US011278320B2

(12) United States Patent
Adams et al.

(10) Patent No.: US 11,278,320 B2
(45) Date of Patent: *Mar. 22, 2022

(54) POLYPECTOMY SYSTEMS, DEVICES, AND METHODS

(71) Applicant: Polygon Medical, Inc., Needham, MA (US)

(72) Inventors: Ronald D. Adams, Holliston, MA (US); Joseph Siletto, Needham, MA (US); Gary R. McCarthy, East Bridgewater, MA (US); James Angelo Libby, Kingston, MA (US); Daniel J. Borsari, Halifax, MA (US); Danial Ferreira, Woodbridge, CT (US)

(73) Assignee: Polygon Medical, Inc., Needham, MA (US)

( * ) Notice: Subject to any disclaimer, the term of this patent is extended or adjusted under 35 U.S.C. 154(b) by 231 days.

This patent is subject to a terminal disclaimer.

(21) Appl. No.: 16/359,860

(22) Filed: Mar. 20, 2019

(65) Prior Publication Data

US 2019/0282269 A1 Sep. 19, 2019

Related U.S. Application Data

(63) Continuation of application No. 16/006,040, filed on Jun. 12, 2018, now Pat. No. 10,285,731.

(Continued)

(51) Int. Cl.
*A61B 17/42* (2006.01)
*A61B 17/32* (2006.01)
(Continued)

(52) U.S. Cl.
CPC .......... *A61B 17/42* (2013.01); *A61B 10/0283* (2013.01); *A61B 10/0291* (2013.01);
(Continued)

(58) Field of Classification Search
CPC . A61B 17/26; A61B 17/221; A61B 17/32056; A61B 17/32; A61B 17/42;
(Continued)

(56) References Cited

U.S. PATENT DOCUMENTS

| 3,606,878 A | 9/1971 | Kellogg, Jr. |
| 3,882,849 A | 5/1975 | Jamshidi |

(Continued)

FOREIGN PATENT DOCUMENTS

| WO | WO 2014/081812 | 5/2014 |
| WO | WO 2018/231778 | 12/2018 |

OTHER PUBLICATIONS

International Search Report and Written Opinion for application No. PCT/US2018/037027, dated Oct. 5, 2018.

(Continued)

*Primary Examiner* — Vi X Nguyen

(57) ABSTRACT

A polyp removal device includes an outer tubular body; an inner tubular body; a tubular cutter coupled to or formed as part of the distal end of the inner tubular body; a spring positioned to bias the inner tubular body in an extended direction with respect to the outer tubular body; a handle coupled to the proximal end of the outer tubular body; an actuation member movably coupled to the handle; and a disconnect mechanism for selectively coupling the actuation member to the inner tubular body and decoupling the actuation member from the inner tubular body, the disconnect mechanism is configured to automatically decouple the inner tubular body from the actuation member when the actuation member is moved in a first direction for a distance greater than a predetermined distance.

20 Claims, 86 Drawing Sheets

Related U.S. Application Data

(60) Provisional application No. 62/519,490, filed on Jun. 14, 2017.

(51) Int. Cl.
    *A61B 10/02*     (2006.01)
    *A61B 10/04*     (2006.01)
    *A61B 10/06*     (2006.01)
    *A61B 17/00*     (2006.01)
    *A61B 17/3201*     (2006.01)
    *A61B 17/3205*     (2006.01)
    *A61B 17/3207*     (2006.01)

(52) U.S. Cl.
    CPC .............. *A61B 10/04* (2013.01); *A61B 10/06* (2013.01); *A61B 17/32002* (2013.01); *A61B 17/320016* (2013.01); *A61B 17/3201* (2013.01); *A61B 17/32053* (2013.01); *A61B 17/320783* (2013.01); *A61B 2017/00269* (2013.01); *A61B 2017/00367* (2013.01); *A61B 2017/00398* (2013.01); *A61B 2017/00473* (2013.01); *A61B 2017/00477* (2013.01); *A61B 2017/320024* (2013.01); *A61B 2017/320044* (2013.01); *A61B 2017/320064* (2013.01); *A61B 2017/4216* (2013.01); *A61B 2217/005* (2013.01)

(58) Field of Classification Search
    CPC ........ A61B 17/3201; A61B 17/320016; A61B 17/32002; A61B 2017/320064; A61B 2017/4216; A61B 10/02; A61B 10/04; A61B 10/06; A61B 10/0283; A61B 17/24; A61B 10/0291
    See application file for complete search history.

(56) References Cited

U.S. PATENT DOCUMENTS

| | | |
|---|---|---|
| 4,603,694 A | 8/1986 | Wheeler |
| 4,620,547 A | 11/1986 | Boebel |
| 4,651,753 A | 3/1987 | Lifton |
| 4,678,459 A | 7/1987 | Onik et al. |
| 4,811,734 A | 3/1989 | McGurk-Burleson et al. |
| 4,958,625 A | 9/1990 | Bates et al. |
| 4,961,430 A | 10/1990 | Sheahon |
| 5,061,238 A | 10/1991 | Shuler |
| D329,092 S | 9/1992 | Carusillo et al. |
| 5,190,542 A | 3/1993 | Nakao et al. |
| 5,201,740 A | 4/1993 | Nakao et al. |
| 5,271,414 A | 12/1993 | Partika et al. |
| 5,327,896 A * | 7/1994 | Schmieding ... A61B 17/320016 600/566 |
| 5,336,227 A | 8/1994 | Nakao et al. |
| 5,347,991 A | 9/1994 | Nakao et al. |
| 5,363,860 A | 11/1994 | Nakao et al. |
| 5,395,313 A | 3/1995 | Naves et al. |
| 5,417,697 A | 5/1995 | Wilk et al. |
| 5,423,830 A | 6/1995 | Schneebaum et al. |
| 5,423,844 A | 6/1995 | Miller |
| 5,439,474 A | 8/1995 | Li |
| D364,463 S | 11/1995 | Pitzen et al. |
| 5,486,182 A | 1/1996 | Nakao et al. |
| 5,505,210 A | 4/1996 | Clement |
| 5,527,332 A | 6/1996 | Clement |
| 5,601,583 A | 2/1997 | Donahue et al. |
| 5,649,547 A | 7/1997 | Ritchart et al. |
| 5,741,271 A | 4/1998 | Nakao et al. |
| 5,741,287 A | 4/1998 | Alden et al. |
| 5,746,747 A | 5/1998 | McKeating |
| 5,759,187 A | 6/1998 | Nakao et al. |
| 5,782,849 A | 7/1998 | Miller |
| 5,797,907 A | 8/1998 | Clement |
| 5,810,806 A | 9/1998 | Ritchart et al. |
| 5,814,052 A | 9/1998 | Nakao et al. |
| 5,871,454 A | 2/1999 | Majlessi |
| 5,873,886 A * | 2/1999 | Larsen ................... A61B 10/06 606/180 |
| 5,906,620 A | 5/1999 | Nakao et al. |
| 5,993,454 A | 11/1999 | Longo |
| 5,997,547 A | 12/1999 | Nakao et al. |
| 6,007,495 A | 12/1999 | Matula |
| 6,022,362 A | 2/2000 | Lee et al. |
| 6,068,603 A | 5/2000 | Suzuki |
| 6,165,137 A | 12/2000 | Milliman et al. |
| 6,171,315 B1 | 1/2001 | Chu et al. |
| 6,383,198 B1 | 5/2002 | Hamilton |
| 6,428,498 B2 | 8/2002 | Uflacker |
| 6,454,727 B1 | 9/2002 | Burbank et al. |
| 6,478,805 B1 | 11/2002 | Marino et al. |
| 6,530,923 B1 | 3/2003 | Dubrul et al. |
| 6,616,659 B1 | 9/2003 | de la Torre et al. |
| 6,626,850 B1 | 9/2003 | Chau et al. |
| 6,638,235 B2 | 10/2003 | Miller et al. |
| 6,887,209 B2 | 5/2005 | Kadziauskas et al. |
| 6,960,172 B2 | 11/2005 | McGuckin, Jr. et al. |
| 7,115,125 B2 | 10/2006 | Nakao et al. |
| D594,983 S | 6/2009 | Price et al. |
| D618,797 S | 6/2010 | Price et al. |
| D620,593 S | 7/2010 | Tran et al. |
| 7,806,894 B1 | 10/2010 | Rosenblatt et al. |
| 7,854,706 B2 | 12/2010 | Hibner |
| D631,965 S | 2/2011 | Price et al. |
| 7,922,737 B1 | 4/2011 | Cesarini et al. |
| 7,988,642 B2 | 8/2011 | Hardin et al. |
| 8,202,229 B2 | 6/2012 | Miller et al. |
| 8,277,393 B2 | 10/2012 | Miller et al. |
| 8,292,909 B1 | 10/2012 | DuBois et al. |
| 8,298,254 B2 | 10/2012 | DuBois et al. |
| D670,380 S | 11/2012 | Sapalev et al. |
| 8,357,103 B2 | 1/2013 | Mark et al. |
| 8,430,825 B2 | 4/2013 | Mark et al. |
| 8,485,989 B2 | 7/2013 | Videbaek |
| D687,549 S | 8/2013 | Johnson et al. |
| D700,966 S | 3/2014 | O'Leary et al. |
| 8,690,793 B2 | 4/2014 | Ranpura et al. |
| D709,194 S | 7/2014 | Miller et al. |
| 8,790,276 B2 | 7/2014 | Ritchart et al. |
| 8,845,621 B2 | 9/2014 | Fojtik |
| 8,893,722 B2 | 11/2014 | Emanuel |
| 8,979,890 B2 | 3/2015 | Boudreaux |
| 9,060,760 B2 | 6/2015 | Sullivan et al. |
| 9,095,366 B2 | 8/2015 | Sullivan et al. |
| D743,547 S | 11/2015 | Chang et al. |
| 9,237,921 B2 | 1/2016 | Messerly et al. |
| 9,339,288 B2 | 5/2016 | Sullivan et al. |
| D759,237 S | 6/2016 | Heath et al. |
| D763,442 S | 8/2016 | Price et al. |
| D785,794 S | 5/2017 | Magno, Jr. |
| 9,700,333 B2 | 6/2017 | Strobl et al. |
| 9,707,012 B2 * | 7/2017 | Adams ............ A61B 17/00234 |
| 9,724,118 B2 | 8/2017 | Schulte et al. |
| D806,245 S | 12/2017 | Halbert et al. |
| 9,848,902 B2 | 12/2017 | Price et al. |
| D847,992 S | 5/2019 | Adams et al. |
| 10,285,731 B2 * | 5/2019 | Adams ................... A61B 10/04 |
| 2002/0082519 A1 | 6/2002 | Miller et al. |
| 2002/0198467 A1 | 12/2002 | Finer |
| 2005/0182339 A1 | 8/2005 | Lee et al. |
| 2006/0144548 A1 | 7/2006 | Beckman et al. |
| 2007/0161925 A1 | 7/2007 | Quick et al. |
| 2007/0185411 A1 | 8/2007 | Hibner |
| 2008/0249553 A1 | 10/2008 | Gruber |
| 2008/0306406 A1 | 12/2008 | Thompson et al. |
| 2009/0204021 A1 | 8/2009 | Shabaz et al. |
| 2010/0152756 A1 | 6/2010 | Mark |
| 2011/0087260 A1 | 4/2011 | Seipel et al. |
| 2012/0172889 A1 | 7/2012 | Chin et al. |
| 2013/0046316 A1 | 2/2013 | Sullivan et al. |
| 2013/0053759 A1 | 2/2013 | McCawley |
| 2013/0103041 A1 | 4/2013 | Regadas |
| 2013/0211321 A1 | 8/2013 | Dubois et al. |

(56) References Cited

U.S. PATENT DOCUMENTS

| | | |
|---|---|---|
| 2015/0025541 A1 | 1/2015 | Furlong et al. |
| 2015/0064165 A1 | 3/2015 | Perry et al. |
| 2015/0141809 A1 | 5/2015 | Costello et al. |
| 2015/0148836 A1 | 5/2015 | Heeren |
| 2015/0238171 A1 | 8/2015 | Shabaz |
| 2015/0335485 A1 | 11/2015 | Rieger et al. |
| 2015/0351788 A1 | 12/2015 | Sullivan et al. |
| 2016/0095615 A1 | 4/2016 | Orczy-Timko et al. |
| 2018/0116694 A1 | 5/2018 | Adams et al. |

OTHER PUBLICATIONS

International Search Report and Written Opinion for application No. PCT/US2016/044417, dated Oct. 20, 2016.

\* cited by examiner

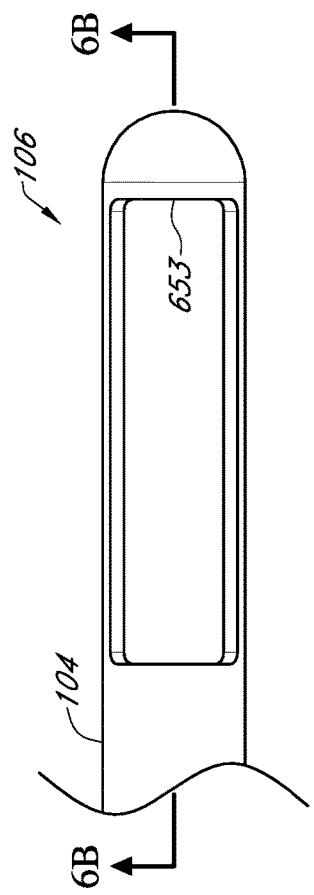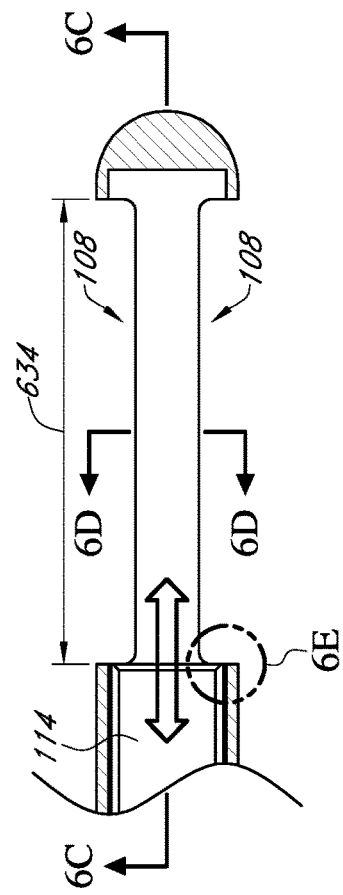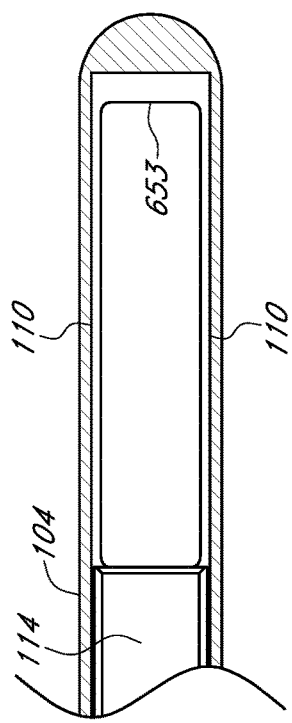

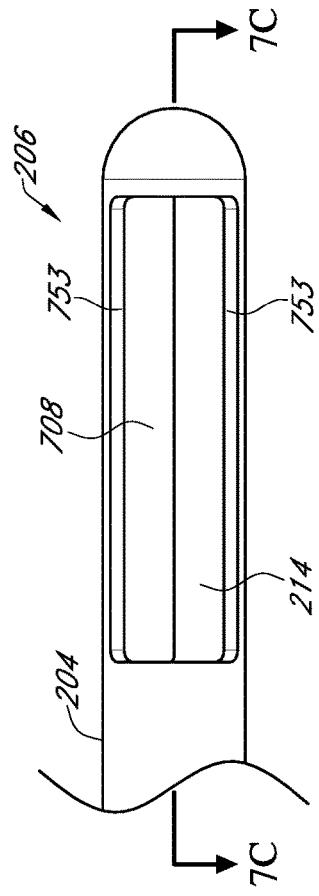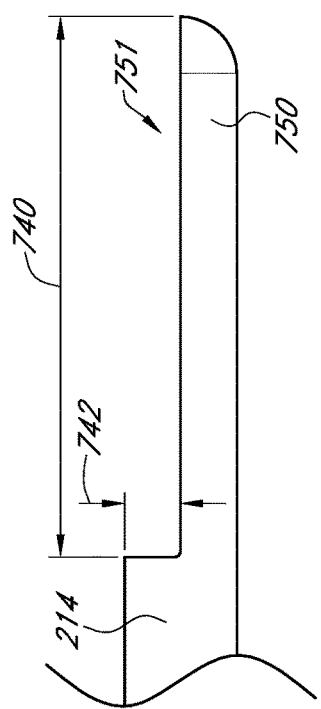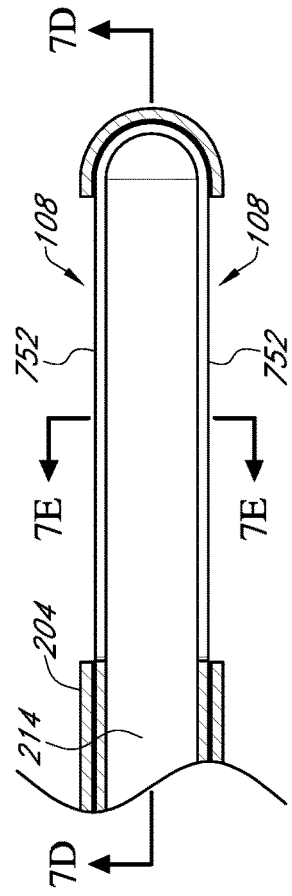

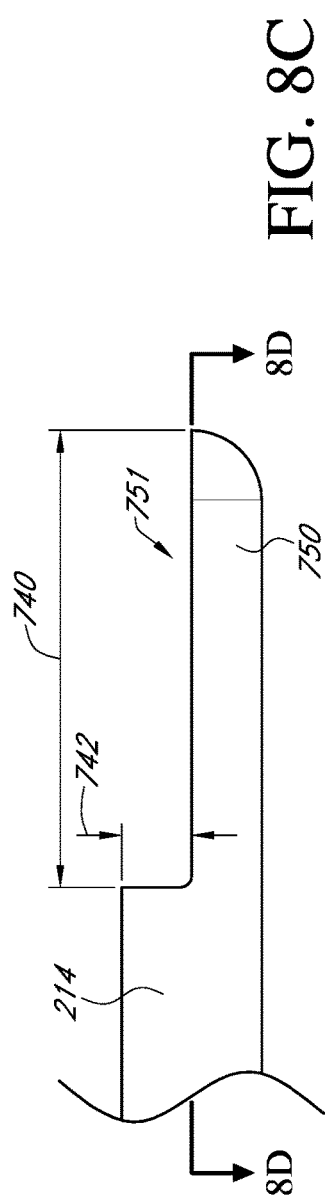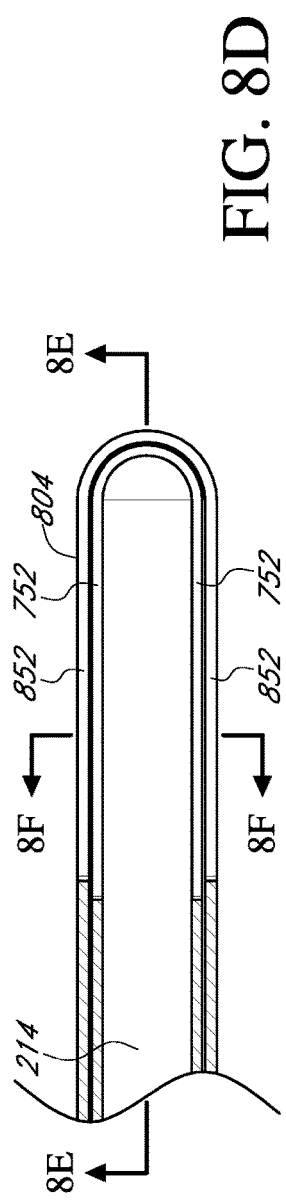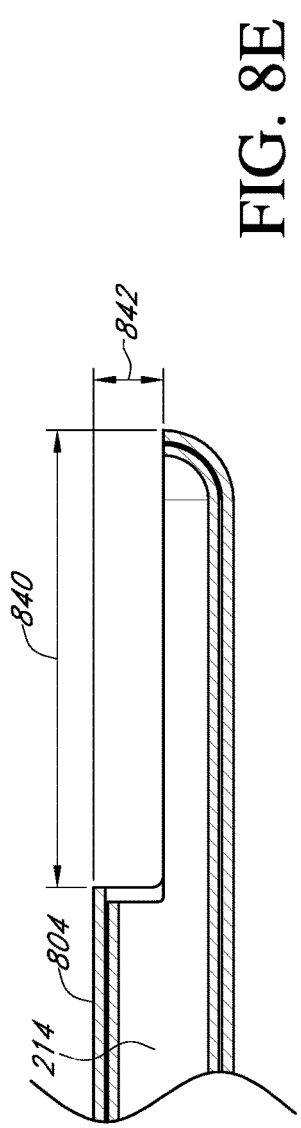

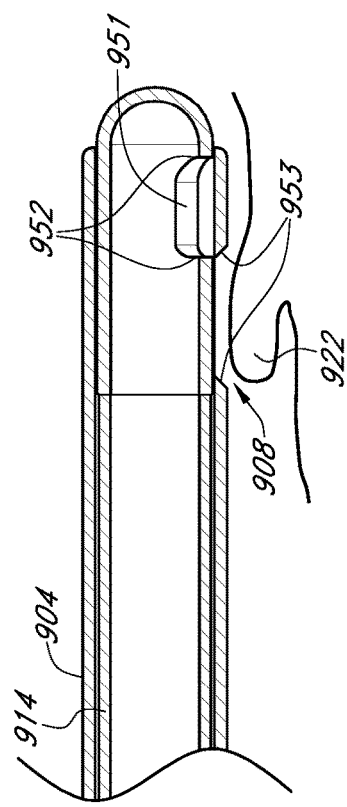
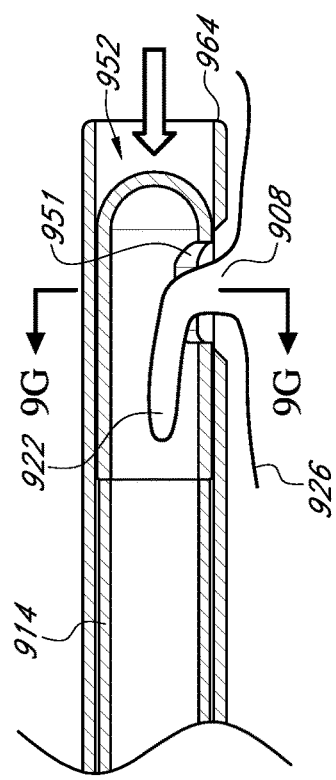
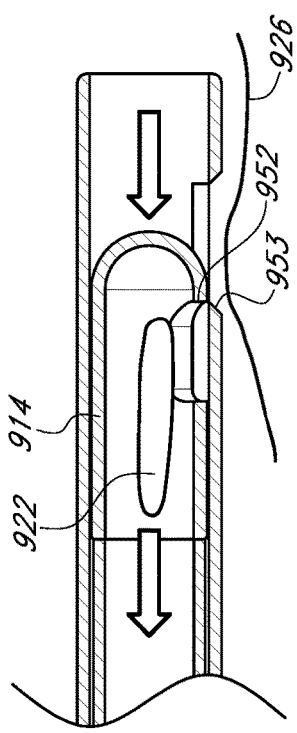
FIG. 9C
FIG. 9D
FIG. 9E

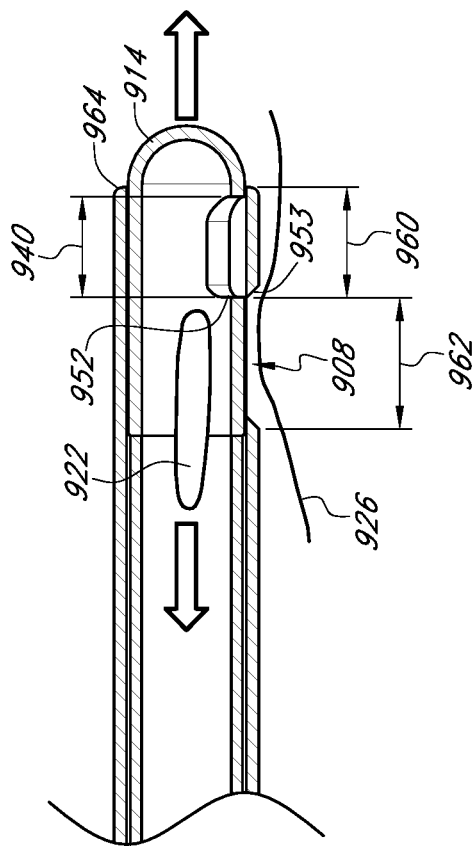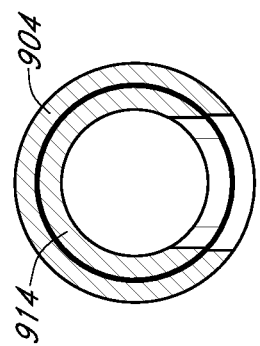

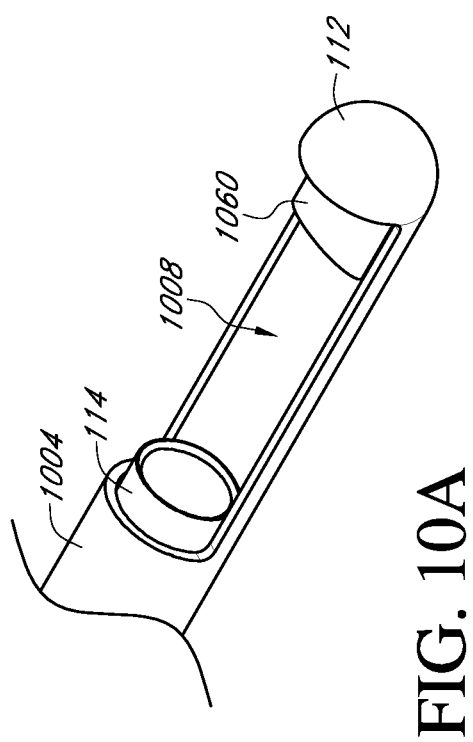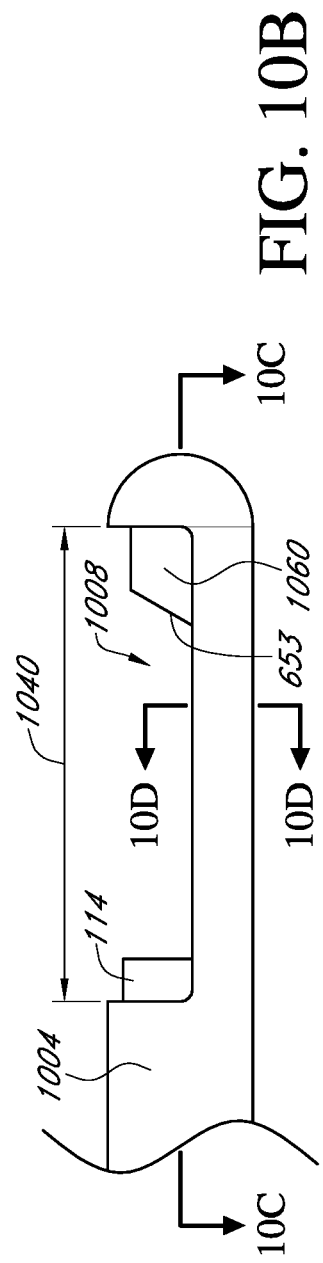

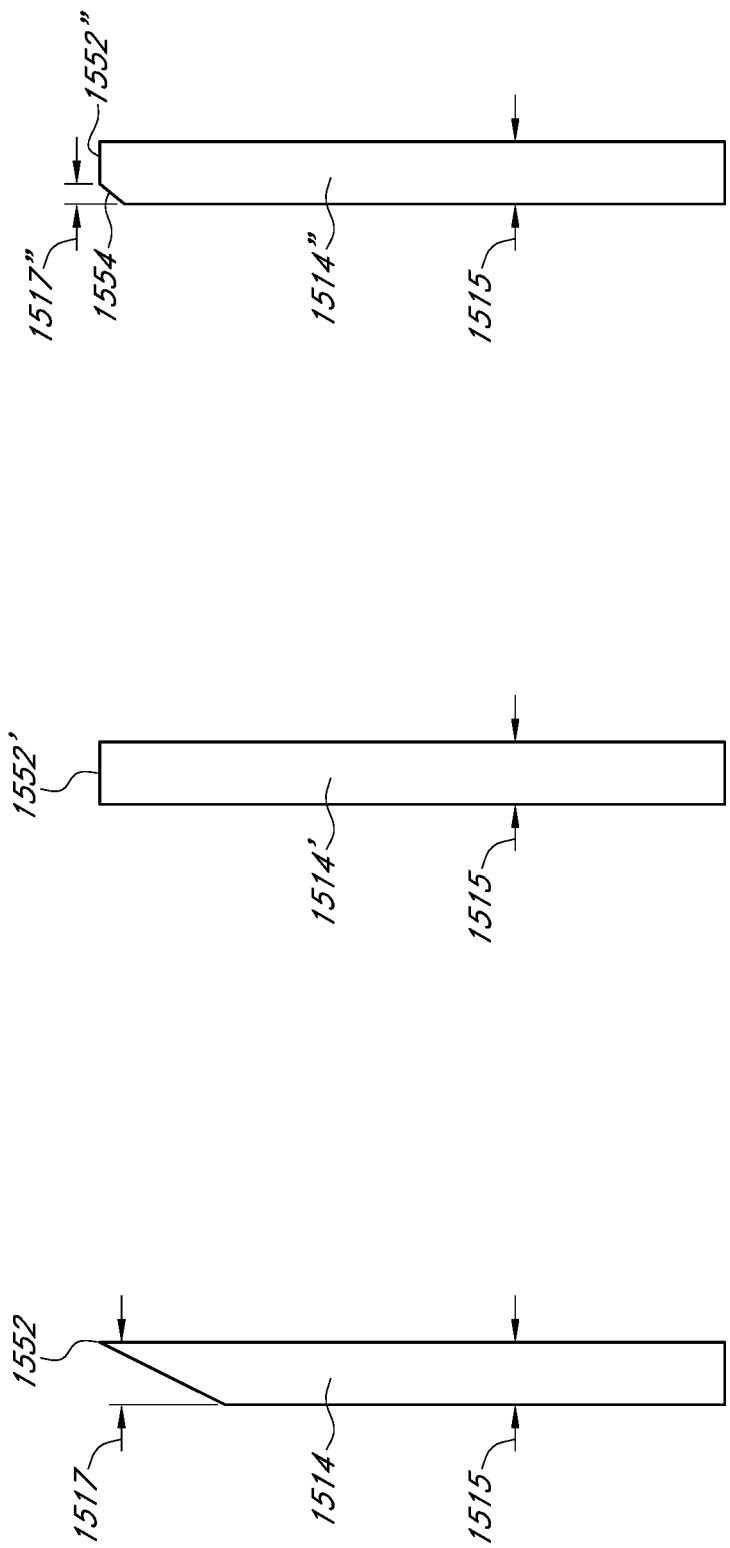

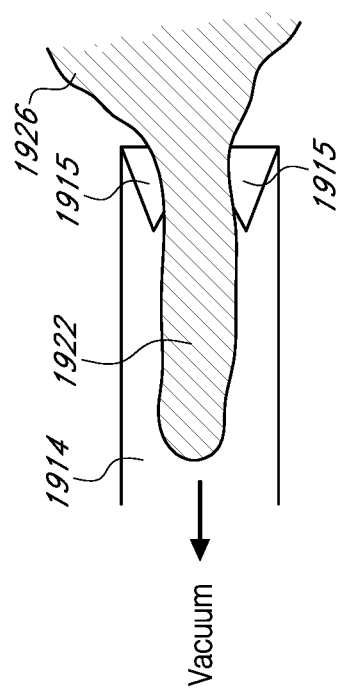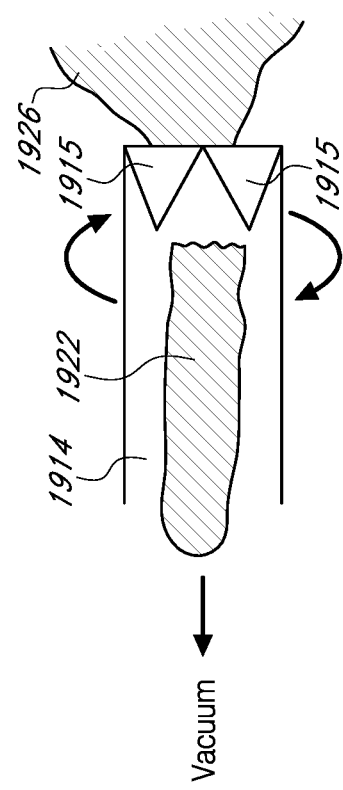

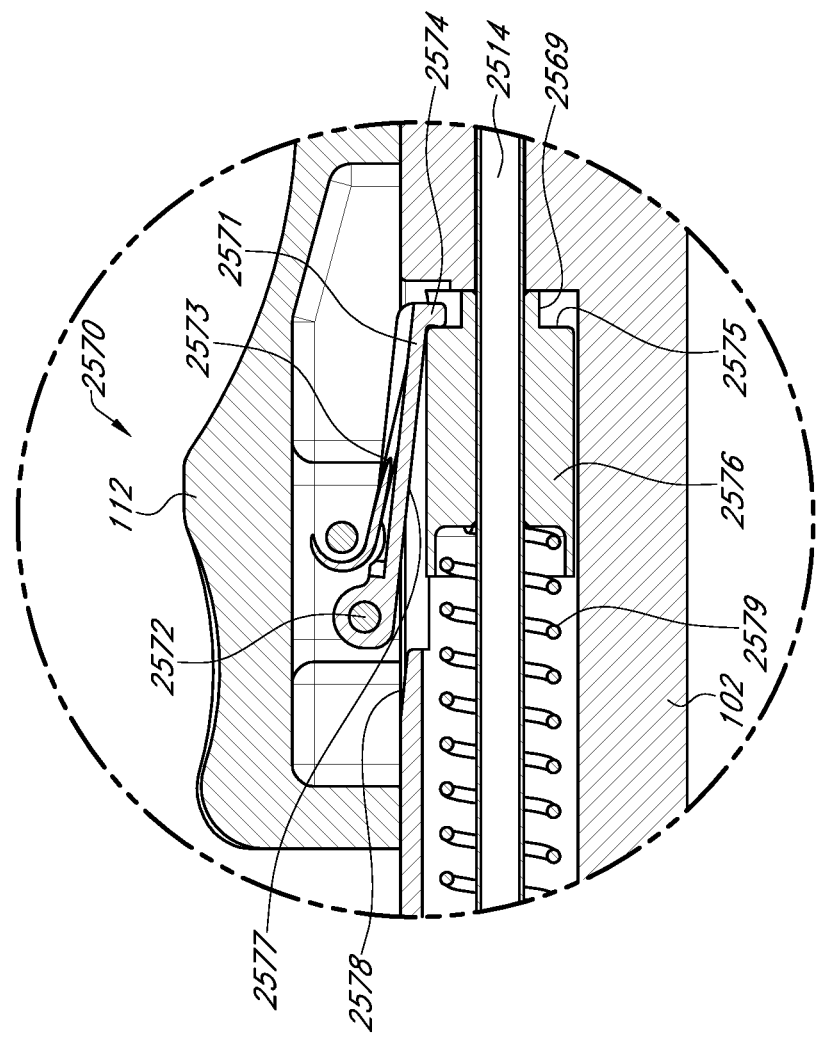
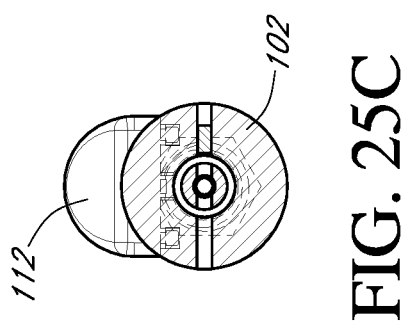

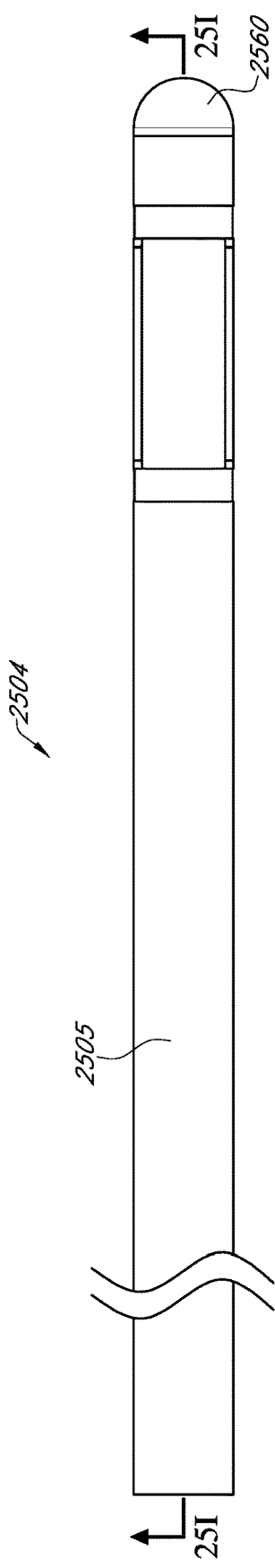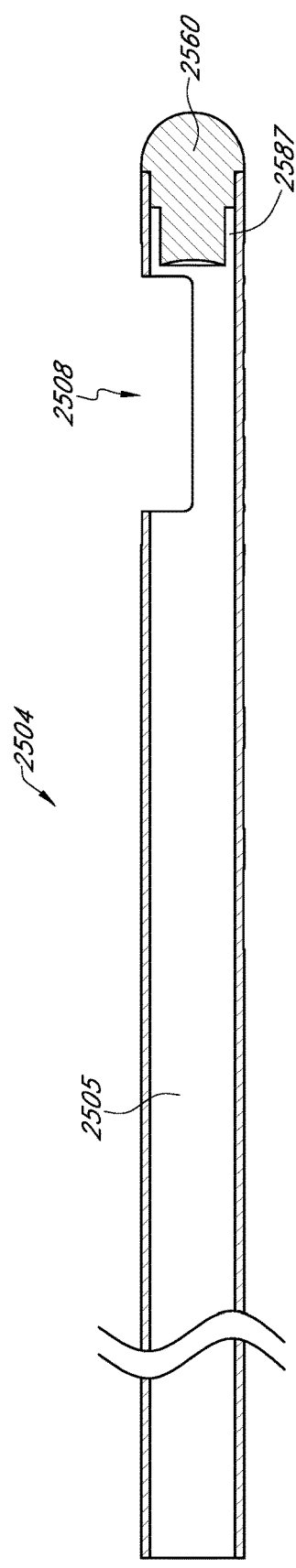
FIG. 25H
FIG. 25I

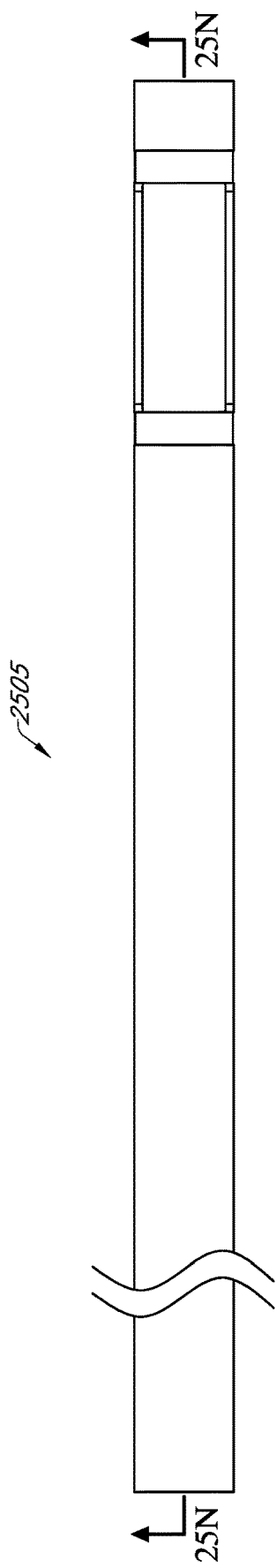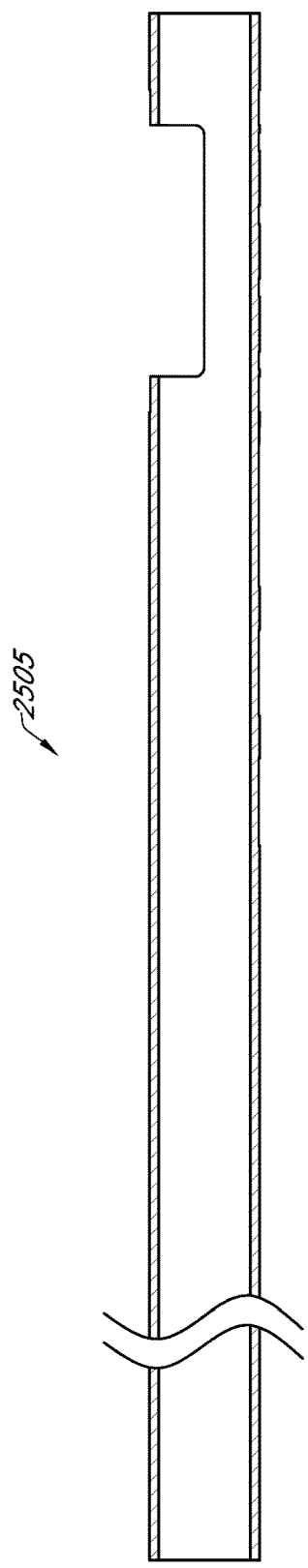

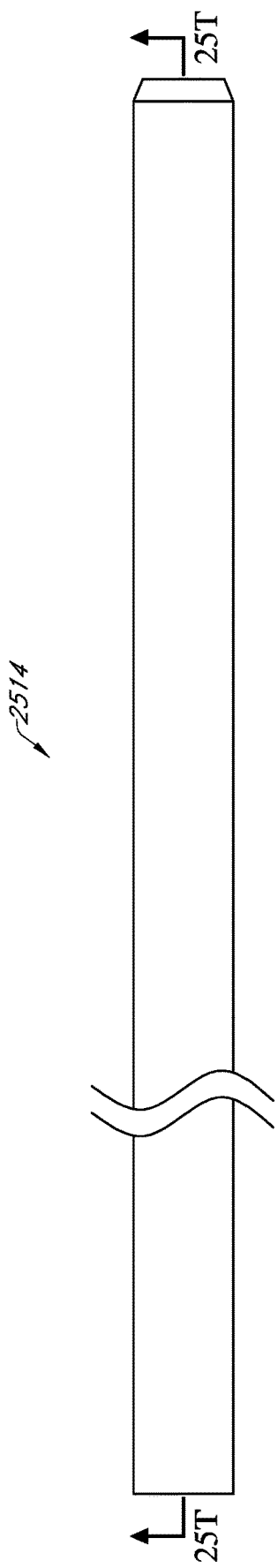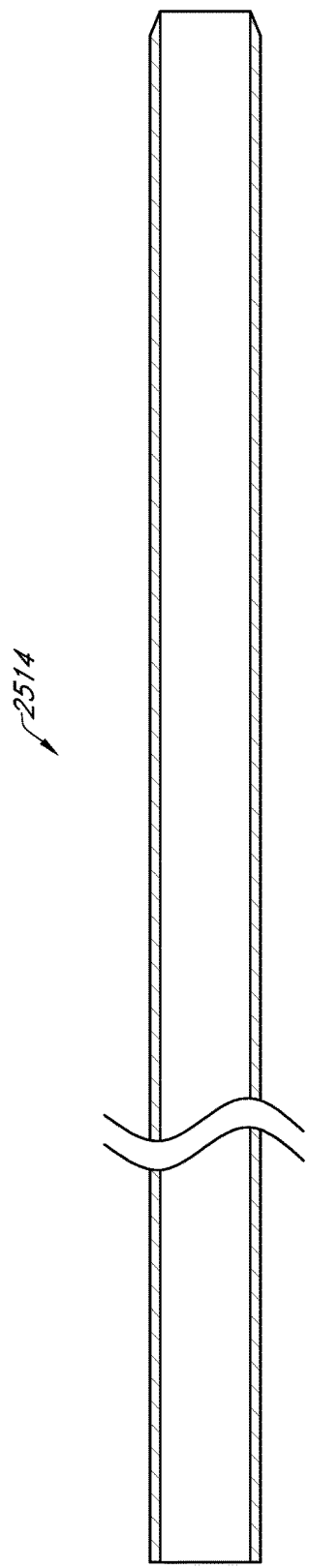

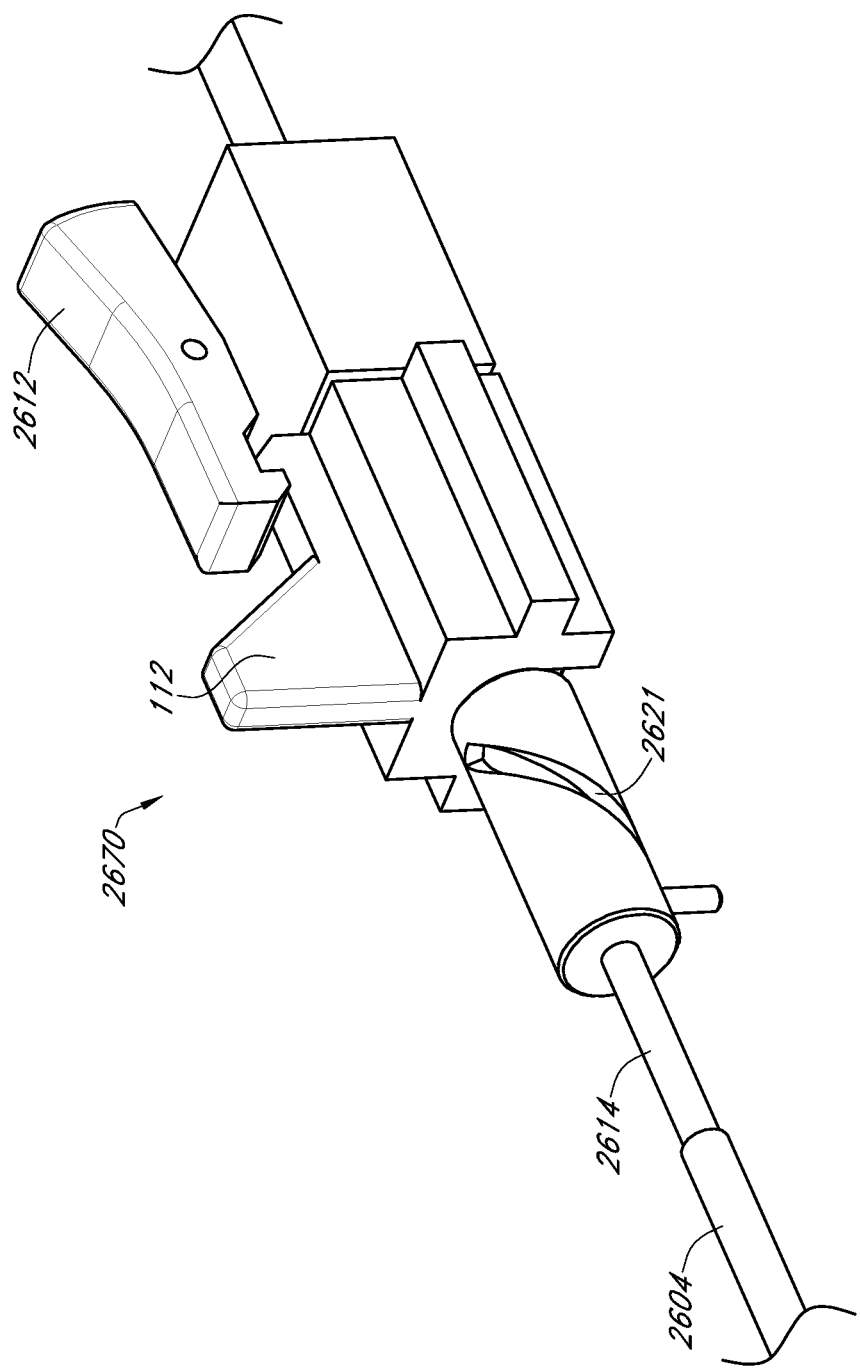

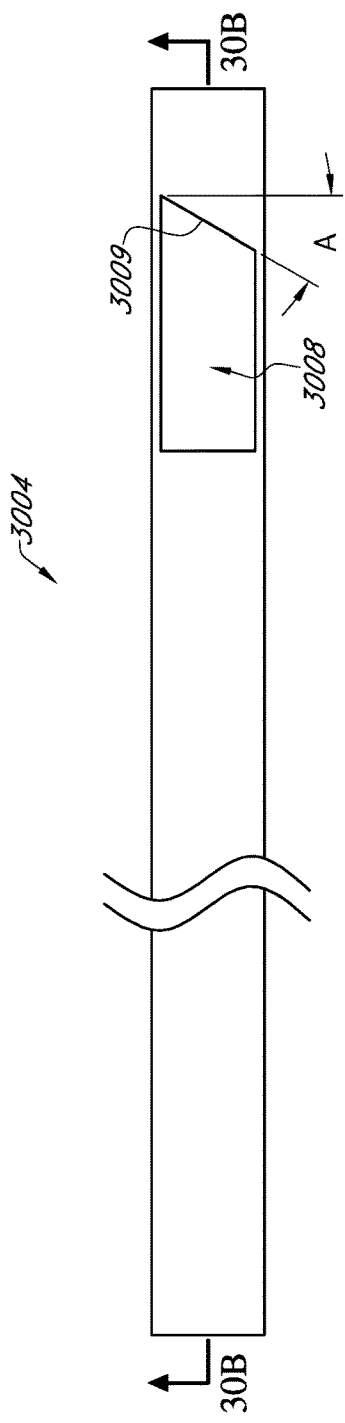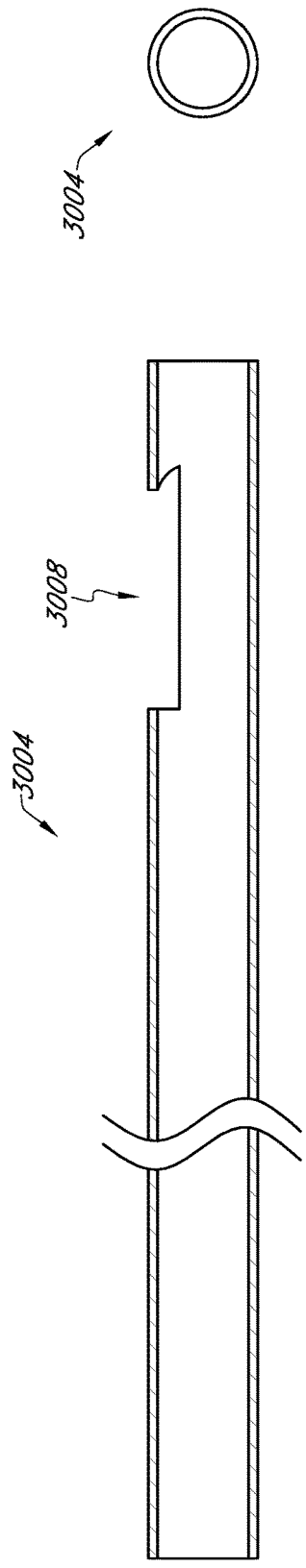
FIG. 30A
FIG. 30B
FIG. 30C

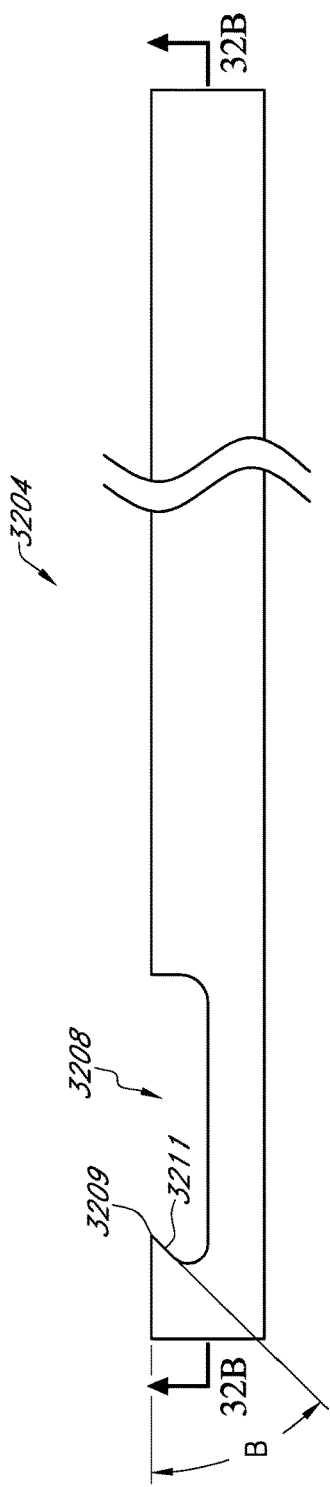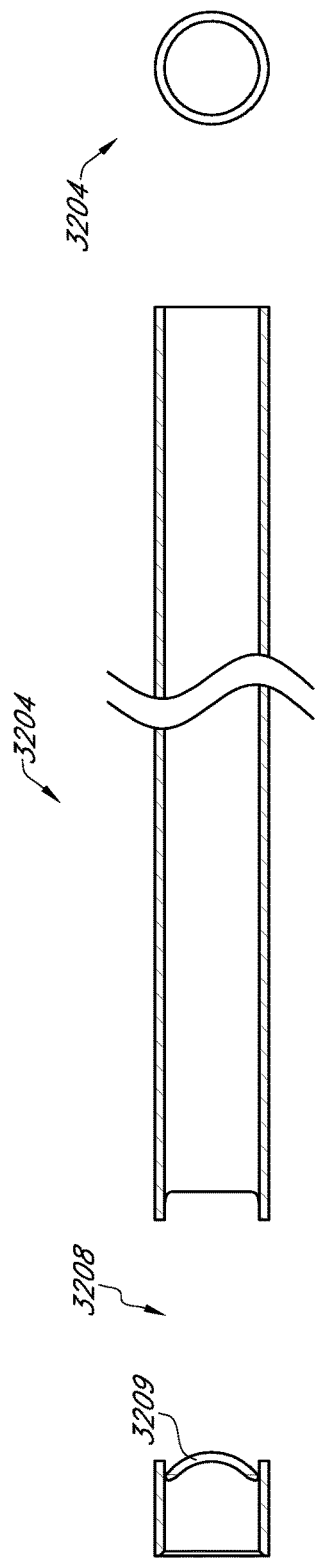

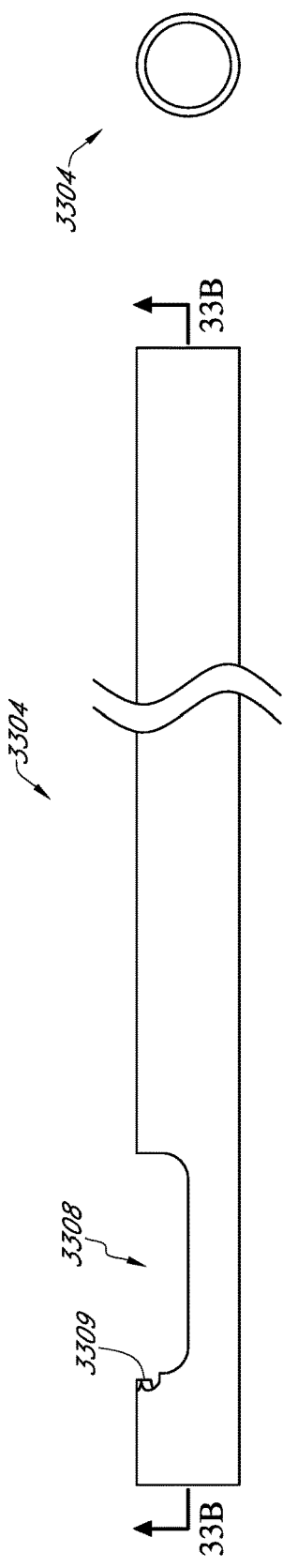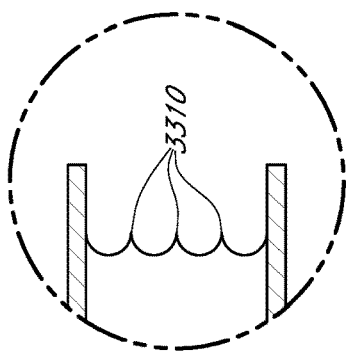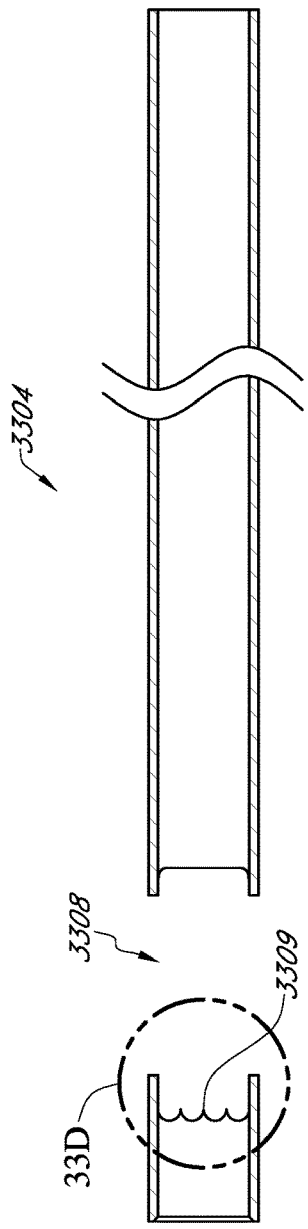

POLYPECTOMY SYSTEMS, DEVICES, AND METHODS

CROSS REFERENCE TO RELATED APPLICATIONS

This application is a continuation of U.S. patent application Ser. No. 16/006,040, titled POLYPECTOMY SYSTEMS, DEVICES, AND METHODS, filed on Jun. 12, 2018, which claims the benefit of U.S. Provisional Patent Application No. 62/519,490, titled POLYPECTOMY SYSTEMS, DEVICES, AND METHODS, filed on Jun. 14, 2017. This application is related by subject matter to U.S. patent application Ser. No. 15/616,148, titled POLYPECTOMY SYSTEMS, DEVICES, AND METHODS, filed on Jun. 7, 2017, which is a continuation of U.S. patent application Ser. No. 15/222,021, titled POLYPECTOMY SYSTEMS, DEVICES, AND METHODS, filed on Jul. 28, 2016, which claims the benefit of U.S. Provisional Patent Application No. 62/199,494, titled POLYPECTOMY SYSTEMS, DEVICES, AND METHODS, filed on Jul. 31, 2015. Each of the foregoing applications is hereby incorporated by reference herein in its entirety.

BACKGROUND

Field

The disclosure relates generally to the field of medicine, and more specifically to devices and methods for performing polypectomies.

Description

A polyp is an abnormal growth of tissue from a mucous membrane. A polypectomy may be performed to remove a polyp. An endometrial or uterine polyp is an abnormal growth attached to an inner wall of the uterus. Uterine polyps are usually benign, but they can be cancerous or eventually turn into cancer.

SUMMARY

This disclosure presents various embodiments of polypectomy systems, methods, and devices for safely removing polyps, such as uterine polyps. In some embodiments, a polypectomy device is configured to be inserted through the vaginal canal into the uterus, and to remove polyps through one or both of vacuum suction and mechanical separation. In some embodiments, the polypectomy devices disclosed herein are specifically designed to remove polyps—which are generally relatively small and gelatinous in consistency—and not necessarily designed to remove a larger and/or firmer object, such as a fibroid. This can enable embodiments disclosed herein to be smaller than, and in some cases mechanically simpler than, more robustly built tools that are intended to remove those larger and/or firmer objects, such as fibroids. The polypectomy devices disclosed herein can be safer, easier to use, lower cost and/or easier to manufacture.

According to some embodiments, a polyp removal device comprises: an outer tubular body having a cylindrical outer surface, proximal and distal ends, and an opening in the cylindrical outer surface at or near the distal end; an inner tubular body positioned within a lumen of the outer tubular body, the inner tubular body having proximal and distal ends and being movable with respect to the outer tubular body; a tubular cutter coupled to or formed as part of the distal end of the inner tubular body, the tubular cutter positioned adjacent the opening of the outer tubular body; a spring positioned to bias the inner tubular body in an extended direction with respect to the outer tubular body; a handle coupled to the proximal end of the outer tubular body; an actuation member movably coupled to the handle, the actuation member configured to be manipulated by a user by at least one of sliding or rotating the actuation member with respect to the handle, the actuation member configured to be movable in at least a first direction and a second direction with respect to the handle; and a disconnect mechanism for selectively coupling the actuation member to the inner tubular body and decoupling the actuation member from the inner tubular body, the disconnect mechanism is configured to keep the inner tubular body coupled to the actuation member while the actuation member is moved in the first direction for a predetermined distance, causing the inner tubular body to retract with respect to the outer tubular body, the disconnect mechanism is further configured to automatically decouple the inner tubular body from the actuation member when the actuation member is moved in the first direction for a distance greater than the predetermined distance, enabling the spring to cause the inner tubular body to extend with respect to the outer tubular body, and the disconnect mechanism is further configured to re-couple the inner tubular body to the actuation member when the actuation member is moved in the second direction.

In some embodiments, the disconnect mechanism comprises: a rotatable connecting link biased in a direction that couples the inner tubular body to the actuation member; and a cam surface positioned to engage the connecting link and cause the connecting link to rotate in a direction that decouples the inner tubular body from the actuation member, responsive to movement of the actuating member in the first direction. In some embodiments, the disconnect mechanism comprises: an elastically bendable connecting link biased in a direction that couples the inner tubular body to the actuation member; and a cam surface positioned to engage the connecting link and cause the connecting link to bend in a direction that decouples the inner tubular body from the actuation member, responsive to movement of the actuating member in the first direction. In some embodiments, the first direction comprises translation of the actuation member in a proximal direction with respect to the handle, and the second direction comprises translation of the actuation member in a distal direction with respect to the handle. In some embodiments, the first direction comprises rotation of the actuation member in a clockwise or counterclockwise direction with respect to the handle, and the second direction comprises rotation of the actuation member in a direction opposite to the first direction with respect to the handle. In some embodiments, the polyp removal device further comprises a cam mechanism configured to cause the inner tubular body to rotate about a longitudinal axis as the inner tubular body extends with respect to the outer tubular body. In some embodiments, the cam mechanism comprises a pin positioned at least partially within a helical groove, wherein the pin is coupled to or formed as part of one of the inner tubular body or the handle, and the helical groove is coupled to or formed as part of the other of the inner tubular body or the handle. In some embodiments, the cam mechanism is configured to cause the inner tubular body to rotate no more than 180 degrees about the longitudinal axis as the inner tubular body extends with respect to the outer tubular body. In some embodiments, the cam mechanism is configured to cause the inner tubular body to rotate no more than 270 degrees about the longitudinal axis as the inner tubular body extends with respect to the outer tubular body. In some embodiments, the polyp removal device further comprises: a cutting block positioned at the distal end of the outer tubular body and at least partially distal to the opening, the cutting block comprising a blunt rounded distal portion that at least partially forms a distal tip of the polyp removal device, the cutting block further comprising a proximally extending cutting portion positioned within the lumen of the outer tubular body, the cutting portion comprising a cylindrical outer surface, a concave proximal face, and a cutting edge where the cylindrical outer surface meets the concave proximal face, wherein the tubular cutter is sized to fit at least partially within an annular shaped void between the lumen of the outer tubular body and the cylindrical outer surface of the cutting portion of the cutting block when the inner tubular body is in an extended position with respect to the outer tubular body. In some embodiments, the tubular cutter comprises a circular cutting edge positioned at an inner diameter of a distal end of the tubular cutter. In some embodiments, the outer tubular body comprises a distal cutting surface at a distal end of the opening, the distal cutting surface comprising a shape that is not perpendicular to a longitudinal axis of the outer tubular body. In some embodiments, the outer tubular body comprises a distal cutting surface at a distal end of the opening, the distal cutting surface comprising a shape that, when viewed perpendicular to a longitudinal axis of the outer tubular body and normal to a center of the opening, comprises one or more rounded portions or comprises one or more portions that are oriented at a non-perpendicular angle with respect to the longitudinal axis. In some embodiments, the outer tubular body is rotatably coupled to the handle, to allow the outer tubular body to rotate about a longitudinal axis with respect to the handle. In some embodiments, the outer tubular body is rotatably coupled to the handle via a hub, the hub comprising at least one radially protruding member for engagement by a user to cause rotation of the hub and outer tubular body with respect to the handle. In some embodiments, the polyp removal device further comprises a ball detent mechanism configured to resist rotation of the hub with respect to the handle until a preload force of the ball detent mechanism is overcome, the ball detent mechanism comprising at least a ball, a ball preload device, and a plurality of detents for the ball to engage. In some embodiments, the tubular cutter comprises a circular cutting edge positioned at an inner diameter of a distal end of the tubular cutter. In some embodiments, the outer tubular body comprises a distal cutting surface at a distal end of the opening, the distal cutting surface comprising a shape that is not perpendicular to a longitudinal axis of the outer tubular body. In some embodiments, the outer tubular body comprises a distal cutting surface at a distal end of the opening, the distal cutting surface comprising a shape that, when viewed perpendicular to a longitudinal axis of the outer tubular body and normal to a center of the opening, comprises one or more rounded portions or comprises one or more portions that are oriented at a non-perpendicular angle with respect to the longitudinal axis.

According to some embodiments, a polyp removal device comprises: an outer tubular body having proximal and distal ends; an inner tubular body positioned within a lumen of the outer tubular body, the inner tubular body having proximal and distal ends and being movable with respect to the outer tubular body; a handle coupled to the proximal end of the outer tubular body; an actuation member movably coupled to the handle, the actuation member configured to cause at least translation of the inner tubular body with respect to the outer tubular body when the actuation member is moved with respect to the handle; a vacuum port for coupling thereto of a vacuum source, the vacuum port being in fluid communication with a lumen of the inner tubular body; an opening near a distal end of the polyp removal device, the opening configured to allow fluid communication between an environment external to the polyp removal device and the lumen of the inner tubular body; a cutting block positioned at the distal end of the outer tubular body and at least partially distal to the opening, the cutting block comprising a blunt rounded distal portion that at least partially forms a distal tip of the polyp removal device, the cutting block further comprising a proximally extending cutting portion positioned within the lumen of the outer tubular body, the cutting portion comprising a cylindrical outer surface, a concave proximal face, and a cutting edge where the cylindrical outer surface meets the concave proximal face; and a tubular cutter positioned at the distal end of the inner tubular body, the tubular cutter sized to fit at least partially within an annular shaped void between the lumen of the outer tubular body and the cylindrical outer surface of the cutting portion of the cutting block when the inner tubular body is in an extended position with respect to the outer tubular body.

In some embodiments, a diametral clearance between an inner diameter of the tubular cutter and an outer diameter of the cylindrical outer surface of the cutting portion of the cutting block is no greater than 0.0025". In some embodiments, the outer tubular body is rotatably coupled to the handle, to allow the outer tubular body to rotate about a longitudinal axis with respect to the handle. In some embodiments, the outer tubular body is rotatably coupled to the handle via a hub, the hub comprising at least one radially protruding member for engagement by a user to cause rotation of the hub and outer tubular body with respect to the handle. In some embodiments, the polyp removal device further comprises a ball detent mechanism configured to resist rotation of the hub with respect to the handle until a preload force of the ball detent mechanism is overcome, the ball detent mechanism comprising at least a ball, a ball preload device, and a plurality of detents for the ball to engage. In some embodiments, the tubular cutter comprises a circular cutting edge positioned at an inner diameter of a distal end of the tubular cutter. In some embodiments, the outer tubular body comprises a distal cutting surface at a distal end of the opening, the distal cutting surface comprising a shape that is not perpendicular to a longitudinal axis of the outer tubular body. In some embodiments, the outer tubular body comprises a distal cutting surface at a distal end of the opening, the distal cutting surface comprising a shape that, when viewed perpendicular to a longitudinal axis of the outer tubular body and normal to a center of the opening, comprises one or more rounded portions or comprises one or more portions that are oriented at a non-perpendicular angle with respect to the longitudinal axis. In some embodiments, a ratio of a longitudinal length of the outer tubular body to an outer diameter of the outer tubular body is at least 100.

According to some embodiments, a polyp removal device comprises: an outer tubular body having a cylindrical outer surface, proximal and distal ends, and an opening in the cylindrical outer surface near the distal end; an inner tubular body positioned within a lumen of the outer tubular body, the inner tubular body having proximal and distal ends and being longitudinally and rotationally movable with respect to the outer tubular body, the inner tubular body comprising an extended position and a retracted position with respect to the outer tubular body; a tubular cutter coupled to or formed as part of the distal end of the inner tubular body, the tubular cutter positioned adjacent the opening of the outer tubular body; a spring positioned to bias the inner tubular body toward the extended position with respect to the outer tubular body; a handle coupled to the proximal end of the outer tubular body; a cam mechanism coupled to the handle and configured to cause the inner tubular body to rotate about a longitudinal axis as the inner tubular body moves from the retracted position to the extended position with respect to the outer tubular body; and a disconnect mechanism coupled to the handle and configured to selectively retain the inner tubular body in the retracted position or release the inner tubular body from the retracted position, allowing the spring to move the inner tubular body toward the extended position.

In some embodiments, the cam mechanism comprises a pin positioned at least partially within a helical groove, wherein the pin is coupled to or formed as part of one of the inner tubular body or the handle, and the helical groove is coupled to or formed as part of the other of the inner tubular body or the handle. In some embodiments, the cam mechanism is configured to cause the inner tubular body to rotate within a range of 90-270 degrees about the longitudinal axis as the inner tubular body extends with respect to the outer tubular body. In some embodiments, the disconnect mechanism comprises a catch that engages an actuation surface of the inner tubular body or a component coupled to the inner tubular body, and wherein the catch is movable out of engagement with the actuation surface to allow the spring to move the inner tubular body toward the extended position. In some embodiments, the catch is pivotally movable to engage or disengage the actuation surface, and the disconnect mechanism further comprises a spring that biases the catch toward engagement with the actuation surface. In some embodiments, the catch is biased toward engagement with the actuation surface, and the catch comprises an elastically bendable material that can bend to disengage the actuation surface. In some embodiments, the disconnect mechanism comprises a manually operable release coupled to or formed as part of the catch to enable manual movement of the catch out of engagement with the actuation surface. In some embodiments, the polyp removal device further comprises: an actuation member movably coupled to the handle and the disconnect mechanism, the actuation member configured to be manipulated by a user by at least one of sliding or rotating the actuation member with respect to the handle; wherein, when the catch of the disconnect mechanism is in engagement with the actuation surface, movement of the actuation member with respect to the handle causes movement of the inner tubular body with respect to the handle; and wherein, when the catch of the disconnect mechanism is not in engagement with the actuation surface, movement of the actuation member with respect to the handle does not cause movement of the inner tubular body with respect to the handle. In some embodiments, the disconnect mechanism further comprises a cam surface positioned to automatically cause the catch to disengage the actuation surface in response to movement of the actuation member with respect to the handle. In some embodiments, the actuation member is coupled to the disconnect mechanism through a geartrain or linkage that converts pivotal movement of the actuation member into sliding movement of at least a portion of the disconnect mechanism. In some embodiments, the outer tubular body is rotatable with respect to the handle, to enable changing of a rotational position of the opening with respect to the handle. In some embodiments, the polyp removal device further comprises: a cutting block positioned at the distal end of the outer tubular body and at least partially distal to the opening, the cutting block comprising a blunt rounded distal portion that at least partially forms a distal tip of the polyp removal device, the cutting block further comprising a proximally extending cutting portion positioned within the lumen of the outer tubular body, the cutting portion comprising a cylindrical outer surface, a concave proximal face, and a cutting edge where the cylindrical outer surface meets the concave proximal face; and wherein the tubular cutter is sized to fit at least partially within an annular shaped void between the lumen of the outer tubular body and the cylindrical outer surface of the cutting portion of the cutting block when the inner tubular body is in the extended position with respect to the outer tubular body. In some embodiments, the tubular cutter comprises a circular cutting edge positioned at an inner diameter of a distal end of the tubular cutter. In some embodiments, the outer tubular body comprises a distal cutting surface at a distal end of the opening, the distal cutting surface comprising a shape that is not perpendicular to the longitudinal axis. In some embodiments, the outer tubular body comprises a distal cutting surface at a distal end of the opening, the distal cutting surface comprising a shape that, when viewed perpendicular to the longitudinal axis and normal to a center of the opening, comprises one or more rounded portions or comprises one or more portions that are oriented at a non-perpendicular angle with respect to the longitudinal axis.

According to some embodiments, a polyp removal device comprises: an outer tubular body having a cylindrical outer surface, proximal and distal ends, and an opening in the cylindrical outer surface near the distal end; an inner tubular body positioned within a lumen of the outer tubular body, the inner tubular body having proximal and distal ends and being movable with respect to the outer tubular body; a cutter coupled to or formed as part of the distal end of the inner tubular body, the cutter positioned adjacent the opening of the outer tubular body; a spring positioned to bias the inner tubular body in a retracted direction with respect to the outer tubular body; a handle coupled to the proximal end of the outer tubular body; an actuation member movably coupled to the handle, the actuation member configured to be manipulated by a user by at least one of sliding or rotating the actuation member with respect to the handle, the actuation member configured to be movable in at least a first direction and a second direction with respect to the handle; and a disconnect mechanism for selectively coupling the actuation member to the inner tubular body and decoupling the actuation member from the inner tubular body, the disconnect mechanism is configured to keep the inner tubular body coupled to the actuation member while the actuation member is moved in the first direction for a predetermined distance, causing the inner tubular body to extend with respect to the outer tubular body, the disconnect mechanism is further configured to automatically decouple the inner tubular body from the actuation member when the actuation member is moved in the first direction for a distance greater than the predetermined distance, enabling the spring to cause the inner tubular body to retract with respect to the outer tubular body, and the disconnect mechanism is further configured to re-couple the inner tubular body to the actuation member when the actuation member is moved in the second direction.

In some embodiments, the disconnect mechanism comprises: a rotatable connecting link biased in a direction that couples the inner tubular body to the actuation member; and a cam surface positioned to engage the connecting link and cause the connecting link to rotate in a direction that decouples the inner tubular body from the actuation member, responsive to movement of the actuating member in the first direction. In some embodiments, the disconnect mechanism comprises: an elastically bendable connecting link biased in a direction that couples the inner tubular body to the actuation member; and a cam surface positioned to engage the connecting link and cause the connecting link to bend in a direction that decouples the inner tubular body from the actuation member, responsive to movement of the actuating member in the first direction. In some embodiments, the first direction comprises translation of the actuation member in a distal direction with respect to the handle, and the second direction comprises translation of the actuation member in a proximal direction with respect to the handle. In some embodiments, the first direction comprises rotation of the actuation member in a clockwise or counter-clockwise direction with respect to the handle, and the second direction comprises rotation of the actuation member in a direction opposite to the first direction with respect to the handle. In some embodiments, the polyp removal device further comprises a cam mechanism configured to cause the inner tubular body to rotate about a longitudinal axis as the inner tubular body retracts with respect to the outer tubular body. In some embodiments, the cam mechanism comprises a pin positioned at least partially within a helical groove, wherein the pin is coupled to or formed as part of one of the inner tubular body or the handle, and the helical groove is coupled to or formed as part of the other of the inner tubular body or the handle. In some embodiments, the cam mechanism is configured to cause the inner tubular body to rotate no more than 180 degrees about the longitudinal axis as the inner tubular body retracts with respect to the outer tubular body. In some embodiments, the cam mechanism is configured to cause the inner tubular body to rotate no more than 270 degrees about the longitudinal axis as the inner tubular body retracts with respect to the outer tubular body. In some embodiments, the outer tubular body is rotatably coupled to the handle, to allow the outer tubular body to rotate about a longitudinal axis with respect to the handle. In some embodiments, the outer tubular body is rotatably coupled to the handle via a hub, the hub comprising at least one radially protruding member for engagement by a user to cause rotation of the hub and outer tubular body with respect to the handle. In some embodiments, the polyp removal device further comprises a ball detent mechanism configured to resist rotation of the hub with respect to the handle until a preload force of the ball detent mechanism is overcome, the ball detent mechanism comprising at least a ball, a ball preload device, and a plurality of detents for the ball to engage.

According to some embodiments, a polyp removal device comprises: an outer tubular body having proximal and distal ends; an inner tubular body positioned within a lumen of the outer tubular body, the inner tubular body having proximal and distal ends and being movable with respect to the outer tubular body; a handle coupled to the proximal end of the outer tubular body; an actuation member movably coupled to the handle, the actuation member configured to cause movement of the inner tubular body with respect to the outer tubular body when the actuation member is moved with respect to the handle; a vacuum port for coupling thereto of a vacuum source, the vacuum port being in fluid communication with a lumen of the inner tubular body; and an opening near a distal end of the polyp removal device, the opening configured to allow fluid communication between an environment external to the polyp removal device and the lumen of the inner tubular body, wherein a size of the opening is variable based on the movement of the inner tubular body with respect to the outer tubular body.

In some embodiments, the inner tubular body is translatable or rotatable with respect to the outer tubular body, but not both. In some embodiments, the polyp removal device further comprises a blunt distal tip. In some embodiments, the opening is formed by unsharpened edges of the outer tubular body and inner tubular body. In some embodiments, the opening is formed by: a first protruding member extending from the distal end of the outer tubular member; and a second protruding member extending from the distal end of the inner tubular member, wherein the first and second protruding members each comprise a semicircular cross-sectional shape at a cross section taken through a transverse plane, and wherein the second protruding member is nested within the first protruding member and is rotatable about a longitudinal axis with respect to the first protruding member. In some embodiments, the opening is formed by: a first protruding member extending from the distal end of the outer tubular member; and a second protruding member extending from the distal end of the inner tubular member, the second protruding member being nested within the first protruding member and rotatable about a longitudinal axis with respect to the first protruding member, wherein the first protruding member comprises an arc-shaped cross-sectional shape, at least at a cross section taken through a transverse plane located at a midpoint of the first protruding member in a longitudinal direction, and wherein the second protruding member comprises an arc-shaped cross-sectional shape, at least at a cross section taken through a transverse plane located at a midpoint of the second protruding member in the longitudinal direction. In some embodiments, angular lengths of the arc-shaped cross-sectional shapes are equal. In some embodiments, an angular length of the arc-shaped cross-sectional shape of the first protruding member is greater than an angular length of the arc-shaped cross-sectional shape of the second protruding member. In some embodiments, an angular length of the arc-shaped cross-sectional shape of the first protruding member is less than an angular length of the arc-shaped cross-sectional shape of the second protruding member. In some embodiments, an angular length of the arc-shaped cross-sectional shape of the first protruding member is equal to or greater than 180 degrees. In some embodiments, a distal tip of the second protruding member comprises a lip extending transversely beyond a longitudinal plane that passes through end points of the arc-shaped cross-sectional shape of the second protruding member. In some embodiments, the lip is sized and positioned such that the lip prevents the second protruding member from translating distally beyond the first protruding member when the second protruding member and first protruding member are positioned rotationally opposite one another. In some embodiments, a distal end of the first protruding member comprises a blunt rounded surface. In some embodiments, the first protruding member comprises a u-shaped cutting edge configured to cooperate with a u-shaped cutting edge of the second protruding member to cut polyp tissue positioned therebetween when the second protruding member rotates with respect to the first protruding member. In some embodiments, a distal end of the first protruding member comprises a flat surface. In some embodiments, the opening is formed by: an outer aperture in a side wall of the outer tubular member, the outer aperture comprising distal and proximal cutting edges; and an inner aperture in a side wall of the inner tubular member, the inner aperture comprising distal and proximal cutting edges, wherein translation of the inner tubular member in a proximal direction with respect to the outer tubular member causes the distal cutting edge of the inner aperture to approach the proximal cutting edge of the outer aperture, and wherein translation of the inner tubular member in a distal direction with respect to the outer tubular member causes the proximal cutting edge of the inner aperture to approach the distal cutting edge of the outer aperture. In some embodiments, the inner tubular member comprises a blunt rounded distal tip, and the outer tubular member comprises an open distal tip, and wherein translation of the inner tubular member in the distal direction with respect to the outer tubular member causes the blunt rounded distal tip of the inner tubular member to protrude distally from the open distal tip of the outer tubular member. In some embodiments, the inner tubular member is translatable with respect to the outer tubular member, but not rotatable with respect to the outer tubular member. In some embodiments, a first longitudinal length, measured from the distal cutting edge of the outer aperture to the distal tip of the outer tubular member, is equal to or greater than a second longitudinal length, measured from the proximal cutting edge of the inner aperture to the distal cutting edge of the inner aperture. In some embodiments, the first longitudinal length is no greater than 110% of the second longitudinal length. In some embodiments, the first longitudinal length is no greater than 120% of the second longitudinal length. In some embodiments, a longitudinal length of the opening at its maximum size is no less than 5 millimeters. In some embodiments, a longitudinal length of the opening at its maximum size is no less than 10 millimeters. In some embodiments, the outer tubular body comprises an outer diameter no greater than 0.125 inches. In some embodiments, the polyp removal device further comprises: a second opening near the distal end of the polyp removal device configured to allow fluid communication between the environment external to the polyp removal device and the lumen of the inner tubular body. In some embodiments, the polyp removal device further comprises: a cutting block positioned at the distal end of the outer tubular body, the cutting block having an outer diameter sized to fit with an inner diameter of the distal end of the inner tubular member, wherein the cutting block comprises a proximal face that is inclined with respect to a transverse plane of the outer tubular member. In some embodiments, the distal end of the inner tubular member comprises a circular cutting edge oriented parallel to the transverse plane. In some embodiments, the distal end of the inner tubular member comprises a cutting edge that is inclined with respect to the transverse plane. In some embodiments, a transverse width of the opening is at least 60% of an outer diameter of the outer tubular member. In some embodiments, the handle comprises a grip portion shaped to be gripped by a human hand and protruding radially, the grip portion protruding in a direction oriented at an angle with respect to the opening within a range of 90-180 degrees.

According to some embodiments, a polyp removal device comprises: an outer tubular body having proximal and distal ends; an inner tubular body positioned within a lumen of the outer tubular body, the inner tubular body having proximal and distal ends and being movable with respect to the outer tubular body; a handle coupled to the proximal end of the outer tubular body; an actuation member movably coupled to the handle, the actuation member configured to cause movement of the inner tubular body with respect to the outer tubular body when the actuation member is moved with respect to the handle; and a vacuum port for coupling thereto of a vacuum source, the vacuum port being in fluid communication with a lumen of the inner tubular body, wherein the distal end of the outer tubular body comprise an opening configured to allow fluid communication between an environment external to the polyp removal device and the lumen of the inner tubular body, and wherein the distal end of the inner tubular body is shaped such that the movement of the inner tubular body with respect to the outer tubular body causes at least a portion of the opening of the outer tubular body to be blocked by the distal end of the inner tubular body.

In some embodiments, the opening of the distal end of the outer tubular body is formed by a first protruding member comprising an arc-shaped cross-sectional shape, at least at a cross section taken through a transverse plane located at a midpoint of the first protruding member in a longitudinal direction. In some embodiments, the distal end of the inner tubular member comprises a second protruding member being nested within the first protruding member and rotatable about a longitudinal axis with respect to the first protruding member, and wherein the second protruding member comprises an arc-shaped cross-sectional shape, at least at a cross section taken through a transverse plane located at a midpoint of the second protruding member in a longitudinal direction.

According to some embodiments, a polyp removal device comprises: an outer tubular body having proximal and distal ends, the distal end comprising an opening configured to allow fluid communication between an environment external to the polyp removal device and a lumen of the outer tubular body; a handle coupled to the proximal end of the outer tubular body, the handle comprising a body and an actuating mechanism; a cutting member disposed within the distal end of the outer tubular body, the cutting member being movable with respect to the outer tubular body, the cutting member comprising at least one cutting edge configured to cut polyp tissue that has been positioned through the opening of the outer tubular body; an actuation member functionally coupled between the actuating mechanism and cutting member, wherein movement of the actuating mechanism with respect to the body of the handle causes the actuation member to move the cutting member with respect to the outer tubular body; and a vacuum port for coupling thereto of a vacuum source, the vacuum port being in fluid communication with the lumen of the outer tubular body.

In some embodiments, the actuating mechanism comprises a trigger. In some embodiments, the actuation member comprises a rod.

According to some embodiments, a method of removing a polyp from a human uterus comprises: inserting a medical instrument into the uterus, the medical instrument comprising a working channel; inserting a polyp removal device through the working channel of the medical instrument; extending a distal end of the polyp removal device into the uterus beyond a distal end of the working channel of the medical device; positioning at least a portion of a polyp through an opening in the distal end of the polyp removal device; operating an actuation member of the polyp removal device, causing the opening in the distal end of the polyp removal device to reduce in size, separating the at least a portion of the polyp from the uterus; and transferring the separated portion of the polyp to a proximal end of the polyp removal device via suction. In some embodiments, the polyp removal device comprises any of the polyp removal devices described herein.

According to some embodiments, a tissue removal device comprises: an outer tubular body that has a proximal end, a distal end with a rounded tip, and an inner lumen therebetween; a housing; and an inner tubular body with distal end with a rounded tip and inner lumen, wherein distal end of the outer tubular body has a cutaway that is at least half of the distal tip and that is at least 90 degrees and comprises non-beveled edges that begin from outer tubular body and terminate at the end of the rounded end of the distal tip of the outer tubular body, and said cutaway serves as an tissue receptacle; wherein inner tubular body has a cutaway that is at least half of the distal tip that is at least 90 degrees, with non-beveled edges that begin from inner tubular body and terminate at the rounded end of the distal tip of the inner tubular body, the inner tubular body cutaway configured as a tissue receptacle, the inner tubular body cutaway forms a chamber that cooperates with the lumen of the outer tubular body when the inner tubular body rotates; and wherein lumen of the inner tubular body is configured to receive tissue that is cut off from the rotation of the inner tubular body when the cutaways of inner tubular body and cutaway of the outer tubular body contain tissue.

According to some embodiments, a tissue removal device comprises: an outer tubular body that has a proximal end, a distal end with a rounded tip, and an inner lumen therebetween housing; an inner tubular body with a distal end with a coaxially removed tip with non-beveled edges; and wherein distal end of the outer tubular body has two parallel cutaways with non-beveled edges, that do not terminate at the distal tip, the cutaways act as a tissue receptacle; and wherein inner tubular body can translate to the distal end of the lumen of the out tubular body, full extension of the inner tubular body forms a chamber that cooperates with the lumen of the outer tubular body when the inner tubular body is translated to the distal tip of the outer tubular body; wherein lumen inner tubular body receives tissue that is cut off from the translation of the inner tubular body when either of the cutaways of the outer tubular body revives tissue; and wherein proximal ends of inner tubular body and outer tubular body that ends in connectors for an exit port that connects to an external vacuum source.

According to some embodiments, a tissue removal device comprises: an outer tubular body that has a proximal end, a distal end with a rounded tip, and an inner lumen therebetween housing a cutter; wherein outer tubular body has an aperture towards the distal end of the tip that is configured as a tissue receptacle; wherein cutter is an inner body with an inner lumen and a distal tip has an aperture with beveled edges towards the distal end of the tip that is configured as a tissue receptacle, aperture of the inner tubular body and aperture of outer tubular body square evenly; wherein translation of inner tubular body, whether elongation or retraction of inner tubular body, creates a chamber with the lumen of the outer tubular body, lumen of inner tubular body holds severed tissue created from translation of the beveled edges of the inner tube; and wherein proximal ends of inner tubular body and outer tubular body ends in connectors for an exit port that connects to an external vacuum source.

BRIEF DESCRIPTION OF THE DRAWINGS

The foregoing and other features, aspects, and advantages of the present invention are described in detail below with reference to the drawings of various embodiments, which are intended to illustrate and not to limit the invention. The drawings comprise the following figures in which:

FIGS. 6A-6E illustrate additional details of a distal tip portion of the polypectomy device of FIG. 2A.

FIGS. 7A-7E illustrate another embodiment of a distal tip configuration of a polypectomy device.

FIGS. 8A-8F illustrate another embodiment of a distal tip configuration of a polypectomy device.

FIGS. 9A-9G illustrate another embodiment of a distal tip configuration of a polypectomy device.

FIGS. 10A-10G illustrate another embodiment of a distal tip configuration of a polypectomy device.

FIGS. 15A-15C illustrate embodiments of material that can be used in a polypectomy device, the material having a sharpened or unsharpened edge.

FIGS. 19A-19I illustrate another embodiment of a polypectomy device.

FIGS. 26A-26F illustrate an embodiment of a mechanism for controlling movement of a cutter.

FIGS. 30A-30C illustrate an embodiment of an outer tubular member of a polypectomy device.

FIGS. 32A-32C illustrate another embodiment of an outer tubular member of a polypectomy device.

FIGS. 33A-33D illustrate another embodiment of an outer tubular member of a polypectomy device.

DETAILED DESCRIPTION OF THE EMBODIMENTS

Figure 1A:
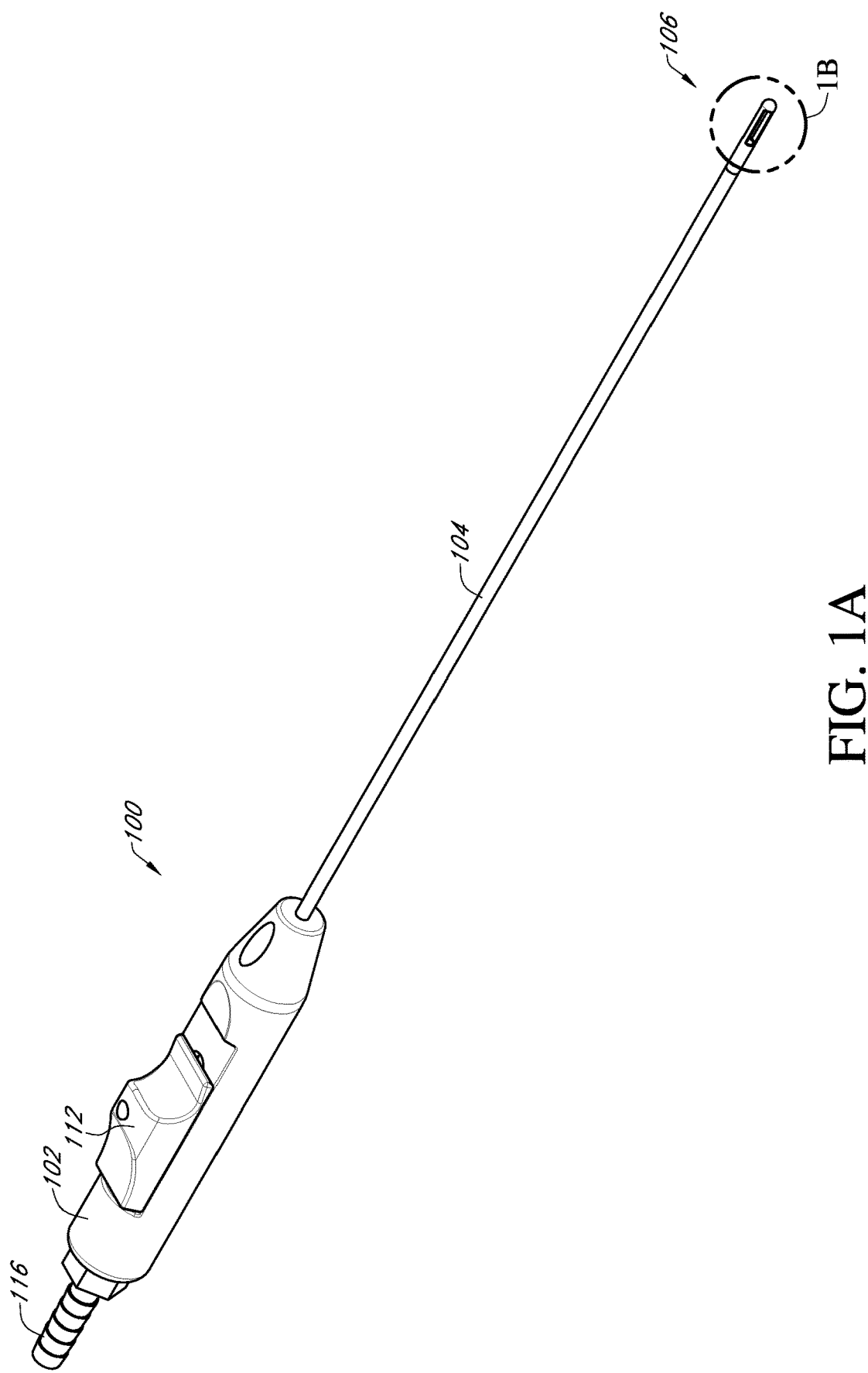
FIGS. 1A and 1B illustrate an embodiment of a polypectomy device that utilizes translation of an inner tubular member to remove polyps.

Although several embodiments, examples, and illustrations are disclosed below, it will be understood by those of ordinary skill in the art that the invention described herein extends beyond the specifically disclosed embodiments, examples, and illustrations and includes other uses of the invention and obvious modifications and equivalents thereof. Embodiments of the invention are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described. Further, it should be understood that any of the examples herein are non-limiting. As such, the inventions disclosed herein are not limited to any particular embodiments, aspects, concepts, structures, functionalities, or examples described herein.

A polyp is an abnormal growth of tissue from a mucous membrane. A polypectomy may be performed to remove a polyp. An endometrial or uterine polyp is an abnormal growth attached to an inner wall of the uterus. Uterine polyps are usually benign, but they can be cancerous or eventually turn into cancer. One method of removing uterine polyps is a hysteroscopic polypectomy, in which a hysteroscopic resectoscope is passed into the uterus along with a loop wire. An electrical current may be passed through the loop wire in order to cut the polyp by increasing the loop temperature by 100° C. to 200° C. Such a technique has its own set of challenges. The surgeon has to manually remove the cut polyp, which is time-consuming. Further, the use of electrocautery to cut the tissues damages the uterine tissues and may impair the ability of the uterus to sustain a pregnancy. For this reason, reproductive endocrinologists may not even use such a technique, for fear that they are liming the tissues where a fertilized egg might implant. Also, a loop wire may not always remove the entire polyp, which can mean repeating the procedure later on. A loop wire also creates a risk of thermal injury to surrounding tissue, and it is especially dangerous if accidentally pushed through the uterine wall contacting sensitive bowel tissues. Morbidity and mortality are known complications of loop uterine perforations creating accidental bowel thermal injuries. Additionally, most patients would require anesthesia in order to mitigate the pain of the heat of the wire loop on sensitive tissues lining the uterus. Finally, if a monopolar wire loop is employed, a non-electrolytic fluid is required for distending the uterus, which may lead to sodium imbalances or fluid overloading in the patient.

Another potential way to remove uterine polyps is to utilize a mechanical device designed to cut uterine fibroids (also called leiomyomas or myomas) from the uterine wall. A fibroid is a growth in the uterus that often grows to be much larger than a typical polyp. Further, a fibroid is typically formed of a tougher, more fibrotic tissue than polyps, which are somewhat gelatinous in consistency. Because of the general size and toughness of fibroids, tools that have been designed to remove fibroids are more robustly built, higher powered tools that utilize a sharpened blade, drilling mechanism, and/or the like to gradually break up and extract a fibroid. Although such a design may be used to remove a polyp, doing so is overkill for the task at hand and can introduce various unnecessary safety risks and mechanically complicated devices. For example, a sharp and robust fibroid removal tool could potentially unintentionally cause trauma to adjacent uterine wall tissue and/or even puncture the uterine wall. Further, because a fibroid removal tool is intended to cut into relatively tough material, the cutting features of the tool are necessarily designed to be relatively robust. This causes the tool to be larger in design and/or use thicker tubing than is desirable or necessary for safe and efficient polyp removal. They also include motorized power delivery systems that are necessary to provide the energy necessary to cut the fibroid.

Ideally, a polypectomy would be able to be performed in a doctor's office setting rather than in a hospital surgical setting. However, because the existing methods for removing polyps, such as uterine polyps, require a high level of skill, expensive equipment, and/or come along with significant levels of risk, polypectomies are typically not performed in an office setting. The devices, systems, and methods disclosed herein, however, can provide for safer and more cost-effective ways of performing polypectomies in an office setting.

The removal of uterine polyps via a hysteroscopic polypectomy poses various challenges as discussed above. Accordingly, there is a demand for devices and methods, as disclosed herein, for addressing some of the shortcomings associated with a traditional hysteroscopic polypectomy.

Various embodiments disclosed herein present safer and more efficient polyp removal devices, methods, and systems. In some embodiments, a polypectomy device comprises an elongate tube having a handle with a trigger or other actuating mechanism at a proximal end and one or more openings (e.g., opening, hole, aperture, window, cutout, and/or the like) at a distal end. The one or more openings at the distal end may be sized and configured (1) to enable a polyp to be aspirated therethrough using vacuum, and/or (2) to mechanically separate the polyp from the uterine wall using a movable member operably coupled to the trigger or other actuating mechanism.

In some embodiments, the configuration of the distal end of the polypectomy device is desirably designed such that a relatively large opening is used, the relatively large opening being big enough to accept as much of a polyp as possible at any one time. This is different than a typical fibroid removal device that needs to gradually cut or grind away at a fibroid and therefore needs to be relatively robust. Because polyps are of a softer consistency than fibroids, the tubing used for the polypectomy device may be thinner than with a fibroid removal tool, enabling the polypectomy device to have a larger inner lumen, thus enabling larger tissue pieces to pass therethrough. Further, because the mechanical stresses present on the cutting features of the distal end of a polypectomy device are less than with a fibroid removal device, larger openings at the distal end of the polypectomy device can be present, thus enabling larger pieces of tissue to be removed at any one time.

In some embodiments, a polypectomy device as disclosed herein comprises one or more openings at its distal end that are sized and configured to accept therethrough an entire polyp, for removal of the entire polyp in one stroke of the cutting blade/surface. The disclosure is not limited to such a configuration, however, and in some embodiments or some instances, only a portion of a polyp may be able to fit through the one or more openings at the distal end of the device at any one time.

The polypectomy devices, systems, and methods disclosed herein provide various benefits, such as easier and safer removal of polyps, faster removal of polyps, more efficient removal of polyps, lower cost and easier manufacturing of the surgical instrument, and/or the like. Some of the features of some of the embodiments disclosed herein that help to provide these features include, but are not limited to, providing a relatively large opening at a distal end of the device; providing more than one opening at the distal end of the device; utilizing an inner tubular member coupled to or comprising a cutting surface that translates or rotates with respect to an outer tubular member, but not both; providing a cutting surface that is unsharpened or blunt; providing a blunt tip to the polypectomy device; providing an opening in a distal end of the polypectomy device that opens on both the side(s) of the distal end and the distal tip of the distal end; providing a cutting member that cuts in two directions, such as in the extend and retract directions or in the clockwise and counterclockwise directions; and/or the like.

In some embodiments, the devices and methods disclosed herein allow for cutting and removing tissue. In some embodiments, the devices and methods disclosed herein allow for cutting and removing tissue simultaneously. This may reduce the operating time needed for a polypectomy procedure. This may reduce the patient's exposed to anesthesia and lower the risk of fluid overloading.

In some embodiments, the devices and methods disclosed herein allow for removal of tissue using vacuum or suction pressure. This may allow for improved removal of the polyp or tissue. This may allow for less damage to occur to the uterus. This may allow for the use of an electrolytically balanced saline solution to distend the uterus, unlike the use of electric current to excise tissue which necessitates the use of non-electrolytic solutions for the same purpose. This may reduce the risk of electrolyte imbalance and/or thermal injury.

Polypectomy Devices

Figure 1B:
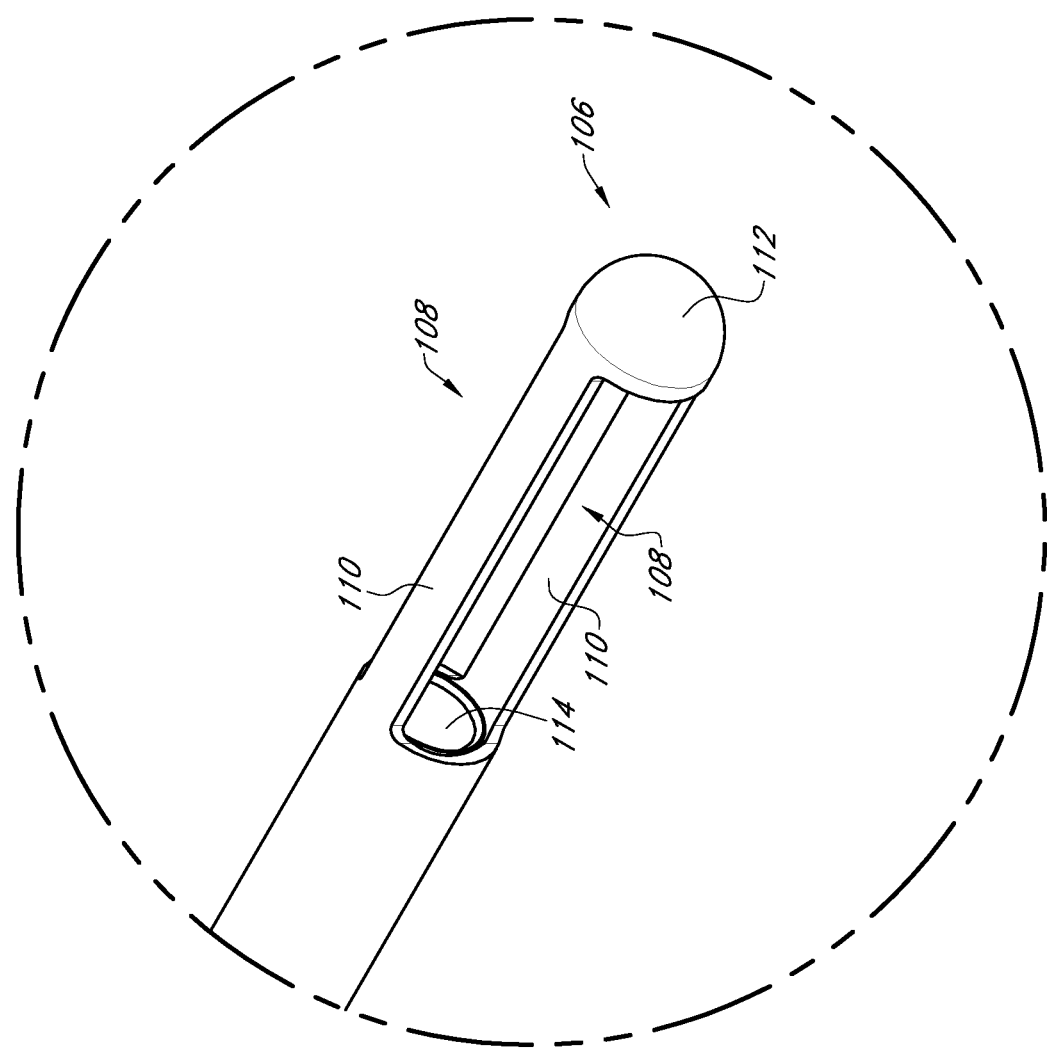
Figure 2A:
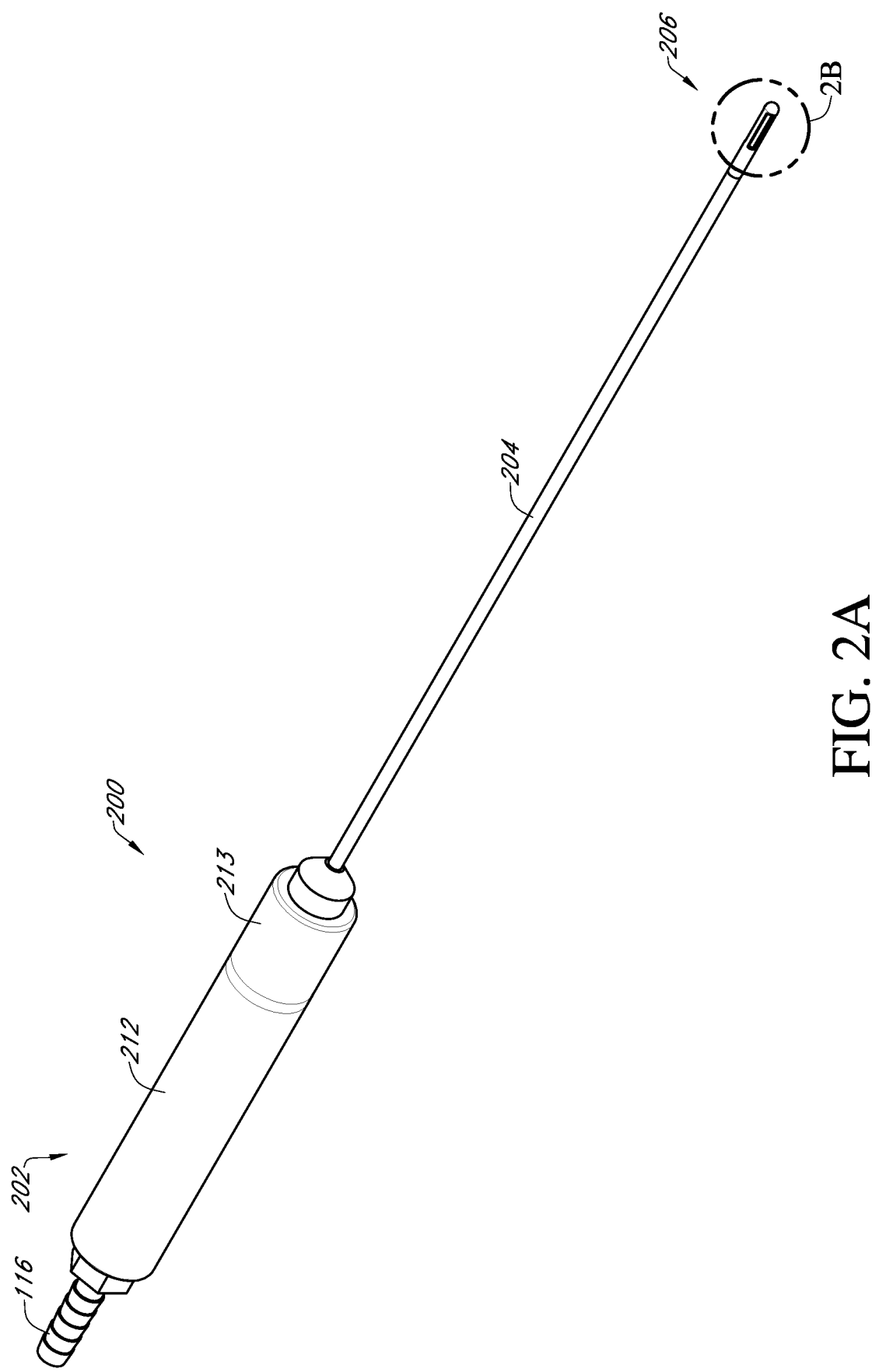
FIGS. 2A and 2B illustrate an embodiment of a polypectomy device that utilizes rotation of an inner tubular member to remove polyps.
Figure 2B:
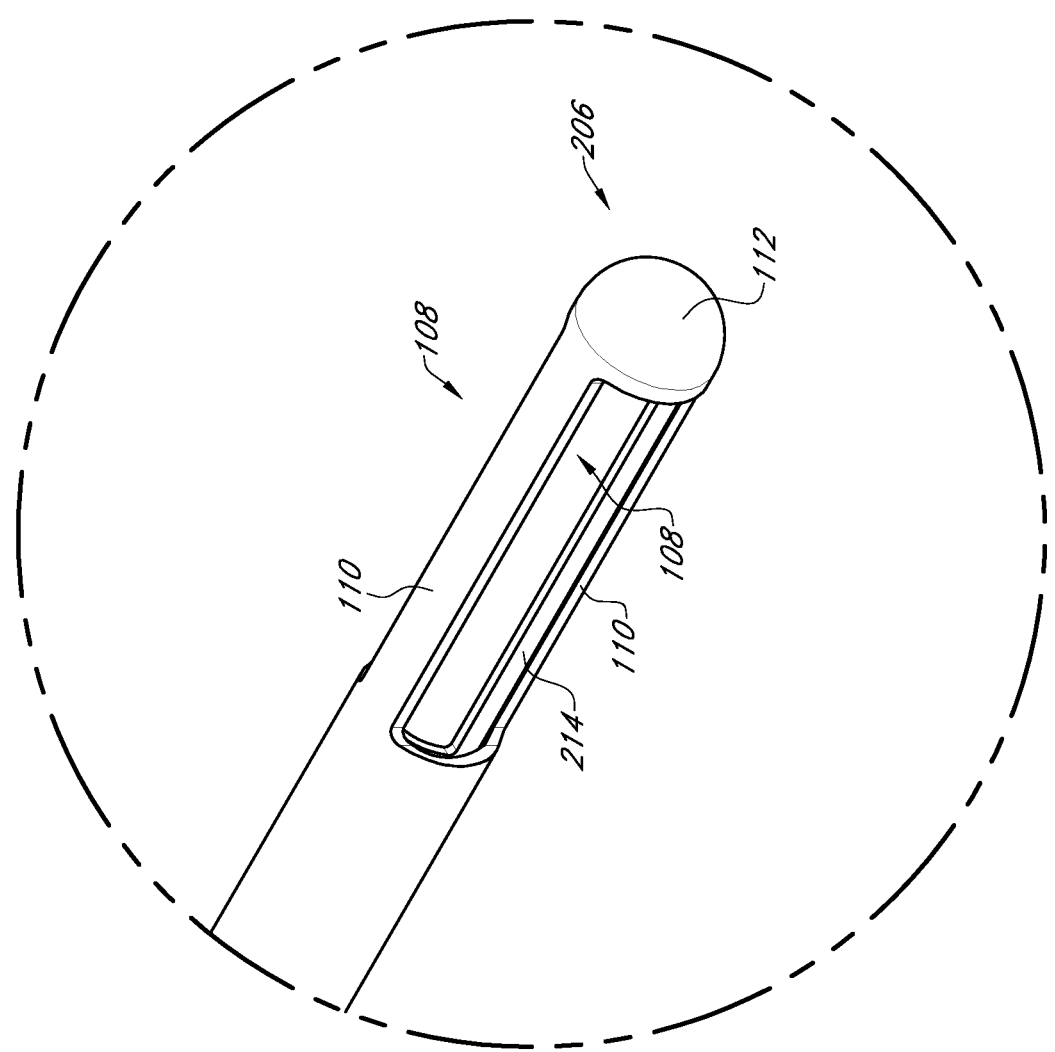

FIGS. 1A and 2A illustrate two example embodiments of polypectomy devices as disclosed herein. FIGS. 1B and 2B illustrate close-up views of the distal ends of the polypectomy devices, respectively. With reference to FIGS. 1A and 1B, the polypectomy device 100 comprises a handle 102 and an outer elongate tubular member 104. The outer tubular member 104 comprises a distal end 106 configured for receiving and removing a polyp. In this embodiment, the distal end comprises two elongate openings 108 positioned opposite one another. These openings 108 are adjacent to supporting arms 110, which support a blunt rounded tip 112 at the distalmost end of the polypectomy device 100. The polypectomy device 100 further comprises an actuating member (e.g., trigger, switch, lever, button, or the like) 112 coupled to the handle 102. In this embodiment, the actuating member 112 is shaped and configured to engage a finger of a human hand, such as a user's thumb or index finger, and is configured to translate back and forth along or parallel to a longitudinal axis of the polypectomy device 100. The actuating member 112 is functionally coupled to an inner tubular member 114 which also translates back and forth along the longitudinal axis along with the actuating member 112. Accordingly, movement of the actuating member 112 causes relative movement of the inner tubular member 114 with respect to the outer tubular member 104.

The polypectomy device 100 further comprises a vacuum port 116 configured to be coupled to a vacuum source, such as via a hose. In this embodiment, the vacuum port 116 is attached to a proximal end of the handle 102 and comprises a fitting that is in fluid communication with an internal lumen of the inner tubular member 114. In use, the outer tubular member 104 of the polypectomy device 100 can be inserted through a working channel of a scope (e.g., the example scope shown in FIG. 3), causing the distal end 106 to protrude into the uterus. The doctor can then position, via manipulation of the handle 102, one or more of the openings 108 adjacent a polyp to be removed. Next, the doctor can activate the vacuum source, such as by activating a foot pedal or the like, causing the polyp (or at least a portion of the polyp) to be aspirated at least partially into one of the openings 108 of the distal end 106. Although this embodiment includes two openings 108, other embodiments may have only one opening or more than two openings. It may be desirable in some embodiments to have only one opening, or to have a way of temporarily blocking other openings (such as a sliding or rotating shutter, window, and/or the like), since, once a polyp is aspirated through one opening, the vacuum suction may start to aspirate distention fluid in through any remaining openings (i.e. through the path of least resistance). If there is only one opening, or the other openings can temporarily be blocked, however, the vacuum suction can be focused on the polyp being removed.

In some embodiments, because polyps typically have a generally gelatinous consistency, vacuum suction alone may be sufficient to separate the polyp from the uterine wall. In that case, the polyp will be aspirated into the inner lumen of the inner tubular member 114 and proceed back through the inner tubular member 114 toward the handle 102 (and potentially out through the vacuum port 116), for collection or disposal. In some embodiments, although vacuum suction alone may be sufficient to separate a polyp from the uterine wall, it can be desirable to also or alternatively have a mechanical means of separating the polyp and/or helping to separate the polyp. For example, with reference to the polypectomy device 100 illustrated in FIGS. 1A and 1B, the inner tubular member 114 is configured to translate forward or distally with respect to the outer tubular member 104, causing narrowing of and/or closure of the openings 108, pinching of the polyp between the distal face of the inner tubular member 114 and the distal edge(s) of the opening(s) 108, and causing the polyp to be separated or sliced off mechanically.

One reason it can be desirable to have a mechanical means of separation in combination with or even in lieu of using vacuum is that, during a procedure such as a polypectomy, the uterus is typically distended using a fluid pumped into the uterus. Any vacuum that aspirates a polyp into the polypectomy device or tool may also cause removal of at least some of the distention fluid from the uterine cavity. If a relatively small amount of fluid is removed, then the procedure may not be substantially affected. However, if a larger amount of fluid is caused to be removed, this may need to be dealt with, such as by reintroducing new fluid while the removal is taking place, stopping the polyp removal procedure and adding more fluid, and/or the like. Such procedures can make a polypectomy a more complicated and difficult surgery, and thus desirably can be avoided by use of various devices disclosed herein.

One way that polypectomy devices disclosed herein can limit the loss of distention fluid is that vacuum suction may be used only to retrieve a removed polyp or portion of a polyp after it has been mechanically separated by, for example, the translation or rotation of the inner tubular member 114 with respect to the outer tubular member 104.

For example, a doctor may (1) manually manipulate the device (e.g., via the handle 102) such that a polyp is positioned through one or more openings 108, (2) manipulate the actuating member 112 to cause the inner tubular member 114 to translate and separate the polyp from the uterus, and (3) then actuate suction to cause the already separated polyp to be aspirated proximally through the inner lumen of the inner tubular member 114 for collection. In this example, very little if any distention fluid would be lost, because the doctor would be able to keep the inner tubular member 114 at a distalmost position, thus substantially or fully closing off the openings 108 during retrieval of the polyp. In some embodiments, at least some leakage from the openings 108 (or elsewhere) to the inner lumen of the inner tubular member 114 may be desirable, even when the inner tubular member 114 is positioned fully forward or distal, to facilitate transfer of the polyp from the distal end to the proximal end.

Another way polypectomy devices disclosed herein can limit loss of distention fluid is that a doctor may use the vacuum or suction to aspirate a polyp (or portion of a polyp) in through one or more openings 108, but then use mechanical motion of the inner tubular member 114 to separate the polyp from the uterine wall. The process of aspirating a polyp or portion of a polyp into an opening 108 will generally require less powerful suction than would be required to actually separate the polyp from the uterine wall using suction alone. Accordingly, by utilizing vacuum or suction to introduce the polyp or portion of a polyp through the openings 108, but then using mechanical means, such as the translating inner tubular member 114, to separate the polyp from the uterine wall, the suction can be most efficiently utilized and loss of distention fluid can be minimized. In some embodiments, at least some suction may still be applied during mechanical operation of the inner tubular member 114, such as to keep the polyp aspirated through the opening 108 during mechanical separation.

It should be noted that, although various embodiments disclosed herein are described in terms of an inner tubular member concentrically positioned within an outer tubular member, and a removed polyp being aspirated through the inner lumen of the inner tubular member, various other designs that accomplish a similar result may be utilized. For example, instead of using an inner tubular member, an actuation rod or other mechanism may be used to move a cutting surface or blade at the distal end of the polypectomy device. In that case, the removed polyp would be aspirated through the lumen of the outer tubular member, because there would be no need for an inner tubular member positioned within the outer tubular member. One example of such a configuration is shown in FIGS. 12A-12F, described in greater detail below. A similar configuration (e.g., using an actuating rod or similar to move the cutting portion at the distal end of the device) could be used with any of the other embodiments disclosed herein, including, but not limited to, the various distal end configurations illustrated in FIGS. 5A-5C, 6A-6E, 7A-7E, 8A-8F, 9A-9G, 10A-10G, 11A-11G, 13A-13C, and 14A-14F. For the embodiments configured to use longitudinal translation of a cutting member at the distal end, such an actuating rod could be directly coupled to the cutting member. For the embodiments configured to use rotational motion of a cutting member at the distal end, such an actuating rod could be coupled to the cutting member through a linkage mechanism, gear train, and/or the like that converts translation of the actuating rod into rotation of the cutting mechanism.

In some embodiments, movement of the inner tubular member 114 may be completely manually controlled by, for example, a doctor moving the actuating member 112 forward and backward along the longitudinal axis. In some embodiments, the actuating member and/or inner tubular member 114 may be biased or spring-loaded, such that the actuating member 112 is configured to be manually actuated in one direction, but will then automatically return to the starting point when the doctor or user releases the pressure used to initially move the actuating member 112. Further, in some embodiments, a polypectomy device may comprise electrical actuation, pneumatic actuation, hydraulic actuation and/or the like. For example, a button, trigger, foot pedal, and/or the like may be configured to actuate or activate a motor that causes movement of the inner tubular member 114 with respect to the outer tubular member 104. Further, although the embodiment illustrated in FIG. 1A illustrates an actuating member or trigger 112 that is directly coupled to the inner tubular member 114, meaning their relative motion is a one-to-one relationship, other embodiments may utilize other actuating or triggering mechanisms. For example, an actuating member may be coupled to a gear train that enables more precise control, provides a mechanical advantage, enables translation of one direction of motion of the actuating member into a different direction of motion of the inner tubular member, converts translating motion into rotating motion and/or vice versa, and/or the like.

As shown in FIG. 1B, the distal end 106 of the polypectomy device 100 comprises a blunt rounded tip 112. It can be desirable to have a blunt tip in a polypectomy device as disclosed herein, because this can help to avoid unintentional trauma or injury to the uterine wall. Accordingly, with a design such as shown in FIG. 1B, if the distal tip of the polypectomy device 100 contacts or rubs up against a portion of the uterine wall, the risk that this contact will cause trauma to the uterine wall is reduced over a design that would have a sharper distal tip. This is in contrast to certain other medical instruments, such as biopsy instruments, that comprise a sharp distal tip, because they are intended to puncture tissue in obtaining a tissue sample. Such a design used with a polypectomy device as disclosed herein could be dangerous, because the sharp tip could unintentionally puncture the uterine wall.

In addition to comprising a blunt tip, various embodiments disclosed herein comprise few, if any, sharpened surfaces at the distal end of the polypectomy device (i.e. the portion of the polypectomy device that will extend out of the scope's working channel into the uterus). For example, although in various embodiments the inner tubular member, such as inner tubular member 114 of FIG. 1B, acts somewhat as a blade to separate the polyp from the uterine wall, because of the generally gelatinous consistency of a polyp, the inner tubular member 114 or similar does not necessarily need to be sharpened. Accordingly, in some embodiments, the inner tubular member or blade or cutting surface of the inner tubular member is not sharpened and/or may comprise a smooth, blunt, and/or the like surface. Further, the edges of the outer tubular member 104 that defined the one or more openings 108 may be unsharpened, smooth, blunt, and/or the like. In such a configuration, where little or no sharp surfaces are present at the distal end of the polypectomy device, the risk of unintentional trauma to the uterine wall is greatly reduced. This can be quite beneficial, particularly when such a device may be used by a doctor that does not typically specialize in uterine surgical procedures. Such a design may enable polypectomy is to be performed by gynecologists in their offices, as opposed to having to send a patient with a polyp to the operating room.

One potential complication with performing uterine polypectomies in a doctor's office setting, as opposed to a hospital's surgical setting, is that in-office procedures may not be reimbursed as much through a health insurance provider as the same or similar procedure performed in a surgical environment would be. For this and other reasons, such as general efficiency, it can be desirable to reduce the complexity of a polyp removal device, thus also potentially reducing the cost of such a device. If a polypectomy device as disclosed herein can be made at a more reasonable cost than heavier duty tools, such as fibroid removal tools, such a tool is more likely to be able to be used in the office setting.

One feature of many of the embodiments disclosed herein that helps to reduce the complexity is that many of the embodiments disclosed herein comprise an inner tubular member (or actuating member), such as the inner tubular member 114, that is configured to move with respect to the outer tubular member, such as outer tubular member 104, but only in one degree of freedom. For example, some embodiments, such as the polypectomy device 100 illustrated in FIG. 1A, allow the inner tubular member to translate along the longitudinal axis with respect to the outer tubular member 104, but the inner tubular member 114 is not configured to move in any other direction, such as rotation about the longitudinal axis. This is in contrast to the embodiment illustrated in FIG. 2A, which allows rotation, but not translation.

FIG. 2A illustrates an embodiment of a polypectomy device 200 that is similar in many respects to the polypectomy device 100 of FIG. 1A. The polypectomy device 200 comprises a handle 202 an elongate outer tubular member 204 extending from a distal end of the handle, and a distal end 106 comprising two openings 108. In this embodiment, however, the inner tubular member 214 is configured to rotate about a longitudinal axis with respect to the outer tubular member 204, instead of translating along the longitudinal axis. To support this difference in movement, the handle 202 is also of a different design than the handle 102. The handle 202 comprises an actuating member 212 that rotates with respect to a nonrotating portion 213. When the actuating member 212 rotates, it causes the inner tubular member 214 to also rotate with respect to the outer tubular member 204, thus narrowing or closing the openings 108, enabling a polyp to be separated or removed from the uterine wall.

As noted above with respect to the polypectomy device 100, the actuating member 212 of the polypectomy device 200 may be designed differently. For example, in this case, the rotating portion 212 is directly connected to the inner tubular member 214 to cause rotation of the inner tubular member 214 with respect to the outer tubular member 204. However, in other embodiments, the handle 202 may be designed differently and comprise various types of manual and/or automatic actuating mechanisms. For example, in some embodiments, a polypectomy device comprises a more ergonomic grip shaped and configured to be comfortably held in a doctor's hand. The ergonomic grip may comprise an actuating member, such as a trigger, button, lever, or the like that is positioned to be operated by, for example, the doctors index finger or thumb, or even all of the doctor's fingers at once.

Polypectomy Device in Use

Figure 3:
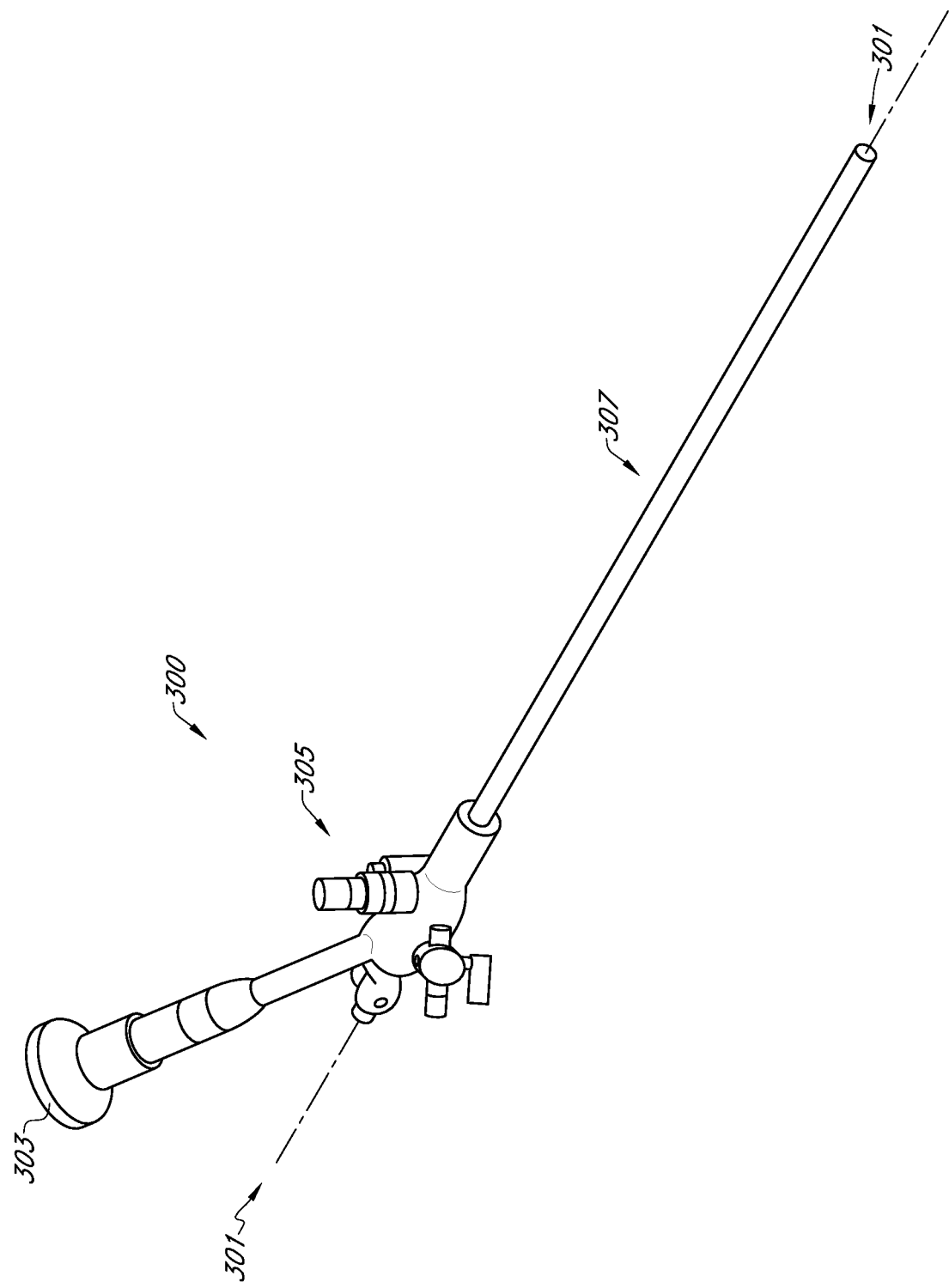
FIG. 3 illustrates an example of a hysteroscope with a straight working channel that may be utilized with embodiments of polypectomy devices disclosed herein.

FIG. 3 illustrates an example of a hysteroscope 300 that may be used in performing a polypectomy along with the various embodiments of polypectomy devices disclosed herein. The hysteroscope 300 comprises an elongate member 307 having a working channel 301 passing therethrough. The working channel 301 can be sized to allow the outer tubular member of a polypectomy device, such as the outer tubular member 104 illustrated in FIG. 1A, to pass therethrough. The hysteroscope 300 further comprises a visualization mechanism 303 that enables a doctor to see within the uterine cavity. The hysteroscope 300 further comprises a plurality of ports 305. These ports 305 may be used to, for example, introduce or remove distention fluid from the uterus.

Although FIG. 3 illustrates one specific example of a hysteroscope 300, the polypectomy devices, methods, and systems disclosed herein may be used with any medical device that has a working channel for the polypectomy device to be inserted therein. Further, in some embodiments, a polypectomy device may be used as a standalone medical instrument that is not passed through the working channel of a scope or other instrument, and/or a hysteroscope or other medical instrument may incorporate any of the one or more features of embodiments of polypectomy devices disclosed herein. For example, an alternative embodiment of the hysteroscope 300 may comprise a distal end configuration having features similar to the distal ends of polypectomy devices disclosed herein that enable a polyp to be aspirated therein and separated from the uterine wall.

Figure 4:
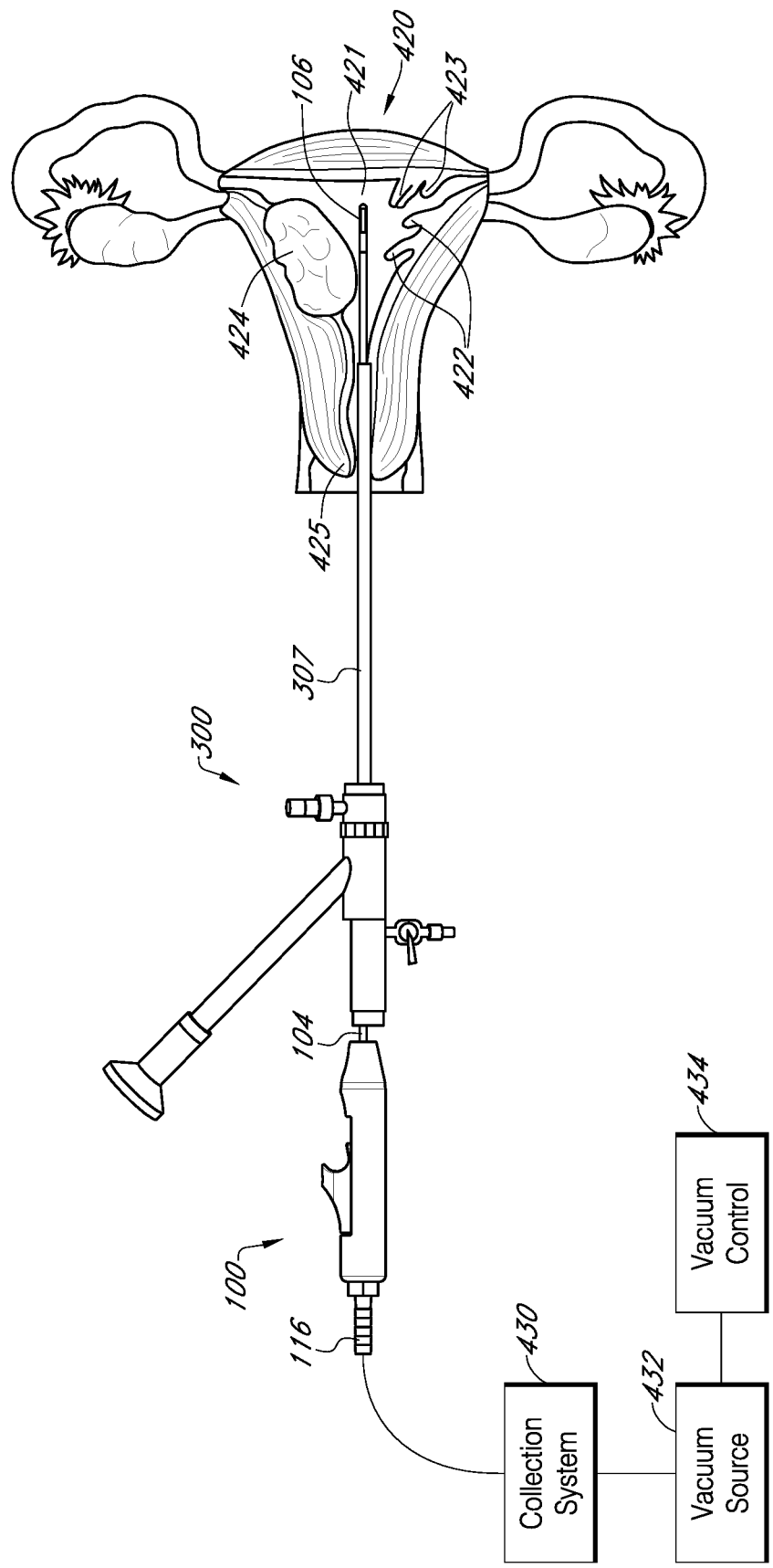
FIG. 4 illustrates an example of the polypectomy device of FIG. 1A in use with the scope of FIG. 3 and a human uterus.

FIG. 4 illustrates a schematic diagram of the polypectomy device 100 of FIG. 1A in use with a patient and the hysteroscope 300 of FIG. 3. In this example, the hysteroscope 300, and specifically the elongate tubular member 307 of the hysteroscope 300, has been passed through the cervix 425 into the inner cavity 421 of the patient's uterus 420. The outer tubular member 104 of the polypectomy device 100 has been passed through the working channel of the hysteroscope 300, causing the distal end 106 of the polypectomy device to extend into the cavity 421 of the uterus 420.

The schematic diagram of a uterus 420 illustrated in FIG. 4 comprises a plurality of polyps 422, 423 and a fibroid 424 attached to the uterine walls. Although all fibroids and polyps are not the same size, the present diagram presents a relatively common size of fibroid 424 and polyps 422, 423. It can be seen that the fibroid 424 is significantly larger than the polyps 422, 423. Further, because of the toughness of a fibroid as compared to polyps, it may be difficult and/or inefficient to remove the fibroid 424 using the present embodiment of a polypectomy removal device 100. However, the present embodiment of a polypectomy device 100 is ideally suited to remove the polyps 422, 423. Because of the relatively large openings 108 (as shown in FIG. 1B) of the distal end 106 of the polypectomy device 100, it is possible that a substantial portion of each of the polyps 422, 423, or even the entire polyp 422, 423 may be aspirated into the polypectomy removal device at one time for separation from the uterine wall. However, even if substantially all or the entire polyp 422, 423 is not able to fit at one time into the distal end 106 of the polypectomy device 100, utilizing a relatively large opening or openings can still make the process more efficient by increasing the amount of tissue that may be removed at any one time over a device that has a smaller opening. Further, as mentioned above, various polypectomy devices disclosed herein are able to have such a larger opening because, among other things, the devices are intended to remove polyps, and not tougher tissue. Another reason is that various polypectomy devices disclosed herein are not intended to be inserted into the body by puncturing tissue and making their own path into the body, which can introduce relatively large stresses into the distal end of an instrument.

As can be seen in FIG. 4, polyps can be located at different portions of the uterus 420. For example, in this diagram, there are two polyps 422 located on a side wall of the uterus, and there are two polyps 423 located on a back wall of the uterus 420. Various embodiments of polypectomy devices disclosed herein can make it easier to reach and remove polyps in these various locations. For example, due to the relatively large openings 108 of the polypectomy device 100, the polypectomy device 100 may be able to remove not only the side wall polyps 422, but also the back wall polyps 423. However, as will be described in greater detail below, other embodiments may be even better suited to easier removal of a back wall polyp 423. For example, the embodiment illustrated in FIG. 8A comprises an opening 808 that extends through a distal tip of the distal end, thus making it even easier to position the opening 808 adjacent to the back wall polyp 423.

The diagram illustrated in FIG. 4 further shows a collection system 430 fluidly coupled to the vacuum port 116 and a vacuum source 432 fluidly coupled to the collection system 430. The vacuum source 432 is further coupled to or comprises a vacuum control 434, such as, for example, a foot pedal, button, switch, trigger, and/or the like. The collection system 430 can optionally be used with some embodiments to enable collection of samples of removed polyps, such as for later analysis by a lab. In some embodiments, the collection system 430 is a separate device or system that is fluidly coupled to the polypectomy device 100. In other embodiments, a collection system may be integrated into the polypectomy device. For example, as will be described in greater detail below with respect to FIG. 19B, a collection system may be integrated into the handle portion of a polypectomy device.

Polyp Removal

Figure 5A:
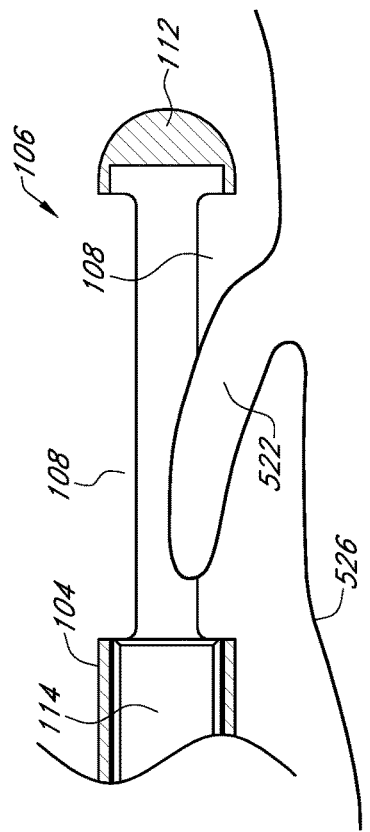
FIGS. 5A-5C illustrate additional details of a distal tip portion of the polypectomy device of FIG. 1A.
Figure 5B:
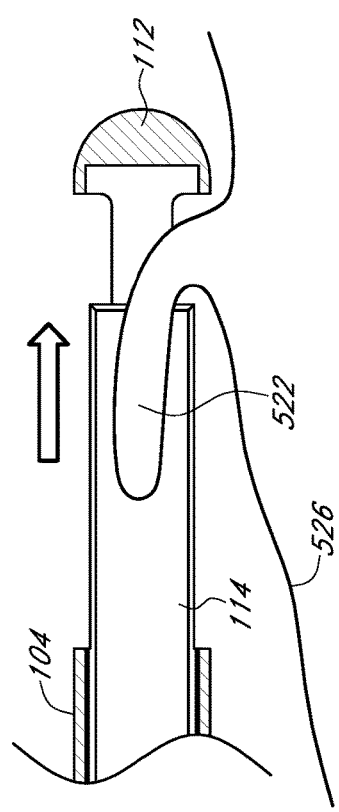
Figure 5C:
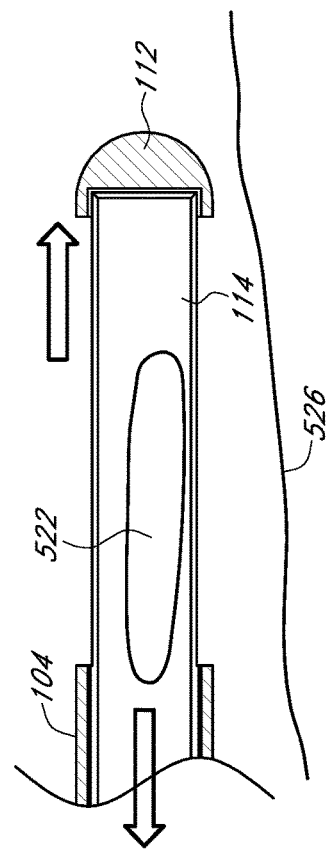

FIGS. 5A-5C illustrate an example process for removing a uterine polyp using a polypectomy device as disclosed herein. Although the embodiment illustrated in FIGS. 5A-5C utilizes the polypectomy device 100 of FIG. 1A, similar techniques may be used with different devices. Further, FIGS. 5A-5C focus on the operation of the distal end 106 of the polypectomy device, and various modifications may be made to the proximal end, while still achieving the same or similar result.

With reference to FIG. 5A, in the present example, a doctor wants to remove a polyp 522 that is attached to a uterine wall 526. Accordingly, using the example polypectomy device 100 of FIG. 1A, the doctor may ensure the inner tubular member 114 is in the retracted position, thus fully opening the openings 108 to enable positioning therethrough of the polyp 522. As can be seen in FIG. 5A, the bottom opening 108 has been maneuvered such that at least a portion of the polyp 522 has passed therethrough. In some embodiments, positioning the polyp 522 through the opening 108 may be performed completely manually, meaning without utilizing suction. However, in some embodiments, at least some suction may be activated to help draw the polyp 522 in through the opening 108.

Further, although this embodiment illustrates having the inner tubular member or blade 114 in a fully retracted position, such that the openings 108 are fully open at the start of the procedure, in other embodiments, it may be desirable to at least partially advance the inner tubular member 114 prior to insertion of the polyp 522 through the opening 108. For example, if suction is to be used to help aspirate the polyp 522 into an opening 108, it may be desirable in some embodiments to advance the inner tubular member 114 somewhat such as to narrow the opening 108 size, thus more narrowly concentrating the suction force. As one of skill in the art will understand, for a given amount of suction applied to the polypectomy device, a smaller opening size 108 at the distal end of the device will create a higher, more concentrated suction force than a larger opening 108. This is similar to the operation of a nozzle, where a smaller orifice size in a nozzle will generate a higher pressure than a larger orifice size, even though the same quantity or similar quantity of fluid may be passing therethrough.

With reference to FIG. 5B, the inner tubular member or blade 114 is now being advanced or extended in a distal direction toward the distal tip 112 of the outer tubular member. The polyp 522, or at least a portion of the polyp 522, is positioned within the inner lumen of the inner tubular member 114. With continued advancement of the inner tubular member 114 and/or with continued or increased application of suction, the polyp 522 will be separated from the uterine wall 526. With reference to FIG. 5C, the inner tubular member 114 has been advanced completely forward to the distal tip of the polypectomy device, and the polyp 522 has been separated from the uterine wall 526. The polyp 522 can now continue to be aspirated through the inner lumen of the inner tubular member 114, to the left as oriented in FIG. 5C, and optionally collected within a collection system, such as the collection system 430 illustrated in FIG. 4.

It should be noted that, although the inner tubular member 114 is positioned completely forward or distally in FIG. 5C, in some embodiments, this may not imply that the inner tubular member 114 is fluidly sealed against the distal tip of the outer tubular member 104. In order to continue suction to cause the polyp 522 to pass through the inner lumen of the inner tubular member 114 after removal, it may be desirable to have at least some fluid communication between the environment external to the polypectomy device, such as the uterine cavity, and the internal lumen of the inner tubular member 114. This fluid communication may occur in one or more of various ways, such as by a distal edge of the inner tubular member 114 not forming a complete seal against the distal end of the outer tubular member 104, the inner tubular member 114 comprising a hole in its side wall that allows distention fluid to pass therethrough, the distal tip 112 of the outer tubular member 104 comprising a hole, and/or the like. In some embodiments, a specific feature, such as a hole, is not necessarily utilized to allow this certain amount of leakage or fluid communication between the uterine cavity and the inner lumen of the inner tubular member 114, but the manufacturing methods or tolerances of the inner and outer tubular members 114, 104 are such that a fluid-tight seal is not formed when the inner tubular member 114 is positioned in its fully extended configuration.

Further, in some embodiments, even if a fluid-tight seal is formed when the inner tubular member 114 is at its distal most or fully extended position, this may be acceptable (or even desirable). For example, in a case where multiple polyps are being removed and/or where a polyp is being removed in multiple steps and not all at once, the doctor may cause the inner tubular member 114 to extend and retract multiple times. For example, the inner tubular member 114 may be extended to cut off a portion of a polyp, and then retracted to allow the next portion of the polyp to be positioned through an opening 108 and within the inner lumen of the inner tubular member 114. The inner tubular member 114 may then be re-extended to separate that next portion of the polyp. This procedure may be repeated as many times as desired or needed to remove the full polyp. In such a case, where the inner tubular member 114 is repeatedly moved back and forth, even if the inner tubular member seals or substantially seals against the outer tubular member 104 in the fully extended position, there may be sufficient fluid communication when the inner tubular member 114 is in a non-fully extended position that polyps or pieces of polyps that have been removed will be able to be transferred through the inner lumen of the inner tubular member 114 and into the collection system 430. Also, even in a case where a polyp is removed in a single cut, it may be desirable for a doctor to be able to control the amount of "leakage" of distention fluid into the inner lumen, such as by manipulating the actuating member of the handle.

Although the process illustrated in FIGS. 5A-5C illustrates an example of a polypectomy device removing a polyp with an inner tubular member 114 that translates with respect to the outer tubular member 104, similar principles may be applied to polypectomy devices that comprise an inner tubular member that rotates with respect to the outer tubular member. Various examples of such devices are described below.

It should be noted that, although various embodiments disclosed herein are described as having a blade or cutting surface as part of an inner tubular member, this should not be interpreted to mean that all embodiments comprise a cutting surface or cutting member integrally formed with the inner tubular member. For example, with the embodiment illustrated in FIGS. 5A-5C, the most cost-effective way to create that device may be to have a single inner tubular member that comprises the distal cutting surface integrally formed at its distal end. However, in some embodiments, a distal portion (e.g., cutting member, cutting portion, blade member, blade portion, and/or the like) may be coupled to the inner tubular member and form the cutting surface or surfaces that are used to cut a polyp. For example, it may be desirable to have an elongate inner tubular member formed of one material, and a cutting portion formed of another material coupled to the end of the inner tubular member. For example, an inner tubular member may comprise a thin-walled stainless steel tube, and a cutting member comprising a polymer, composite, or other material may be coupled to the end of the stainless steel tube. This could, for example, enable the main elongate portion of the inner tubular member to be relatively thin and have a relatively large inner lumen, while enabling the distalmost cutting member or cutting portion to be relatively complicated in design and/or have tighter tolerances than the rest of the inner tubular member. Any cutting member or other portion that is attached to the distal end of the inner or outer tubular member may be attached through various manufacturing methods, such as, for example, laser welding, adhesives, mechanical fasteners, and/or the like.

Distal End Configurations

Various configurations of the distal end of a polypectomy device (e.g., the portion that protrudes from the working channel of a scope into the uterus) may be used with the embodiments disclosed herein. Some of the common features among many of these embodiments comprise an outer tubular member and an inner tubular member, wherein the inner tubular member is movable in at least one degree of freedom with respect to the outer tubular member. In many of the embodiments disclosed herein the outer tubular member is configured to be stationary with respect to the handle of the device, and the inner tubular member is configured to move with respect to the outer tubular member and handle. However, some embodiments may be configured to move the outer tubular member with respect to the handle and inner term tubular member, while keeping the inner tubular member fixed with respect to the handle. Further, some embodiments may be configured to move both the outer and inner tubular members with respect to the handle and with respect to one another.

Further, various embodiments disclosed herein, as mentioned above, are configured to have one degree of freedom between the inner and outer tubular members. Specifically, many of the embodiments disclosed herein are configured to have the inner tubular member be translatable along a longitudinal axis with respect to the outer tubular member, or rotatable about the longitudinal axis with respect to the outer tubular member, but not both. Some embodiments, however, may include both rotation and translation of the inner tubular member with respect to the outer tubular member.

It should be noted that, when the present disclosure refers to tubular members, namely the outer tubular member and inner tubular member, this is not intended to restrict the embodiments disclosed herein to a configuration where the inner and/or outer tubular member comprises a cylindrical or annular shape along its entire length. Rather, the term tubular member is intended to refer to a member of the polypectomy device that comprises at least an outer wall that extends in a longitudinal direction and forms a lumen defined by an inner surface of the member. In many embodiments, the tubular members are cylindrical or annular in shape, at least for a significant portion of their length. It is envisioned, however, that some embodiments could include a non-cylindrical shape for the inner and/or outer tubular members. Further, although in some embodiments the inner and outer tubular members may comprise a generally cylindrical or annular shape along a majority of their length (e.g., the central portion that is intended to be positioned within a working channel of a scope or other medical instrument), the shape or configuration of the tubular members may be different at the distal end of the polypectomy device, where the openings for insertion therethrough of polyps are located, and/or at the proximal end, where the inner and outer tubular members interface with the handle.

Described below are various embodiments of distal end configurations. Each of these distal end configurations may be used with a variety of polypectomy device designs, including polypectomy devices having different shapes and configurations of handles, polypectomy devices having integrated vacuum suction and/or polyp collection features, polypectomy devices without integrated suction and/or collection features, manually operated polypectomy devices, electrically, pneumatically, or hydraulically operated polypectomy devices, and/or the like. Further, these various distal end configurations may be integrated into a different medical device, such as a hysteroscope, other scope device, and/or the like.

In some embodiments, the various distal end configurations disclosed herein are integrally formed into the inner and/or outer tubular members. For example, a cylindrical tube may have one or more openings or other features cut into it to form the distal end configuration. In some embodiments, however, the distal end configurations may be formed by joining one or more separate components to the inner and/or outer tubular members. For example, to form a blunt rounded tip of the outer tubular member, a blunt rounded portion may be attached to the end of the outer tubular member, such as via laser welding, adhesives, and/or other affixation methods. Further, the inner tubular member may comprise a substantially cylindrical or annular elongate portion that has a blade or cutting portion affixed to its distal end, with that affixed blade or cutting portion being the portion that mechanically contacts the polyp to help separate the polyp from the uterine wall.

It should also be noted that, as discussed in greater detail below, although portions of polypectomy devices disclosed herein are described as having a blade, cutting feature, and/or the like, this is not necessarily intended to imply that the blade, cutting portion, and/or the like is sharpened. As mentioned above, because polyps are generally of a relatively gelatinous consistency, a "blade" configured to separate a polyp from the uterine wall may not need to be sharpened, and may comprise a blunt edge. This can have multiple benefits. For example, risk of unintentional trauma to the uterine wall can be reduced by having an unsharpened edge of the blade or cutting surface. Further, manufacturing costs may be reduced if a sharpening operation does not need to be performed to create the cutting surface. This can further help to bring the cost of such a polypectomy device down to the point that it is practical for use in doctor's office setting, as opposed to a hospital surgical setting.

In various embodiments, various materials may be used to form the inner and/or outer tubular members of a polypectomy device disclosed herein. For example, the inner and/or outer tubular members may be formed from surgical grade stainless steel tubing. Other materials may also be used, however, such as, for example, liquid crystal polymer tubing. Further, in some embodiments, the inner and/or outer tubes are composite designs, meaning two or more materials may be joined together to form the final component. For example, the inner and/or outer tubular members may be formed from stainless steel tubing that forms a majority of the elongate portion of the tubular member, but a different material, such as a polymer, carbon fiber, composites, and/or the like, may be used to form the distal end that comprises the opening or openings for the polyp to pass therethrough and/or the blade/cutting surface. These different materials may be coupled together using various manufacturer practices, such as laser welding, friction welding, adhesives, fasteners, and/or the like.

Following are descriptions of several groups of figures which illustrate various embodiments of distal end configurations of polypectomy devices as disclosed herein. The different configurations can generally be grouped into two types of configurations, namely, translating or rotating. As mentioned above, to maintain relative simplicity in manufacturing and operation, and to keep manufacturing costs down, it can be desirable to design a polypectomy device that operates using a relatively simple mechanical actuation, such as translation of the inner tubular member or rotation of the inner tubular member, but not both. It should be noted, however, that various other embodiments of polypectomy devices as disclosed herein may comprise more than one degree of freedom in the actuation.

Figure 6E:
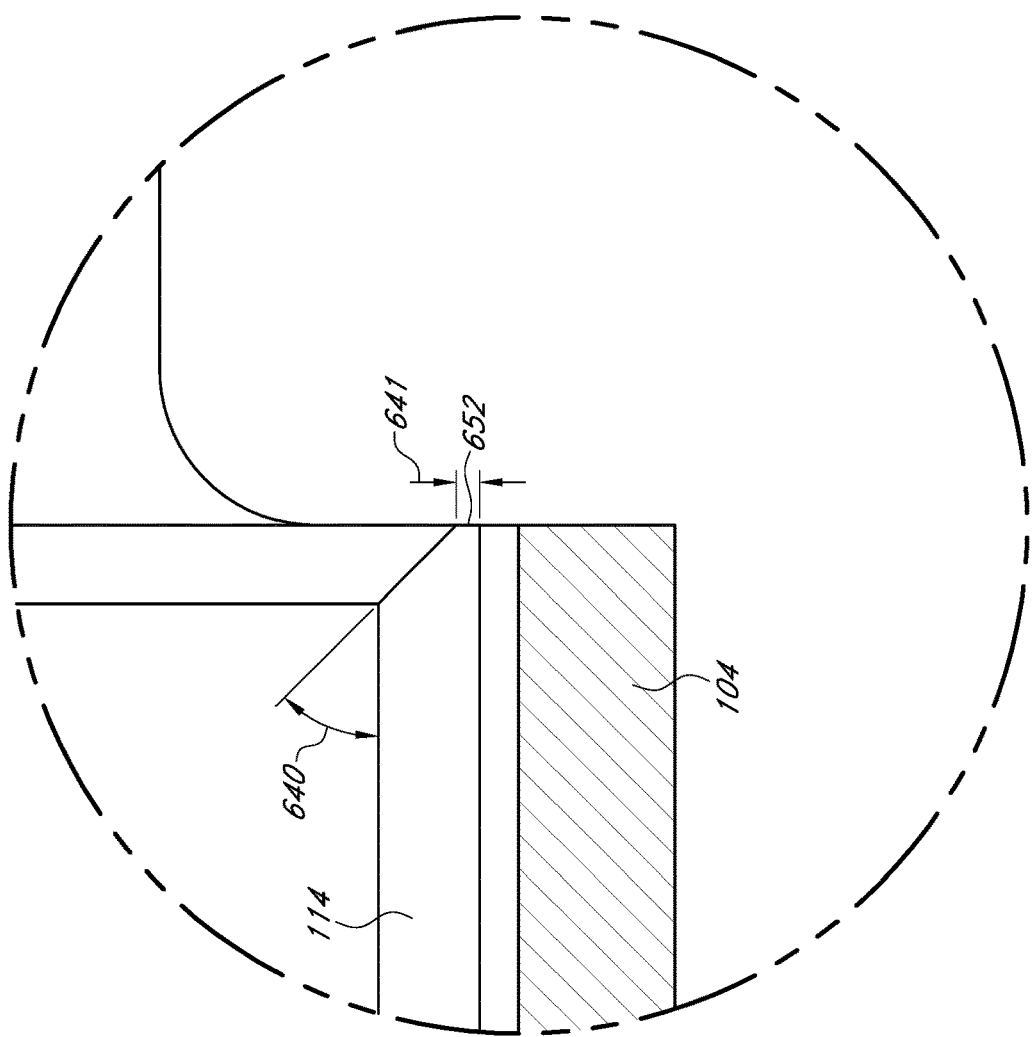

FIGS. 6A-6E illustrate an embodiment of a distal end configuration that utilizes a translating inner tubular member 114. The embodiment illustrated in FIGS. 6A-6E provides additional details of the design introduced in FIGS. 1A and 1B. With reference to FIG. 6B, the inner tubular member 114 comprises a substantially cylindrical tube nested concentrically inside of a substantially cylindrical outer tubular member 104. The outer tubular member 104 comprises two openings 108 positioned opposite one another. The two openings 108 are separated by two supporting arms 110, also positioned opposite one another.

It can be beneficial in some embodiments to have more than one opening 108, such as is shown in the present embodiment to, among other things, enable removal of polyps that are located in various locations of the uterine cavity without requiring excessive rotation of the outer tubular member 104 and the handle attached thereto. For example, in an embodiment that comprises a pistol grip type handle, similar to as described below with reference to FIGS. 18A and 18B, it may be desirable to have the pistol grip handle oriented such that it is pointed directly downward or not too far away from being pointed downward. For example, it may be desirable to use the tool with the pistol grip handle pointing downward or within 45° clockwise or counterclockwise from directly downward. With a configuration as illustrated in FIGS. 6A-6E, it is likely that a doctor will be able to reach all or nearly all polyps that may need to be removed without needing to rotate the handle outside of that 90° range.

In some embodiments, the outer tubular member 104 may be rotatable along the longitudinal axis with respect to the handle. This may, for example, enable selective angular positioning of the opening(s) 108 without having to rotate the entire handle. For example, a knob or wheel connected to the handle may allow a doctor to rotate the outer tubular member with respect to the handle.

Figure 6D:
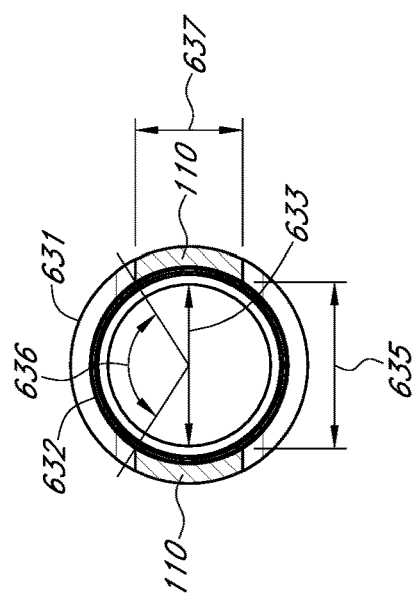

FIG. 6D is a cross sectional end view that provides additional detail as to the shape and size of the openings 108. Since these openings 108 are positioned opposite one another it can be considered that radial or angular midpoints of the two openings 108 are positioned 180° from one another. In some embodiments, that angle may be different. For example, the relative orientation of midpoints of the two openings 108 may be, for example, exactly, about, no more than, or no less than 180°, 170°, 160°, 150°, 140°, 130°, 120°, 110°, 100°, or 90°. As the relative angular position of the openings 108 with respect to each other is reduced, there will become a point, depending on the size of the openings 108, that the size of the openings may need to be decreased or one of the supporting arms 110 between the openings would go away and the two openings would merge into a single opening.

With further reference to FIG. 6D, the outer tubular member 104 comprises an outer diameter 631, and the inner tubular member 114 comprises an outer diameter 632. The outer diameter 632 may be sufficiently smaller than an inner diameter of the outer tubular member 104, to enable translating or sliding motion of the inner tubular member 114 with respect to the outer tubular member 104. The inner tubular member 114 further comprises an inner diameter 633. It can be desirable to have the inner diameter 633 be as large as possible, such as to enable easy passage of relatively large polyps or pieces of polyps that have been removed.

This and other embodiments disclosed herein may utilize various sizes of tubing in manufacturing the polypectomy devices. For example, the outer tubular member 104, and/or various other outer tubular members disclosed herein, may comprise in some embodiments an outer diameter 631 of 0.12 inches and a wall thickness of 0.01 inches. This leads to a nominal inner diameter of 0.10 inches. Further, the inner tubular member 114, and/or various other inner tubular members disclosed herein, may comprise in some embodiments an outer diameter 632 of 0.095 inches with a material thickness or wall thickness of 0.0065 inches. This creates a nominal inner diameter 633 of 0.082 inches. The size of the outer tubular member 104 may correspond to standard hypodermic tubing of gauge 11 TW.

In various embodiments, various other tubing sizes may be used for the inner and outer tubular members, depending on, among other things, the size of the scope working channel through which the outer tubular member is intended to be inserted, the size of the openings 108 in the distal end of the tubing, the expected stresses the tubing will be subjected to in use, the torsional stresses needing to be transferred through a rotating inner tubular member, and/or the like. For example, the outer diameters 631 and 632 of the outer and inner tubular members, respectively, in any of the embodiments disclosed herein may be approximately, exactly, no greater than, or no less than 0.203 inches, 0.188 inches, 0.180 inches, 0.172 inches, 0.165 inches, 0.156 inches, 0.148 inches, 0.141 inches, 0.134 inches, 0.126 inches, 0.120 inches, 0.115 inches, 0.109 inches, 0.1 inches, 0.095 inches, 0.089 inches, 0.083 inches, 0.078 inches, 0.072 inches, 0.068 inches, 0.065 inches, 0.062 inches, 0.059 inches, 0.058 inches, or 0.050 inches, corresponding to 6 through 18 gauge hypodermic tubing sizes. Further, in any of the embodiments disclosed herein, the outer and/or inner tubular members' wall thicknesses may be approximately, exactly, no greater than, or no less than 0.015 inches, 0.014 inches, 0.013 inches, 0.012 inches, 0.011 inches, 0.010 inches, 0.009 inches, 0.008 inches, 0.007 inches, 0.006 inches, 0.005 inches, 0.004 inches, 0.003 inches, or 0.002 inches, also corresponding to 6 through 18 gauge hypodermic tubing sizes. Desirably, the outer diameter 632 of the inner tubular member is slightly smaller than the inner diameter of the outer tubular member, to enable sliding and/or rotational relative motion.

The openings 108 also comprise a plurality of dimensions defining their shape. The openings 108 comprise a longitudinal length 634, a transverse width 635, and an angular opening size or width 636. The longitudinal length 634 is measured in the longitudinal direction from the radial outermost edge of the outer tubular member 104. The width 635 is measured in the transverse direction from the radially innermost edge of the outer tubular member 104, at approximately a longitudinal midpoint of the openings 108, as shown in the cross-section of FIG. 6D. Similarly, the angular width 636 is measured from the innermost radial edge of the outer tubular member 104, at approximately a longitudinal midpoint of the openings 108, as shown in the cross-section of FIG. 6D, with reference to the centerline or longitudinal axis of the outer tubular member 104. The supporting arms 110 also comprise a transverse width 637, measured at approximately a longitudinal midpoint of the openings 108, as shown in the cross-section of FIG. 6D.

In this embodiment, the longitudinal length 634 is desirably approximately 10 mm, the transverse width 635 is desirably approximately 2.138 mm, and the transverse width 637 of the arms is desirably approximately 1.37 mm. Other dimensions may be used in this and other embodiments, however. For example, it may be desirable for the length 634 of the openings 108 to be longer, such as to enable insertion therethrough of a larger portion of a polyp, or to be shorter, such as to make the design stiffer or more robust, or to cut smaller portions of polyps to help prevent clogging. For example, in various embodiments, the length 634 of the opening 108 may be approximately, exactly, no greater than, or no less than, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. Further, the width 637 of the arms 110, related to the radial depth of the openings 108, may vary in various embodiments based on, for example, the desirable size of the opening and/or the desired robustness of the design. For example, in some embodiments, the width 637 of the arms 110 may be approximately, exactly, no greater than, or no less than, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, or 3.0 mm. Further, the transverse width 635 of the openings 108 may be varied in various embodiments based on, for example, the desirable size of the openings and/or the desired robustness of the design. For example, in some embodiments, the width 635 may be approximately, exactly, no greater than, or no less than, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, or 3.5 mm. Further, the angular width 636 of the openings 108 may vary in different embodiments based on, for example, the desirable size of the opening and/or the desired robustness of the design. For example, in some embodiments, the angular width 636 of the openings 108 may be approximately, exactly, no greater than, or no less than, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 170°, 180°, 190°, 200°, 210°, 220°, 230°, 240°, 250°, 260°, or 270°. In some embodiments, the number of openings 108 may be more or less, depending on, among other things, the angular width 636 of each of the openings. For example, as the angular width 636 approaches 180°, the device may be limited to a single opening, or a second or additional openings may need to have an angular width 636 substantially less than 180°, to leave room for supporting arms 110. On the other hand, as the angular width 636 becomes less than 120°, the polypectomy device may be able to have three or more openings 108. Further, in various embodiments, the two or more openings 108 do not have to comprise the same nominal dimensions. For example, one opening may be longer and/or wider than another.

In various embodiments, the opening length 634 versus width 635 may be various ratios. For example, in the present embodiment, the ratio is approximately 4.7. In other embodiments, it may be desirable to have a smaller ratio, such as approximately, exactly, no greater than, or no less than 0.5, 1.0, 1.5, 2.0, 2.5, 3.0, 3.5, 4.0, or 4.5. In other embodiments, it may be desirable to have a larger ratio, such as approximately, exactly, no greater than, or no less than 5.0, 5.5, 6.0, 6.5, 7.0, 7.5, 8.0, 8.5, 9.0, 9.5, or 10.0.

As mentioned above, because the embodiments disclosed herein are intended to remove polyps, and not necessarily tougher body tissue, such as fibroids, the openings 108 of the present embodiment, or similar openings in various other embodiments disclosed herein, may be relatively large in comparison to the size and/or thickness of the tubing through which the opening is cut. This is because the expected stresses, such as bending or torsional stresses, may be lower than if the tool were intended to cut or remove tougher tissue. For example, with reference to the embodiment of FIGS. 6A-6E, the length 634 of the openings 108 is approximately 10 mm, and the outer diameter 631 of the outer tubular member 104 is approximately 3.048 mm, or 0.12 inches. Accordingly, the nominal ratio of opening length to outer tubular member outer diameter is approximately 3.28. In various embodiments, including the present embodiment and the various other embodiments disclosed herein, the ratio of longitudinal length of an opening in the outer tubular member to the outer diameter of the outer tubular member can be approximately, exactly, no greater than, or no less than, 1.0, 1.5, 2.0, 2.5, 3.0, 3.28, 3.5, 4.0, 4.5, 5.0, 5.5, 6.0, 6.5, 7.0, 7.5, or 8.0. This relatively large opening with respect to the size of the outer tubular member may also be defined as a ratio of the longitudinal length 634 of the opening 108 with respect to the wall thickness of the outer tubular member. For example, the present embodiment comprises a longitudinal length 634 of the opening 108 of approximately 10 mm, or 0.394 inches, and an outer tubular member wall thickness of approximately 0.01 inches. Accordingly, the nominal ratio of opening length to outer tubular member wall thickness is approximately 39.4. In various embodiments, including the present embodiment and various other embodiments disclosed herein, the ratio of longitudinal length of an opening in the outer tubular member to the wall thickness of the outer tubular member can be approximately, exactly, no greater than, or no less than, 20, 25, 30, 35, 39.4, 40, 45, 50, 55, 60, 65, 70, 75, or 80.

This relatively large opening with respect to the size of the outer tubular member may also be defined as a ratio of the transverse width 635 of the opening 108 with respect to the outer diameter 631 of the outer tubular member. For example, the present embodiment comprises a transverse width 635 of the opening of approximately 2.138 mm, or 0.084 inches, and the outer diameter 631 of the outer tubular member is approximately 0.12 inches. Accordingly, the nominal ratio of transverse width of the opening with respect to the outer diameter of the outer tubular member is approximately 0.7. In various embodiments, including the present embodiment and various other embodiments disclosed herein, the ratio of transverse width of the opening to the outer diameter of the outer tubular member can be approximately, exactly, no greater than, or no less than, 0.3, 0.4, 0.5, 0.6, 0.7, 0.8, or 0.9. Because the transverse width 635 may be somewhat dependent on the outer tube wall thickness, particularly with higher ratios, a smaller tube thickness may be desirable as the ratio increases. Further, this relatively large opening with respect to the size of the outer tubular member may also be defined as a ratio of the transverse width 635 of the opening 108 with respect to the wall thickness of the outer tubular member. For example, the present embodiment comprises a transverse width 635 of the opening of approximately 2.138 mm, or 0.084 inches, and the wall thickness of the outer tubular member is approximately 0.01 inches. Accordingly, the nominal ratio of transverse width of the opening with respect to the wall thickness of the outer tubular member is approximately 8.4. In various embodiments, including the present embodiment and various other embodiments disclosed herein, the ratio of transverse width of the opening to the wall thickness of the outer tubular member can be approximately, exactly, no greater than, or no less than, 5, 6, 7, 8, 8.4, 9, 10, 11, 12, 13, 14, 15, 16, 17, 18, 19, or 20.

This relatively large opening with respect to the size of the outer tubular member may also be defined as a percentage of the circumference of the outer tubular member that is cut away (e.g., removed or otherwise not present), forming openings therethrough. For example, with reference to the cross-sectional view shown in FIG. 6D, this embodiment illustrates an example where the outer circumference of the outer tubular member 631 is greater than 50% cut away to form the two openings 108, and thus less than 50% of the outer circumference remains to form the supporting arms 110. It can be desirable in some embodiments to maximize the percentage of the outer circumference of the outer tubular member that is cut away to form one or more openings through the outer tubular member, while leaving enough material to sufficiently resist any expected bending and/or torsional stresses that will be applied to the outer tubular member. In some embodiments, the outer circumference of the outer tubular member, at a longitudinal location approximately centered in the one or more openings 108, is approximately, exactly, no greater than, or no less than, 30%, 40%, 50%, 60%, 70%, or 80% cut away to form the one or more openings 108.

The various dimensions and ratios given herein that help to define the bounds of the size of the opening or openings with respect to the outer tubular member may be used with any of the embodiments disclosed herein, even though the specific shape of the openings in other embodiments may be somewhat different in some other embodiments. For example, the dimensions and ratios given with respect to the longitudinal length 634 may also apply to longitudinal length 840 shown in FIG. 8E, a longitudinal length of the opening 908 illustrated in FIG. 9F, longitudinal length 1040 of FIG. 10B, longitudinal length 840 of FIG. 14E, and the like. As another example, the dimensions and ratios given with respect to the transverse width 635 of the opening may also apply to a transverse width of opening 808 of FIG. 8A, a transverse width of opening 908 of FIG. 9A, a transverse width of opening 1008 of FIG. 10A, a transverse width of opening 1408 of FIG. 14A, and the like. Further, the percentages given above of the outer circumference of the outer tubular member that are cutaway to form one or more openings may apply to various other embodiments, such as the embodiments illustrated in FIG. 7E, FIG. 8F, FIG. 9G, FIG. 10D, FIG. 11D, FIG. 14F, and the like.

FIG. 6E is a detail view of the cross-section shown in FIG. 6B, which shows enlarged detail of the distal end of the inner tubular member 114, which acts as a blade or cutting surface. As mentioned above, it can be desirable in polypectomy devices disclosed herein to utilize a blade or cutting surface that is not actually sharpened as a blade typically would be. This can promote safety and also reduce manufacturing costs. As can be seen in FIG. 6E, the distal end of the inner tubular member 114 in this embodiment does comprise a chamfered or beveled edge defined by angle 640. However, unlike a design where a sharp edge is desired, the chamfered or beveled edge does not extend through the outer radial edge of the inner tubular member 114, thus leaving a blunt distal cutting surface 652 having transverse width 641. In this embodiment, width 641 is approximately 0.04 mm. In other embodiments, however, the width 641 may be larger, smaller, or may even be the full width of the material (e.g., if there is no chamfer). The cutting surface 652 is positioned to cooperate with opposing cutting surfaces 653 of the outer tubular member in cutting polyps. Additional examples of cutting edge or surface configurations, dimensions, and ratios are given below with reference to FIGS. 15A-15C.

FIGS. 7A-7E illustrate a distal end configuration embodiment having some similarities to the embodiment illustrated in FIGS. 6A-6E, except that the inner tubular member 214 is configured to rotate instead of translate. In this embodiment, the outer tubular member 204 is similar in design to the outer tubular member 104 of FIGS. 6A-6E, and the opposing openings 108 in outer tubular member 204's distal end are similar to those in FIGS. 6A-6E. Accordingly, the same reference numbers have been used with respect to the openings 108, and the description, dimensions, and ratios given above with respect to FIGS. 6A-6E can also apply to the design illustrated in FIGS. 7A-7E.

One difference in the embodiment illustrated in FIGS. 7A-7E is that the inner tubular member 214 comprises a protruding member 750 that extends longitudinally in a distal direction. The protruding member 750 comprises a cutout or opening 751 which, depending on the instant radial orientation of the inner tubular member 214 with respect to the outer tubular member 204, allows a polyp to be aspirated in through an outer opening 108 and the cutout 751, and into the inner lumen of the inner tubular member 214. In this embodiment, instead of using a distal end face as a cutting surface, such as the face or surface 652 shown in FIG. 6E, the protruding member 750 comprises cutting surfaces 752 positioned opposite one another and positioned to separate a polyp from the uterine wall when the cutting surfaces 752 approach the edges 753 of the supporting arms 110 of the outer tubular member 204. As the inner tubular member 214 rotates, the radial movement of the cutting edges 752 causes an effective opening size (e.g., the size of the combined opening from an external environment into the inner lumen of the inner tubular member created by the relative orientation of the inner and outer tubular members) of the one or more openings 108 to vary. For example, with reference to FIG. 7A, the effective opening size 708 is approximately 50% of the full opening size 108 in the present orientation. If the inner tubular member 214 were rotated 90° from this position, one of the openings 108 would be fully open into the inner lumen of the inner tubular member, and the other opening 108 would be fully blocked from the inner lumen by the protruding member 750.

As the inner tubular member 214 rotates and reduces the effective opening size 708, a polyp that is positioned there through is eventually pinched off and separated from the uterine wall. As with various other embodiments, the surfaces or edges 752 and/or the sides 753 of the supporting arms 110 which pinch off the polyp do not necessarily need to be sharpened, due to the generally gelatinous consistency of polyps.

Figure 7D:
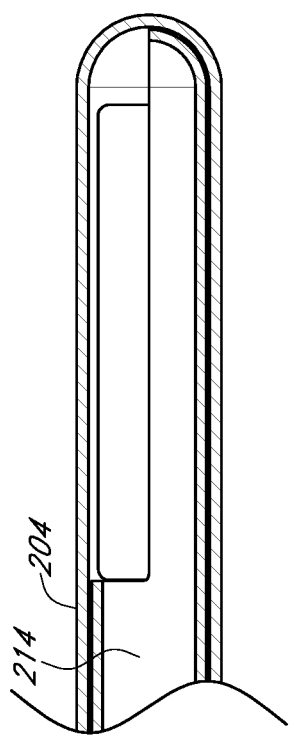
Figure 7E:
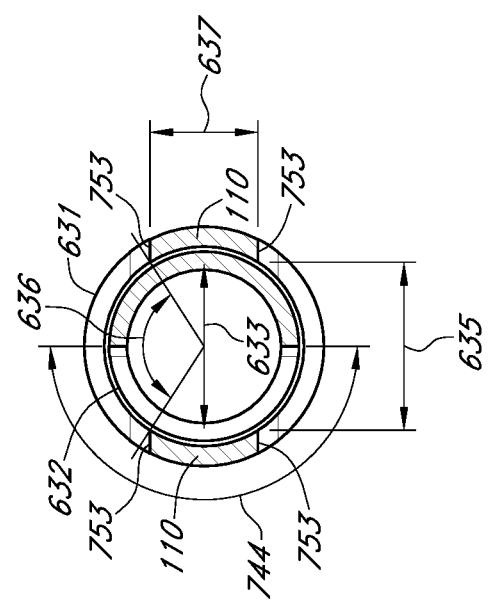

With reference to FIGS. 7B and 7E, the cutout or opening 751 in this embodiment comprises a longitudinal length 740 and a radial depth 742. Further, the cutout 751 comprises an angular width 744 as shown in FIG. 7E. In this embodiment, the angular width 744 is desirably 180°, meaning approximately half of the distal end of the inner tubular member 214 has been "cut away." In various embodiments, however, the angle 744 may be more or less than 180°. For example, the angle 744 may be, about, substantially, no more than, or no less than, 90° 100°, 110°, 120°, 130°, 140°, 150°, 160°, 170°, 180°, 190°, 200°, 210°, 220°, 230°, 240°, 250°, 260°, or 270°.

In this embodiment, the longitudinal length 740 of opening or cutout 751 is approximately 11.6 mm, and the radial or transverse depth 742 of the cutout or opening 751 is approximately 1.2 mm. Further, the outer diameter of the inner tubular member 214 is approximately 2.4 mm or 0.095 inches, with a tubing wall thickness of approximately 0.229 mm or 0.009 inches. Similarly to as discussed above with reference to openings 108, the cutout or opening 751 can be a relatively large size with respect to the size and/or thickness of the inner tubular member 214, given that the medical instrument is intended to remove polyps and not necessarily tougher material, such as fibroids.

As with the openings in the outer tubular member, the opening or cutout 751 in the inner tubular member may comprise various dimensions and ratios. For example, the length 740 of the cutout 751 may be described as a ratio versus the outer diameter or wall thickness of the inner tubular member 214. For example, the present embodiment comprises a length 740 of approximately 11.6 mm or 0.457 inches and an outer diameter of the inner tubular member 214 of approximately 0.095 inches, giving a ratio of about 4.8. In various other embodiments, including embodiments similar to as shown in FIG. 7B or in any other embodiments herein, this ratio may be different, such as approximately, exactly, no greater than, or no less than, 1, 2, 3, 4, 4.8, 5, 6, 7, 8, 9, or 10. As a ratio of cutout length 740 to material thickness of the inner tubular member, the present embodiment comprises a length 740 of approximately 0.457 inches and a tubular wall thickness of approximately 0.009 inches, giving a ratio of approximately 50.8. In other embodiments, this ratio may be larger or smaller, such as approximately, exactly, no greater than, or no less than, 10, 15, 20, 25, 30, 35, 40, 45, 50, 50.8, 55, 60, 65, 70, 75, 80, 85, 90, 95, or 100. Further, the depth 742 of the cutout 751 in the present embodiment is approximately 50% of the outer diameter of the inner tubular member 214. In some embodiments, the depth 742 of the cutout 751 can be more or less, such as exactly, approximately, no greater than, or no less than, 20%, 30%, 40%, 50%, 60%, 70%, or 80%. In general, a lower percentage will lead to a more rigid design but smaller overall opening 751. On the other hand, a higher percentage will lead to a less rigid design but larger overall opening 751.

With respect to absolute dimensions, the length 740 of the cutout 751 may in other embodiments comprise various other lengths, such as, for example, approximately, exactly, no greater than, or no less than, 3 mm, 4 mm, 5 mm, 6 mm, 7 mm, 8 mm, 9 mm, 10 mm, 11 mm, 11.6 mm, 12 mm, 13 mm, 14 mm, 15 mm, 16 mm, 17 mm, 18 mm, 19 mm, or 20 mm. Further, the depth 742 of the cutout 751 may comprise various depths, such as, for example, approximately, exactly, no greater than, or no less than, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, or 3.0 mm. In general, as the outer diameter of the inner tubular member is increased, the depth 742 of the cutout 751 may also be increased while maintaining a same or similar level of torsional or bending stiffness.

Figure 14A:
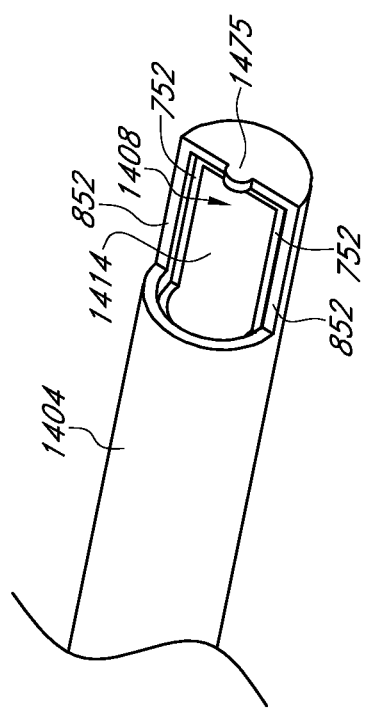
FIGS. 14A-14F illustrate another embodiment of a distal tip configuration of a polypectomy device.
Figure 14B:
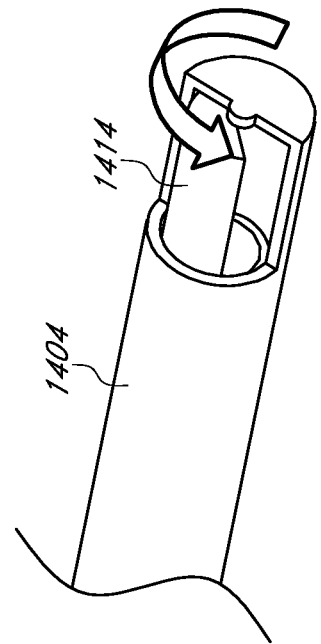
Figure 14F:
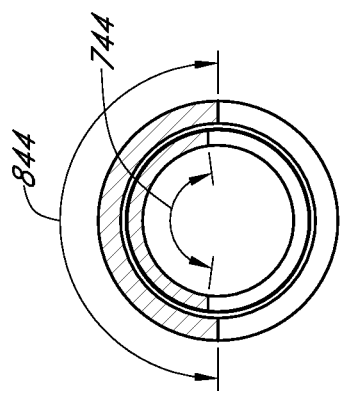
Figure 14C:
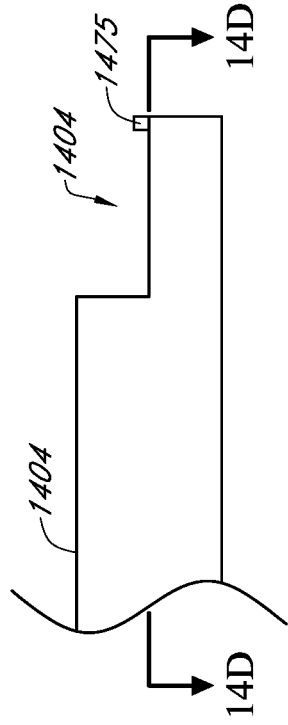
Figure 14D:
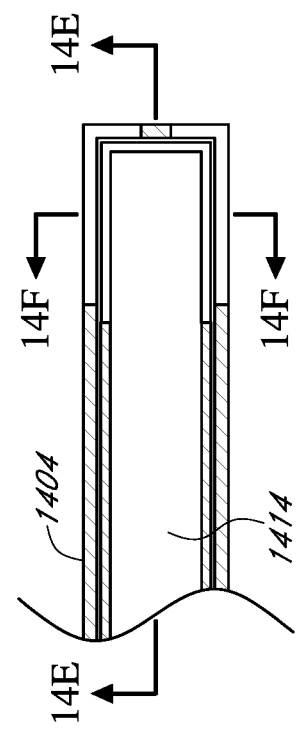
Figure 14E:
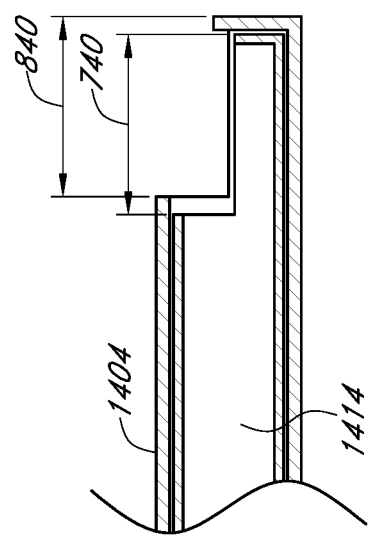

The dimensions and ratios given herein with respect to cutout 751 may also apply to other embodiments, such as the cutout 751 shown in FIG. 8C, or the cutout in inner tubular member 1414 shown in FIG. 14E.

FIGS. 8A-8F illustrate another embodiment of a distal end configuration that utilizes relative rotation of the inner tubular member 214 with respect to outer tubular member 804 to separate polyps from a uterine wall. In this embodiment, the inner tubular member 214 is similar in design to the inner tubular member 214 illustrated in FIGS. 7A-7E. Accordingly, similar reference numbers are used, and the descriptions and various dimensions and ratios described above with reference to FIGS. 7A-7E also apply to the inner tubular member 214 of FIGS. 8A-8F. One difference in the embodiment illustrated in FIGS. 8A-8F is that the outer tubular member 804 is different than the outer tubular member 204 of FIGS. 7A-7E. In this embodiment, the outer tubular member 804 comprises a single opening 808 which is similar in design to the cutout or opening 751 of the inner tubular member 214. Instead of having two supporting arms 110 that separate two openings 108, the outer tubular member 804 comprises a single protruding member 850 having an opening or cutout 808 similar to the opening or cutout 751 of the inner tubular member 214.

In operation, the inner tubular member 214 is caused to rotate with respect to the outer tubular member 804, and the blades or cutting edges or surfaces 752 and 852 are caused to approach one another and eventually come together to close the effective opening 808. As the blades or cutting surfaces 752, 852 approach one another, a polyp is caused to be pinched off and separated from the uterine wall.

Similar to the cutout or opening 751, the cutout or opening 808 of the outer tubular member 804 comprises a longitudinal length 840, a radial depth 842, and an angular width 844. In this embodiment, the angular width 844 is desirably 180°, which is identical to the angular width 744 of the cutout 751 of the inner tubular member 214. In some embodiments, it can be desirable to have angular width 844 of the opening in the outer tubular member 804 be larger or smaller. For example, if the angular width 844 of the opening 808 is smaller than 180°, and the angular size of the opening in the inner tubular member 744 is larger than the angular size of the opening in the outer tubular member, then the protruding member 750 of the inner tubular member 214 will be constrained by the protruding member 850 in the transverse or radial direction as it rotates. This may help to resist any bending moments that may be placed on the distal tip of the protruding member 750 during cutting of a polyp. However, if the angular size 844 of the opening 808 of the outer tubular member 804 is only slightly less than 180°, it is possible the protruding member 750 of the inner tubular member 214 may become jammed in the opening 808, due to manufacturing tolerances and/or elastic bending of the protrusion 750 during use. Accordingly, if it is desired in a particular embodiment to have the angular opening size 844 of the opening 808 be less than 180°, it can be desirable to make sure that angle is sufficiently smaller than 180° that jamming of the protruding member 750 is unlikely to occur, taking into account manufacturing tolerances and anticipated bending moments that may be applied to the protruding member 750.

The shape and size of the cutout or opening 751 can have the same or similar dimensions 740, 742 as described above with reference to FIG. 7B. Further, the opening 808, having corresponding dimensions 840 and 842, may comprise similar dimensions to the cutout 751, but scaled up to a larger diameter tubing. For example, in this embodiment, the length 840 and length 740 are both the same, being approximately 10 mm. In some embodiments, however, the lengths of the two openings may be different. The same absolute lengths and ratios of length to tubing diameter and/or tubing thickness can apply to the length 840 with respect to the outer tubular member as described above for length 740 with respect to the inner tubular member. Further, the same dimensions and ratios as discussed above with respect to depth 742 can apply to depth 842 of FIG. 8E, but with respect to the outer tubular member instead of the inner tubular member.

Figure 24B:
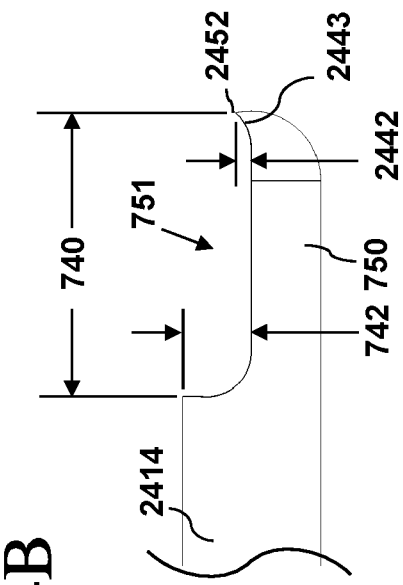
FIGS. 24A-24C illustrate another embodiment of a distal tip configuration of a polypectomy device.
Figure 24C:
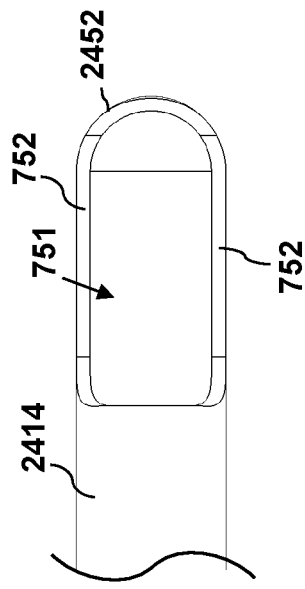
Figure 24A:
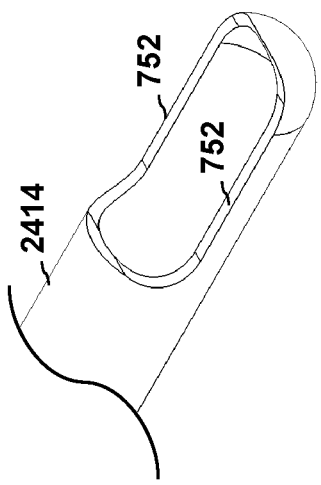

FIGS. 24A-24C illustrate an alternative embodiment of an inner tubular member 2414 that can replace inner tubular member 214 of the embodiment illustrated in FIGS. 8A-8F. Similar reference numbers are used to reference features that are similar to or the same as the embodiment illustrated in FIGS. 8A-8F. One difference with the inner tubular member 2414 versus the inner tubular member 214 is that the longitudinal length 740 of the opening 751 is shorter in this embodiment. For example, this embodiment may comprise a length 740 of approximately 5 mm, instead of 10 mm. Any of the various other dimensions given above with respect to longitudinal length 740 may also apply to this embodiment, however.

Another difference with the embodiment illustrated in FIGS. 24A-24C is that the cutout or opening 751 does not comprise a substantially flat U-shaped cutting surface 752, as in the embodiment illustrated in FIGS. 8A-8F. Rather, with reference to FIGS. 24A and 24B, the inner tubular member 2414 comprises a cutout 751 defined at least in part by two surfaces 752 on transversely opposite sides of the cutout 751, the cutting surfaces 752 extending in a direction parallel to the longitudinal axis of the inner tubular member 2414. At the distal tip of the cutout 751, however, the cutting surface rises or extends upward from the cutting surfaces 752 to form a raised lip or additional cutting edge 2452.

This raised lip or cutting edge 2452 positioned at the distal tip of the inner tubular member 2414 can provide multiple benefits. For example, in some embodiments, such as in an embodiment where the angular widths 744 and 844 of the openings in the inner and outer tubular members are both 180 degrees, the lip 2452 can stop the inner tubular member 2414 from being able to translate distally in a longitudinal direction with respect to the outer tubular member when the opening 808 is in a completely closed configuration (e.g., the protruding members 750 and 850 are positioned rotationally opposite one another). If the protruding edge or lip 2452 were not present (for example, as with the embodiment shown in FIGS. 8A-8F), it may potentially be possible for the protruding member 750 of the inner tubular member to translate distally beyond the protruding number 850 of the outer tubular member (e.g., to slide past the protruding member 850) when the inner tubular member is oriented at an angular position that is 180° from the position illustrated in FIG. 8F, which could, for example, stop the inner tubular member from being able to rotate. Note that this is assuming the inner tubular member is not otherwise restricted or restrained from translating longitudinally with respect to the outer tubular member. In some embodiments, however, the inner tubular member may be restricted, at least somewhat, in the longitudinal direction with respect to the outer tubular member by, for example, the connection of the inner tubular member to the handle of the device. However, given the relatively small size of such a medical device, and the tolerances inherent in manufacturing processes, it may be desirable to have the inner tubular member 2414 be biased in a distal direction with respect to the outer tubular member 804, such as by a spring or other feature located in the handle or elsewhere, and to have the distal tip of the protruding member 750 pressing against an interior distal tip surface of the protruding member 850 be the mechanical feature that limit distal longitudinal translation of the inner tubular member with respect to the outer tubular member. This can help to keep the cutting edge 2452 as close as possible to the corresponding cutting edge or surface 852 in the distal tip of the outer tubular member, thus increasing cutting efficiency. This can be analogous to scissors, where, if the two cutting edges are kept tightly against one another, cutting can be relatively efficient; however, if there is slop between the two cutting edges, cutting efficiency can drop.

Figure 8A:
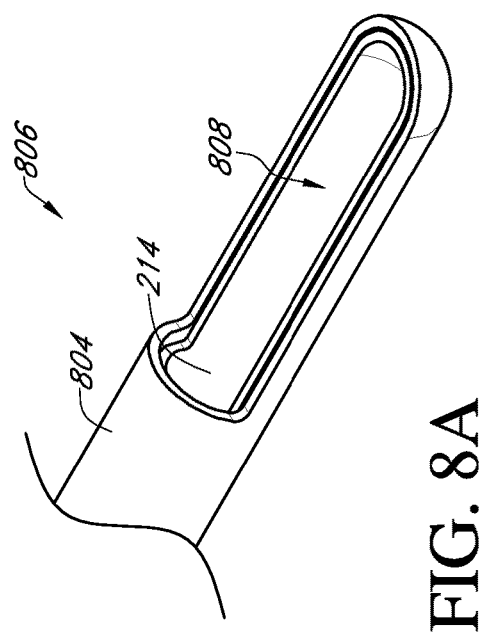
Figure 8B:
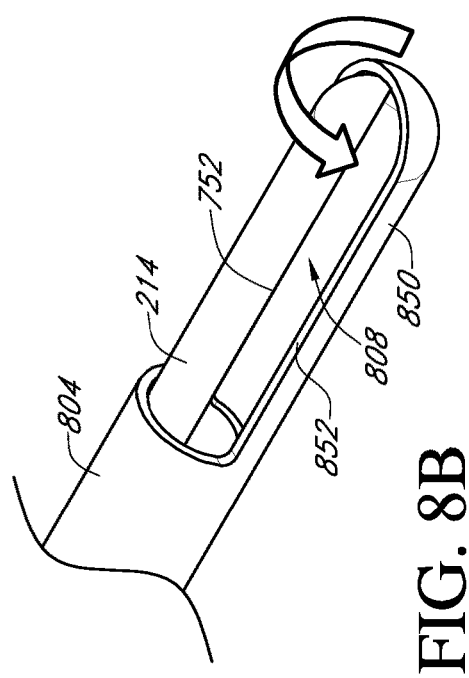
Figure 8F:
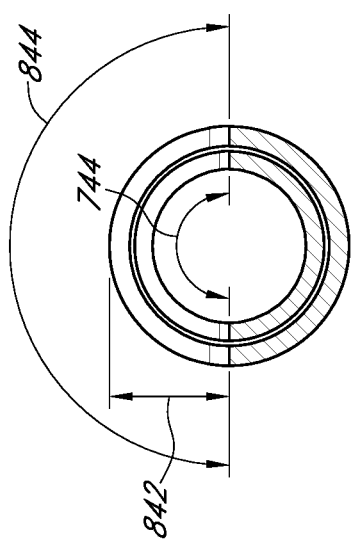

Another benefit of the protruding member 750 of FIGS. 24A-24C comprising the lip or protruding cutting edge 2452 is that the cutting edge 2452 may more efficiently cut or shear polyp tissue that is positioned at or through the distal tip of the opening 751 than the design shown in FIG. 8B, where two semicircular edges come together at the distal tip. In some embodiments, the outer tubular member may additionally or alternatively comprise a raised lip or cutting edge similar to the raised lip or cutting edge 2452 of the inner tubular member. With the lip 2452 of the inner tubular member, the lip 2452 desirably comes to a point or edge positioned at a distal (or outer) side of the material that forms the rounded distal tip of the protruding member 750. If the protruding member 850 of the outer tubular member comprises a similar lip, it would desirably come to a point or edge positioned at a proximal (or inner) side of the material that forms the rounded distal tip of the protruding member 850, since that is the side of the material that would interface with the inner tubular member.

In this embodiment, the cutting edge or lip 2452 comprises a height 2442 with respect to transverse surfaces 752. This height 2442 may comprise various sizes in various embodiments. For example, height 2442 may be exactly, approximately, no more than, or no less than, 0.005 inches, 0.006 inches, 0.007 inches, 0.008 inches, 0.009 inches, 0.010 inches, 0.011 inches, 0.012 inches, 0.013 inches, 0.014 inches, 0.015 inches, 0.020 inches, 0.025 inches, 0.030 inches, 0.035 inches, 0.040 inches, 0.045 inches, or 0.050 inches. In some embodiments, a ratio of the height 2442 of the lip to the height 742 of the cutout may be exactly, approximately, no more than, or no less than, 0.1, 0.2, 0.3, 0.4, or 0.5. In some embodiments, the raised edge or lip 2452 is formed with a gradual radiused profile 2443 shown in the side view of FIG. 24B. It can be desirable to have such a radiused profile 2443 to, for example, make the tip or lip 2452 more durable and/or resisting of deformation. In some embodiments, the profile 2443 may be of a different shape, such as, for example, a ramp, a radius of a smaller or larger size, and/or the like.

FIGS. 9A-9G illustrate another example distal end configuration embodiment that utilizes translation of the inner tubular member 914 with respect to outer tubular member 904 to separate polyps from the uterine wall. In this embodiment, the outer tubular member comprises an opening 908 positioned on a distal end side wall of the outer tubular member 904. In this embodiment, the opening 908 is substantially rectangular in shape. However, in other embodiments, the opening 908 may be shaped differently, and/or more than one opening 908 may be included at different angular locations about the outer tubular member 904 and/or at different longitudinal locations.

In this embodiment, the outer tubular member 904 further comprises an opening 952 at its distal end tip. This opening 952 allows a blunt rounded tip 950 of the inner tubular member 904 to pass therethrough. One benefit of this configuration is that it enables the opening 908 to be positioned longitudinally relatively close to the end face or surface 964. In this embodiment, the distalmost portion of the opening 908 is positioned a longitudinal distance 960 from the end face 964. This length 960 is desirably equal to or greater than the longitudinal length 940 of the opening or cutout 951 in the inner tubular member 914.

In the present embodiment, the length 940 of opening 951 is approximately 0.08 inches, the length 962 of opening 908 is approximately 0.094 inches, and the length 960 that defines the position of the distalmost edge of opening 908 is approximately 0.088 inches. In other embodiments, these dimensions may be different. For example, the length 962 of opening 908 may be, for example, approximately, exactly, no greater than, or no less than, 0.05 inches, 0.06 inches, 0.07 inches, 0.08 inches, 0.09 inches, 0.094 inches, 0.10 inches, 0.11 inches, 0.12 inches, 0.13 inches, 0.14 inches, 0.15 inches, 0.16 inches, 0.17 inches, 0.18 inches, 0.19 inches, 0.20 inches, 0.25 inches, 0.30 inches, 0.35 inches, or 0.40 inches. As another example, the length 940 of opening 951 may be, for example, approximately, exactly, no greater than, or no less than, 0.05 inches, 0.06 inches, 0.07 inches, 0.08 inches, 0.09 inches, 0.094 inches, 0.10 inches, 0.11 inches, 0.12 inches, 0.13 inches, 0.14 inches, 0.15 inches, 0.16 inches, 0.17 inches, 0.18 inches, 0.19 inches, 0.20 inches, 0.25 inches, 0.30 inches, 0.35 inches, or 0.40 inches. As another example, the length 960 may be, for example, approximately, exactly, no greater than, or no less than, 0.05 inches, 0.06 inches, 0.07 inches, 0.08 inches, 0.09 inches, 0.094 inches, 0.10 inches, 0.11 inches, 0.12 inches, 0.13 inches, 0.14 inches, 0.15 inches, 0.16 inches, 0.17 inches, 0.18 inches, 0.19 inches, 0.20 inches, 0.25 inches, 0.30 inches, 0.35 inches, or 0.40 inches. It can be desirable for the length 940 to be equal to or less than length 960 in some embodiments.

In some embodiments, the lengths 962, 940, and 960 can be described as a ratio versus the outer or inner tubular member's outer diameter or material thickness. For example, the present embodiment comprises an outer diameter of the outer tubular member 904 of approximately 0.115 inches. Accordingly, the lengths 962, 940, and 953 of the present embodiment can be described as having a ratio of approximately 0.82, 0.70, or 0.77, respectively, with respect to the outer diameter of the outer tubular member 904. Any of these three lengths may have a ratio in other embodiments with respect to the outer diameter of the outer tubular member 904 of approximately, exactly, no greater than, or no less than, 0.5, 0.6, 0.7, 0.77, 0.8, 0.82, 0.9, 1.0, 1.1, 1.2, 1.3, 1.4, 1.5, 2.0, 2.5, 3.0, 3.5, or 4.0. Similar or identical ratios may apply to these lengths with respect to the outer diameter of the inner tubular member. It should be noted that, however, if it is desirable for the opening 951 to not extend beyond the end face 964 of the outer tubular member when cutting a polyp on the forward stroke, as the length 940 increases, the length 960 must also increase, thus pushing the opening 908 backward or proximally. In some embodiments, accordingly, it can be desirable to have a shorter length 940, thus enabling the opening 908 to be closer to the distal interface 964, such as for removing polyps that are positioned toward the back of the uterus.

The tubing wall thickness of the outer tubular member 904 of the present embodiment is approximately 0.01 inches. Accordingly, the lengths 962, 940, and 953 of the present embodiment can be described as having a ratio of approximately 9.4, 8.0, and 8.8, respectively, with respect to the wall thickness of the outer tubular member 904. Any of these three lengths may have a ratio in other embodiments with respect to the wall thickness of the outer tubular member 904 of approximately, exactly, no greater than, or no less than, 5, 6, 7, 8, 8.8, 9, 9.4, 10, 11, 12, 13, 14, 15, 16, 17, 18, 19, or 20. Similar or identical ratios may apply to these lengths with respect to the wall thickness of the inner tubular member.

In this embodiment, the opening 908 in the outer tubular member 904 and the opening 951 in the inner tubular member 914 are positioned and configured to cooperate to separate a polyp from the uterine wall on either the forward stroke or rearward stroke of the inner tubular member 914 with respect to the outer tubular member 904. FIGS. 9C through 9F illustrate an example of using this embodiment to remove a polyp. In FIG. 9C, the opening 908 is positioned adjacent a polyp 922. In this view, the opening 951 is presently positioned such that the opening 908 is fully blocked off (e.g., its effective opening size is at its minimum or 0%), and the polyp 922 cannot yet be aspirated into or positioned through the opening 908.

With reference to FIG. 9D, the inner tubular member 914 has been pulled rearward or in the proximal direction with respect to the outer tubular member 904. Accordingly, the opening 951 has been positioned adjacent to the opening 908, and thus the polyp 922 is able to be positioned therethrough. At this point, the polyp 922 may be separated from the uterine wall 926 by either continuing to translate the inner tubular member 914 rearward, or by translating the inner tubular member 914 back forward or in the distal direction. FIG. 9E illustrates the inner tubular member 914 having been pulled further in the proximal direction, thus causing cutting surfaces 952 and 953 to separate the polyp 922 from the uterine wall 926. FIG. 9F illustrates an example where the inner tubular member 914 was returned in the distal direction or forward direction, thus causing surfaces 952 and 953 to separate the polyp 922 from the uterine wall 926. In either case, the polyp 922 can then be aspirated through the inner lumen of the inner tubular member 914 for extraction and/or collection.

In this embodiment, cutting surfaces 952 of the inner tubular member are substantially blunt surfaces, and cutting surfaces 953 of the outer tubular member comprise beveled or sharpened edges. In various other embodiments, however, this relationship may be flipped, meaning the surfaces 952 are beveled or sharpened and the surfaces 953 are blunt. Further, in some embodiments, all of the surfaces 952, 953 may be beveled or sharpened, or all of the surfaces 952, 953 may be blunt or un-sharpened.

Figure 9A:
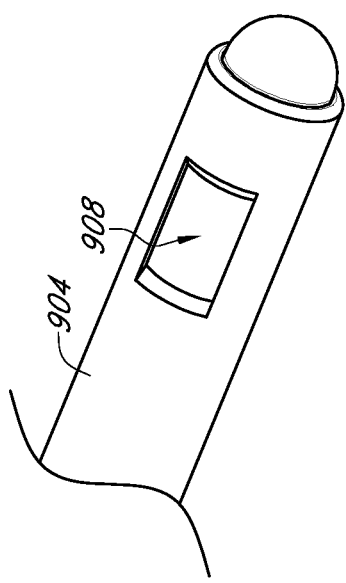
Figure 9B:
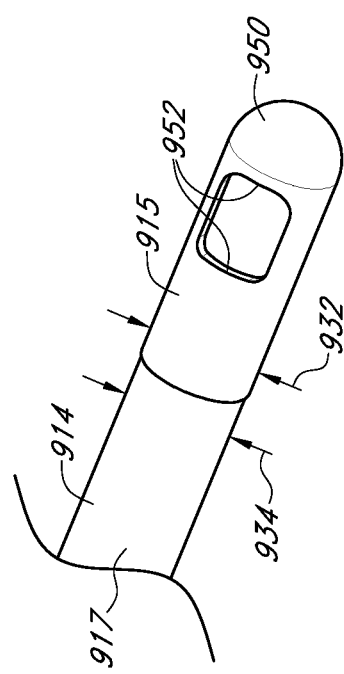

With reference to FIG. 9B, this embodiment illustrates a configuration where the inner tubular member 914 comprises a composite structure, with a distal tip portion 915 being coupled to a proximal portion 917. One advantage of this design is that the outer diameter 932 of the distal tip portion 915 may be slightly larger than the outer diameter 934 of the proximal portion 917. This larger diameter 932 may form a closer fit with the inner diameter of the outer tubular member 904, thus controlling the sliding friction between the inner and outer tubular members and/or controlling an amount of lateral movement and/or seepage or leakage of distention fluid that may pass between the inner and outer tubular members. In practice, when manufacturing a tool such as disclosed herein, it may be easier to control a relatively close fit of just of the distal tip portion 915 with the outer tubular portion 904 than it would be to have the same relatively close fit along the entire length of the inner tubular portion 914. In some embodiments, a seal, such as an O-ring, is included to help stop leakage of distention fluid between the inner and outer tubular members.

In this embodiment, the outer diameter 934 of the main elongate portion of the inner tubular member is approximately 0.089 inches. The outer diameter 932 of the distal tip portion 915 is approximately 0.092 inches. Further, the inner diameter of the outer tubular member 904 is approximately 0.095 inches. Accordingly, in this embodiment, there is nominally 0.006 inches of total clearance between the main elongate portion of the inner tubular member 914 and the inner diameter of the outer tubular member 904. There is nominally half as much total clearance, 0.003 inches, between the distal tip portion 915 and the inner diameter of the outer tubular member 904. Various other specific dimensions may be used in other embodiments; however, the general principle of having a tighter clearance between the distal tip portion 915 and the outer tubular member 904 than between the elongate portion of the inner tubular member 914 and the outer tubular member 904 can be desirable in various embodiments. In some embodiments, having a relatively tight clearance between the distal tip portion and the outer tubular member (such as, for example, approximately or no more than 0.001, 0.002, 0.003, 0.004, or 0.005 inches) can help to smoothly guide the inner tubular member with respect to the outer tubular member when the inner tubular member is translated in a longitudinal direction with respect to the outer tubular member. In some embodiments, different, or additional mechanisms are used to help guide the inner tubular member with respect to the outer tubular member, such as, for example, a linear track, one or more bearings, and/or the like.

Figure 10C:
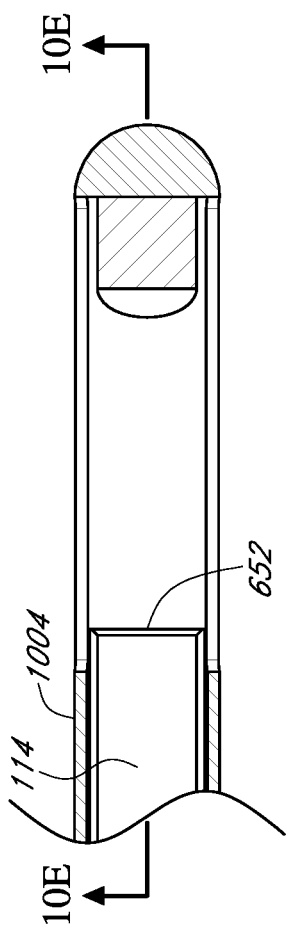
Figure 10D:
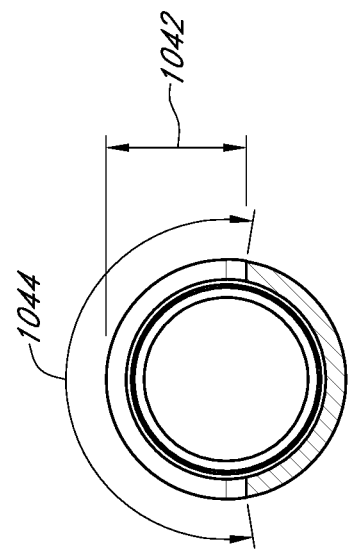

FIGS. 10A-10G illustrate another example embodiment of a distal end configuration of a polypectomy device. The embodiment illustrated in FIGS. 10A-10G shares some similar features to other embodiments disclosed herein, and also include some differences. This embodiment comprises an outer tubular member 1004, an inner tubular member 114, and a cutting block 1060. The inner tubular member 114 is similar in design to the inner tubular member 114 of the embodiment illustrated in FIGS. 6A-6E, and all characteristics and dimensions discussed elsewhere with respect to inner tubular member 114 can apply to this inner tubular member 114. Further, the outer tubular member 1004, its opening 1008, and its blunt tip 112 are similar in design to the outer tubular member 104 illustrated in FIGS. 6A-6E. However, instead of having two openings 108 positioned opposite one another, the present embodiment comprises a single opening 1008 that, in the current embodiment, desirably comprises an angular width 1044, as shown in FIG. 10D, of greater than 180°. Angular width 1044 is measured to the radially outermost edges of the opening 1008, as shown in FIG. 10D. Further, the opening 1008 comprises a depth 1042 that is greater than 50% of the outer diameter of the outer tubular member, although various other depths may be used, such as described above with reference to depth 842. This opening 1008 is similar in design to the opening 808 as shown in FIGS. 8A-8F. However, instead of the opening extending completely through the distal tip of the outer tubular member, the opening 1008 ends before the blunt distal tip 112. There can be trade-offs in these two designs. For example, including a full blunt distal tip 112, as shown in FIG. 10A, can be helpful to make the tool less likely to cause trauma if the tool is unintentionally poked into the wrong tissue. An embodiment that has at least a portion of the distal tip open, as illustrated in FIG. 8A, may, however, make it easier to reach polyps that are on the back or end wall of the uterus, such as the polyps 423 illustrated in FIG. 4.

With reference to FIG. 10B, the length 1040 of the opening 1008 can comprise any of the same dimensions described above, for example, with reference to length 634 shown in FIG. 6B. The angular opening width 1044 of the opening 1008, as shown in FIG. 10D, can comprise any of the dimensions described herein, for example, with respect to angle 844 illustrated in FIG. 8F. Further, the thickness of the outer and inner tubular members, in this embodiment and any other embodiments disclosed herein may be of any thickness as described elsewhere herein.

Another difference in the embodiment of FIGS. 10A-10G as compared to the embodiment of FIGS. 6A-6E is that this distal and configuration comprises a cutting block 1060 positioned at a distal end of the opening 1008. The cutting block 1060 is generally cylindrical in shape and sized with an outer diameter 1064 that fits within the inner diameter of the inner tubular member 114. A proximal surface of the cutting block 1060 comprises an inclined shape shown by angle 1062, which forms a cutting surface 653 which can be used to help cut the polyp 1022 to remove the polyp from the uterine wall 1026. The inclined proximal surface can help to act like a guillotine or other angled blade, which can make it easier to cut the body tissue by gradually cutting the tissue as the inner tubular member 114 is advanced, instead of trying to cut through the entire polyp at the same time. The cutting block 1060 further comprises a longitudinal length 1066, defined in FIG. 10E as the distance from the distal end of the opening 1008 of the outer tubular member 1004, to the closest point of the angled proximal surface of the cutting block 1060. In this embodiment, angle 1062 is approximately 30°. In other embodiments, the angle 1062 can be greater or less, such as, for example, approximately, exactly, no greater than, or no less than, 10°, 20°, 30°, 40°, 45°, 50°, or 60°.

Figure 10E:
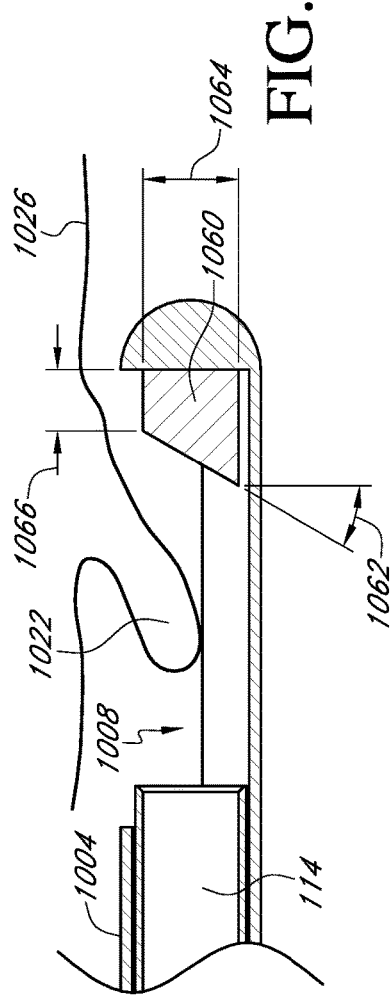
Figure 10F:
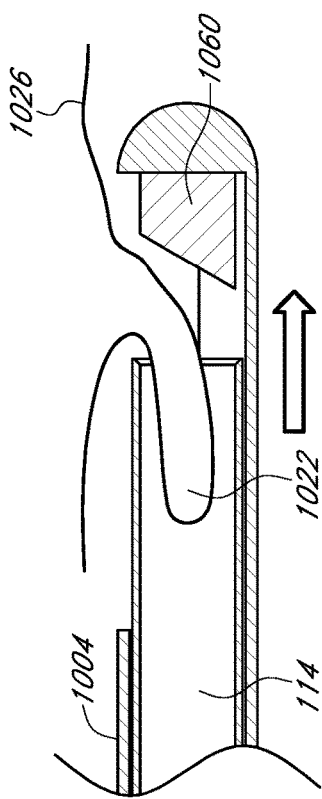
Figure 10G:
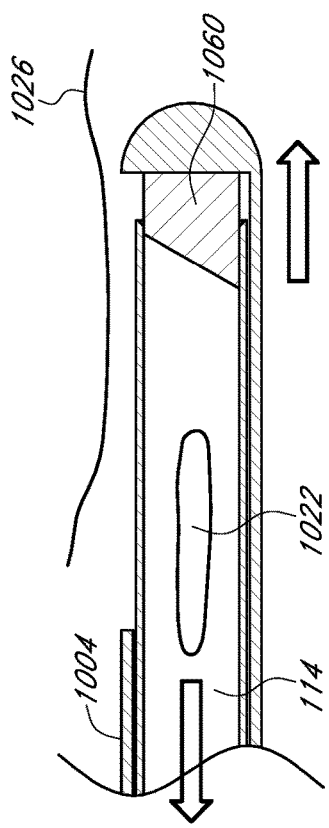

FIGS. 10E-10G illustrate an example of using this embodiment to remove a polyp 1022. In FIG. 10E, the polyp 1022 has been positioned through the opening 1008. In FIG. 10F, the inner tubular member 114 has been advanced forward and is approaching the cutting block 1060. In FIG. 10G, the inner tubular member 114 has been advanced forward far enough that there is no gap left between the end opening of the inner tubular member 114 and the cutting block 1060, and the polyp 1022 has been separated from the uterine wall 1026. With continued vacuum suction, the polyp 1022 can be aspirated through the inner lumen of the inner tubular member 114. In some embodiments, the cutting block comprises an angle 1062 of zero degrees, and the front cutting edge 652 of the inner tubular member 114 is instead angled (using any of the angles described above with reference to angle 1062).

FIGS. 11A-11G illustrate another embodiment of a distal end configuration for a polypectomy device. The embodiment illustrated in FIGS. 11A-11G is the same as the embodiment described above with respect to FIGS. 10A-10G, with the exception of different designs for the inner tubular member 1114 and cutting block 1160. The opening 1108 is similar to opening 1008 and can have similar dimensions. The cutting block 1160 is similar to the cutting block 1060, and can comprise the same range of proximal surface angles 1062 as the cutting block 1060 of FIG. 10E. The longitudinal length 1066 of the cutting block 1160, however, is desirably longer than the length of the cutting block 1060, because the inner tubular member 1114 comprises an angled surface configured to engage the cutting block 1160, instead of a straight distal surface, as illustrated in FIG. 10E.

Figure 11A:
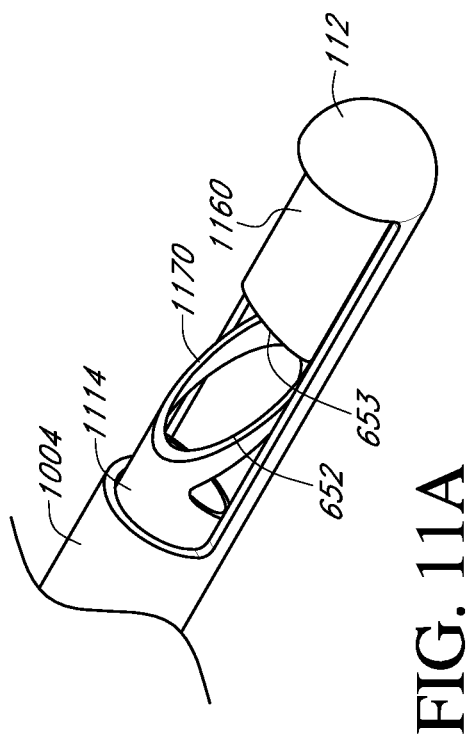
FIGS. 11A-11G illustrate another embodiment of a distal tip configuration of a polypectomy device.
Figure 11B:
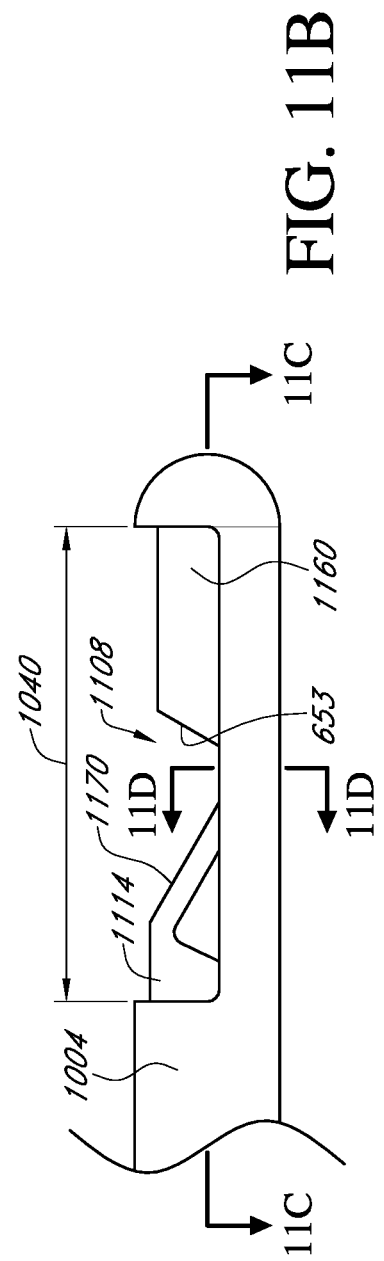
Figure 11C:
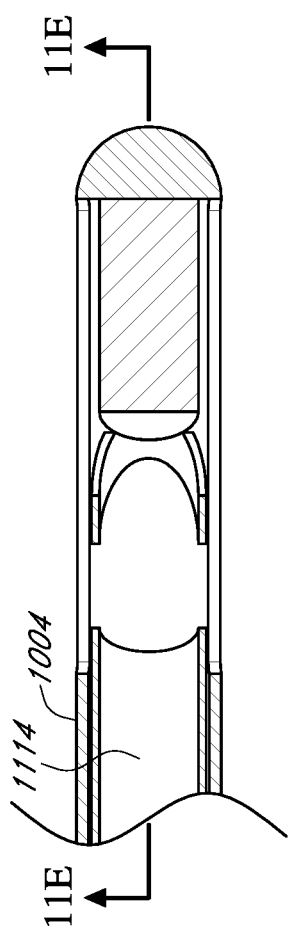
Figure 11D:
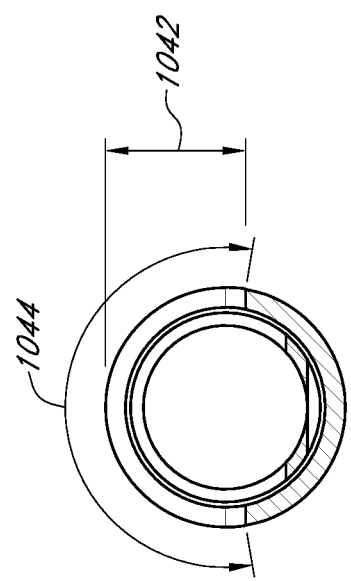
Figure 11E:
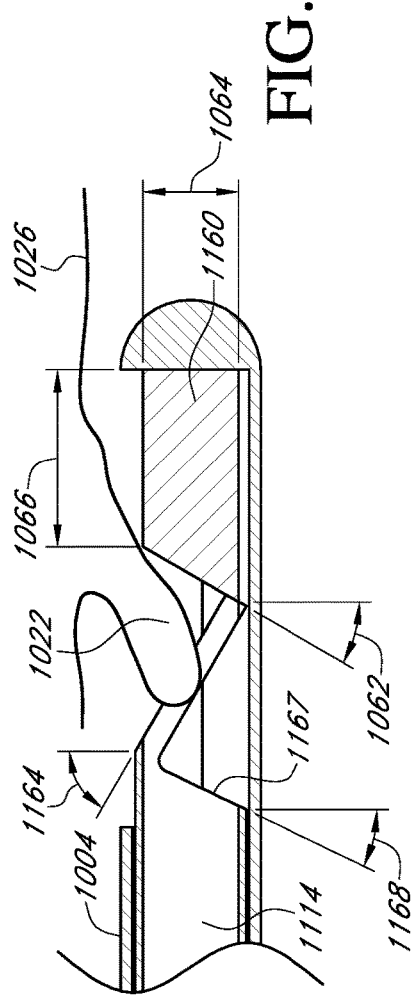
Figure 11F:
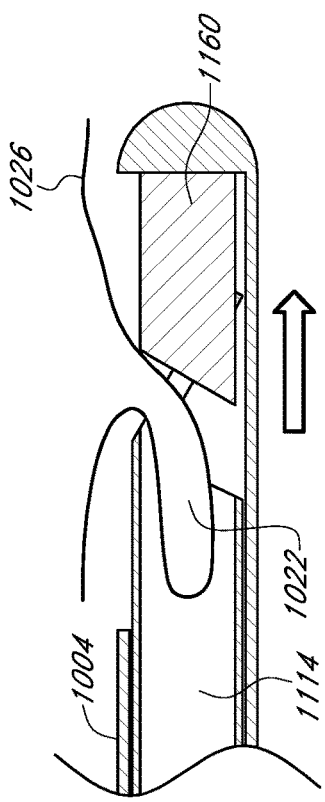
Figure 11G:
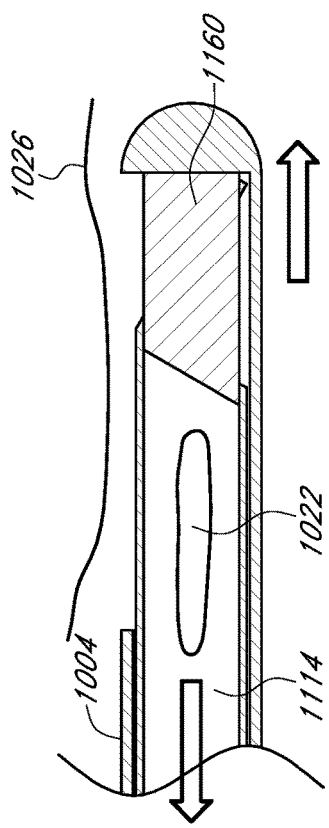
Figure 12A:
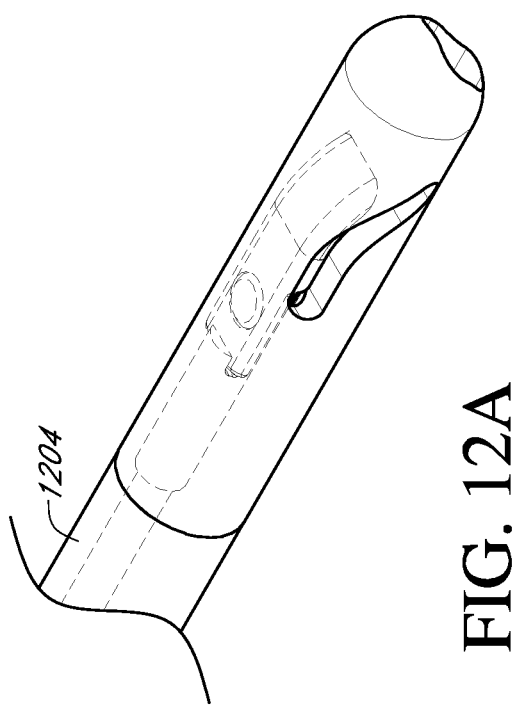
FIGS. 12A-12F illustrate another embodiment of a distal tip configuration of a polypectomy device.
Figure 12B:
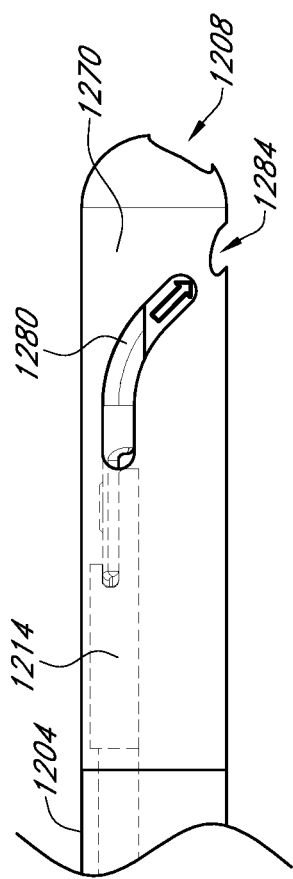
Figure 12C:
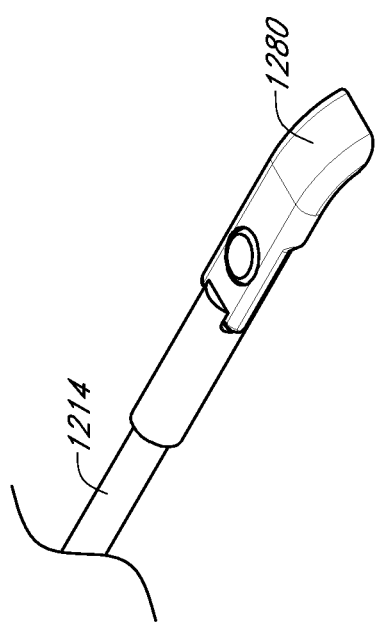
Figure 12D:
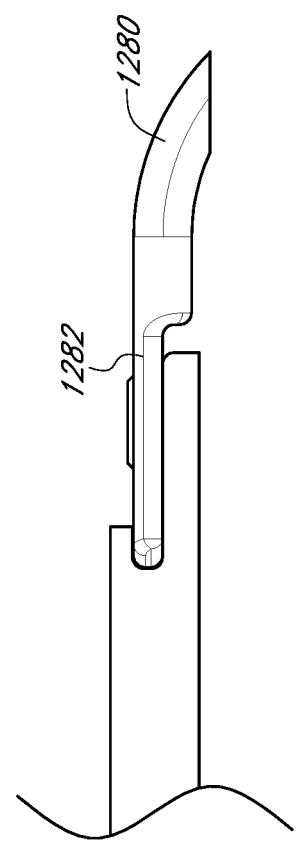
Figure 12E:
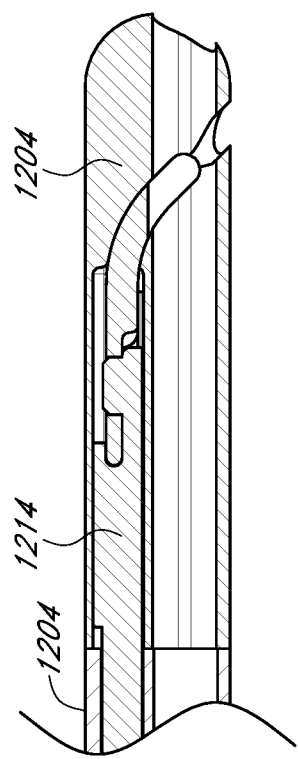
Figure 12F:
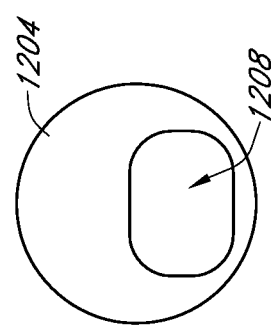

The inner tubular member 1114, instead of having a flat cylindrically shaped or annularly shaped distal surface 652, as shown in FIG. 10E, comprises an angled ring portion 1170 extending from the distal end of the inner tubular member 1114 and having distal cutting surface 652. This ring member 1170 is sized and shaped to fit around the outside of the cutting block 1160, enabling cutting surface 652 to cooperate with cutting surface 653 to cut a polyp. The ring member 1170 and the cutting block 1160 work together to slice polyp material from the uterine wall. The ring member 1170 is angled back or comprises a distal face positioned at angle 1164 as measured from a vertical plane as illustrated in FIG. 11E. Further, a distal surface 1167 of the inner tubular member 1114, positioned behind the distal surface of the ring member 1170, is angled back at an angle 1168 with reference to the vertical plane. The distal surface 1167 and/or the surface 652 can act as cutting surface, depending on where a polyp is positioned during the cutting process.

In this embodiment, angle 1062 can have similar dimensions as discussed above with reference to FIG. 10E. Angle 1164 is approximately 60° in the present embodiment. In other embodiments, however, angle 1164 may be a different dimension, such as, for example, approximately, exactly, no greater than, or no less than, 10°, 20°, 30°, 40°, 50°, 60°, 70°, or 80°. In this embodiment, angle 1168 is approximately 25.6°. Further, a distal tip surface of the ring member 1170 may comprise an angle similar to or the same as angle 1062, as can be seen in FIG. 11E where that surface is shown coincident with angle 1062. Each of these angles may be different in other embodiments, such as, for example, approximately, exactly, no greater than, or no less than, 10°, 20°, 30°, 40°, 50°, 60°, 70°, or 80°.

FIGS. 12A-12F illustrate another embodiment of a distal end configuration of a polypectomy device. This embodiment comprises an outer tubular member 1204 but does not comprise an inner tubular member as shown in many of the other embodiments disclosed herein. With many of the other embodiments disclosed herein, the inner tubular member is what comprises an inner lumen through which a separated polyp will pass for collection or disposal. In this embodiment, however, the outer tubular member 1204 comprises the inner lumen for extraction or collection of separated polyps.

The outer tubular member 1204 has a cutter mechanism 1270 attached to the distal end of the outer tubular member 1204. The cutting mechanism 1270 comprises an opening 1208 that provides a passageway into the central lumen of the outer tubular member 1204. The cutting mechanism 1270 further comprises a flexible cutter 1280 positioned therein, the flexible cutter 1280 being coupled to an actuation member (e.g., actuation member, rod, link, linkage, pushrod, and/or the like), in this case an actuation rod 1214. The actuation rod 1214 can be connected to, for example, the trigger or actuation mechanism of the handle in a way similar to the inner tubular members of other embodiments (e.g., movement of the trigger or actuation mechanism of the handle causes translation of the actuation rod 1214). In the retracted state shown in FIG. 12B, the flexible cutter 1280 is retracted within the cutting mechanism 1270. After a polyp has been aspirated or otherwise positioned into the cutting mechanism 1270 through the opening 1208 in the distal end of the cutting mechanism 1270, the actuation rod 1214 can be translated forward, causing the flexible cutter 1280 to move forward and downward through the cutter channel 1284, thus separating the polyp from the uterine wall.

In some embodiments, the flexible cutter 1280 may be formed from, for example, a polymer or other material that enables the flexible cutter 1280 to flex and bend downward to be pushed through the cutter channel 1284. In some embodiments, with reference to FIG. 12D, the flexible cutter 1280 may comprise a thinner portion 1282 that may help to enable the flexible cutter 1280 to flex.

Figure 13A:
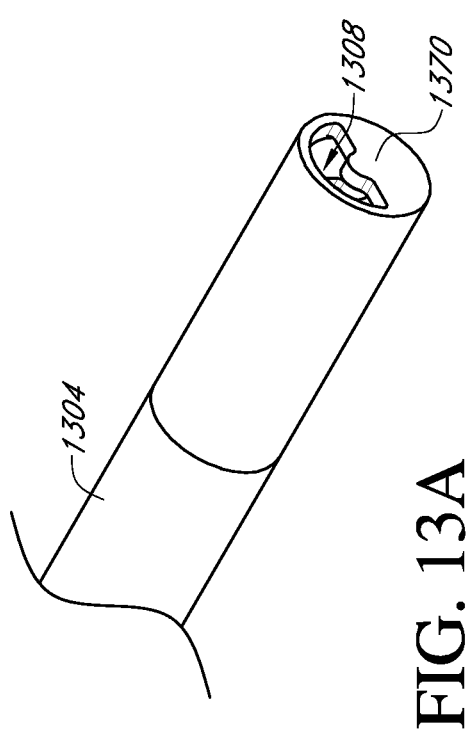
FIGS. 13A-13C illustrate another embodiment of a distal tip configuration of a polypectomy device.
Figure 13B:
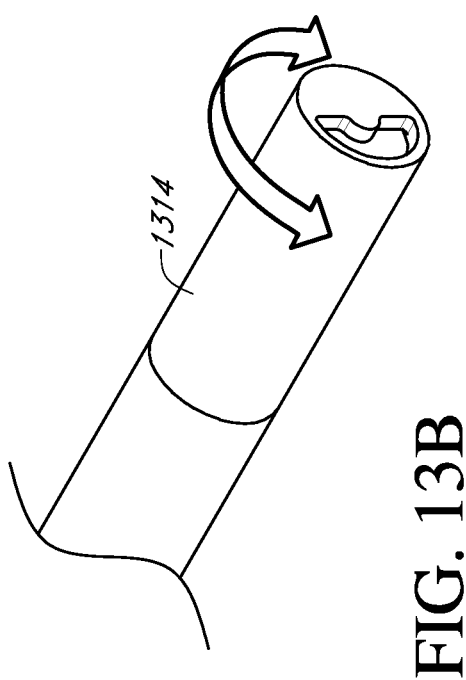
Figure 13C:
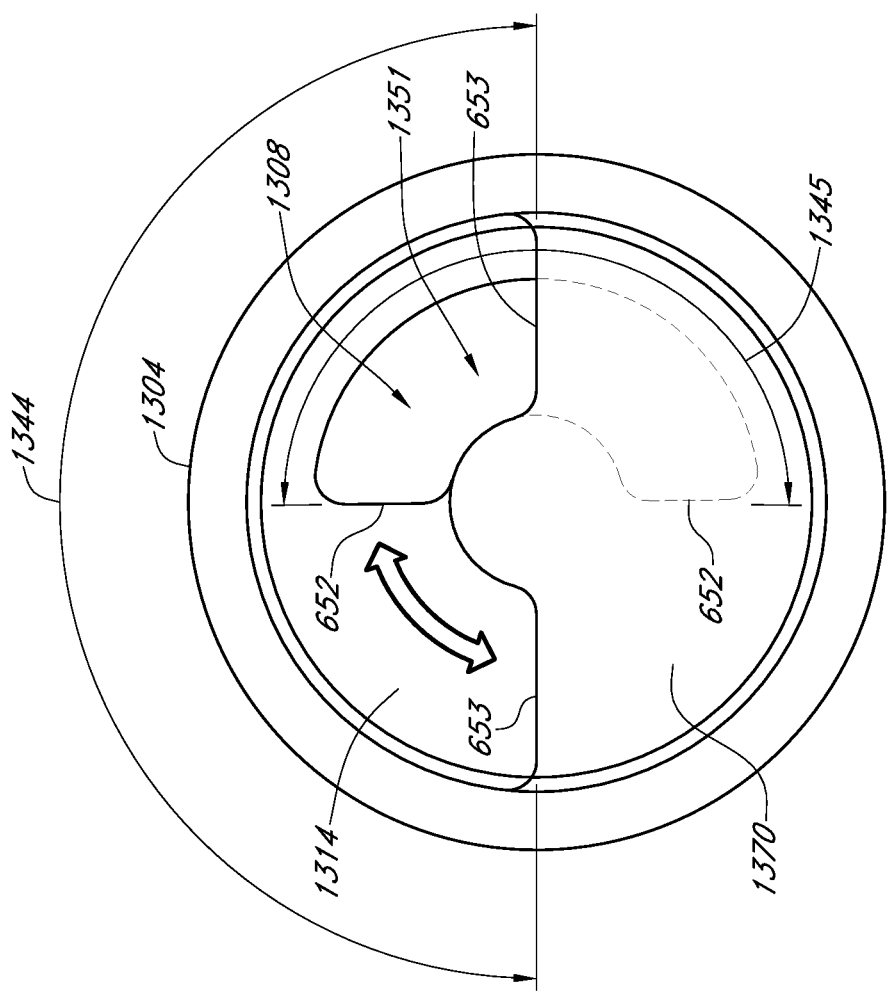

FIGS. 13A-13C illustrate another embodiment of a distal end configuration of a polypectomy device. One difference in this embodiment from some of the other embodiments disclosed herein is that the opening 1308 for passing therethrough of a polyp for removal from the uterine wall is positioned on the distal tip of the instrument instead of on a side wall of the distal end of the instrument. This is similar, at least with respect to positioning of the opening 1308, to the positioning of the opening 1208 illustrated in FIG. 12F.

In the embodiment illustrated in FIGS. 13A-13C, the instrument comprises an outer tubular member 1304 shown in FIG. 13A, and an inner tubular member 1314, shown in FIG. 13B (with the outer tubular member 1304 hidden). FIG. 13C illustrates an end view of the polypectomy device, with the inner tubular member 1314 being shown partially in hidden lines because part of the inner tubular member 1314 is blocked from view by the distal end face 1370 of the outer tubular member 1304. As can be seen in FIG. 13C, the cutout or opening 1351 in the distal end surface of inner tubular member 1314 can be rotated with respect to the outer tubular member 1304, thus causing the effective opening size of opening 1308 into the inner lumen of the inner tubular member 1314 to vary. In this embodiment, the openings in the outer and inner tubular members each comprise an angular width of 1344 and 1345, respectively, that are approximately 180°. Accordingly, in this embodiment, the cutout or opening 1351 of the inner tubular member 1314 can be selectively completely exposed through opening 1308, completely hidden by end face 1370 of the outer tubular member 1304, or anything in between. In other embodiments, the angular widths 1344 and 1345 may vary. For example, if angle 1344 of the outer tubular member 1304 is greater than 180°, and angle 1345 of the inner tubular member 1314 remains as 180°, the opening 1351 into the inner lumen of the inner tubular member 1314 will never be fully covered by the end surface 1370. This may be desirable in some embodiments, such as to provide at least a small controlled amount of leakage of distention fluid into the inner lumen of the inner tubular member 1314. This may be desirable to enable or facilitate more efficient suction of a removed polyp through the inner tubular member 1314 and into a collection chamber.

In some embodiments, a polypectomy device may comprise both a distal end opening, such as is shown in FIG. 13A, and a side opening, such as is shown in FIG. 7A. One advantage of having both end openings and side openings is that an end opening may be more desirable for use with polyps positioned at the back uterine wall, such as polyps 423 shown in FIG. 4, and a side opening may be more desirable for polyps positioned at the side wall of the uterus, such as polyps 422 shown in FIG. 4. Further, an opening positioned along the side of the tubes may be able to have a larger effective opening size than an opening positioned at the distal end, since the opening at the distal end is limited by the diameter of the tubes. In some embodiments, the benefits of both side opening and end opening designs are combined into a single opening, such as is shown in FIG. 8A. With the embodiment shown in FIG. 8A, the opening 808 extends from the side of the outer tube 804 all the way through the distal end of the instrument.

FIGS. 14A-14F illustrate another embodiment of a distal end configuration of a polypectomy device. This embodiment is similar to the embodiment illustrated in FIGS. 8A-8F, as described above, with the exception of the distal tip configuration. The present embodiment comprises a flat distal tip as opposed to the rounded distal tip of FIG. 8A. Further, the embodiment of FIG. 14 A comprises a protrusion 1475 which may, for example, be configured to act as a pivot point for the inner tubular member 1414 as it rotates. Although not shown in these figures, the inner tubular member 1414 may comprise a pin or other protrusion that fits into a hole or depression of the protrusion 1475, thus enabling the protrusion 1475 to act as a pivot point. In some embodiments, the protrusion 1475 may help to limit translation of the inner tubular member 1414 distally beyond the outer tubular member 1404, similar to as described above with reference to the raised lip 2452 of FIGS. 24A-24C.

The dimensions 840 and 844 of outer tubular member 1404 may be similar or identical to the dimensions 840 and 844 of the embodiment of FIGS. 8A-8F, and these dimensions may take any of the numbers given above. Further, the dimensions 740 and 744 of the inner tubular member 1414 may be similar or identical to any of the numbers given above for dimensions 740 and 744 of inner tubular member 214 illustrated in FIGS. 8C and 8F. As shown in FIG. 14F, in this embodiment, angular width 844 is approximately 180 degrees, but angular width 744 is less than 180 degrees, thus leading to the inner tubular member's cutting surfaces being desirably recessed somewhat with respect to the outer tubular member, when the inner and outer tubular members are rotationally aligned as shown in FIG. 14F.

Blade or Cutter Configurations

As mentioned above, various embodiments of polypectomy devices disclosed herein may comprise sharpened or un-sharpened blades or cutting surfaces configured to separate a polyp from the uterine wall. Because polyps are relatively soft or gelatinous, particularly as compared to other objects in need of removal, such as fibroids, a less sharp or blunter surface may be acceptable in a polypectomy device to cut or remove the polyp. Further, a blunter or less sharp surface may even be desirable, because it can be safer by having less risk of causing trauma if that surface were to contact a portion of body tissue that is not intended to be cut.

FIG. 6E, as discussed above, illustrated one example of a cutting surface 652 having a chamfered surface next to it, but not coming to a point like a typical blade would. These concepts can be applied to any of the embodiments disclosed herein. FIGS. 15A-15C illustrate a simplified example of cutting faces, edges, or surfaces 1552, 1552', and 1552" that may be used with any of the embodiments disclosed herein (e.g., with cutting surfaces 652, 653, 752, 753, 852, 952, 953, 1167, or similar surfaces shown in various figures).

FIG. 15A illustrates a cross-sectional view of an inner or outer tubular member having material thickness 1515 and having a sharpened cutting edge 1552 formed by a chamfer being created that is of thickness 1517, equal to the full thickness 1515 of the material. This provides an example of a sharpened cutter or blade. FIG. 15B illustrates a version of an inner or outer tubular member 1514' having an un-sharpened cutting face or surface 1552'. In this embodiment, the material thickness is 1515 and the cutting face 1552' has a thickness equal to the material thickness 1515.

In practice, it can be difficult to form an edge or surface that does not have some sort of chamfer or imperfection at its edges. Further, if a surface like the surface 1552' were used, with no chamfer or rounding at all at the corners, the side edges of the surface 1552' may still be relatively sharp. Accordingly, it may be desirable in some embodiments to have a cutting face that is not sharpened (for example, using a manufacturing process that makes the cutting edge come to a point) but that may still have some sort of chamfer, round, or imperfection at its edge. FIG. 15C illustrate such an example, wherein inner or outer tubular member 1514" comprises a cutting face or surface 1552" and a chamfer 1554 at its edge. In this example, the width 1517" of the chamfer 1554 is less than the width 1515 of the material of the tubular member 1514". The example shown in FIG. 15C is similar to the example shown in FIG. 6E, but may be used with any other embodiments, also. The chamfer, round, or imperfection 1554 may be formed in various ways. For example, it may be formed using a secondary operation, such as a cutting, grinding, or deburring operation. It may also be formed into the material during injection molding or the like. In some embodiments, the chamfer, round, or imperfection 1554 may be a result of whatever manufacturing process is used to create the cutting surface 1552" and may not require a secondary operation. In some embodiments, both sides of the surface 1552" comprise a chamfer, round, or imperfection, but at least a portion of the surface 1552" remains flat or blunt (e.g., not sharpened to a point).

As discussed above, tubing used to create portions of the polypectomy devices disclosed herein, including the example blade or cutting surfaces shown in FIGS. 15A-15C, may comprise a variety of thicknesses. For example, tubing thickness, and thus thickness 1515 shown in FIGS. 15A-15C, may be in some embodiments somewhere within the range of 0.015 inches to 0.002 inches, or approximately, exactly, no greater than, or no less than, 0.015 inches, 0.014 inches, 0.013 inches, 0.012 inches, 0.011 inches, 0.010 inches, 0.009 inches, 0.008 inches, 0.007 inches, 0.006 inches, 0.005 inches, 0.004 inches, 0.003 inches, or 0.002 inches, corresponding to 6 through 18 gauge hypodermic tubing sizes. The chamfer, round, or imperfection 1517" may in various embodiments be various percentages of the overall width 1515. For example, in some embodiments, the width 1517" may be approximately, exactly, no less than, or no greater than, 5%, 10%, 15%, 20%, 25%, 30%, 40%, 50%, 60%, 70%, or 75% of the total material thickness 1515.

Polypectomy Device Handles

Various human interface features may be used with polypectomy devices disclosed herein. For example, various embodiments disclosed herein comprise a handle portion sized and configured to be held and/or manipulated by a human hand during use. The handle portion may comprise features that enable the user to grip the handle and reposition the polypectomy device, such as by rotating the device about a longitudinal axis of the outer tubular member and/or inserting or retracting the outer tubular member into or out of the patient's uterus (e.g., through the working channel of a scope or other instrument). The handle portion may further comprise one or more actuating members, such as a trigger, button, lever, and/or the like that enables the user to cause relative motion of the inner tubular member with respect to the outer tubular member, and/or relative motion of another actuating member with respect to the outer tubular member, such as the actuation rod 1214 of FIG. 12C.

Figure 16A:
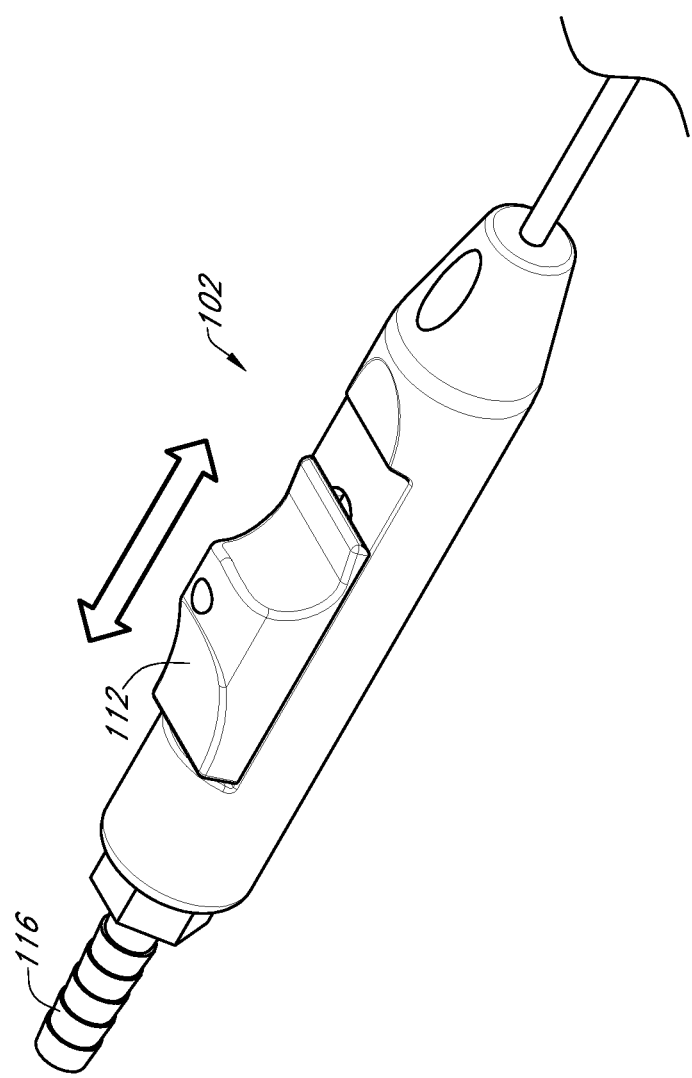
FIGS. 16A and 16B illustrate additional details of the handle portion of the embodiment of FIG. 1A.
Figure 16B:
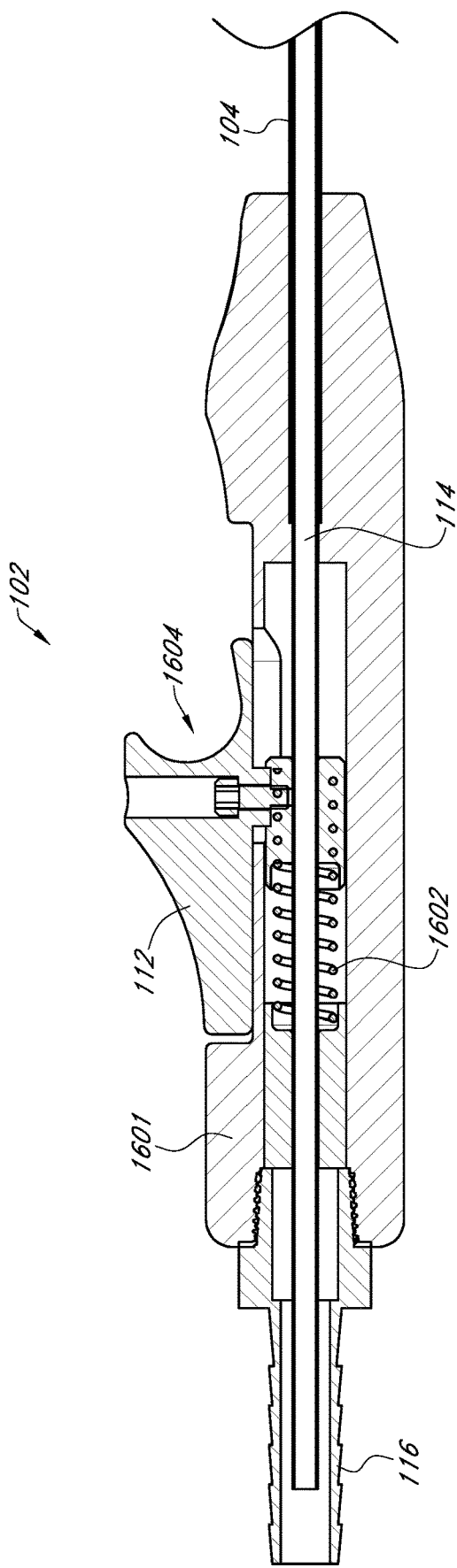

FIGS. 16A and 16B illustrate additional details of the handle 102 of the polypectomy device 100 of FIG. 1A. The handle 102 comprises a main body 1601 having an actuating member 112 slidably coupled therewith. The actuating member 112 can translate back and forth to cause back and forth translating motion of the inner tubular member 114 with respect to the outer tubular member 104. The handle 102 further comprises a spring 1602 positioned to bias the actuating member 112 in one direction. In this embodiment, the actuating member 112 is biased by the spring 1602 in the forward or distal direction. However, in other embodiments, the actuating member 112 may be biased in the proximal direction (or even biased to a central position between the proximal and distal extents). The actuating member 112 further comprises a finger surface 1604 shaped to engage a human finger. The surface 1604 may, for example, be shaped to engage the index finger or thumb or other finger of a user's hand.

In this embodiment, the outer tubular member 104 is affixed to the main body 1601 of the handle 102, and the inner tubular member 114 is coupled to and moves along with the actuating member 112. In this embodiment, the inner tubular member 114 extends into the vacuum port 116, and thus enables polyps or portions of polyps that have been removed from the uterine wall and aspirated through the inner tubular member 114 to be expelled at the vacuum port 116, desirably into a collection system fluidly coupled with the vacuum port 116.

Figure 17A:
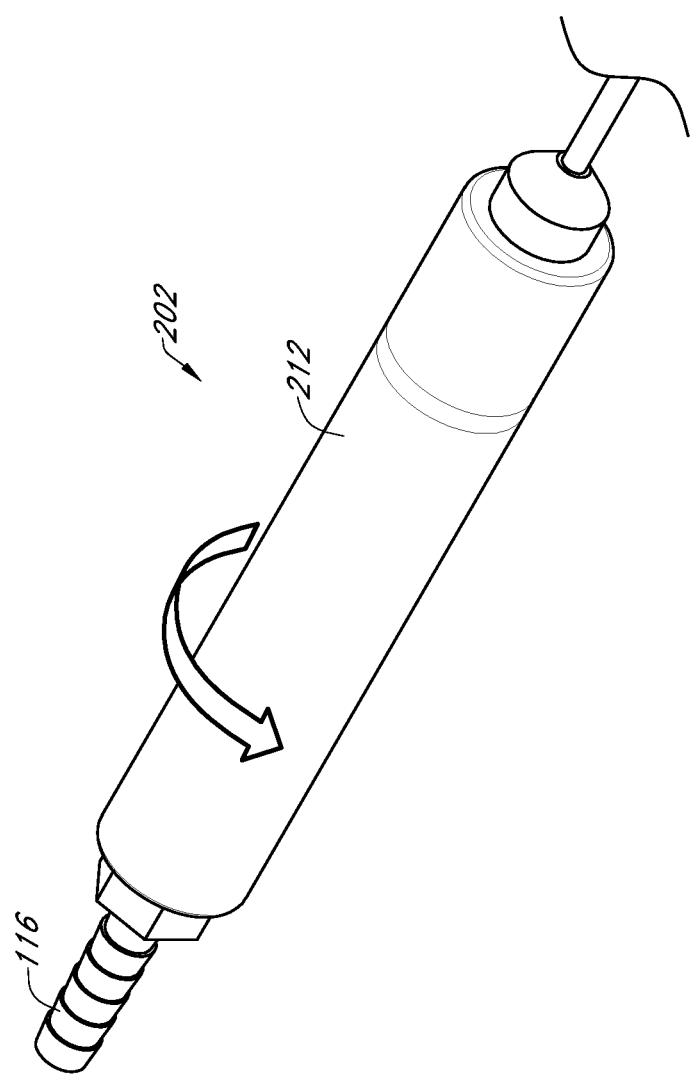
FIGS. 17A and 17B illustrate additional details of the handle portion of the embodiment of FIG. 2A.
Figure 17B:
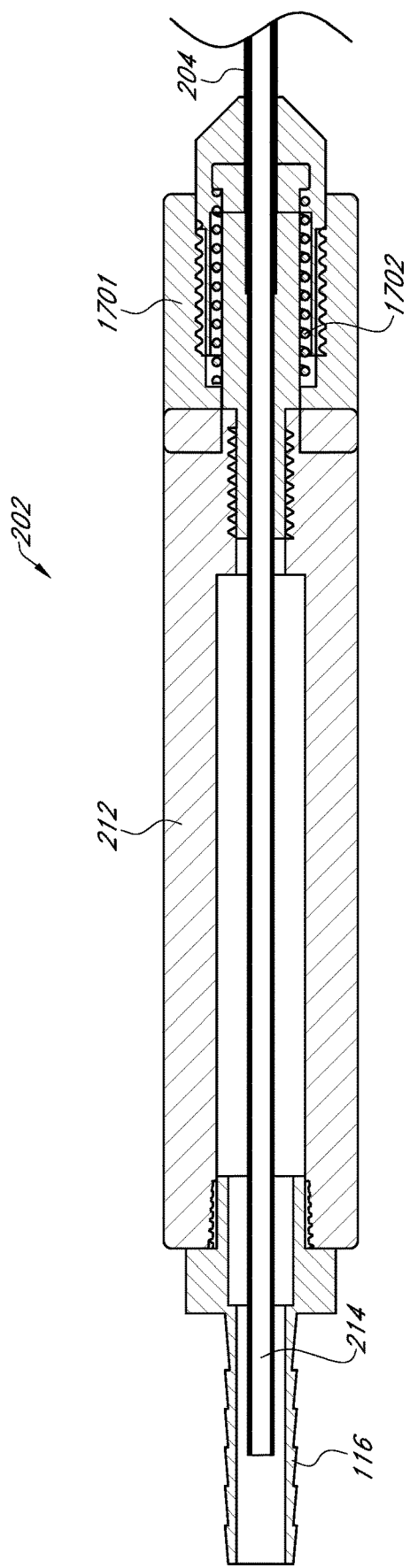

FIGS. 17A and 17B illustrate additional details of the handle portion 202 of the embodiment illustrated in FIGS. 2A and 2B. In this embodiment, the handle portion 202 comprises a main body 1701 affixed to the outer tubular member 204. The handle 202 further comprises an actuating member 212 coupled to the inner tubular member 214 such that the rotation of the actuating member 212 with respect to the main body 1701 causes relative rotation of the inner tubular member 214 with respect to outer tubular member 204. A spring 1702 provides a compression or tension force that keeps the actuating member 212 and main body 1701 from freely rotating with respect to one another. Accordingly, depending on the strength of the spring 1702, a particular predetermined torque force on the actuating member 212 will have to be applied to begin rotation of the rotating member 212 with respect to the main body 1701.

Figure 18A:
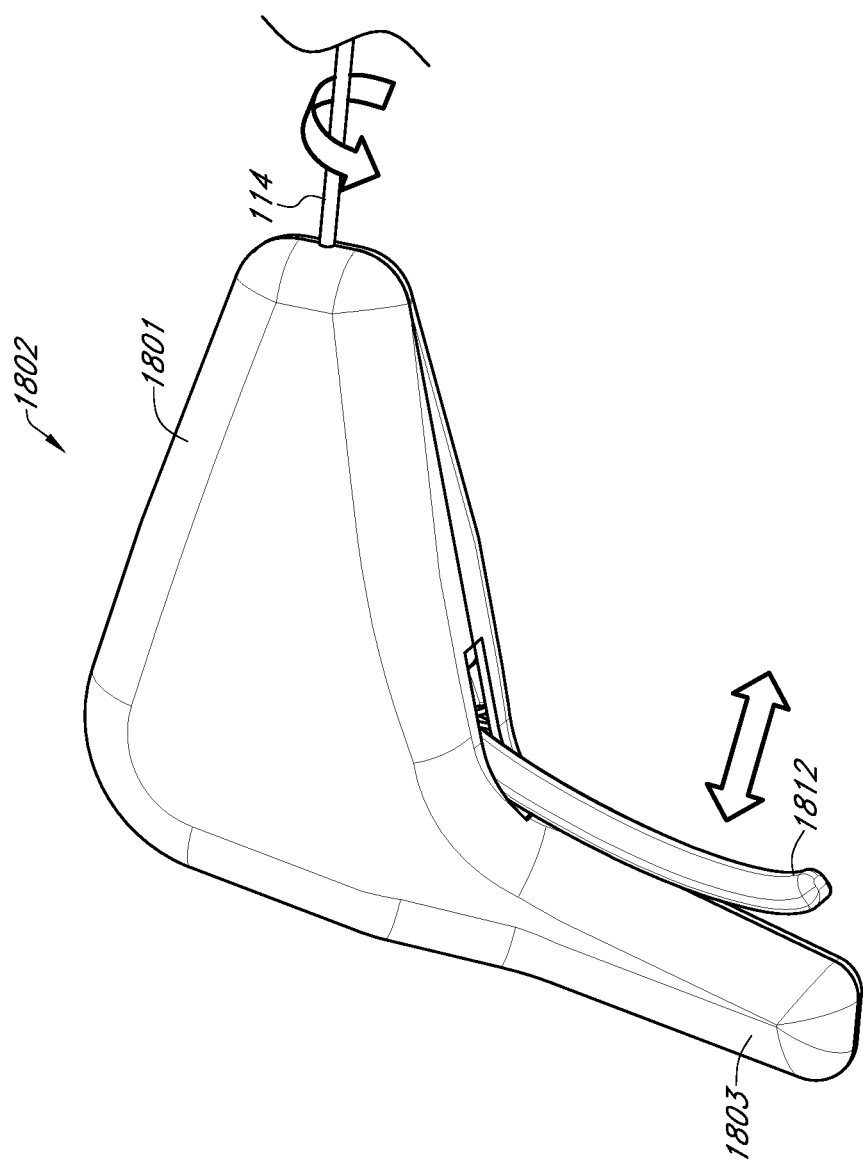
FIGS. 18A and 18B illustrate another embodiment of a handle portion of a polypectomy device.
Figure 18B:
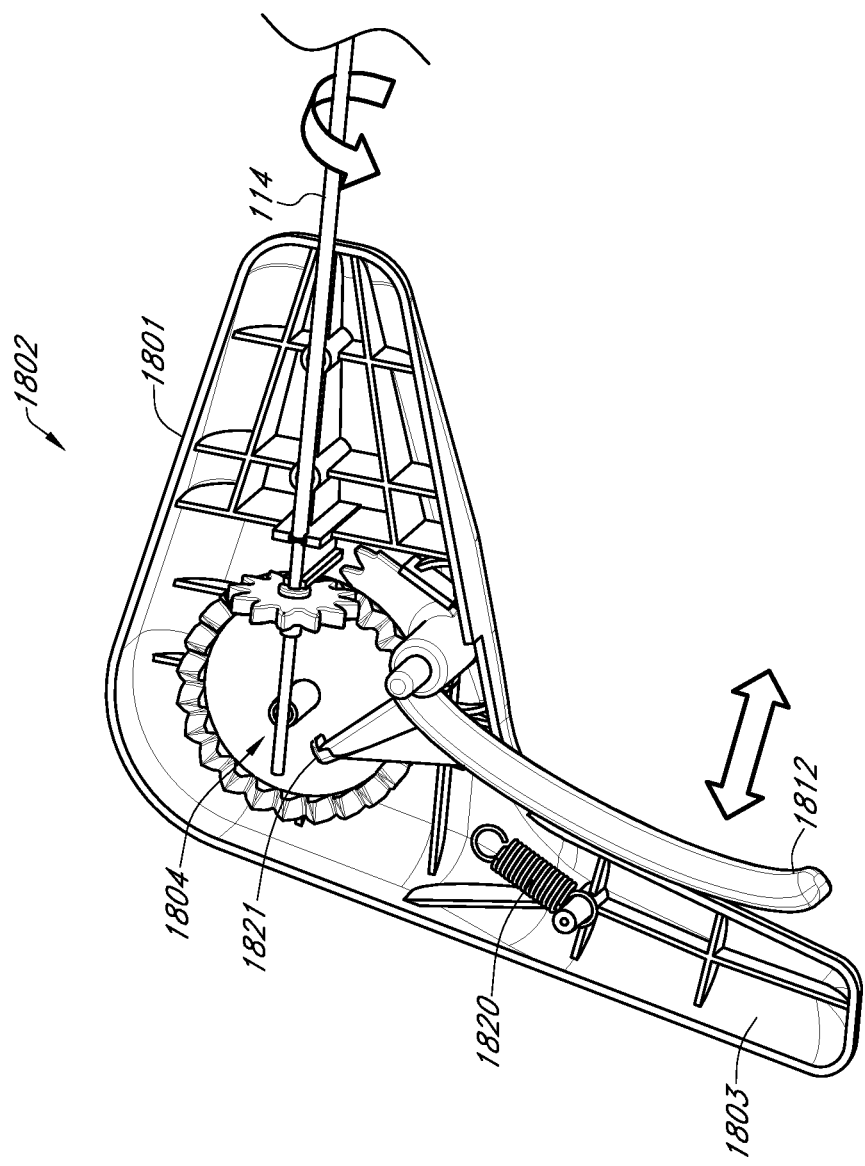

It should be noted that the handle designs of FIGS. 16A-16B and 17A-17B are relatively minimalistic designs that can be used to create a functioning device at relatively low cost. It may be desirable, however, in some embodiments to have an at least somewhat more complicated handle design that may be easier and/or more comfortable to use. For example, the embodiment illustrated in FIGS. 18A and 18B illustrates an example of a handle 1802 that is more ergonomically shaped. The handle 1802 comprises a housing 1801 having two halves (for example, two injection-molded polymer halves that can be joined during assembly). The handle 1802 further comprises a trigger or actuating member 1812 that is biased in an extended position by spring 1820, when spring 1820 is connected to protruding member 1821 of the actuating member 1812 (although FIG. 18B shows spring 1820 disconnected from protruding member 1821). A user, when using the handle 1802, can repeatedly compress the trigger or actuating member 1812, i.e. pull it toward the protruding member 1803, to cause rotation of the inner tubular member 114 with respect to outer tubular member 104 (not shown). In various embodiments, the protruding member 1803 is shaped to be gripped by a human hand and protrudes radially in a direction oriented at a specific angle with respect to an opening (e.g., opening 808 of FIG. 8A, or any other distal end opening disclosed herein). For example, the protruding member 1803 may be oriented at 90 degrees with respect to the opening (similar to as shown in FIG. 1A, where the actuating member 112 is oriented at approximately 90 degrees from the openings 108). In various embodiments, this orientation can be various angles. In some embodiments, the angle is desirably configured such that the protruding member 1803 is pointing in a downward direction when removing polyps in the most common locations. For example, in some embodiments, the orientation is in the range of 90-180 degrees. In this embodiment, the handle 1802 further comprises a geartrain 1804 or plurality of gears 1804 that convert the pivoting motion of the trigger or actuating member 1812 into rotation about a different axis of the inner tubular member 114. Other embodiments may use different geartrain configurations, and other embodiments may use a configuration that converts the rotating motion of the trigger 1812 into translating motion of the inner tubular member instead of rotational motion.

The polypectomy devices disclosed herein are not limited to being used with handles of the specific designs shown in the figures of the present application. One of skill in the art will recognize that various other handle and triggering mechanisms may be used to cause relative motion of one member with respect to another member within the uterus.

Additional Embodiments

In some embodiments, the devices and methods disclosed herein allow for removal of tissue using a rotating motion combined with a blade or cutting edge or surface (sharpened or unsharpened). In some embodiments, the devices and methods disclosed herein allow for removal of tissue using a mechanical biting motion by a set of cutting jaws. In some embodiments, the devices and methods disclosed herein allow for removal of tissue through a stationary jaw and a movable wire. The use of mechanical motion to remove tissue may further allow for the use of a saline solution to distend the uterus, which may reduce the risk of electrolyte imbalance and prevent thermal injury.

Following are descriptions of various additional polypectomy device embodiments, any of which may comprise features that can be combined with any of the other polypectomy devices disclosed herein. For example, the handle and drive mechanism configurations discussed below may be combined with any of the distal end configurations described above or below.

Figure 19A:
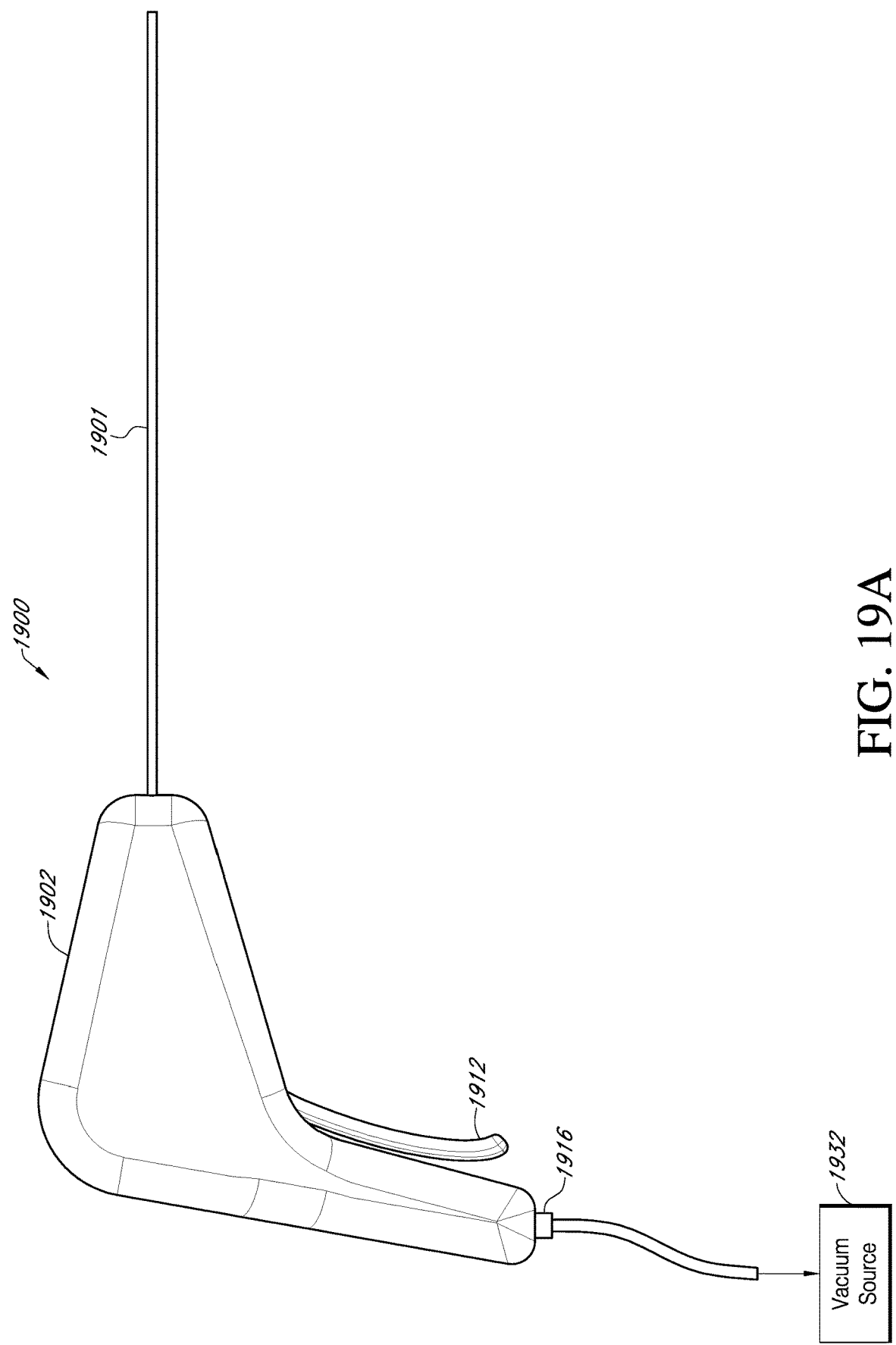

FIGS. 19A-19I illustrate another embodiment of a polypectomy device 1900. FIG. 19A illustrates a side view of the polypectomy device 1900. The device may have a shaft 1901, handle 1902, trigger 1612, a port 1916, and/or a vacuum source 1932. The vacuum source 1932 may be in fluid connection with the handle 1902 or shaft 1901 via the port 1916.

Figure 19B:
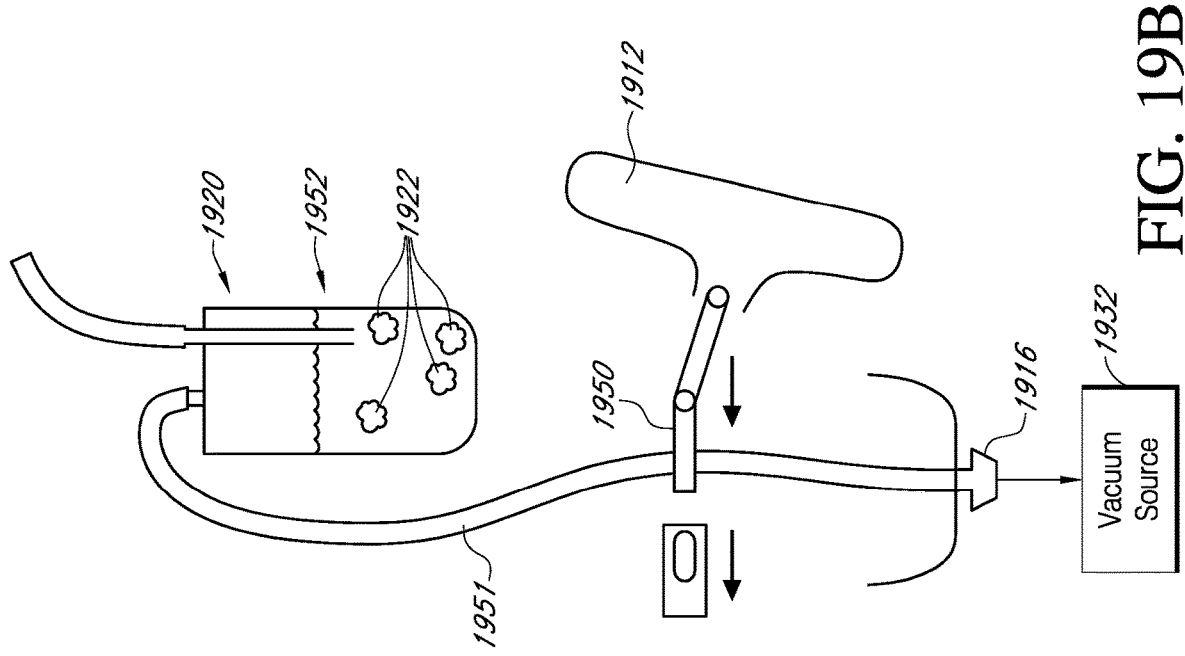
Figure 19C:
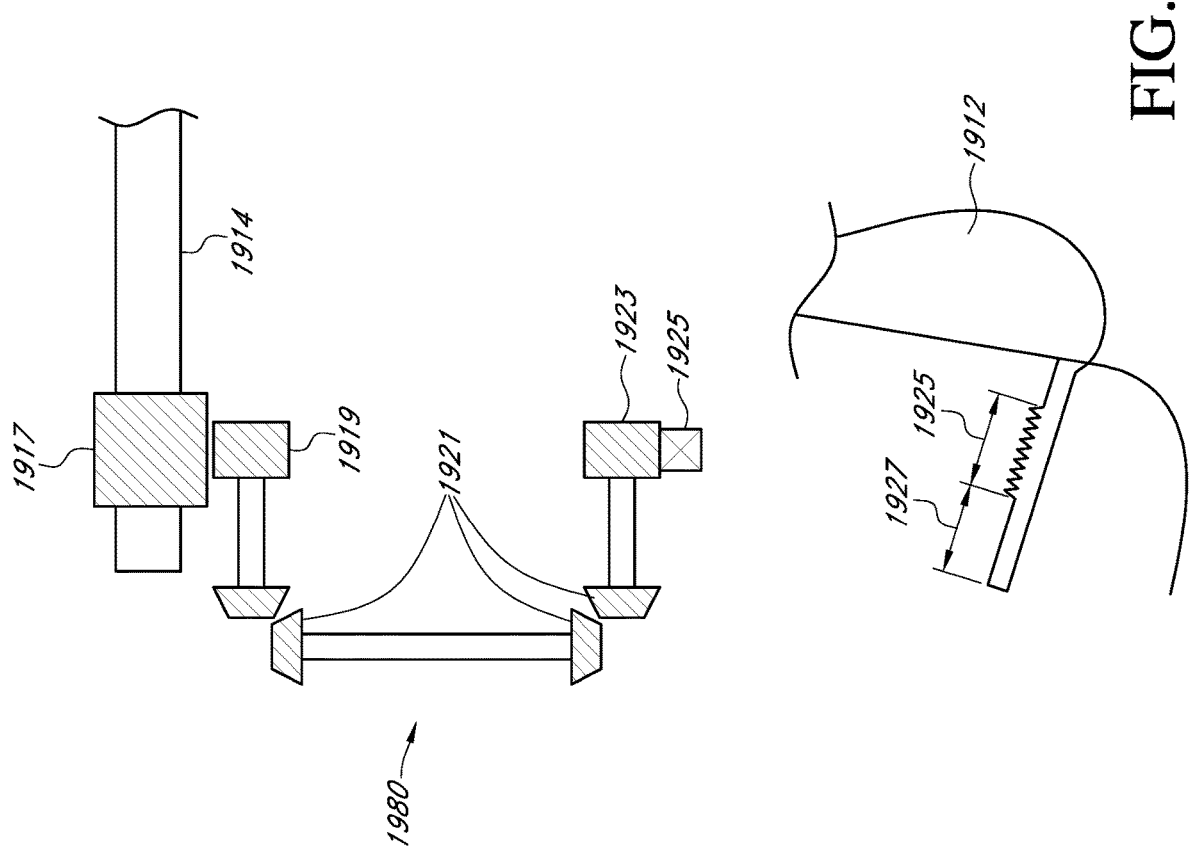
Figure 19D:
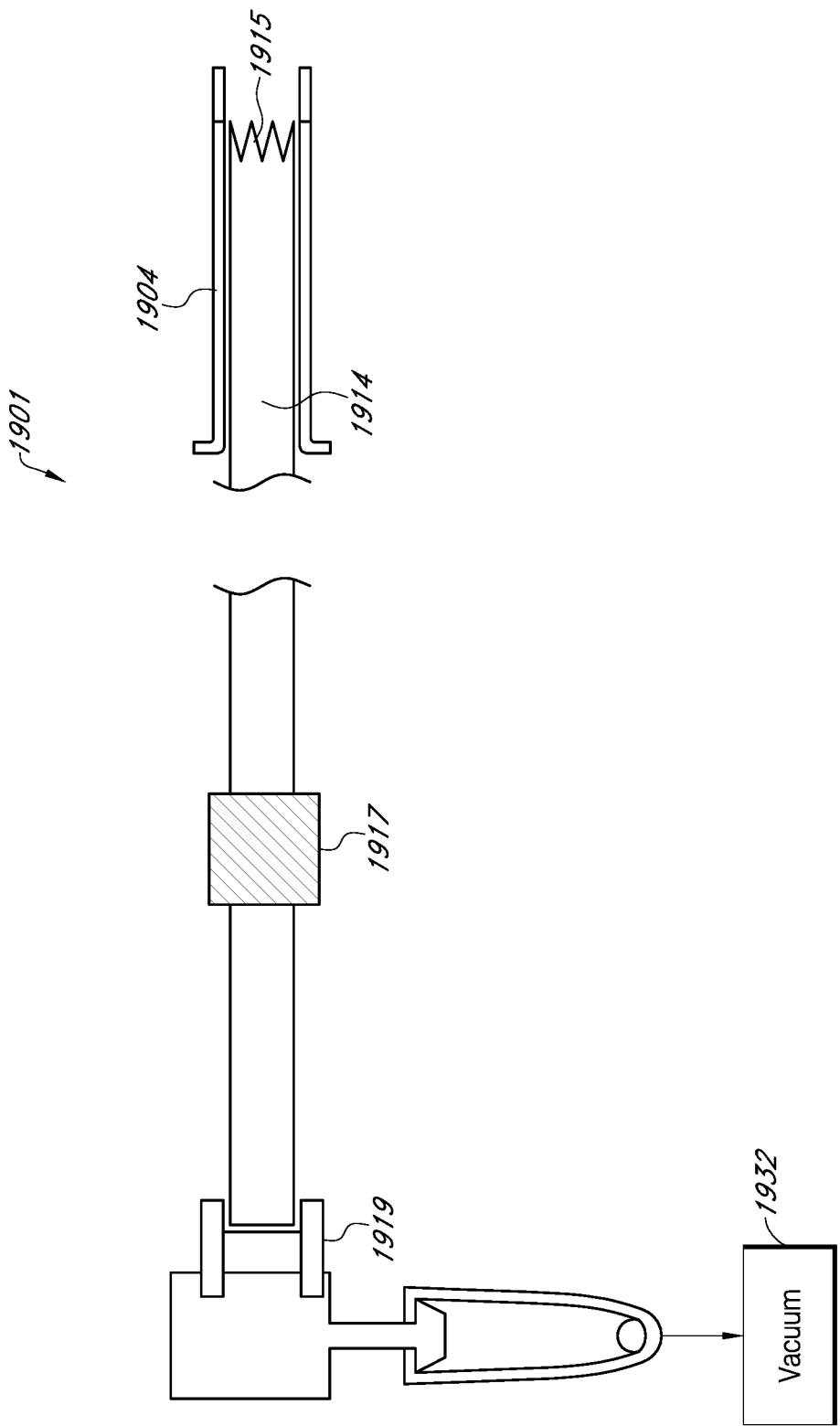
Figure 19E:
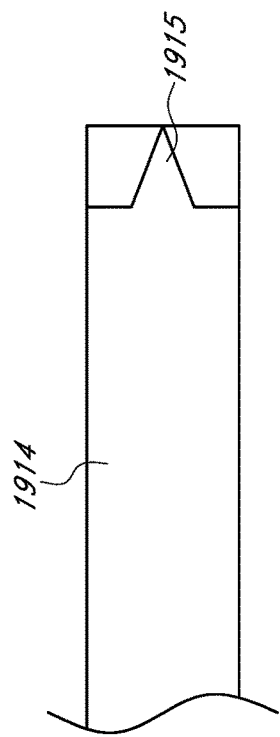
Figure 19F:
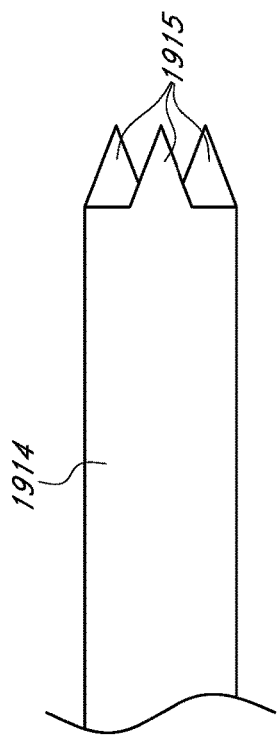
Figure 19G:
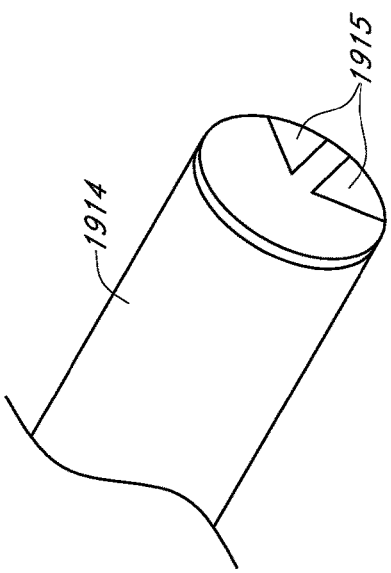

The device 1900 may be a handheld device that mechanically rotates a tube with "blades." The blades may have been formed by bending some cut out sections of a thin walled tube (as shown in FIGS. 19E-19G). The device may be connected to a vacuum source that is used to pull the specimen (such as a polyp) into the distal tip of the device shaft. The vacuum pressure may, in some embodiments, be applied to the shaft only when the trigger has been pressed. The control of the vacuum may be important in maintaining the distention of the uterus. In some embodiments, however, the vacuum may be controlled by another element, such as a foot pedal.

The shaft 1901 may comprise a pair of concentrically aligned tubes (e.g., outer and inner tubular members, similar to as described above with respect to other embodiments). The inner tube may be modified to create a cutting edge to sever the polyp once it has been suctioned into the inner tube (e.g., as shown in FIGS. 19E-19G).

The polypectomy device 1900 would be introduced into the uterus using a scope similar to the scope of FIG. 3 to provide visualization and an inflow port for saline solution needed to distend the uterus.

The trigger 1912 may have multiple positions. The trigger may have three positions. In the first position, suction in the device may be turned off. In the second position, suction in the device may be turned on. In the third position, the blades of the device may be activated. This may be desirable to, among other things, only activate suction just before cutting the polyp, to minimize loss of distention fluid. In some embodiments, however, the suction may be controlled by a foot pedal or other device, instead of being controlled by a multi-stage trigger 1912.

FIG. 19D illustrates the shaft 1901 of the improved polypectomy device 1900 in more detail, according to one embodiment. The shaft 1901 may have an outer tube 1904, an inner tube 1914 with cutting edges 1915, a drive gear 1917, and a bearing 1919. The shaft may be connected to a vacuum source 1932.

There may be a gear 1917 that is welded (or otherwise coupled) to the inner tube 1914 and enables the inner tube 1914 to be rotated by a set of gears in the handle (for example, similar to the gear train 1804 of FIG. 18B). The rotation of the inner tube 1914 may allow for the cutting edges 1915 to cut tissue. In some embodiments, polyps may be transected using suction or vacuum alone. The cutting efficiency of the blades may not be very high. This may be intentional, such as by not sharpening the blades, which can increase safety and reduce manufacturing costs. The torque and rotational speed of the shaft rotation may not be very high, because, for example, the inner tube 1914 may be rotated by a human hand manipulating the trigger 1912, as opposed to a motor spinning the tube 1914.

In this and various other embodiments disclosed herein, the speed of reciprocation (e.g., cutter translating and/or rotating back and forth) can be, for example, approximately, exactly, no greater than, or no less than, 0.5, 1, 2, 3, 4, or 5 cycles per second. It may be desirable in some embodiments to have a relatively low speed (e.g., cycles per second), to enable manual positioning of the opening for each cut.

FIGS. 19E-19G illustrate an example process for forming the cutting edges 1915 of the improved polypectomy device in more detail, according to one embodiment. The cutting edges 1915 may be formed in the inner tube 1914 of the device.

The cutting edges 1915 may be formed, for example, by cutting and trimming the tip of a hypotube to enable points to be formed. The points may comprise teeth, which may be created by removing adjacent material (e.g., as shown in FIG. 19E). Once the points are formed (e.g., as shown in FIG. 19F), they may be bent or folded back inside the tip of the tube to form one or more reverse facing cutting edges (e.g., as shown in FIG. 19G).

FIGS. 19H and 19I illustrate how the cutting edges 1915 of the improved polypectomy device 1900 may remove tissue, according to one embodiment. A vacuum may pull the polyp or tissue specimen 1922 into the tube 1914, through the end of the tube with cutting edges 1915. While the vacuum continues to be applied, spinning the tube 1914 allows the cutting edges 1915 to shear the polyp or specimen 1922, disconnecting it from the uterine wall or other body tissue 1926. Afterwards, the vacuum may further prevent the specimen from falling out of the tube.

FIG. 19B illustrates how tissue capture may be performed by the improved polypectomy device 1900, according to one embodiment. In the embodiment shown in FIG. 19B, the device may be able to capture the tissue that is cut off and removed. The device may have a tissue capture chamber 1920 in the handle 1902 that would enable the physician to send the specimen 1922 to the pathology lab with no need for an auxiliary tissue trap. The capture chamber 1920 may eliminate the risk of biohazardous material handling.

The trigger 1912 may have a member 1950 attached that translates through a slot in the handle to provide a means for controlling the vacuum. For example, gate 1950 may selectively block off or open up tube 1951, to selectively enable vacuum to be applied to tube 1951, and thus the tissue capture chamber 1920. It may be important to limit the vacuum duration as the pressure will empty the uterus of its distention fluid and force the use of larger volumes of the fluid. It may be ideal if the total volume of distention fluid can be <1 liter to minimize safety concerns and efforts to exchange multiple fluid bags.

The tissue capture chamber 1920 may be in fluid communication with the cutting tube 1914. The tissue capture chamber 1920 may be removable, such that the device may operate without the tissue capture chamber 1920. The tissue capture chamber 1920 may have a screen 1952 disposed within it. The tissue capture chamber 1920 may contain a fluid for holding any collected specimens. The tissue capture chamber 1920 may be in fluid connection to a vacuum source, such as by means of a hose, tube, or vacuum line 1951.

The vacuum line may pass through a gate 1950. The gate 1950 may have an open configuration and a closed configuration. When the gate 1950 is closed, the flow path of the vacuum line 1951 may be closed. When the gate 1950 is open, the flow path of the vacuum line 1951 may be open.

When the trigger 1912 of the device is pressed, the gate 1950 may slide across the vacuum line 1951 into its open configuration and the flow path of the vacuum line may be opened.

FIG. 19C illustrates how cutting tube 1914 rotation may be performed by the improved polypectomy device 1900, according to one embodiment. In the embodiment of FIG. 19C, there is a drive mechanism 1980 that links the translation of the trigger 1912 to the rotation of the cutting tube 1914. The inner tube 1914 may be connected to a drive gear 1917, and the drive gear 1917 may be in mechanical communication with a second spur gear 1919. The second spur gear 1919 may be in mechanical communication with a set of bevel gears 1921. The set of bevel gears 1921 may be in mechanical communication with a first spur gear 1923. The trigger may have a rack 1925 that would drive a pinion gear (or first spur gear) 1923 and a set of bevel gears 1921 to translate the motion and energy.

As the trigger 1912 is pressed, the rack 1925 may engage the first spur gear 1923, creating a rotation of the set of bevel gears 1921 and the second spur gear 1919. The rotation of the second spur gear 1919 would rotate the drive gear 1917, causing the rotation of the cutting tube 1914. In some embodiments, the trigger 1912 comprises a dead zone 1927 that, for example, enables the vacuum suction to start (e.g., via movement of gate 1950 of FIG. 19B) prior to starting rotation of the inner tube 1914.

Figure 20A:
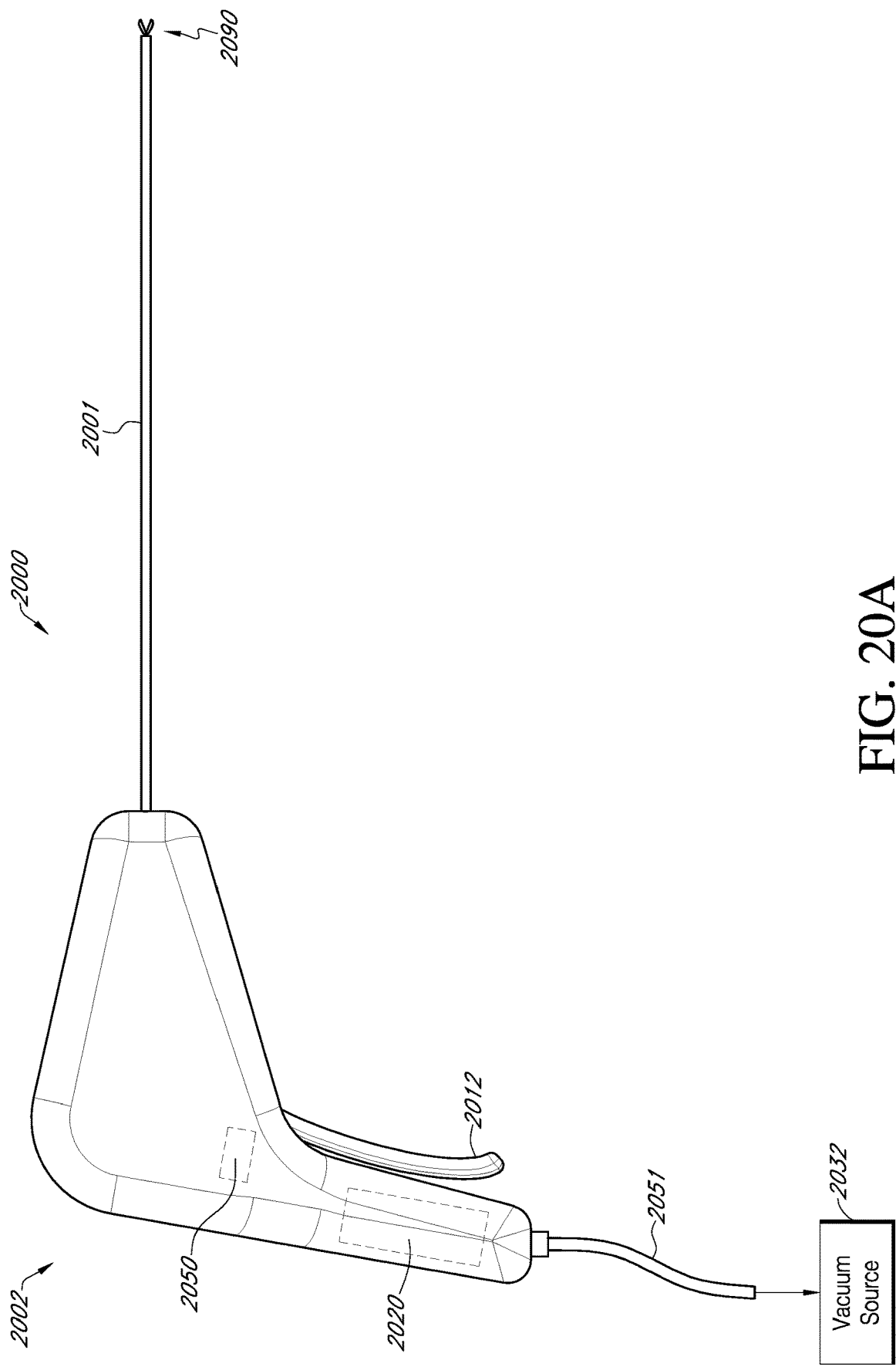
FIGS. 20A-20C illustrate another embodiment of a polypectomy device.
Figure 20B:
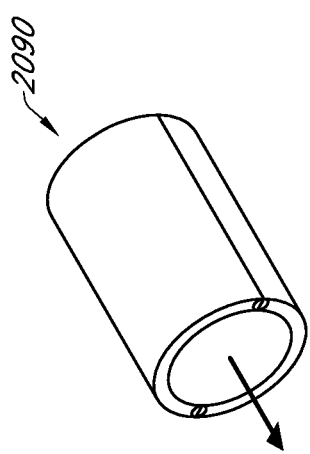
Figure 20C:
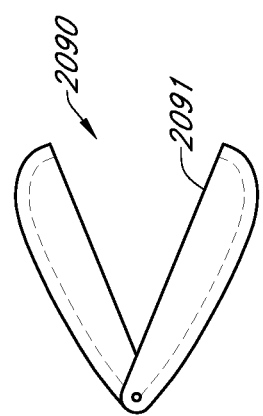

FIGS. 20A-20C illustrate another embodiment of an improved polypectomy device 2000. The device 2000 shown may be a handheld device that mechanically opens and closes jaws 2090 to take bites of the polyp, rather than cutting the polyp through the rotation and/or translation of a cutting edge. There may be a shaft 2001 with cutting jaws 2090, a handle 2002, a trigger 2012, a removable tissue chamber 2020, a vacuum gate 2050, and/or a vacuum line 2051 connecting a vacuum source 2032. The removable tissue chamber 2020 and vacuum gate 2050 may be within the handle 2002, along with portions of the vacuum line 2051, and may be similar to, for example, tissue chamber 1920 and vacuum gate 1950 of FIG. 19B. There may be a port that connects portions of the vacuum line to the handle. The handle may include a vacuum control gate concept similar to the one shown in FIG. 19B.

The cutting jaws 2090 may have an open tissue path at their proximal attachment point where vacuum is applied to remove the specimen from the jaws. A "cutting edge" 2091 may formed at the tip of one jaw (or both jaws) by utilizing a thin wall at the jaw tip. The cutting jaws 2090 may have an open configuration (e.g., FIG. 20C) and a closed configuration (e.g., FIG. 20B). In the open configuration, the cutting jaws 2090 may be positioned around a polyp or tissue specimen. In the closed configuration, the cutting jaws 2090 may move towards each other so that the cutting edge 2091 may cut off the polyp.

The trigger 2012 may have multiple positions. The trigger 2012 may have two positions. In the first position, the jaws 2090 may be in the open configuration and the vacuum turned off. In the second position, the jaws 2090 may move to their closed configuration and the vacuum turned on. The trigger 2012 may comprise a dead zone, such that the vacuum is not enabled at the same time as when the jaws 2090 begin moving.

Figure 21:
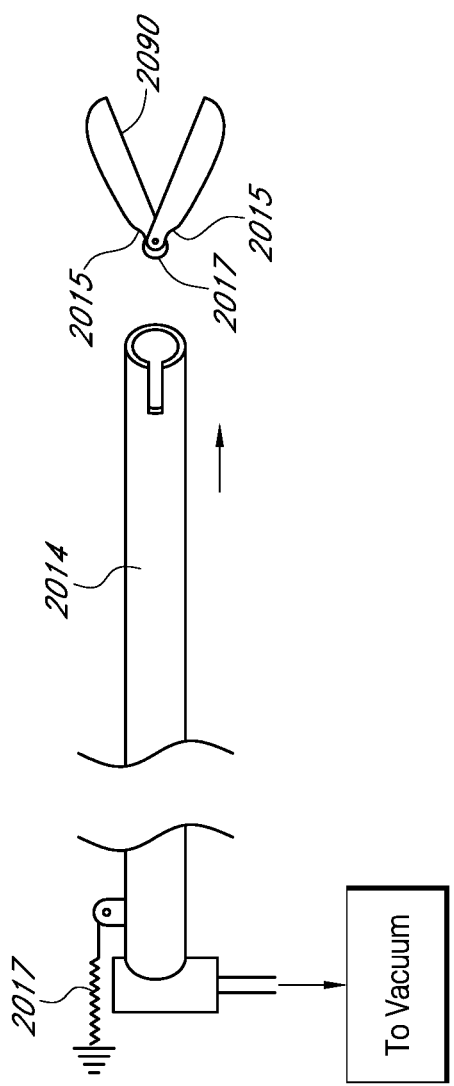
FIG. 21 illustrates a portion of another embodiment of a polypectomy device.

FIG. 21 illustrates how the cutting jaws 2090 may be opened and closed, according to one embodiment. The jaws 2090 may be closed by use of a translating tube 2014 that slidably engages a cam surface 2015 on the jaw to force it to close. The trigger may be used to slide the translating tube 2014. A spring or elastic member 2017 may be used to return the jaws 2090 to an open position once cutting is completed. A coil spring 2017 may also keep the jaws 2090 open until the translating tube 2014 cams them closed.

Figure 22A:
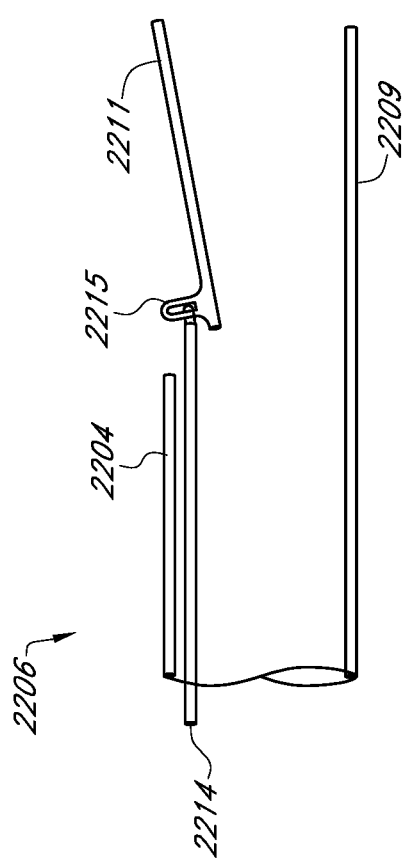
FIGS. 22A-22C illustrate details of a distal tip portion of another embodiment of a polypectomy device.
Figure 22C:
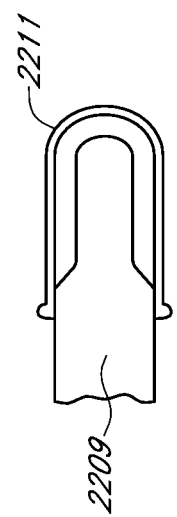
Figure 22B:
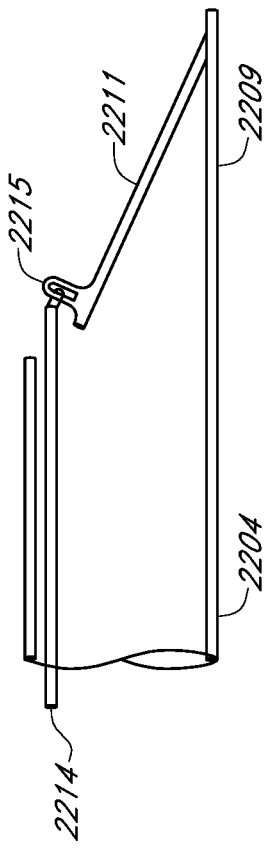

FIGS. 22A-22C illustrate how a distal end 2206 of an improved polypectomy device may use a polyp slicer, according to one embodiment. The device may be a handheld device that mechanically opens and closes to take bites of the polyp. The cutting mechanism may involve a stationary lower jaw 2209, such as by forming the outer tube 2204, and a movable wire 2211. Thus, the cutting jaws 2090 shown in FIGS. 20A-20C are not used, although the handle and shafts may be identical or similar.

The lower cutting jaw has been replaced by a fixed plane 2209 made by sculpting the outer tube 2204. The upper jaw has been replaced by a thin wire 2211 strong enough to cut the tissue, but thin enough to slice the tissue. The wire 2211 would desirably be set to bypass the lower jaw 2209 to create a shearing action similar to the blades of a scissor. The formed wire upper jaw 2211 may be closed by use of a translating tube 2214 that slidably engages a surface 2215 on the jaw to force it to close. A spring (similar to spring 2017 of FIG. 21) may be used to return the jaw 2211 to an open position once cutting is completed.

Additional/Alternative Features

Following are various options/features that may be included in any of the various embodiments of polypectomy devices disclosed herein. In some embodiments, the cutting tube may be a thin-walled tube. In some embodiments, the distal end of the cutting tube may not be bulbous-shaped. In some embodiments, the device may be configured to approach polyp tissue straight on (e.g., with an opening in a distal end). In some embodiments, the distal end of the cutting tube may be open for receiving polyp tissue. In some embodiments, a side window may or may not be present in the cutting tube. In some embodiments, the inner tube and the outer tube in the shaft may be concentrically aligned tubes, both of which have open distal ends. In some embodiments, the blades or cutting edges (which may or may not be sharpened) are bent inwards (towards the proximal end of the cutting tube) back into the device, such that any engaged tissue cannot escape or fall out of the device once the tissue is pulled into the tube.

In some embodiments, the vacuum function of the device may be used alone to sever and capture polyps. The vacuum may not need to be paired with another cutting mechanism. In some embodiments, the device may not need a mechanical action to sever and retrieve polyp tissue, with some examples of mechanical action including using a lasso or wire loop, or rotating a tube with blades in it. In some embodiments, the device may keep the uterus distended or maximize uterus distention in the course of removing polyps. In some embodiments, the device may help conserve distention fluid over the course of a polypectomy. In some embodiments, the device may have a dual trigger design for engaging a mechanism used to mechanically cut the polyp and for varying the suction power of the vacuum source. In some embodiments, the device has a single trigger that may control both the functions of cutting (such as the rotation of a tube), and the suction (such as varying the power of the vacuum source). In some embodiments, the device has a single trigger that may be a multi-function trigger.

In some embodiments, the device may have a thin-walled cutting tube with a non-bulbous tip, and the tip may be open at the distal end for receiving tissue. The cutting tube may not have any openings in the side wall. In some embodiments, the device may have cutting jaws that can simultaneously cut, envelope, and retrieve polyp tissue. The retrieving of the polyp tissue may be aided by suction. In some embodiments, the device may use gear mechanisms to rotate the device's shaft or cutting element.

Polypectomy Methods

Figure 23:
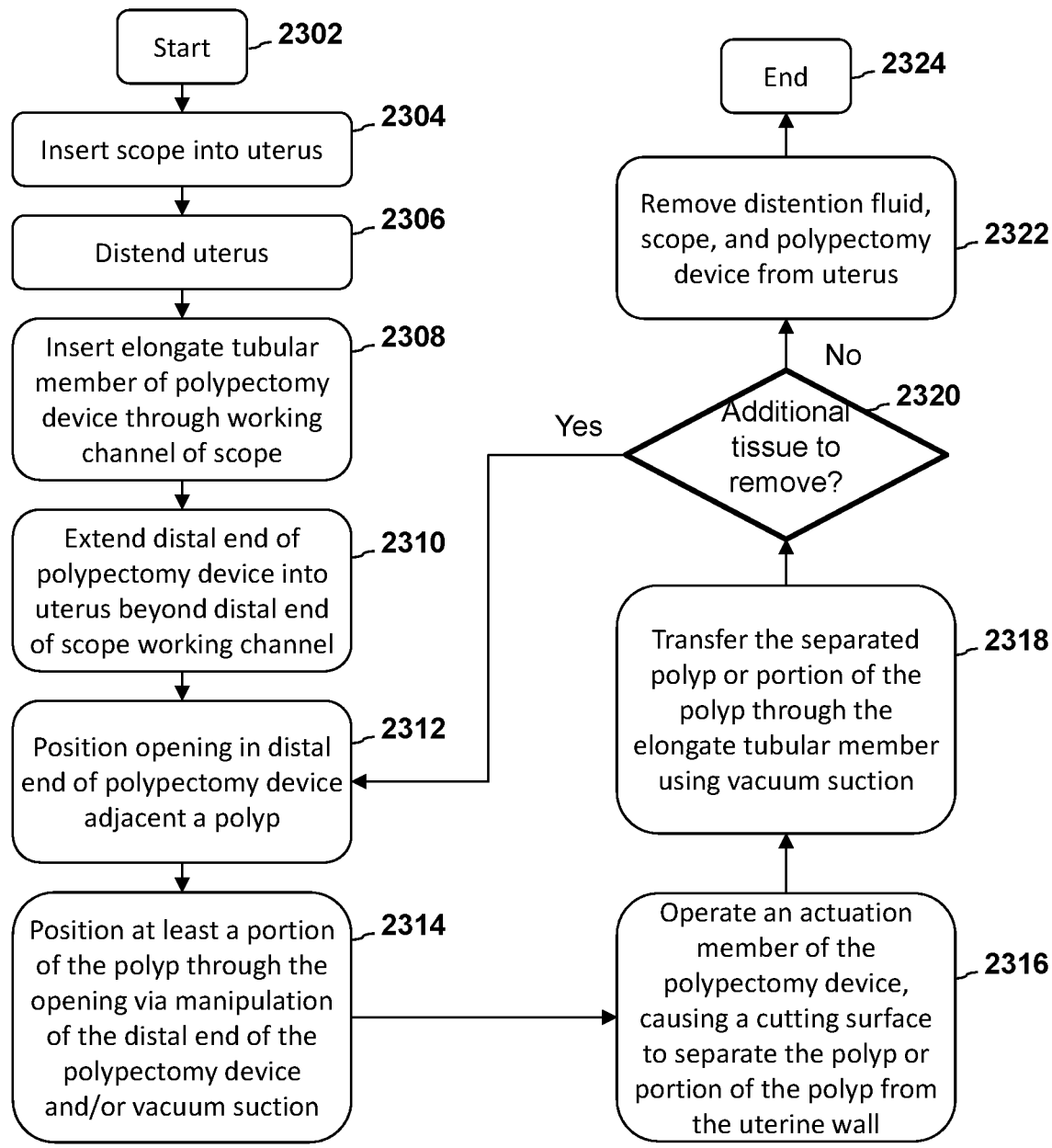
FIG. 23 illustrates an embodiment of a method of performing a polypectomy.

Various methods described herein may be used to remove polyps or portions of polyps using polypectomy devices disclosed herein. FIG. 23 illustrates one example embodiment of such a process; however, the process flow illustrated in FIG. 23 is not the only process that can be used to remove polyps with the devices disclosed herein.

The process flow begins at block 2302. At block 2304, a doctor inserts a scope into the uterus, such as the scope 300 shown in FIGS. 3 and 4. At block 2306, the doctor distends the patient's uterus. For example, the doctor may cause distention fluid to pass through the scope and into the uterus. At block 2308, the doctor inserts an elongate tubular member of a polypectomy device through a working channel of the scope. For example, outer tubular member 104 illustrated in FIG. 4 may be inserted through the working channel of the scope of 300. At block 2310, upon further insertion of the elongate tubular member into the working channel of the scope, the doctor causes the distal end of the polypectomy device to extend into the uterus beyond the distal end of the scope working channel. An example of this can be seen in FIG. 4, where the distal end 106 is protruding into the uterus 420.

At block 2312, the doctor positions an opening in the distal end of the polypectomy device adjacent a polyp. For example, the doctor may manipulate the handle of the polypectomy device to cause an opening in the distal end to be positioned adjacent a polyp for removal. At block 2314, the doctor causes at least a portion of the polyp to be positioned through the opening. This may be accomplished via manipulation of the distal end of the polypectomy device and/or activating a vacuum suction that causes a portion of the polyp to be aspirated through the hole.

At block 2316, the doctor operates an actuation member, such as a trigger, button, and/or the like, causing a cutting surface to separate the polyp or a portion of the polyp from the uterine wall. For example, the doctor may manipulate a trigger that causes an inner tubular member to translate and/or rotate with respect to an outer tubular member, and causes a cutting surface or cutting surfaces to separate the polyp or portion of the polyp from the uterine wall.

At block 2318, the separated polyp or portion of the polyp is cause to be transferred through the elongate tubular member using vacuum suction. For example, the doctor may manually activate the vacuum suction, such as by using a foot pedal or other activating member, and/or the vacuum suction may be automatically activated using a multistage trigger, and/or the like. This vacuum may cause the removed polyp or portion of the polyp to be aspirated through the inner or outer tubular members and aspirated into a collection system.

At block 2320, the process flow varies depending on whether additional tissue needs to be removed, such as additional polyps or an additional portion of the same polyp. If additional tissue needs to be removed, the process flow proceeds back to block 2312 and proceeds as described above. If no additional tissue needs to be removed, the process flow proceeds to block 2322. At block 2322, distention fluid is removed, such as through the scope, and the polypectomy device and scope are removed from the uterus. The process flow ends at block 2324.

Additional Embodiments of Polypectomy Devices

Figure 25A:
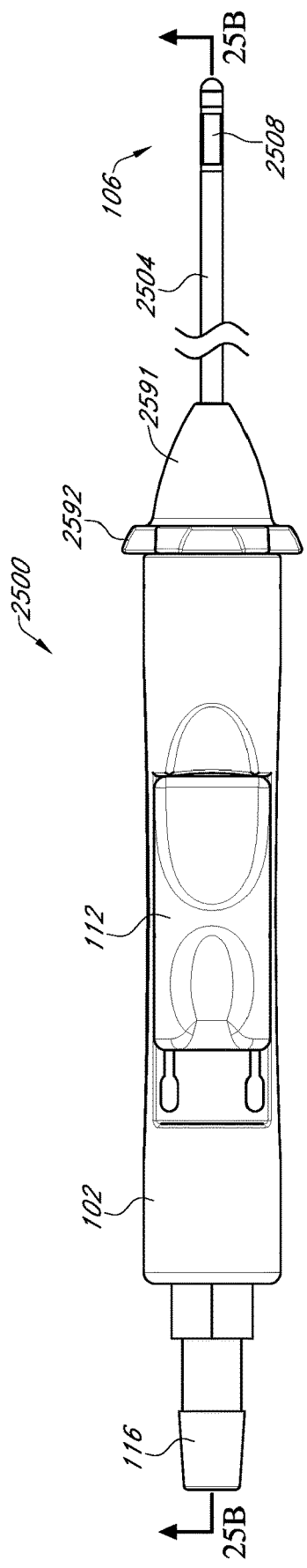
FIGS. 25A-25U illustrate another embodiment of a polypectomy device.
Figure 25B:
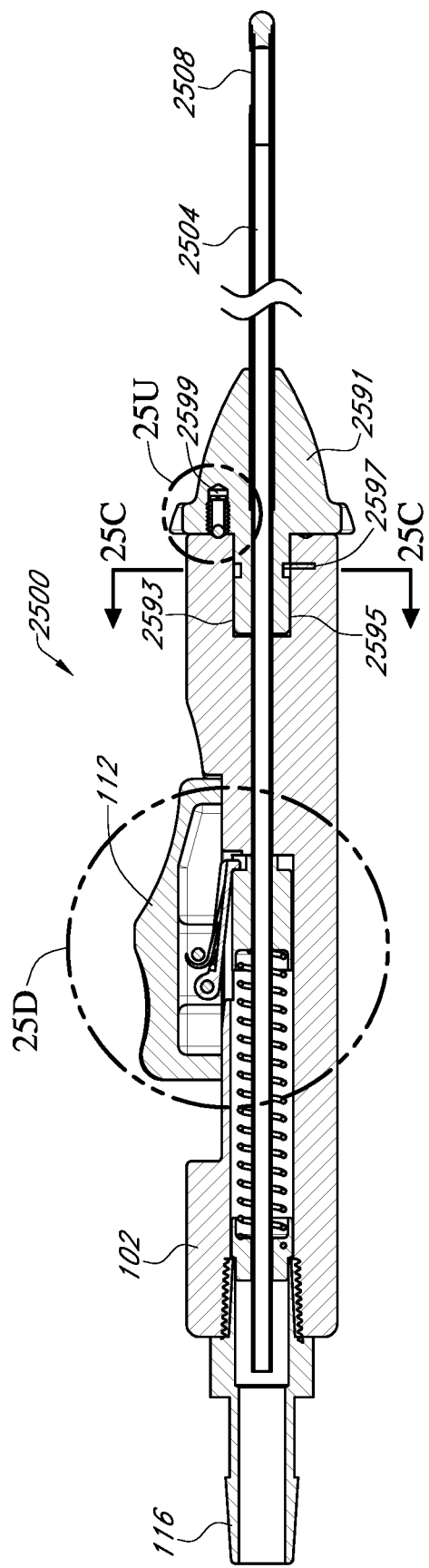
Figure 25E:
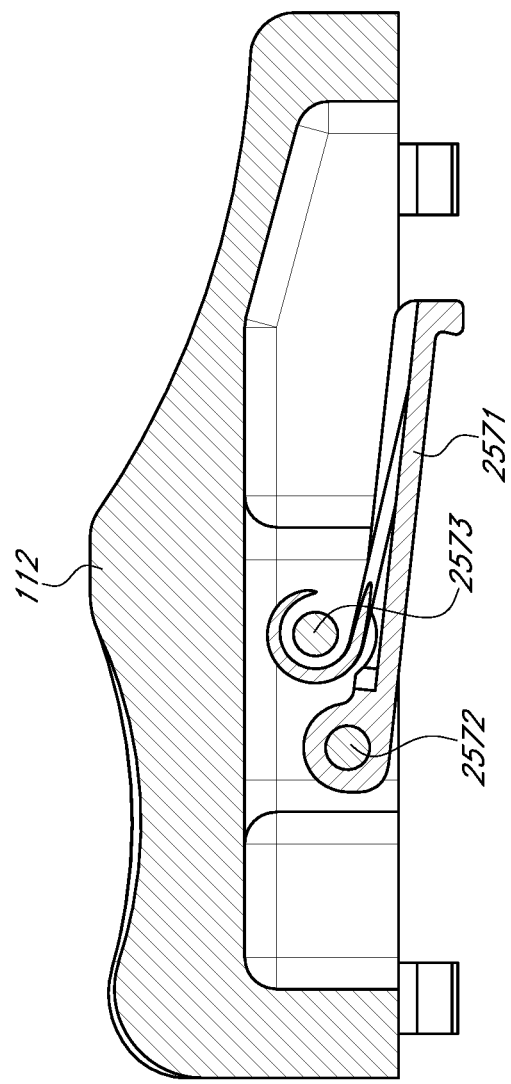
Figure 25F:
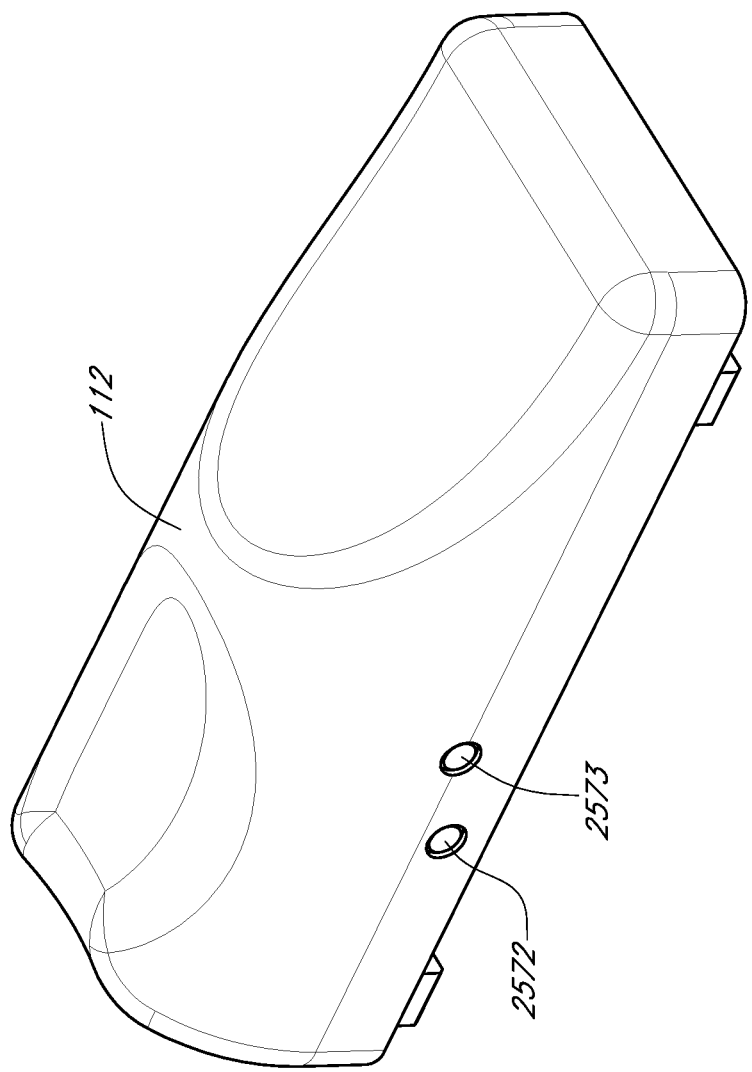
Figure 25G:
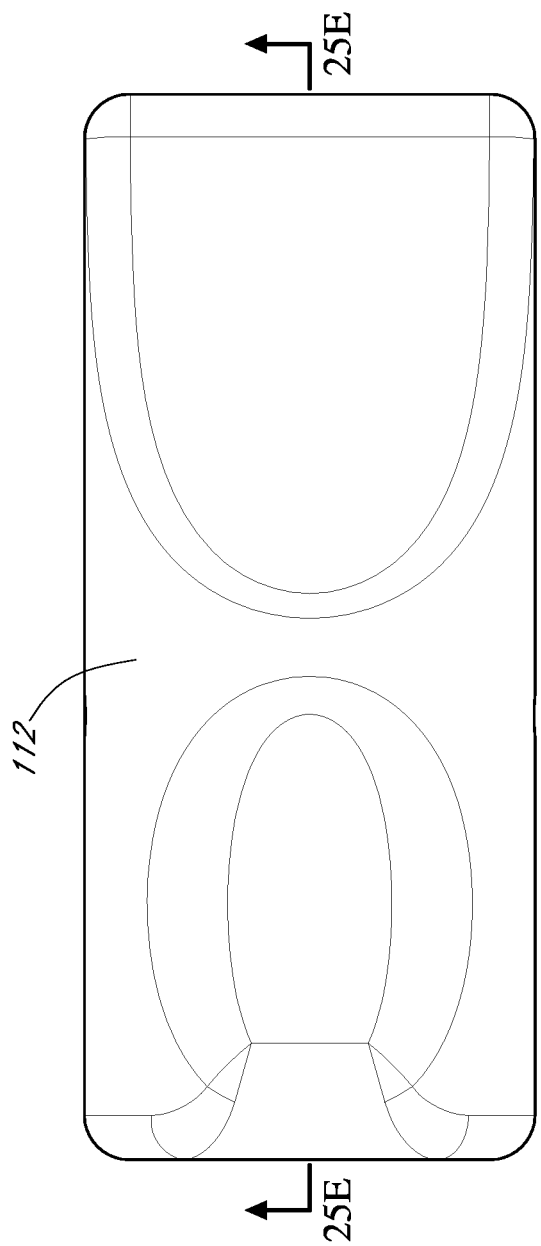
Figure 25J:
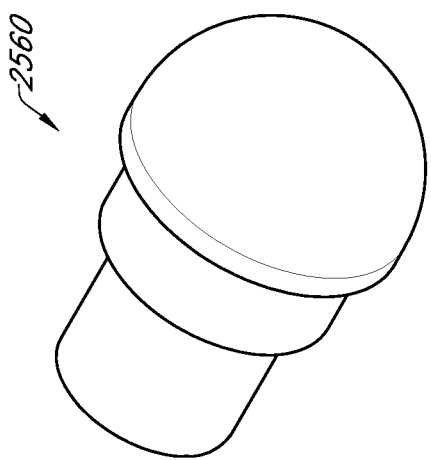
Figure 25L:
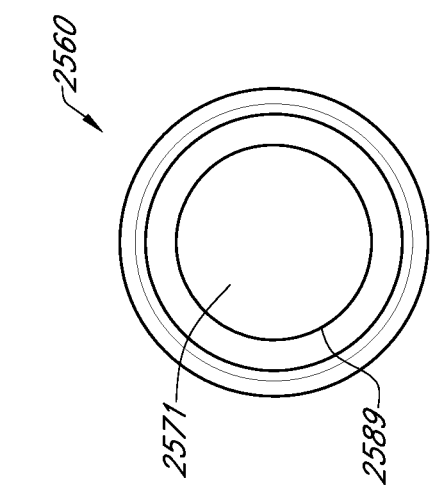
Figure 25K:
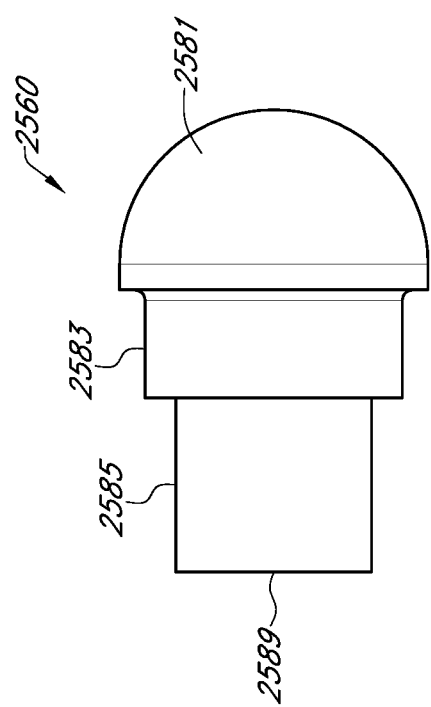
Figure 25O:
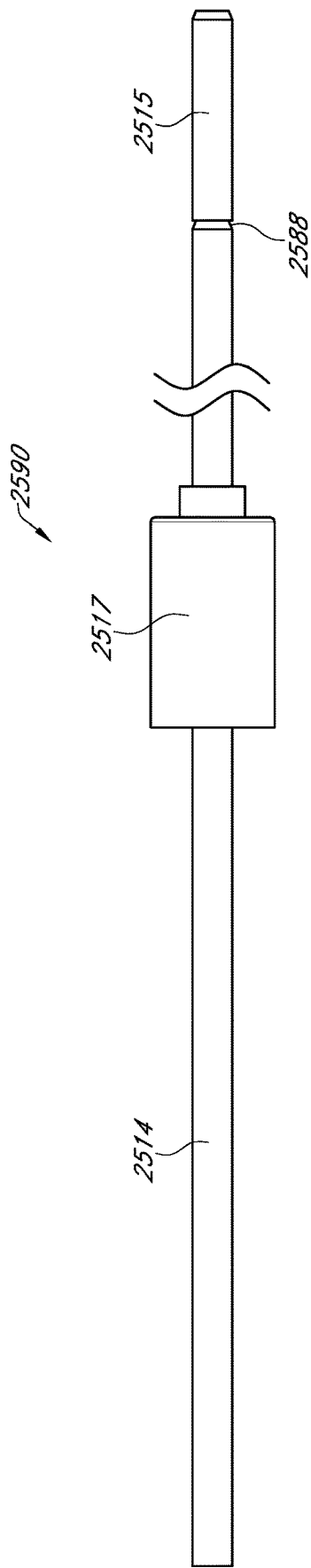
Figure 25Q:
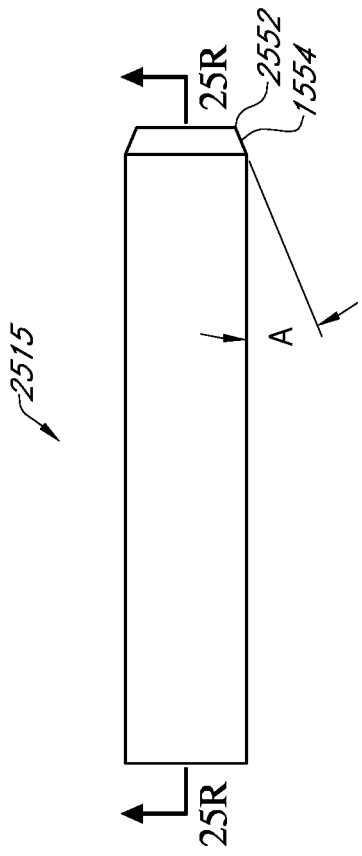
Figure 25R:
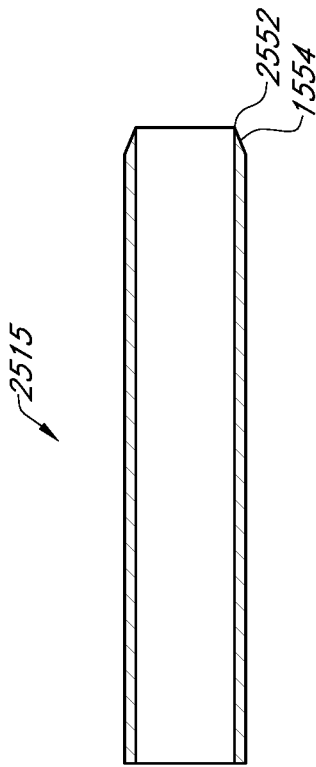
Figure 25P:
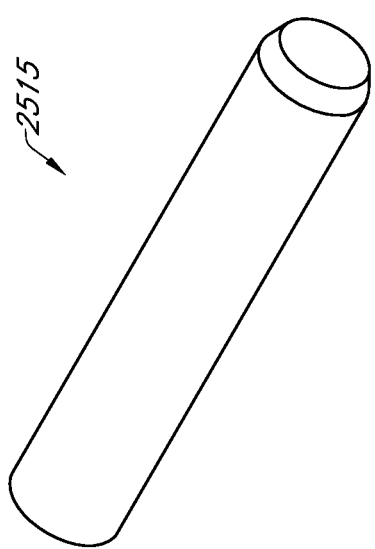
Figure 25U:
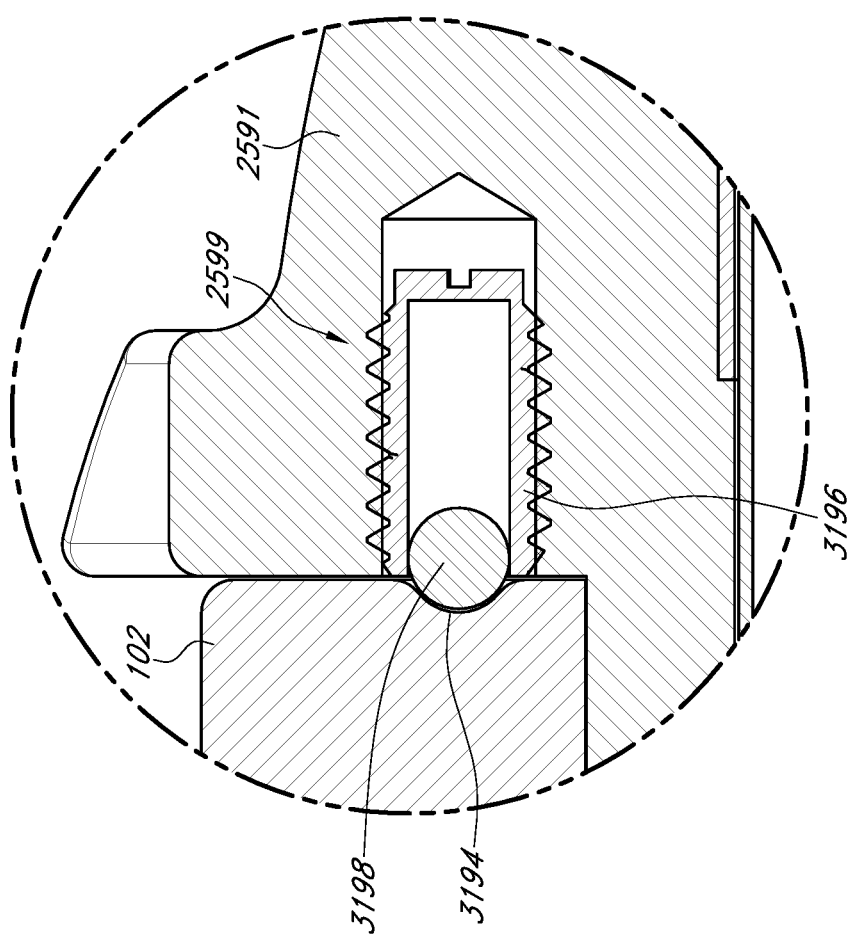
Figure 26A:
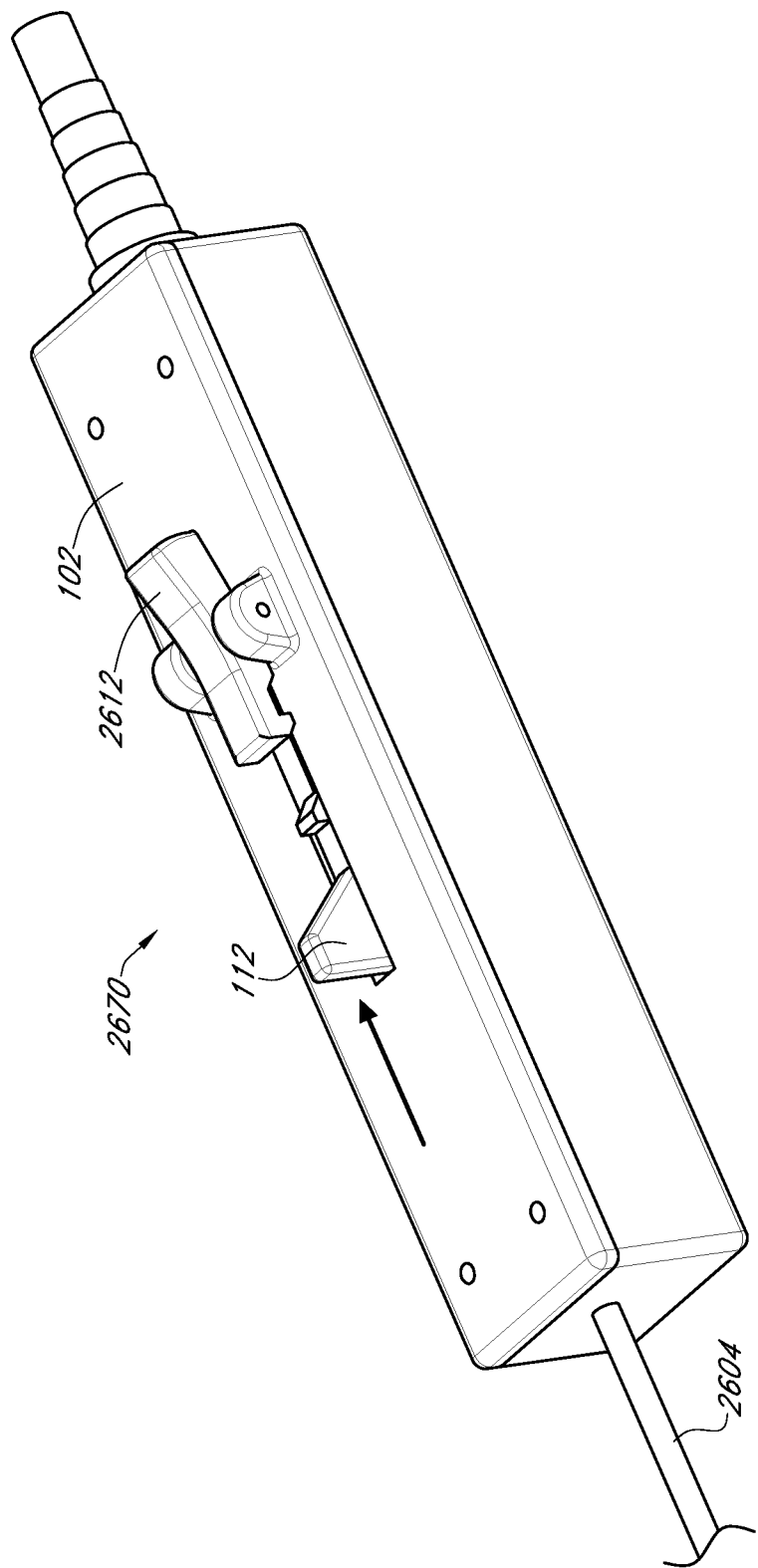
Figure 26B:
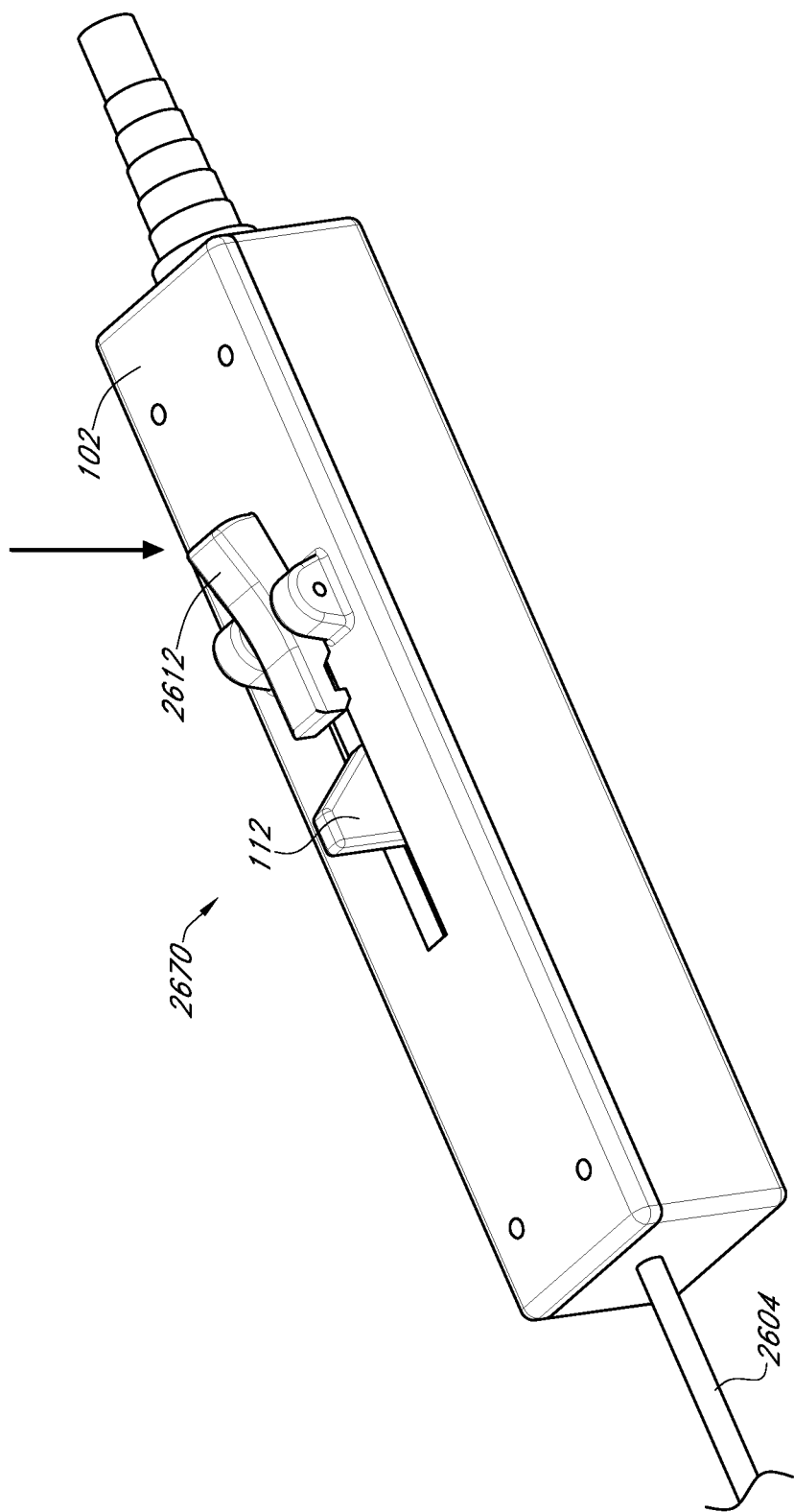
Figure 26C:
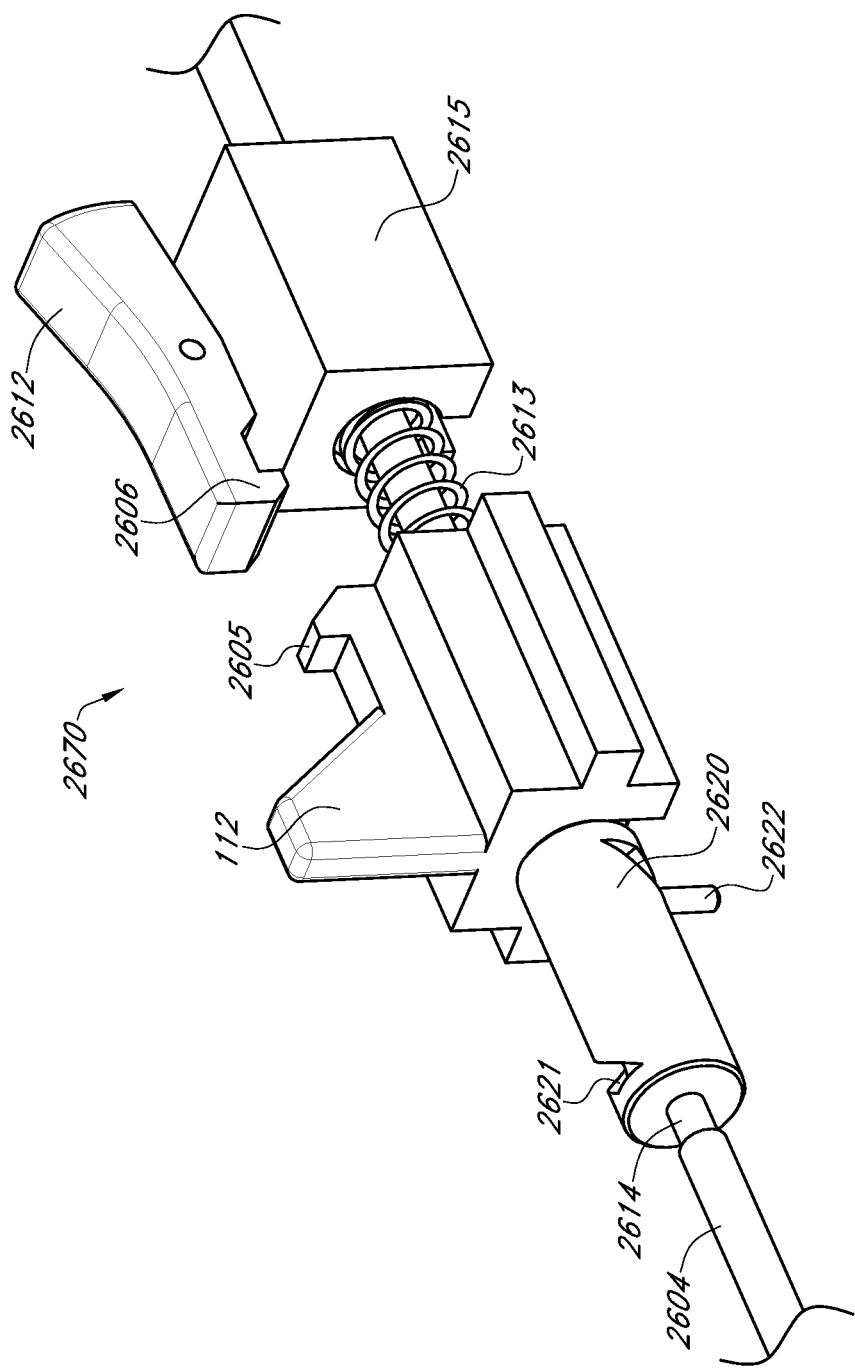
Figure 26E:
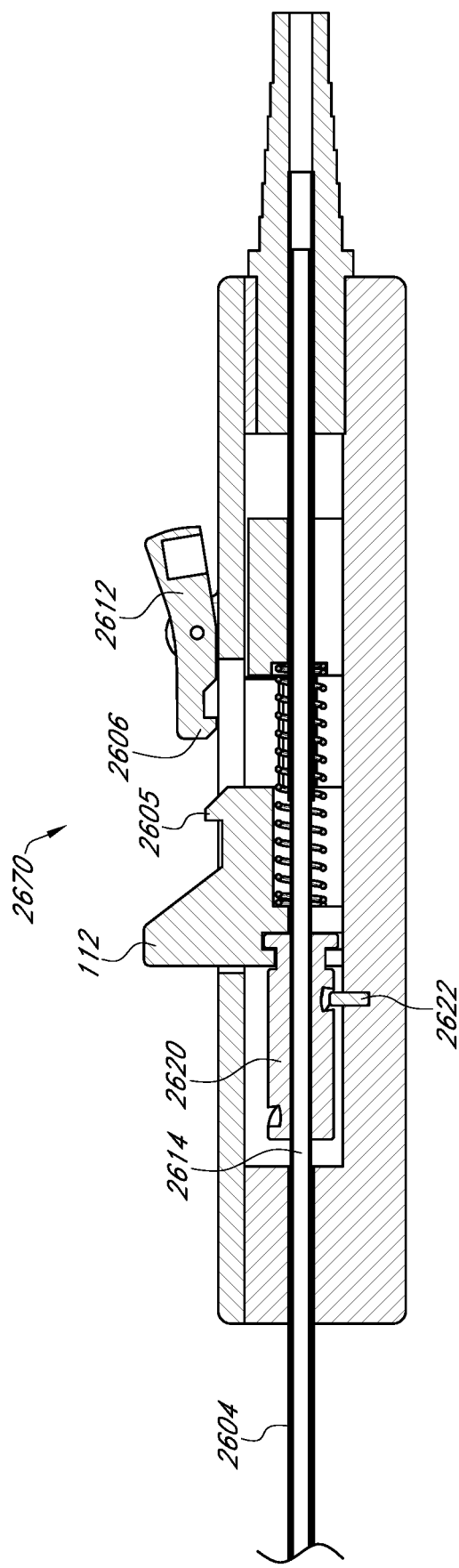
Figure 26F:
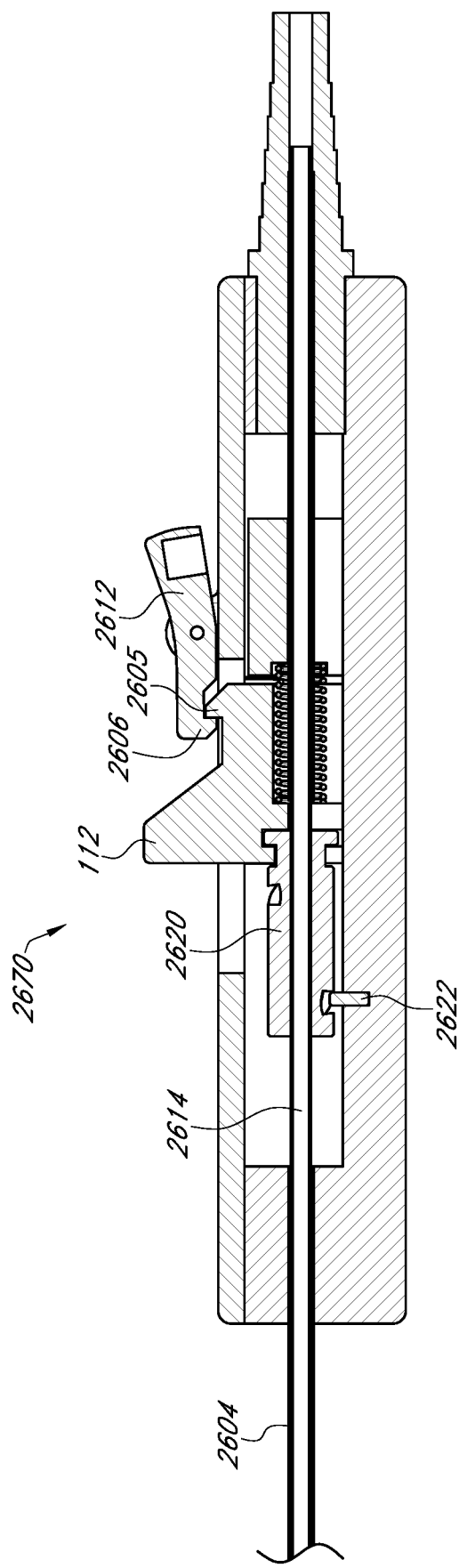

FIGS. 25A-25U illustrate another example embodiment of a polypectomy device 2500. FIGS. 25A and 25B illustrate side and cross-sectional views, respectively, of the entire assembly. FIGS. 25C and 25D illustrate detail cross-sectional views. FIGS. 25E-25G illustrate various views of an actuating member or trigger of the assembly. FIGS. 25H and 25I illustrate an outer tubular member assembly 2504. FIGS. 25J through 25L illustrate a cutting block 2560, and FIGS. 25M and 25N illustrate an outer tubular member 2505, which can be coupled to the cutting block 2560 to form the outer tubular member assembly 2504. FIG. 25O illustrates an inner tubular member assembly 2590 that comprises an inner tubular member 2514, a tubular cutter 2515, and a guide member 2517. FIGS. 25P through 25R illustrate additional details of the tubular cutter 2515. With reference to FIG. 25O, the tubular cutter 2515 may be attached to the inner tubular member 2514 at junction 2588. In this figure, and also some of the other figures, such as FIGS. 25S and 25T, a chamfer at the distal end of the inner tubular member 2514 (e.g., at junction 2588) is illustrated, although such a chamfer may not be visible in the finished product. Such a chamfer may, for example, help with the joining process, such as laser welding or other processes. When the joining process is complete, the chamfered area at the distal end of the inner tubular member 2514 may be filled in. FIGS. 25S & 25T illustrates additional details of the inner tubular member 2514. FIG. 25U illustrates additional details of a ball detent mechanism 2599. Individual components or subassemblies of this embodiment may be used with any other embodiment disclosed herein. For example, additional figures described below, including but not limited to FIGS. 26A-26F, 27A-27D, 28A-28D, 29A-29C, and 31A-31D, focus on a proximal portion of a polypectomy device (e.g., the handle portion), but any of those designs may be used with the distal portion of a polypectomy device shown in FIGS. 25A-25U (e.g., including the inner and outer tubular bodies and cutting portions near the distal end).

The polypectomy device 2500 is similar in many respects to the polypectomy device 100 described above, and similar reference numbers are used to refer to similar items. Further, for efficiency, the descriptions given herein for this and other following embodiments are focused on differences from the embodiments described above. The polypectomy device 2500 comprises several differences from the embodiments described above, and particularly the polypectomy device 100 illustrated in FIG. 1A.

Rotatable Outer Tubular Member

One difference is that, in the polypectomy device 2500, the outer tubular member 2504 is configured to be rotatable about the longitudinal axis of the device with respect to the handle 102. Allowing rotation of the outer tubular member 2504 with respect to the handle 102 can be beneficial in some embodiments, because this can allow rotational positioning of the opening 2508 in the distal end of the device without rotating the handle 102. Accordingly, if a doctor wishes to position the handle 102, and the actuating member or trigger or knob 112 in a particular orientation that is most comfortable and/or controllable for that doctor, the doctor can do so, and then rotate the outer tubular member 2504 with respect to the handle 102 to achieve a rotational orientation of the opening 2508 that is most desirable for removal of the present polyp.

In this embodiment, rotation of the outer tubular member or outer tubular body 2504 is desirably accomplished by rotating a hub 2591 which is affixed to the outer tubular member 2504 and rotationally coupled to the main body of the housing 102. In this embodiment, the hub 2591 comprises a protruding shaft 2593 that fits into a corresponding hole 2595 of the main body of the handle 102. The shaft 2593 is desirably sized to have a slip fit with the hole 2595, thus enabling rotation about the longitudinal axis of the hub 2591 with respect to the main body of the handle 102. Further, a retaining ring or pin 2597 is desirably utilized to limit translation along the longitudinal axis of the hub 2591 with respect to the handle 102. Some embodiments may further comprise a bearing, sleeve, and/or the like operatively positioned between the main body of the housing 102 and the shaft 2593 to reduce friction between the hub 2591 and handle 102 and/or to allow more controlled rotation. Further, other embodiments may utilize other mechanical methods of enabling rotation of the outer tubular member 2504 with respect to the handle 102.

In this embodiment, the hub 2591 comprises a radially protruding member 2592 that comprises a plurality of concave depressions desirably sized for engagement by a human finger. For example, the radially protruding member 2592 and/or its plurality of concave depressions may enable a user of the device to place his or her thumb on the radially protruding member 2592 and press sideways to cause rotation of the radially protruding member 2592, and thus the hub 2591 and outer tubular member 2504. Although such a design can be relatively ergonomic, various other embodiments may comprise various other types of protruding members, knurled or other friction-increasing surfaces, and/or the like that enable a user to use his or her fingers to cause rotation of the outer tubular member 2504. Further, some embodiments may comprise a geartrain, linkage mechanism, and/or the like configured to transform motion of a trigger, button, and/or the like into rotational motion of the outer tubular member 2504.

Although it can be desirable to enable rotation of the outer tubular member 2504 with respect to the main body of the handle 102, it can also be desirable to selectively restrict such rotation, such as to avoid inadvertent rotation of the outer tubular member 2504 with respect to the handle 102 during use. The present embodiment accomplishes such a feature by including a ball or pin detent mechanism 2599. In this embodiment, with reference to FIG. 25U, the ball detent mechanism 2599 comprises a spring-loaded ball or plunger 3198 that extends at least partially beyond a proximal surface of the hub 2591, and a plurality of detents, depressions, grooves, and/or the like 3194 in a distal surface of the housing 102. The spring-loaded ball or plunger 3198 can be held at least partially within one of the detents, depressions, grooves, and/or the like 3194 under its internal biasing force (e.g., a spring 3196 operatively positioned between the ball and the hub), which can keep the outer tubular member 2504 in a specific rotational orientation with respect to the handle 102 until a sufficient rotational force is applied to force the ball or plunger 3198 out of the detent 3194. Although FIG. 25U shows only one of the plurality of detents 3194, the housing 102 may comprise a plurality of detents 3194 similar to as shown in FIG. 31D.

Although this embodiment uses a ball detent mechanism to selectively limit rotation of the outer tubular member 2504 with respect to the handle 102, other mechanisms may be used in lieu of a ball detent mechanism or in addition to a ball detent mechanism. For example, a collet type mechanism may be used that enables a user to flip a lever, rotate a member, and/or the like, to unlock rotational movement of the outer tubular member 2504 with respect to the housing 102, and then reverse the movement of that lever, member, and/or the like to relock the rotational orientation of the outer tubular member 2504 with respect to the handle 102. Such an embodiment may allow a firmer or stiffer locking of the rotation of the outer tubular member 2504 than a detent type mechanism. However, a detent type mechanism may be desirable because it may be simpler for a user to use.

One reason a rotatable outer tubular member 2504 may be more desirable in the present embodiment than in the embodiment illustrated in FIGS. 1A and 1B is that the present embodiment comprises a single opening 2508, whereas the embodiment illustrated in FIG. 1B comprises two openings 108. With an embodiment that has more than one opening in the distal end, less rotation of the outer tubular member may be needed in order to align any particular opening with a particular polyp. However, as discussed above, there can also be benefits to having only one opening in the distal end, such as to allow more precise control of aspiration. By including a single opening 2508, but also including the ability of the outer tubular member 2504 to rotate with respect to the handle 102, a polypectomy device with relatively fine control of aspiration and relatively easy alignment of the opening with a polyp can be provided.

Alternative Cutting Block

Another difference of the polypectomy device 2500 with respect to the polypectomy device of FIG. 1A is the use of a cutting block 2560 at the distal end. The configuration of the cutting block 2560 is illustrated in the outer tubular member assembly views of FIGS. 25H and 25I, and the individual views of the cutting block 2560 in FIGS. 25J through 25L. The cutting block 2560 is somewhat similar to the cutting block 1060 described above with reference to FIGS. 10A through 10G. One difference with the cutting block 2560, however, is that the cutting block 2560 comprises a blunt rounded distal surface 2581 that is configured to be the distal tip of the polypectomy device after the cutting block 2560 is assembled into the distal end of the outer tubular member 2505 illustrated in FIGS. 25M and 25N. Such a configuration can be easier and cheaper to manufacture, and can also result in a smoother, less traumatic distal tip of the polypectomy device. This can be desirable, for example, to reduce the chance of trauma when the distal tip of the polypectomy device contacts uterine tissue during a polypectomy procedure.

With reference to FIG. 25K, the cutting block 2560 further comprises a cylindrical surface 2583 sized to fit within and be coupled to an inner diameter of the outer tubular member 2505 illustrated in FIG. 25N. The cylindrical surface 2583 may in some embodiments comprise a press fit to hold the two components together. In some embodiments, the two components may be held together with adhesive, a threaded junction, laser welding, and/or the like.

The cutting block 2560 further comprises a proximal cylindrical surface 2585 that is sized to fit within the inner diameter of the outer tubular member 2505, and create an annular shaped gap between the cylindrical surface 2585 and the inner surface of the tubular member 2505. This annular shaped gap or void is labeled element 2587 in FIG. 25I. Similarly to as shown in FIG. 10G as described above, the inner tubular member and/or tubular cutter at the end of the inner tubular member can be sized to fit around the cylindrical surface 2585 and pass into the gap or void 2587 to help with separating polyp tissue. In some embodiments, it can be desirable to control a clearance between the outer surface 2585 of the cutting block 2560 and the inner surface of the inner tubular member or cutter (e.g., inner surface 2586 illustrated in FIG. 25R). A tighter clearance may help to efficiently separate polyp tissue, while too tight of a clearance could lead to jamming of the tool. In some embodiments, it is desirable to have a diametral clearance between the inner surface 2586 and outer surface 2585 (i.e. the diameter of the inner surface 2586 minus the diameter of the outer surface 2585) within a range of 0.0005-0.0015, 0.001-0.002, 0.001-0.003, or 0.002-0.005 inches. In some embodiments, it can be desirable to have a relatively deep gap or void 2587 (measured in the longitudinal direction as the longitudinal depth beyond the distal edge of the opening 2508). A relatively deep gap or void 2587 can increase the likelihood of polyp tissue being completely and efficiently severed, by allowing the cutting end of the inner tubular body to move beyond the distal edge of the opening 2508. In some embodiments, it is desirable for the gap or void 2587 to have a longitudinal depth that is at least 25%, 30%, 40%, 50%, 60%, 70%, 80%, 90%, or 100% of the inner diameter of the outer tubular body.

The cutting block 2560 further comprises a circular shaped cutting edge 2589 at the junction between the proximal most edge of the outer cylindrical surface 2585 and a proximal concave surface 2571. Although some embodiments may comprise a flat (or other shaped) proximal surface, instead of the concave proximal surface 2571, the concave proximal surface 2571 can help to create a sharper cutting edge 2589 that can interact with the inner tubular member and/or tubular cutter attached to the distal end of the inner tubular member to sever or shear polyp tissue. It may be desirable to utilize a proximal concave surface 2571 having a spherical radius within a range of 0.100-0.200 or 0.150-0.250 inches. In some embodiments, a ratio of the spherical radius of the proximal concave surface 2571 divided by the outer diameter of the outer cylindrical surface 2585 is desirably within a range of 1.0-2.0, 1.5-2.0, or 1.0-3.0. Although in this example embodiment the sharpened cutting edge 2589 is created by the junction of the outer surface 2585 and a concave spherical surface, other embodiments may create a sharpened cutting-edge 2589 in various other ways.

Another difference in the cutting block 2560 with respect to the cutting block 1060 is that the cutting edge 2589 lies in a plane that is substantially perpendicular to the longitudinal axis of the tool. In the embodiment illustrated in FIG. 10E, however, the proximal surface of the cutting block 1060 is angled at angle 1062 with respect to a plane that is perpendicular to the longitudinal axis. Both designs can help to cut polyp tissue. One benefit of the design illustrated in FIG. 25K, however, is that it may be easier and/or cheaper to manufacture a cutting block that has a round cutting-edge 2589 created by adding the concave proximal surface 2571. Further, with reference to FIG. 25I, in this embodiment, the proximal cutting edge (e.g., cutting edge 2589 shown in FIGS. 25K and 25L) of the cutting block 2560 can be recessed distally beyond the distal edge of the opening 2508, helping to maximize the use of space within the tool and/or to position the distal end of the opening 2508 closer to the distal tip of the polypectomy device. Other embodiments may have the proximal cutting edge approximately aligned with the distal edge of the opening 2508, or may have the proximal cutting edge extend somewhat longitudinally proximately into the opening area 2508. Further, some embodiments may have the cutting edge 2589 oriented at a non-perpendicular angle with respect to the longitudinal axis, such as any of the angles discussed above with respect to cutting block 1060.

Spring-Loaded Cutter

Another difference in the polypectomy device 2500 is that the polypectomy device 2500 comprises a spring-loaded cutter release or disconnect mechanism 2570 illustrated in the detail cross-sectional view of FIG. 25D and also partially in FIGS. 25E through 25G. The spring-loaded cutter release mechanism 2570 is desirably configured to enable the inner tube assembly 2590 illustrated in FIG. 25O to automatically move forward with respect to the outer tubular member in response to the actuating member or trigger 112 being pulled beyond a predetermined point (or otherwise being activated, such as described below in reference to other spring-loaded embodiments). It can be desirable in some embodiments to allow the inner tube and/or the cutter integrated into or coupled to the distal end of the inner tube to move or extend with respect to the outer tube in a relatively quick fashion to aid in cutting polyp tissue. As an example, with reference to FIG. 25D, the spring-loaded cutter release or disconnect mechanism 2570 comprises a trigger 112 having an actuator link 2571 rotatably coupled thereto. In this embodiment, the actuator link 2571 is rotatably coupled to the trigger 112 via the pin 2572. The actuator link 2571 is desirably biased in a downward or clockwise direction in this embodiment (e.g., a direction toward engagement with actuation surface 2575 of actuation member 2576, as described below) by a torsion spring 2573. By biasing the actuator link 2571 downward or in a clockwise direction, this causes a protruding member or catch portion 2574 to engage a distal surface or actuation surface 2575 of an actuation member 2576. The actuation member 2576 is desirably coupled to the inner tubular member 2514. Accordingly, with continued reference to FIG. 25D, if the trigger 112 is translated in a proximal or retraction direction (to the left as oriented in FIG. 25D), the catch portion 2574 will cause the actuation member or block 2576 to also translate to the left or in the retract direction along with the trigger 112. Once the trigger 112 is translated in the retract direction a sufficient amount, the bottom surface 2577 of the actuator link 2571 will engage a ramp or cam portion 2578 of the handle 102. Continued translation of the trigger 112 in the retract direction will cause the ramp 2578 to force the actuator link 2571 upward or in a counterclockwise direction (e.g., a direction away from engagement with actuation surface 2575). Once the actuator link 2571 rotates sufficiently in the counterclockwise direction, the catch portion 2574 will no longer engage the actuation surface 2575 of the actuation member 2576, and the actuation member 2576 and inner tubular member 2514 will desirably spring forward in the extended direction under the biasing force of the spring 2579 (which is operably positioned between the handle 102 and the actuation member 2576).

The ramp or cam portion 2578 and the bottom surface 2577 of the actuator link 2571 are desirably designed such that the catch portion 2574 will release the actuation member 2576 when the trigger 112 has been moved a predetermined distance. The predetermined distance that results in releasing the actuation member 2576, and thus springing the cutter forward, can desirably be selected based on a desired position of the distal end of the inner tubular body and/or the cutting edge 2552 of the tubular cutter with respect to the opening 2508. For example, it may be desirable for the predetermined distance to be selected such that the cutting edge 2552 will be retracted such that it is in line with the proximal end of the opening 2508, or even behind (or proximal to) the proximal end of the opening 2508 before springing forward. Such designs may be desirable, because they can enable the full length of the opening 2508 to be accessible for tissue to be inserted therethrough before springing the cutter forward. In some embodiments, it may be desirable to design the cam or ramp portion 2578 and bottom surface 2577 such that the predetermined distance that results in springing the cutter forward will occur before the cutting edge 2552 of the tubular cutter reaches the proximal end of the opening 2508. For example, the opening 2508 comprises a length in the longitudinal direction, and it may be desirable to set the predetermined distance such that a longitudinal distance from the proximal end of the opening 2508 to the cutting edge 2552 when the disconnect mechanism releases the inner tubular body is no greater than ⅓, ¼, or ⅛ of the longitudinal length of the opening. Such a design may be desirable, for example, because not retracting the cutting edge 2552 completely to the proximal end of the opening 2508 may help to avoid clogging by potentially cutting off smaller pieces of polyp tissue than if the cutting edge 2552 were retracted all the way to or beyond the proximal end of the opening 2508. It should be noted that, although this disclosure regarding the design of the disconnect mechanism to release the cutter when the cutting edge of the tubular cutter reaches a particular position with respect to the opening is described with reference to the embodiment of FIGS. 25A-25T, the same design considerations and predetermined distances may apply to other disconnect mechanisms described herein. For example, the disclosure regarding designing the ramp or cam surface 2578 and bottom surface 2577 to release the mechanism when the cutter is in a particular position may also apply to the cam surfaces 3178 and bottom or angled surfaces 3177 described below.

The user can then move or allow the trigger 112 to move back to a starting position as shown in FIG. 25D, where the catch portion 2574 will be forced downward or rotated in a clockwise direction by the torsion spring 2573 and reengage the distal surface 2575 of the actuation member 2576. In some embodiments, a biasing member, such as a spring, is used to automatically return the trigger 112 to its forward or starting position (for example, similar to spring 3153 of the embodiment shown in FIG. 31B). To allow clearance for the catch portion 2574 to re-engage with the distal surface 2575 of the actuation member 2576, the actuation member 2576 further comprises a distally extending protrusion 2569 that stops the actuation member 2576 from translating far enough in the extend direction that there would not be room left for the catch portion 2574 to engage the distal surface 2575.

This embodiment illustrates merely one example of a spring-loaded cutter release mechanism, which may also be known as a disconnect mechanism, that enables selective and/or automatic disconnecting or decoupling of the inner tubular member from the trigger. Somewhat similar functionality could potentially be accomplished by using an embodiment like the embodiment shown in FIG. 1A, and having the user simply remove his or her finger from the trigger after pulling the trigger back, allowing the spring to return the trigger and inner tubular member to an extended position. It can be desirable, however, to automate this release of the inner tubular member with a disconnect or decoupling mechanism, because it can be easier for a user to operate and can also allow or enable faster extension of the inner tubular member. For example, by disconnecting or decoupling the trigger 112 from the inner tubular member 2514, there is less mass for the spring 2579 to accelerate forward in the extension direction. Accordingly, a spring 2579 will desirably move the inner tubular member 2514 to the extended position more quickly when the inner tubular member 2514 has been decoupled from the trigger 112 than if the inner tubular member 2514 were not decoupled from the trigger 112. As a non-limiting example, an embodiment that does not decouple the trigger from the inner tubular member may have an extension speed of approximately 20 inches/second, and a similar embodiment that does decouple the trigger from the inner tubular member may have an extension speed of approximately 65 inches/second. Such an increase in speed may help to more efficiently and/or more cleanly cut polyp tissue. In some embodiments, it can be desirable to have a higher spring rate for the spring 2579 to increase the speed of extension of the inner tubular member 2514 when released. In some embodiments, it can be desirable for the spring 2579 to comprise a spring rate that is approximately, no greater than, or no less than 1, 2, 3, 4, 4.5, 5, or 6 pounds/inch. In some embodiments, it can be desirable for the spring 2579 to comprise a spring rate within the range of 2.5-3.5 pounds/inch. In some embodiments, it can be desirable to provide a mechanism for cocking or moving the assembly to the retracted position that provides a mechanical advantage, instead of requiring a user to directly apply such axial force. For example, as will be described in more detail below with respect to the embodiments illustrated in FIGS. 27A-27D, 28A-28D, 29A-29C, and 31A-31D, some embodiments may comprise a trigger that utilizes a linkage mechanism, a gear train, and/or the like to provide a mechanical advantage. Such embodiments of trigger mechanisms may be used with all other features of the embodiment of FIGS. 25A-25T. In some embodiments, such mechanical advantage is configured to be approximately, exactly, no less than, or no greater than 1.5, 2.0, 2.5, or 3.0.

In some embodiments, it may be desirable to include a damping feature to dampen a shock load imparted into the inner tubular member assembly and/or handle at the end of the extension stroke. For example, an o-ring, gasket, or other resilient member may be positioned between the distally extending protrusion 2569 and a corresponding mating surface of the housing 102.

Various other methods of decoupling the inner tubular member from the trigger or actuating member may be used, and some of these other methods are described below with reference to additional figures. Further, although various embodiments described herein describe a spring-loaded cutter that springs forward (e.g., toward the distal end of the device), similar features may be used with a cutter that springs backward (e.g., toward the proximal end of the device. For example, such a design could be used with a cutter similar to as shown in FIGS. 9C-9E, which cuts polyp tissue as the cutter is retracting. For example, a spring could be used to bias the cutter in the retracted direction, and movement of the actuating member or trigger by the user could cause the cutter to move in the extend direction, until the disconnect mechanism releases the cutter to allow it to spring back. Accordingly, the disconnect mechanism design could be essentially the opposite of the designs shown in FIGS. 25B, 26E, 27B, 28B, 29C, and 31B. One reason such a design may be desirable is that the cutter would be moving in the same direction as the vacuum pressure (which would be pulling the polyp tissue toward the proximal end of the device), which may help to produce larger specimens with each cut.

Spring-Loaded Cutter with Rotation

FIGS. 26A-26F illustrates an example embodiment of a mechanism for a polypectomy device that incorporates a spring-loaded release or decoupling feature for the cutting tube or inner tubular member 2614, and also incorporates an automatic rotation mechanism that causes the inner tubular member 2614 to rotate with respect to the outer tubular member 2604 as the inner tubular member 2614 is also translating with respect to the outer tubular member 2604. Incorporating at least some rotation of the inner tubular member 2614, and thus the cutting blade or surface at the distal end of the inner tubular member 2614, can help to make an efficient cut in the polyp tissue as the inner tubular member 2614 translates forward with respect to the outer tubular member 2604. One reason for this increase in cutting efficiency is that the absolute speed of the cutting edge of the inner tubular member 2614 with respect to a corresponding cutting surface coupled to or formed by the outer tubular member 2604 may be increased. Another reason for this increase in cutting efficiency is that the rotation in combination with translation can tend to lead to more of a slicing action than with simply a translation motion.

The embodiment illustrated in FIGS. 26A-26F is a simplified design intended to show how such a decoupling and rotation mechanism 2670 may operate. Accordingly, the housing 102 is merely a rectangular box, but in other embodiments could comprise an ergonomic handle as illustrated in some of the other embodiments illustrated herein. Further, the decoupling and rotation mechanism 2670 comprises a trigger 112 that can be manually cocked and then manually released by a user pressing release 2612 (for example, a lever, button, trigger, latch, and/or the like). It may be more desirable, however, in some embodiments, to have the inner tubular member automatically release when the trigger 112 reaches a certain point, similar to as described above with respect to the polypectomy device 2500. In this simplified example, however, the assembly is cocked by a user sliding the trigger 112 in a retraction direction until a catch 2605 engages a corresponding catch 2606 of the rocker or latch 2612. In doing so, spring 2613 is compressed. When a user manipulates the rocker or latch 2612, the catches 2605, 2606 will disengage, enabling the spring 2613 to push the trigger 112 in the extend direction, thus also translating the inner tubular member 2614 in the extend direction with respect to the outer tubular member 2604. In some embodiments, including this embodiment and others disclosed herein, the spring that biases the inner tubular body forward (e.g., spring 2613) may be positioned against a spring seat (e.g., spring seat 2615) that is adjustable (for example, slidable in the longitudinal direction) to adjust the preload force of the spring. Additionally or alternatively, the spring may be replaced with a spring having a different spring rate and/or length to adjust the preload force of the spring.

Another feature of the decoupling and rotation mechanism 2670 is that the mechanism comprises a body 2620 coupled to the inner tubular member 2614. The body 2620 comprises a helical cam groove 2621 having a pin 2622 positioned therein. The pin 2622 is desirably held stationary with respect to the housing (not shown in FIGS. 26C and 26D for clarity). Accordingly, when the inner tubular member 2614 and attached body 2620 are forced forward by the spring 2613, the body 2620 and inner tubular member 2614 will also be caused to rotate with respect to the outer tubular member 2604 as the pin 2622 tracks the path of the helical cam groove 2621. In some embodiments, the pin 2622 is coupled to the inner tubular member 2614 and tracks a groove that is coupled to or part of the housing (essentially the opposite of the configuration shown in FIGS. 26C and 26D). This can enable less rotational mass, and thus potentially faster movement of the inner tubular member 2614. Further, some embodiments may comprise more than one pin (or equivalent feature), such as two, three, or four pins equally spaced about the inner tubular member 2614 or body 2620.

In some embodiments, it can be desirable for the helical cam groove 2621 to have a relatively high lead or pitch. For example, it can be desirable for the helical cam groove 2621 to have a lead or pitch that causes the inner tubular member 2614 to rotate only 180° as the inner tubular member 2614 translates from a fully retracted position to a fully extended position. Using such a relatively high pitch or lead can reduce friction, thus enabling the inner tubular member 2614 to translate and/or rotate faster. In various embodiments, the helical cam groove 2621 may be configured to cause the inner tubular member 2614 to rotate or partially rotate a smaller or greater amount as the inner tubular member moves from the fully retracted to the fully extended position, such as, for example, approximately, no less than, or no more than 45, 90, 135, 180, 225, 270, 315, or 360°. In some embodiments, the device is configured to cause the inner tubular member 2614 to rotate within a range of 160-200 degrees, 90-270 degrees, or 45-315 degrees as the inner tubular member moves from the fully retracted to the fully extended position. Further, some embodiments may comprise a variable pitch or lead, or even a non-helical groove. For example, some embodiments may comprise a groove shaped such that the inner tubular member rotates back and forth, such as at least once in a clockwise direction and at least once in a counterclockwise direction, as the inner tubular member extends from the fully retracted position to the fully extended position. In some embodiments, the body 2620 may comprise a material configured to reduce the friction between the cam groove 2621 of the body 2620 and the pin 2622. For example, the body 2620 may comprise an acetal polymer that has Polytetrafluoroethylene (PTFE) formulated into it. Further, some embodiments may comprise a grease, oil, bearing, and/or the like to reduce such friction. Some embodiments may comprise a lead screw coupled to a lead nut to cause rotation of the inner tubular member when the inner tubular member translates.

Alternative Automatic Decoupling Mechanisms

FIGS. 27A-27D, 28A-28D, and 29A-29C illustrate three alternative embodiments of automatic decoupling or release mechanisms 2770, 2870, and 2970, respectively. These automatic decoupling mechanisms desirably operate on a similar principle to the automatic decoupling mechanism 2570 illustrated in FIG. 25D, but with different trigger configurations. Further, any of these automatic decoupling mechanism may comprise automatic rotation features as described above with reference to FIGS. 26A-26F. The automatic decoupling mechanisms 2770, 2870, and 2970 each comprises a trigger 112 that is rotatably or pivotally coupled to the handle 102 at pivot axis 2780 instead of being slidably coupled to the handle 102. Accordingly, instead of a user sliding a trigger 112 in the retract direction to cause the inner tubular member 2514 to move in the retract direction, a user can squeeze the trigger 112 to cause the inner tubular member 2514 to move in the retract direction. Such a configuration may in some cases be more ergonomic than a sliding trigger. Such a configuration may also enable a greater mechanical advantage than a sliding trigger.

Figure 27A:
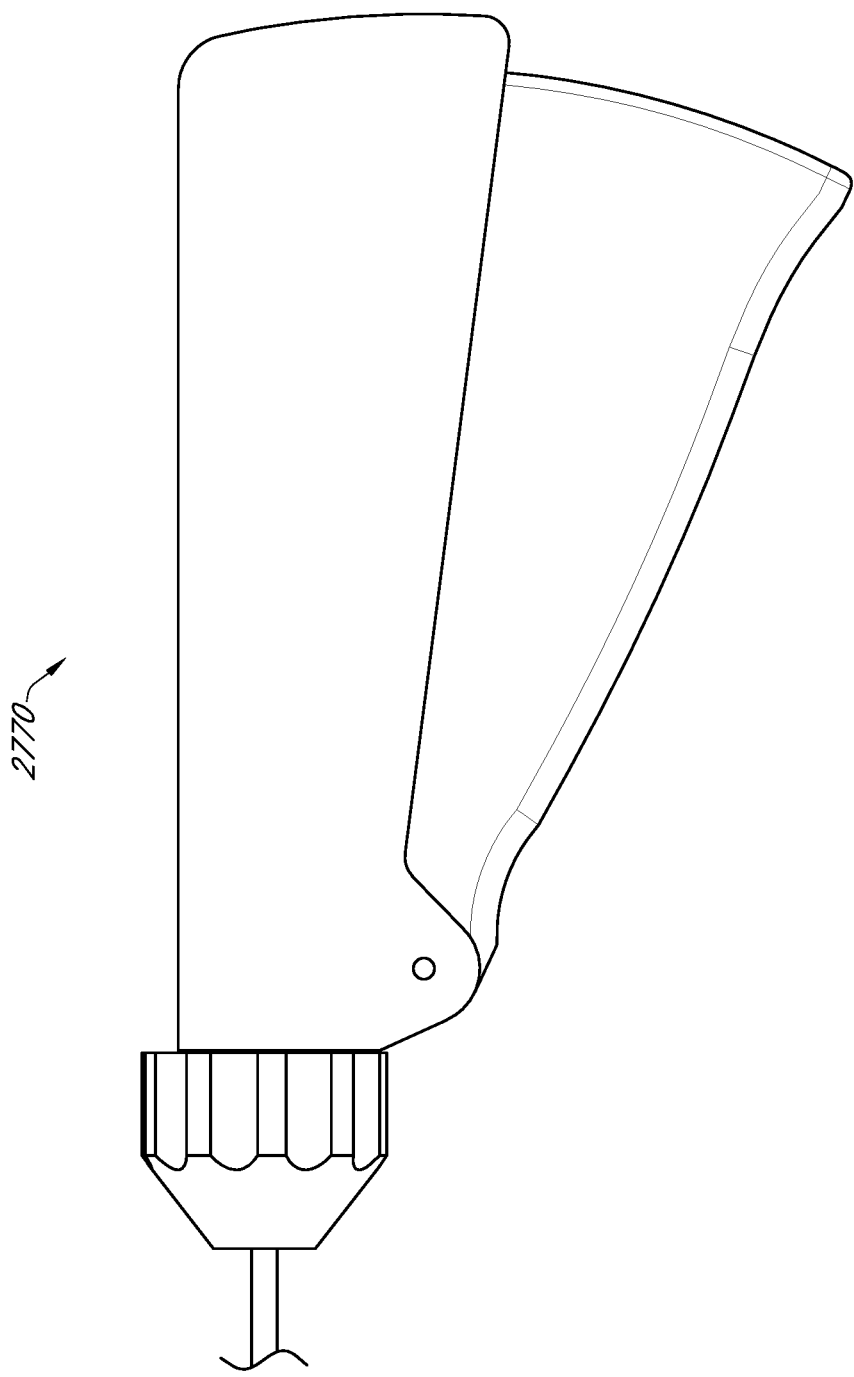
FIGS. 27A-27D illustrate another embodiment of a mechanism for controlling movement of a cutter.
Figure 27B:
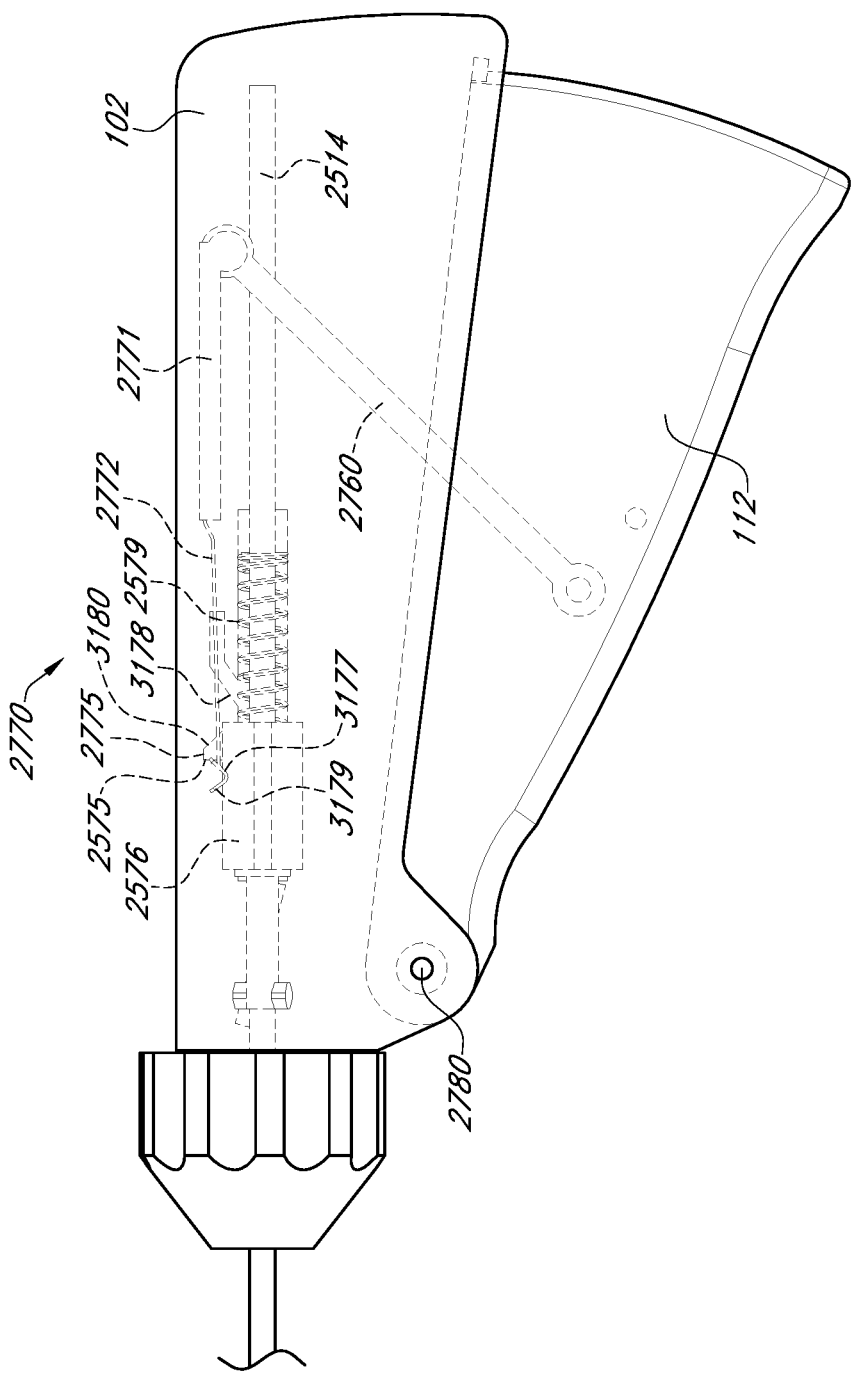
Figure 27C:
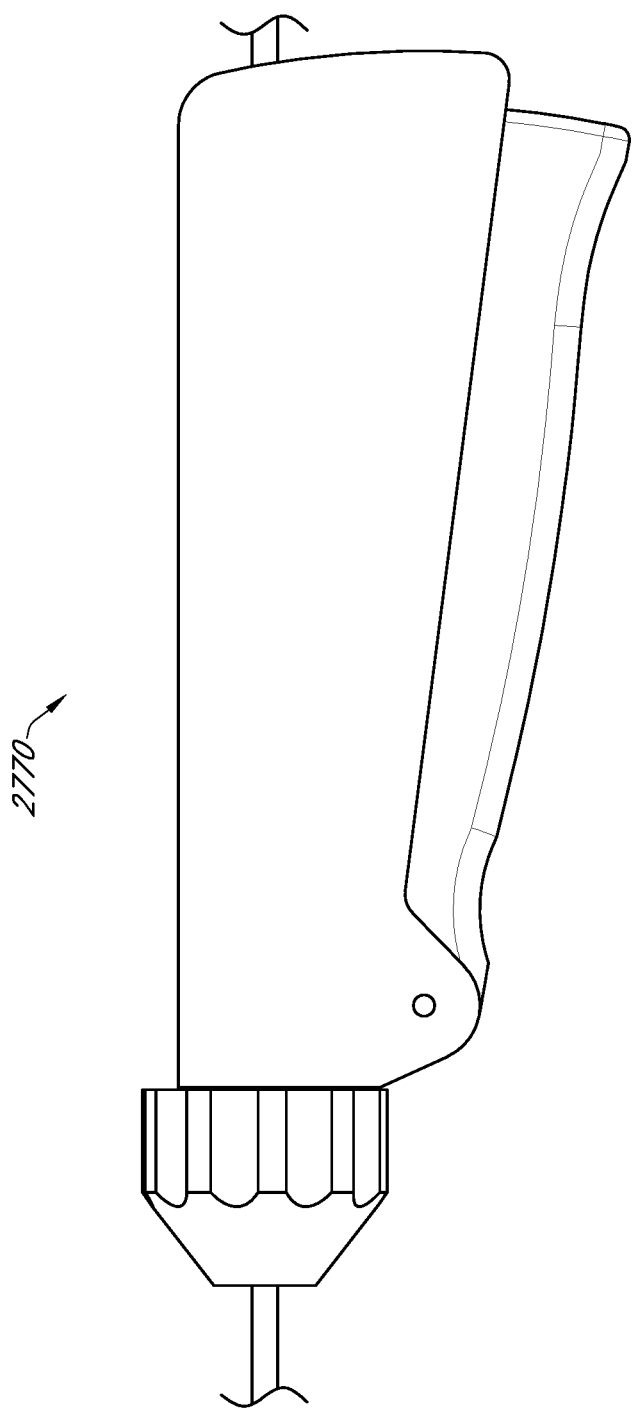
Figure 27D:
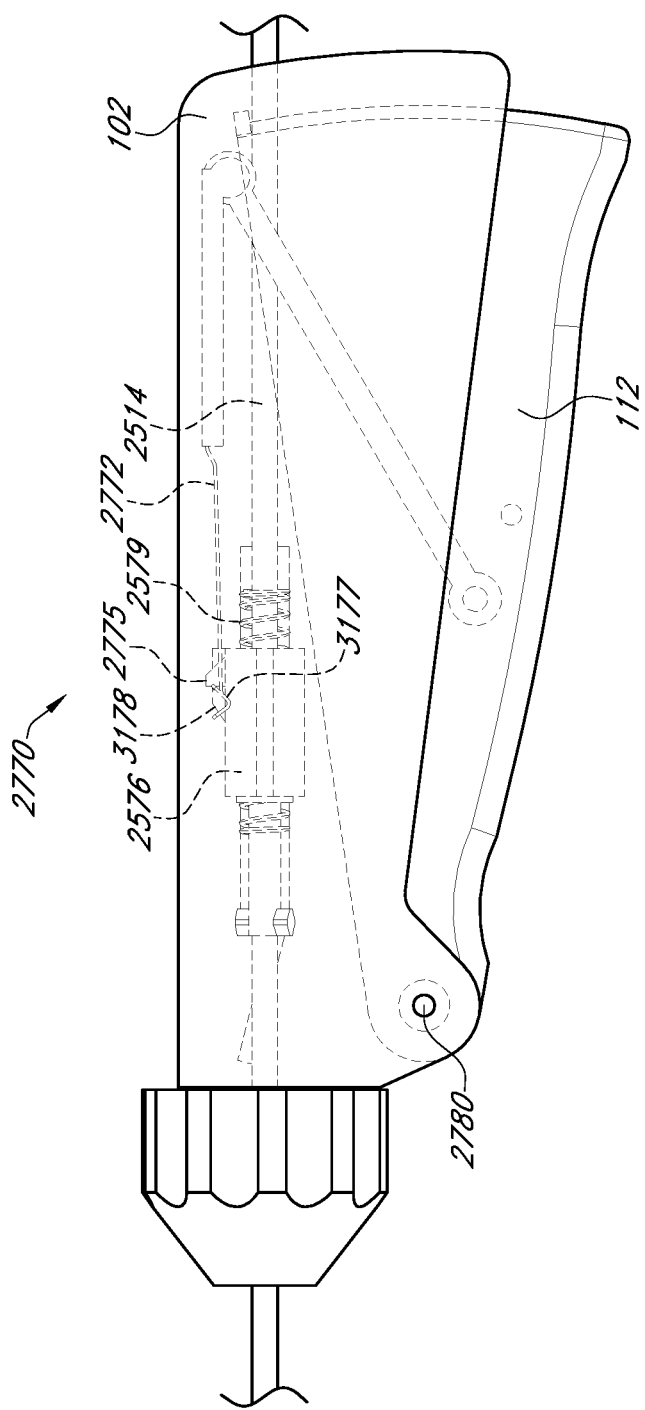

With reference to FIG. 27B, the decoupling mechanism 2770 comprises an actuator link 2771 that has a spring-loaded or elastically bendable connecting link or portion 2772 that engages a catch 2775 of actuation member 2576. As the trigger 112 is squeezed, linkage 2760, which is pivotally coupled to the trigger 112 and the actuator link 2771, causes the actuator link 2771 to be pulled in the retract direction, thus causing catch 2775 and actuation member 2576 to also be pulled in the retract direction. This also causes the inner tubular member 2514 to be pulled in the retract direction. As the actuator link 2771 is pulled in the retract direction, a bottom or angled portion 3177 of the bendable connecting link 2772 will desirably engage a cam surface or ramp 3178 coupled to or integrated into an interior of the handle 102. As the actuator link 2771 continues to be pulled in the retract direction, the cam surface 3178 will eventually force the bendable portion 2772 outward (e.g., away from the actuation member 2576) and out of engagement with the catch 2775, thus decoupling the trigger 112 from the actuation member 2576 and inner tubular member 2514. This can allow the spring 2579 to release or launch the inner tubular member 2514 forward or in the extension direction. FIG. 27D illustrates a configuration where the trigger 112 has been fully compressed. In this case, the spring-loaded portion 2772 is still shown to be engaging the catch 2775. However, desirably, as described above, in this position of the trigger 112, the cam surface 3178 will have moved the bendable portion 2772 out of engagement with the catch 2775. The bendable portion 2772 in this and other embodiments may comprise spring steel, plastic, or another material having sufficient elasticity to be bent out of engagement with the catch 2775 without plastic deformation.

With continued reference to FIG. 27B, the bendable portion 2772 further comprises another bottom or angled surface 3179 positioned to engage cam surface 3180 of the actuation member 2576. The angled surface 3179 and cam surface 3180 are positioned to cooperate to push the distal end of bendable portion 2772 up and over the catch 2775 to allow the bendable portion 2772 to re-engage the catch 2775 as the trigger 112 is released. The bendable portion 2772 may engage the catch 2775 similar to as shown in FIG. 31C, described below.

Figure 29A:
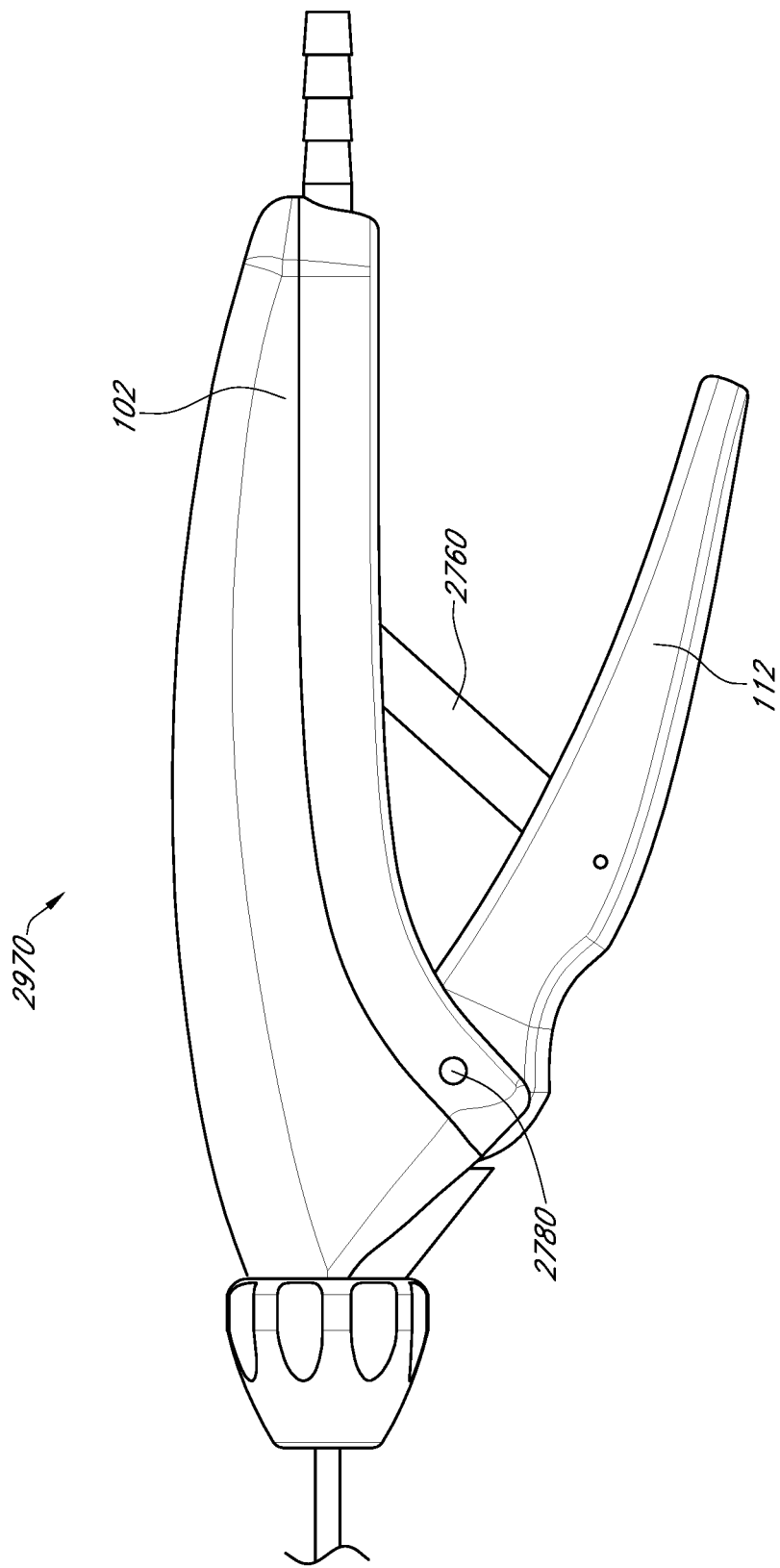
FIGS. 29A-29C illustrate another embodiment of a mechanism for controlling movement of a cutter.
Figure 29B:
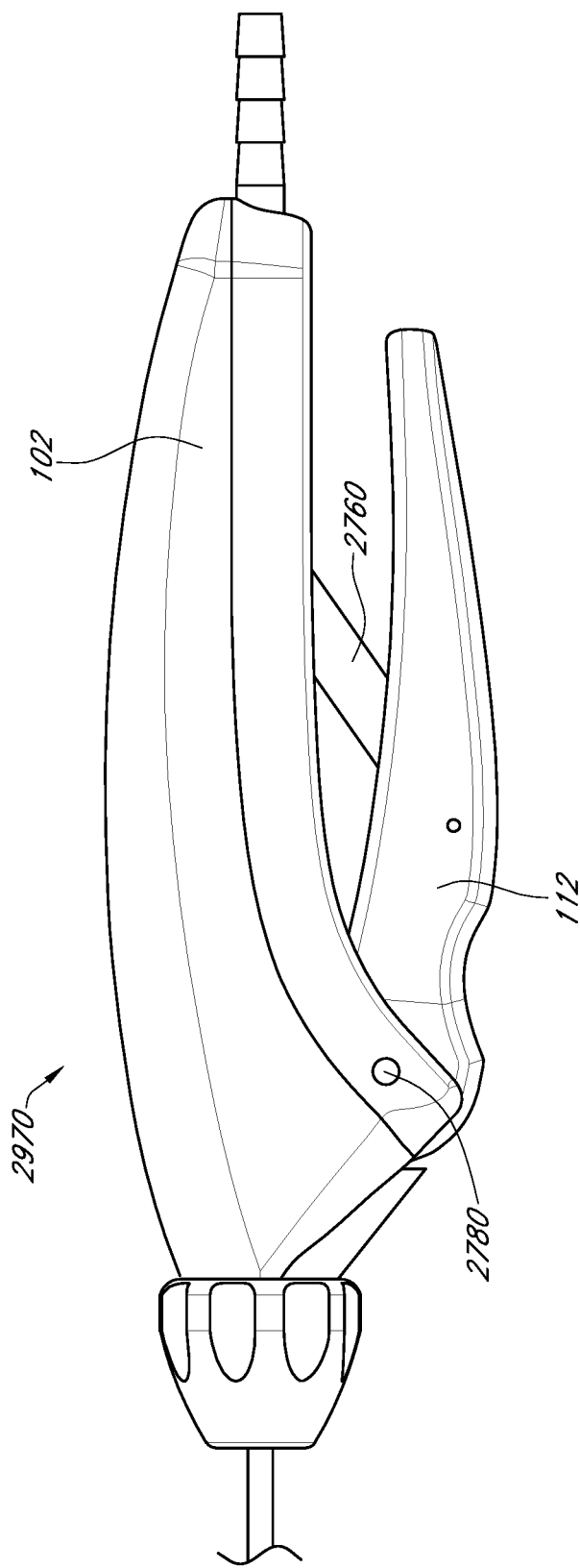
Figure 29C:
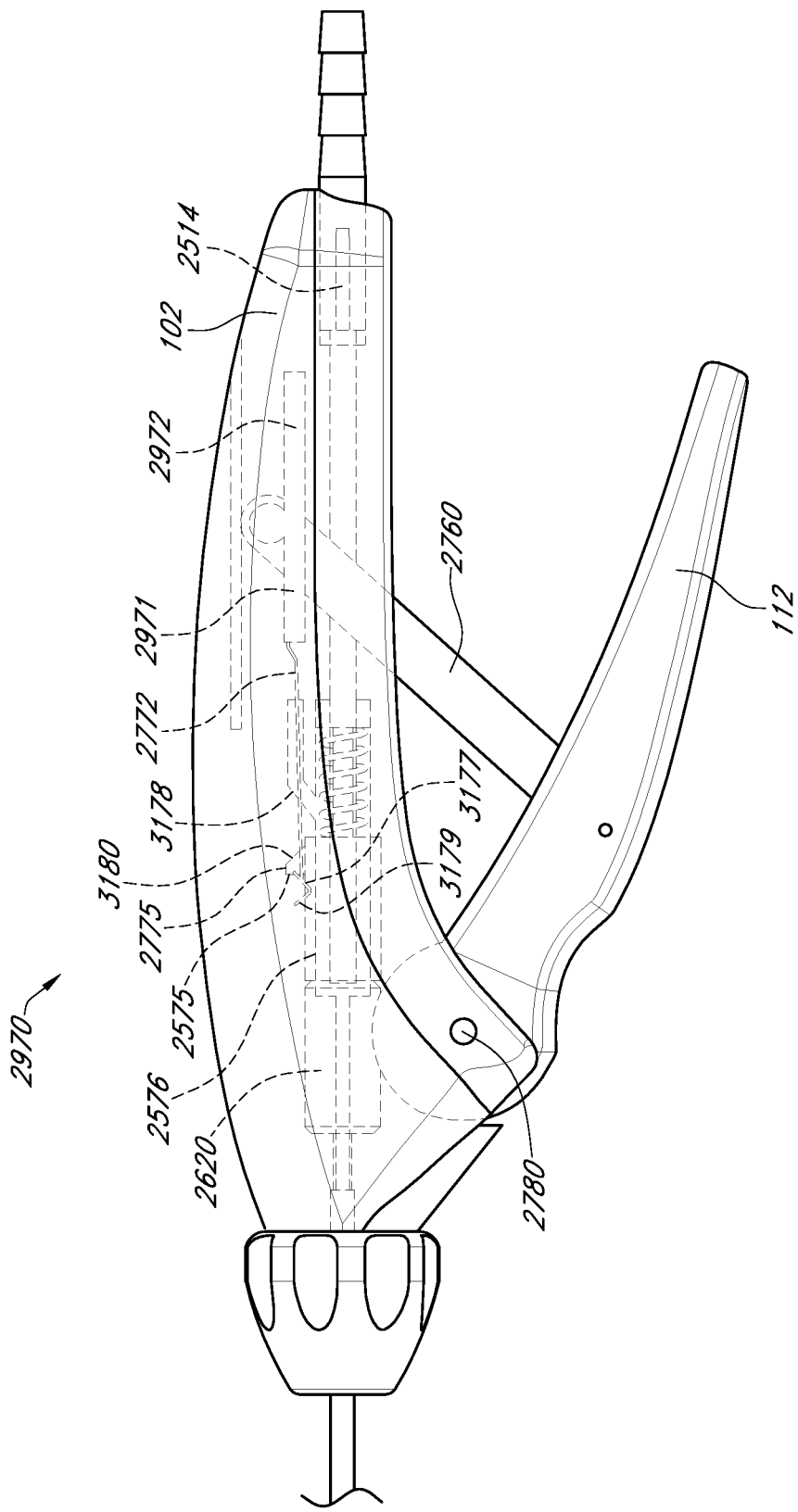

The embodiment illustrated in FIGS. 29A-29C, namely the decoupling mechanism 2970, is similar in design to the embodiment 2770 illustrated in FIGS. 27A-27D, with similar reference numbers used to refer to similar elements. Some differences in the embodiment of the decoupling mechanism 2970 are that the housing and trigger 102, 112 comprise a different shape, and the actuator link 2971 is coupled to linkage 2760 at a different point. In this embodiment, linkage 2760 is pivotally coupled to the actuator link 2971 at a point forward of a proximally protruding member 2972 (instead of at a proximal end of the actuator link), which can change the mechanical advantage provided by the linkage 2760. Further, the embodiment illustrated in FIGS. 29A-29C includes a body 2620 similar to as described above with reference to FIGS. 26A-26F, to cause rotation of the inner tubular body as it extends.

Figure 28A:
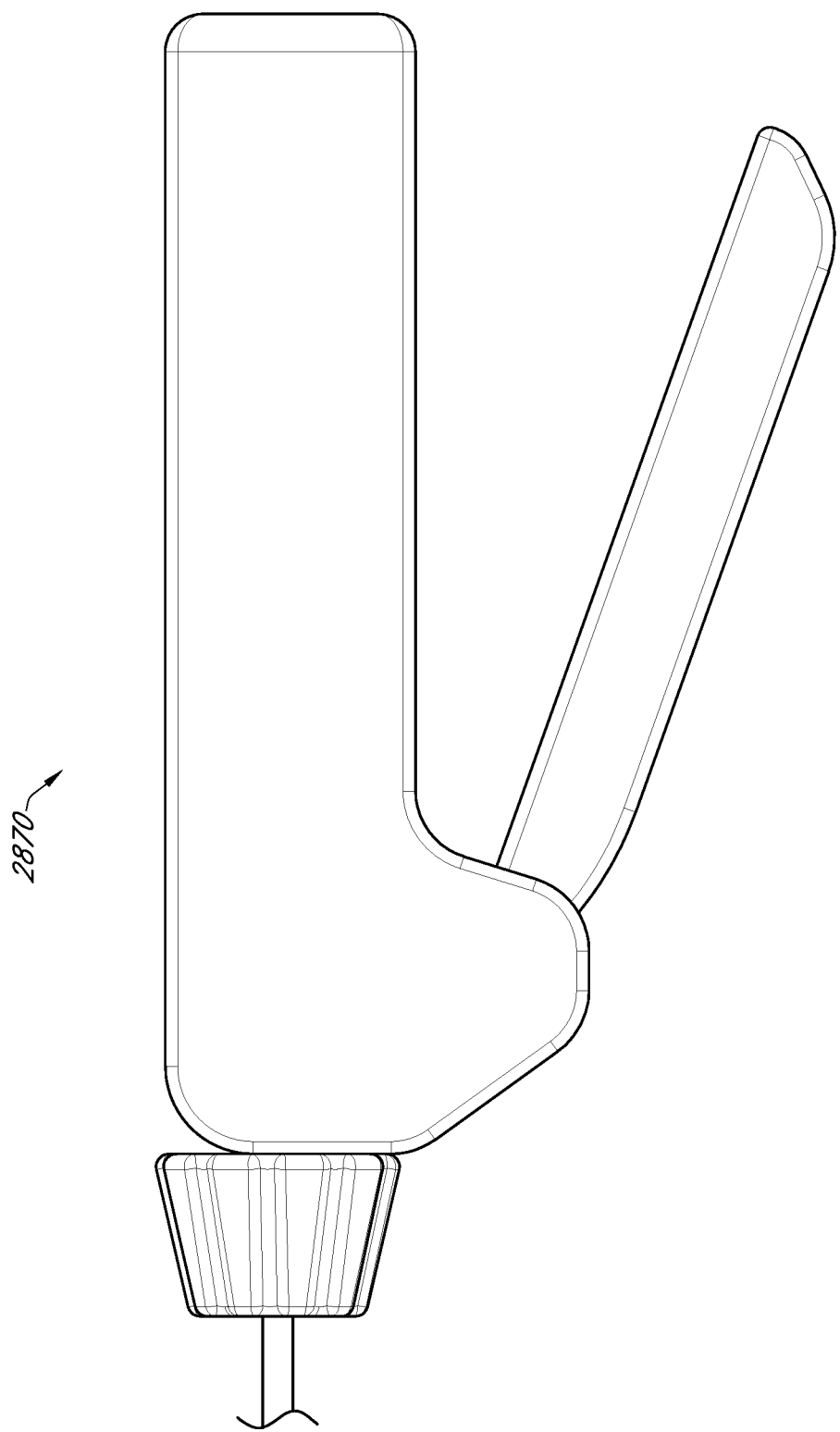
FIGS. 28A-28D illustrate another embodiment of a mechanism for controlling movement of a cutter.
Figure 28B:
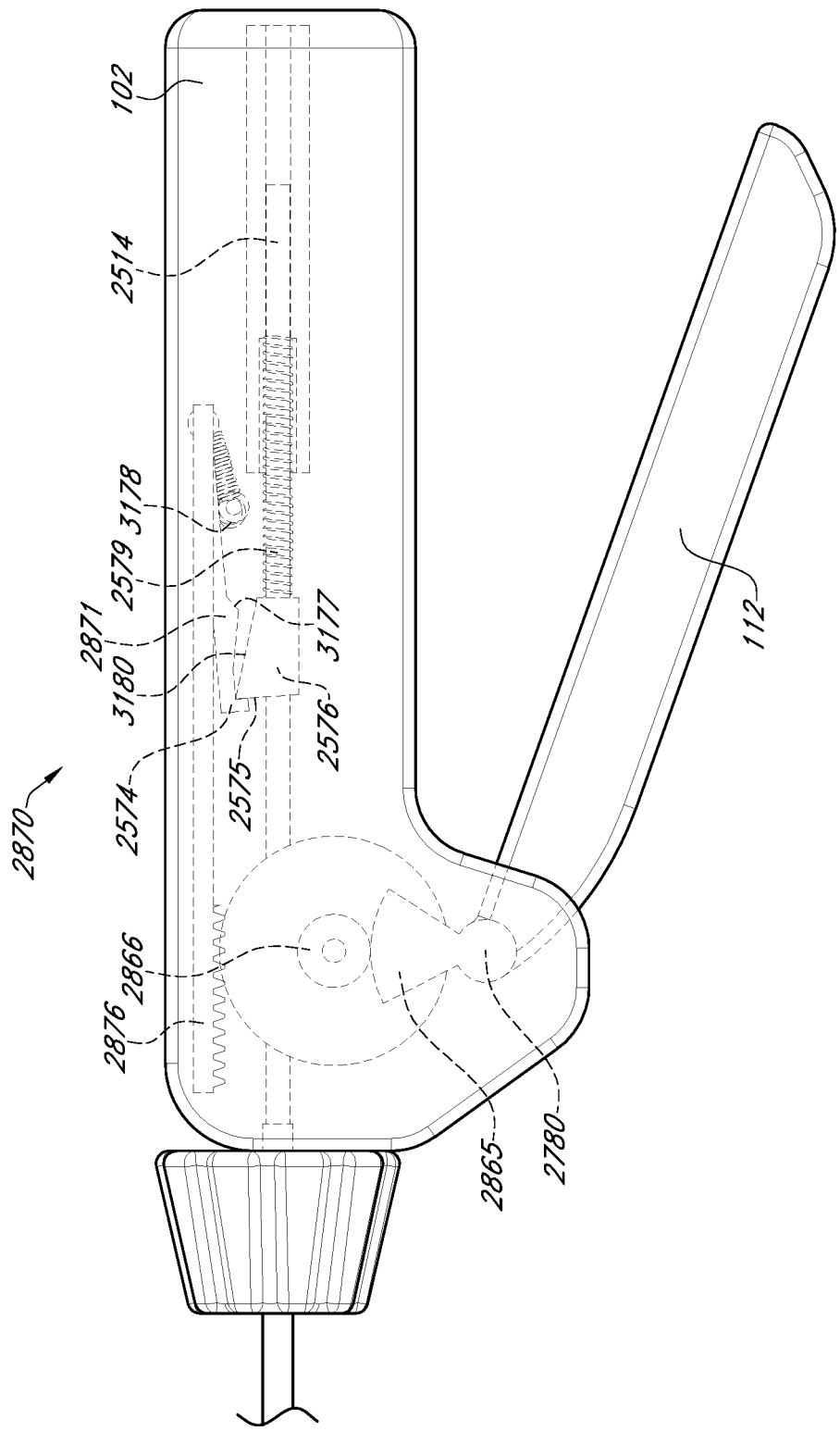
Figure 28C:
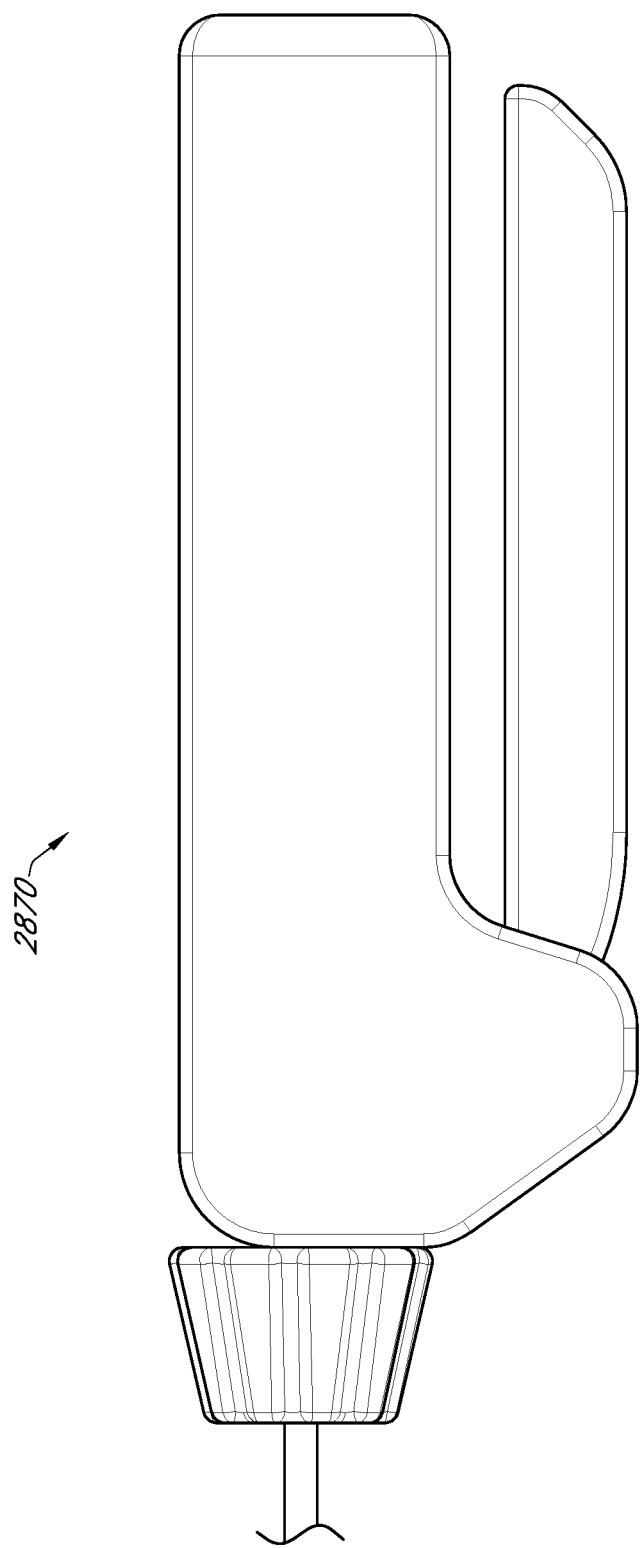
Figure 28D:
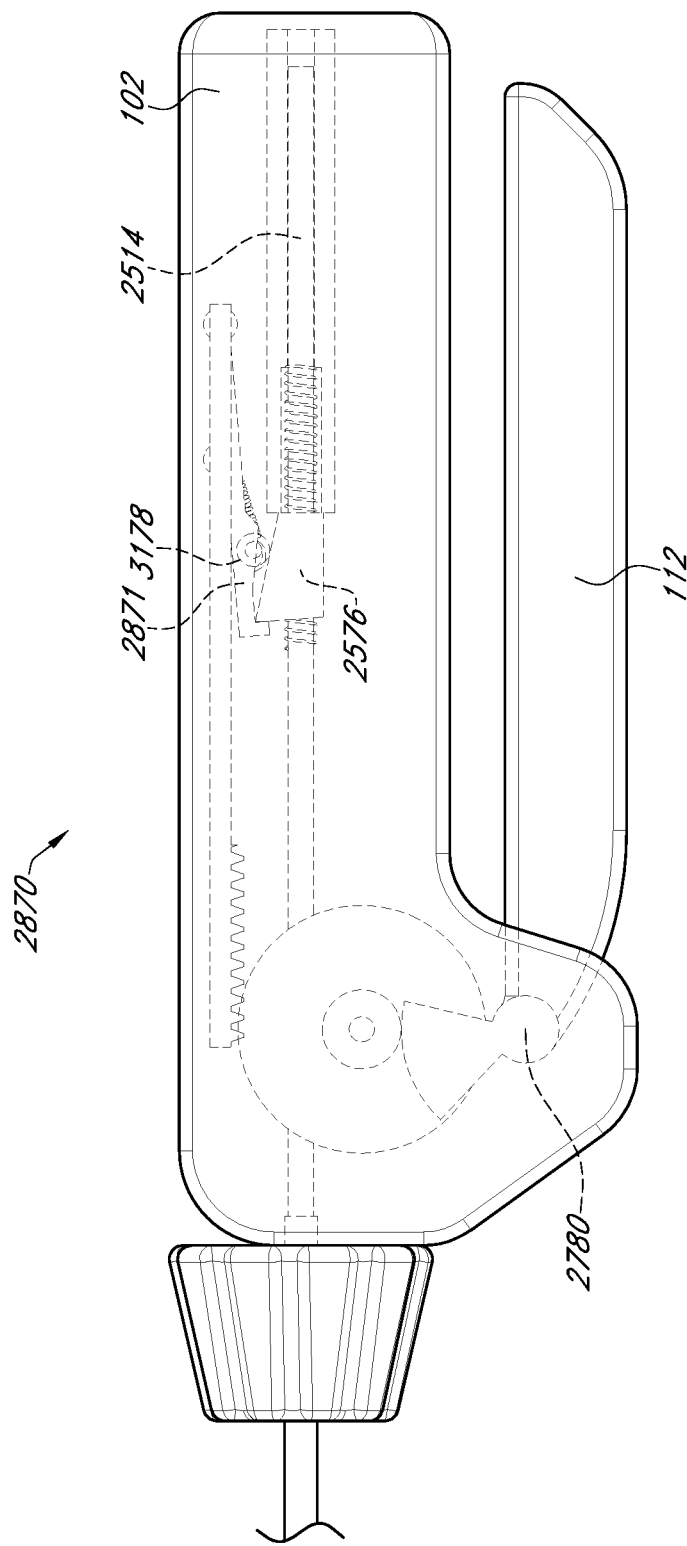

FIGS. 28A-28D illustrate another alternative embodiment of a disconnect mechanism 2870. This mechanism is somewhat similar to the disconnect mechanism 2770, with similar reference numbers used to refer to similar elements, but using a gear driven mechanism instead of a linkage mechanism to convert rotational motion of the trigger 112 into translational motion of the actuator link 2871. In this embodiment, when the trigger 112 is squeezed, this causes a first gear 2865 to rotate a second gear 2866, which causes translation or sliding of a gear rack 2867. With reference to FIG. 28B, if the trigger 112 is squeezed (i.e. rotating counterclockwise as shown in FIG. 28B), the gear 2866 will be caused to rotate clockwise and thus move the rack 2867 to the right, or in the retracted direction. The rack 2867 is pivotally coupled to the actuating link 2871 at their proximal ends, thus causing the actuating link 2871 to also move in the retract direction. In this embodiment, once the actuating link 2871 has been retracted sufficiently, the bottom surface 3177 of the actuating link 2871 will desirably contact a cam surface, ramp, or equivalent feature 3178 coupled to the housing 102 that will cause the catch portion 2574 to disengage or decouple from the actuation member 2576, thus allowing the inner tubular member 2514 to automatically extend forward under the energy of the spring 2579. FIG. 28D shows the fully compressed trigger position, except that the actuating link 2871 would be lifted up away from the actuating member 2576 instead of still engaging the actuating member 2576. Returning to FIG. 28B, the actuating member 2576 further comprises a cam surface 3180 that can push the catch 2574 up and over the actuating member 2576 as the trigger is released from the compressed position, thus allowing the catch 2574 to re-engage the actuating member 2576 when the trigger 112 is in the extended position.

Alternative Openings

FIGS. 30A-30C, 32A-32C, and 33A-33D illustrate alternative embodiments of outer tubular members 3004, 3204, and 3304, respectively, that could be used with any of the embodiments disclosed herein, including the embodiment of the outer tubular member assembly 2504 illustrated in FIGS. 25H and 25I and other figures. With reference to FIGS. 30A-30C, one difference of the outer tubular member 3004 with respect to the outer tubular member 2505 of FIG. 25H is that the outer tubular member 3004 comprises an opening 3008 having a distal cutting surface 3009 that is angled or inclined with respect to a transverse plane (for example, a plane oriented perpendicular to the longitudinal axis of the outer tubular member). In this embodiment, the distal cutting surface 3009 is oriented at an approximately 30° angle A with respect to the transverse plane; however, other embodiments could position the distal cutting surface 3009 at a different angle A, such as, for example, approximately, exactly, no less than, or no more than 10, 20, 30, 40, 50, 60, 70, or 80°. In some embodiments, the angle A may be within a range of 10-50°, or 20-40°.

Further, some embodiments may comprise a distal cutting surface that is curved, rounded, radiused, and/or the like, instead of being positioned at a specific angle. For example, FIGS. 32A-32C illustrate another example embodiment of an outer tubular member 3204 that is similar to the outer tubular member 3004 except for the design of the opening 3208. In this embodiment, the outer tubular member 3204 comprises a distal cutting surface 3209 that is rounded when viewed perpendicular to the longitudinal axis of the outer tubular body and normal to a center of the opening 3208, for example as oriented in FIG. 32B. In this embodiment, the distal cutting surface 3209 comprises a single convex rounded shape when viewed perpendicular to the longitudinal axis and normal to the center of the opening 3208. Other embodiments may comprise multiple rounded shapes and/or concave shapes instead of convex shapes. For example, FIGS. 33A-33D illustrate another example embodiment of an outer tubular member 3304 that is similar to the outer tubular member 3004 except for the design of the opening 3308. In this embodiment, the outer tubular member 3304 comprises a distal cutting surface 3309 that comprises a plurality of concave rounded surfaces when viewed perpendicular to the longitudinal axis of the outer tubular member 3304 and normal to a center of the opening 3308, for example, as oriented in FIG. 33B. The design shown in FIG. 33B, which includes a plurality of concave surfaces, also results in a plurality of pointed portions 3310 that can help with severing of tissue more efficiently.

Returning to FIG. 32A, the outer tubular member 3204 further comprises a recess 3211 when viewed perpendicular to the longitudinal axis and from the side of the opening 3208, for example, as oriented in FIG. 32A. The recess 3211 is at least partially defined by the distal cutting surface 3209 extending into the opening 3208 at an angle B. In this embodiment, the angle B is approximately 45°. In other embodiments, however, the angle B may be approximately, no greater than, or no less than 20°, 30°, 40°, 50°, 60°, or 70°. In some embodiments, the angle B may be within a range of 30 to 60°. The recess 3211 may help to form the rounded cutting surface 3209 into a shape that can help with severing of tissue more efficiently. It may be desirable to have a distal cutting surface of the opening that is angled, rounded, or otherwise not parallel with a transverse plane to, for example, help with severing of tissue more efficiently. The embodiments disclosed herein, including the embodiments shown in FIGS. 30A-30C, 32A-32C, and 33A-33D, may further help to prevent the polyp tissue from slipping out of the cutting bay (e.g., the opening 3008, 3208, 3308) once the cutter tube (e.g., tubular cutter 2515) strikes the tissue. For example, the distal cutting surface 3009, 3209, 3309 may help to "capture" the tissue between the distal cutting surface and the tubular cutter, to prevent the tubular cutter from pushing the tissue out of the opening as the tubular cutter strikes the tissue.

Further, the angular width of the openings 3008, 3208, 3308, or any other outer tubular member openings disclosed herein, may comprise various values. For example, with reference to the discussion above regarding angle 636 shown in FIG. 6D, the same range of angular widths 636 may apply to the openings 3008, 3208, 3308, or any other outer tubular member openings disclosed herein. For example, the openings 3008, 3208, or 3308 may comprise an angular width, as defined above with respect to angular widths 636, that is approximately, exactly, no greater than, or no less than, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 170°, 180°, 190°, 200°, 210°, 220°, 230°, 240°, 250°, 260°, or 270°. In some embodiments, it may be desirable to have an opening having an angular width greater than 90°, such as 120°, 150°, 180°, or any of the other angles given above, to increase the size of polyp tissue that may pass through the opening and be severed at any one time, thus increasing the efficiency of the polypectomy device. In some embodiments, it may be desirable to have an angular width of the opening that is within a range of 100°-140°. Testing results confirm such a desirable range, as shown in the two tables below, which compare the size of cut (in grams/cut) for a device with a 120 degree opening (Table 1) and a device with a 90 degree opening (Table 2).

TABLE 1

Device Configuration: 120° window (e.g., angle 636), blade rotation (e.g., rotation of the inner tubular member with respect to the outer tubular member as the inner tubular member moves from the retracted to extended position), 30° blade grind (e.g., the chamfer angle A shown in FIG. 25Q, measured with respect to a longitudinal plane, 3 lbf/in spring (e.g., the spring 2579, 3151, or the like)

| | Trial | | | | | |
|---|---|---|---|---|---|---|
| | 1 | 2 | 3 | 4 | 5 | 6 |
| Number of Cuts | 23 | 35 | 34 | 24 | 24 | 20 |
| Grams/Cut | 0.21 | 0.12 | 0.08 | 0.23 | 0.10 | 0.20 |

TABLE 2

Device Configuration: 90° window (e.g., angle 636), blade rotation (e.g., rotation of the inner tubular member with respect to the outer tubular member as the inner tubular member moves from the retracted to extended position), 30° blade grind (e.g., the chamfer angle A shown in FIG. 25Q, measured with respect to a longitudinal plane), 3 lbf/in spring (e.g., the spring 2579, 3151, or the like)

| | Trial | | | | | |
|---|---|---|---|---|---|---|
| | 1 | 2 | 3 | 4 | 5 | 6 |
| Number of Cuts | 32 | 41 | 37 | 40 | 41 | 37 |
| Grams/Cut | 0.04 | 0.06 | 0.07 | 0.06 | 0.10 | 0.08 |

The efficiency of the polypectomy device can in some embodiments also be increased by changing the angle and/or direction of the chamfer that forms the distal cutting edge of the tubular cutter of the inner tubular member. For example, with reference to FIG. 25Q, the tubular cutter 2515 in this embodiment comprises an approximately 22.5° chamfer 1554 (measured with respect to a longitudinal plane at angle A) that forms the distal cutting edge 2552. In other embodiments, this angle A may be lower or higher (measured with respect to a longitudinal plane). For example, this angle A may be approximately, exactly, no greater than, or no less than 45°, 40°, 30°, 22.5°, or 20°. In some embodiments, angle A may be within a range of 40-50 degrees, 30-60 degrees, 18-26 degrees, or 15-30 degrees. In some embodiments, this chamfered cutting edge is desirably formed using a grinding process, to generate a sharper cutting edge than typical machining processes. In some embodiments, as illustrated in FIG. 25Q, the tubular cutter is designed such that the cutting edge 2552 is positioned at an inner diameter of the tubular cutter. Stated another way, the chamfer 1554 that forms angle A is positioned radially outward of the cutting edge 2552. Positioning the cutting edge 2552 inward of the chamfer 1554 and/or at the inner diameter of the tubular cutter (as opposed to positioning the cutting edge 2552 at a position radially outward of the inner diameter) can help to increase the efficiency of the device and/or reduce clogging. This is because a cutting edge positioned more radially outward may produce larger diameter pieces of tissue, which may be harder to pass through the inner lumen of the tubular cutter 2515 and/or the inner tubular member 2514. In this embodiment, the cutting edge 2552 comprises a circular cutting edge that is oriented such that the circle lies in a plane that is perpendicular to the longitudinal axis of the tubular cutter. Other embodiments may comprise differently shaped cutting edges, such an oval shaped cutting edge that is oriented such that the oval lies in a plane that is not perpendicular to the longitudinal axis of the tubular cutter.

Alternative Release Mechanism

Figure 31A:
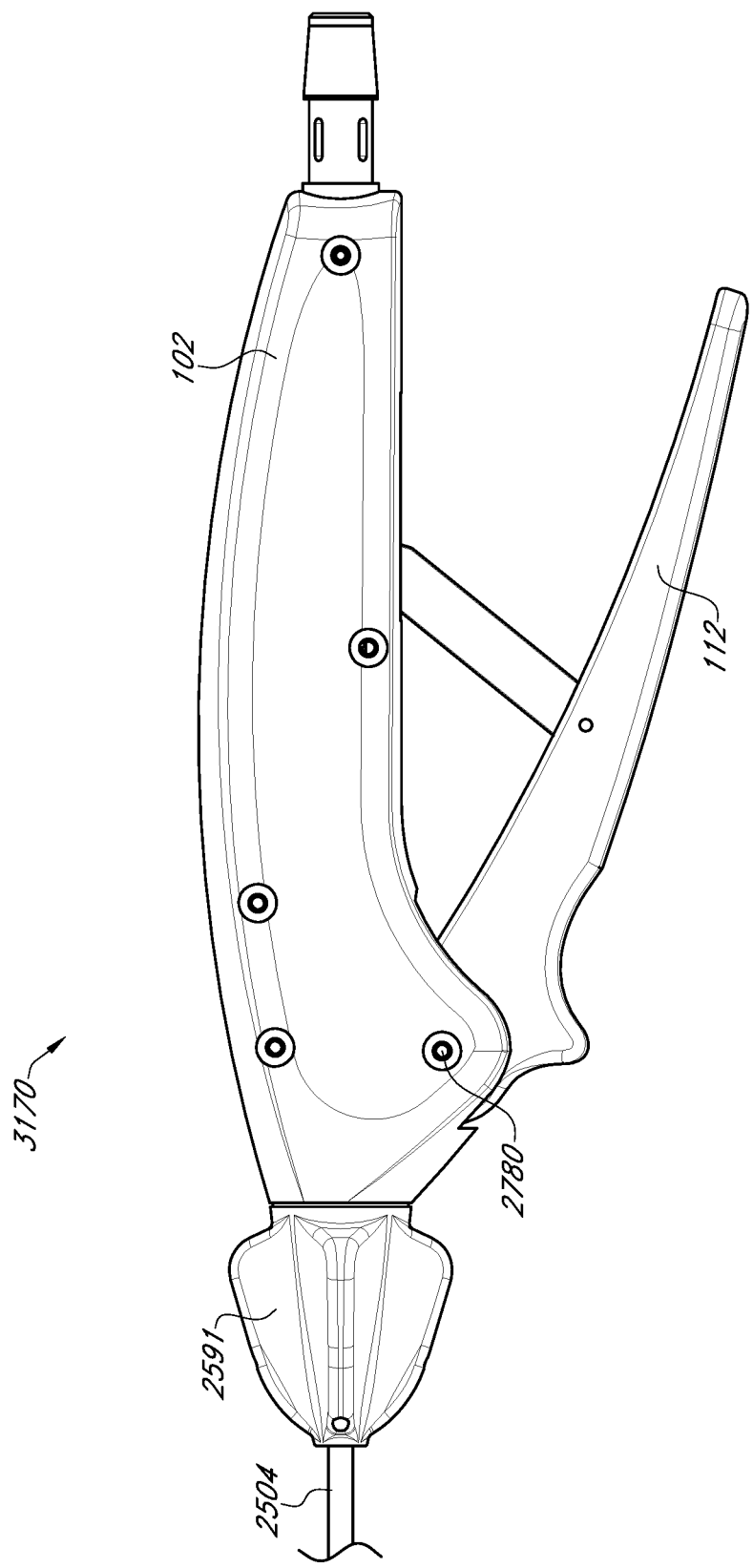
FIGS. 31A-31D illustrate another embodiment of a mechanism for controlling movement of a cutter.
Figure 31B:
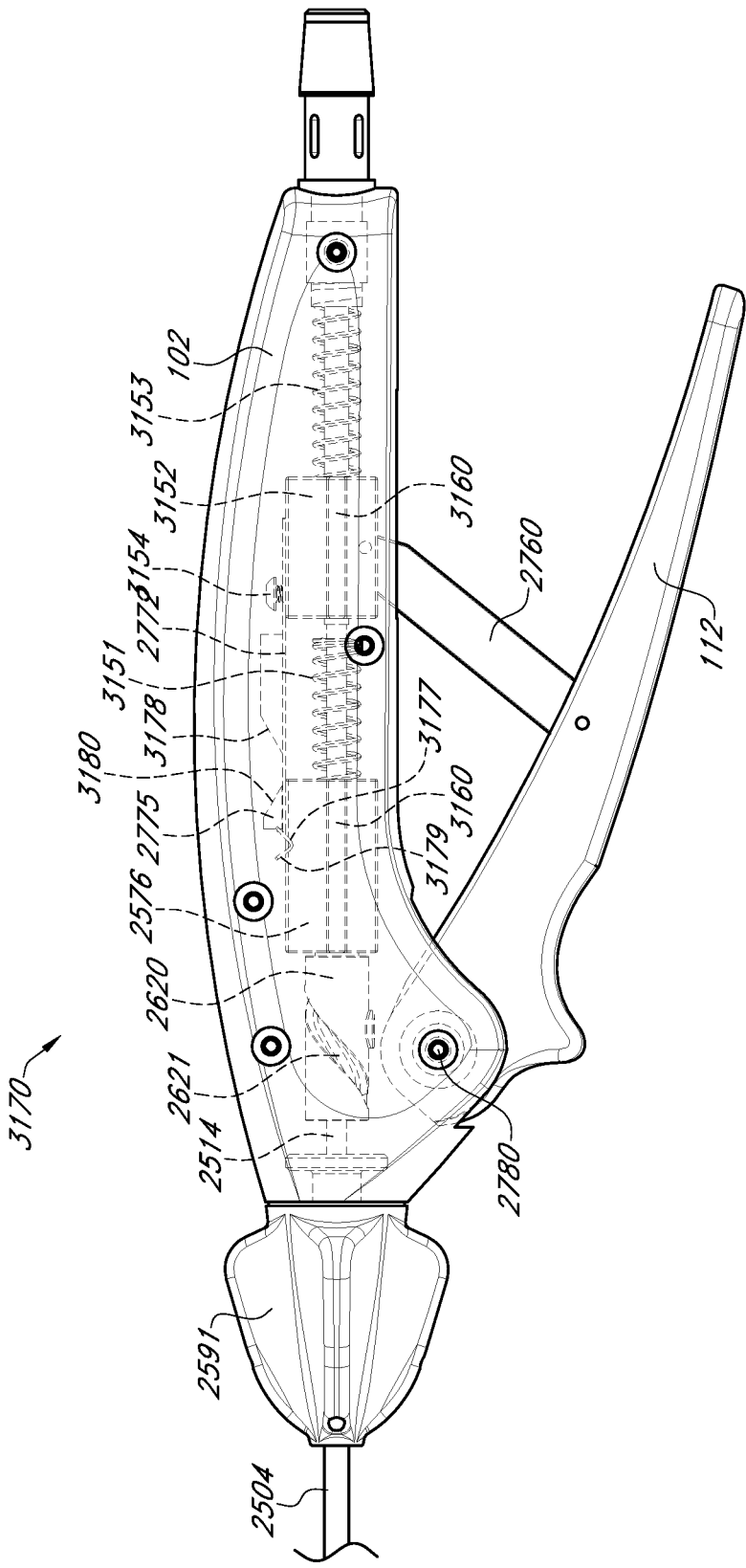
Figure 31C:
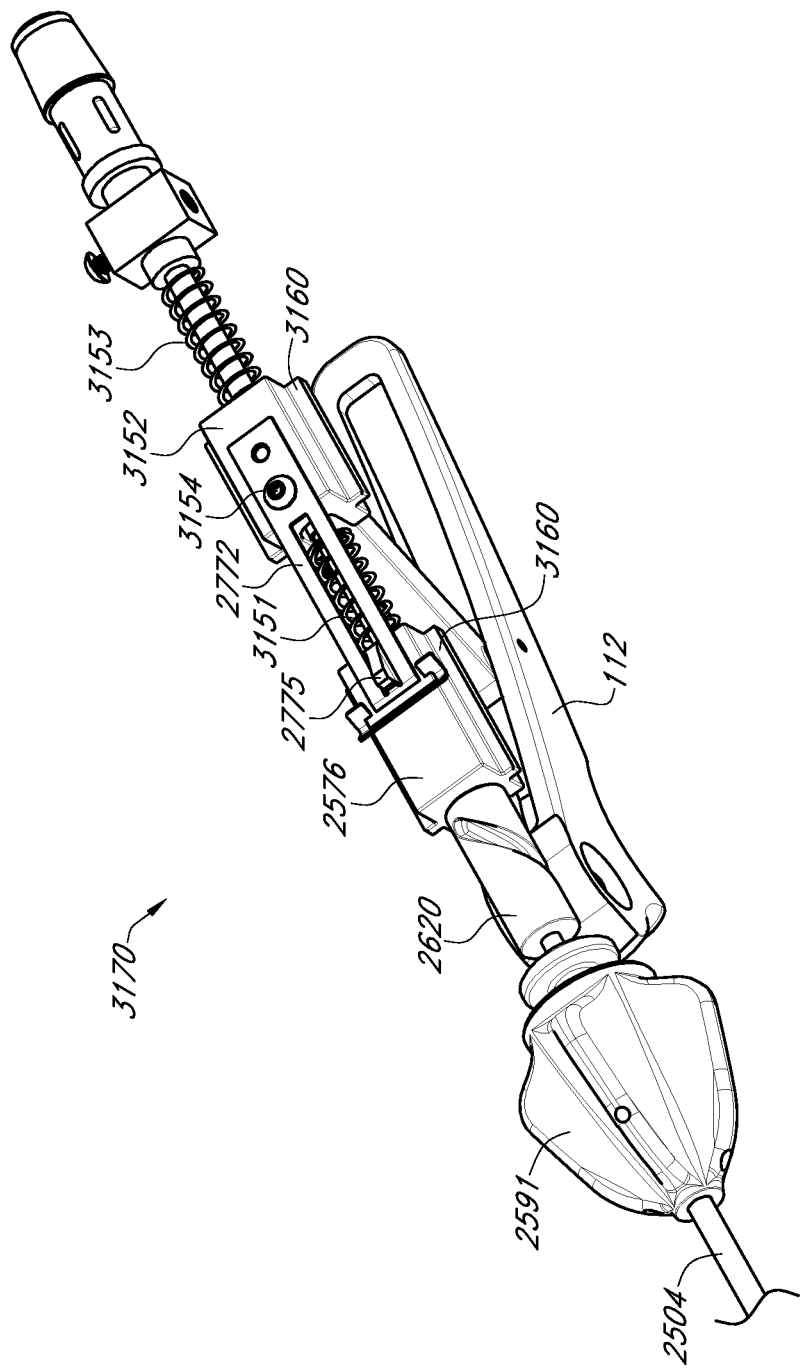
Figure 31D:
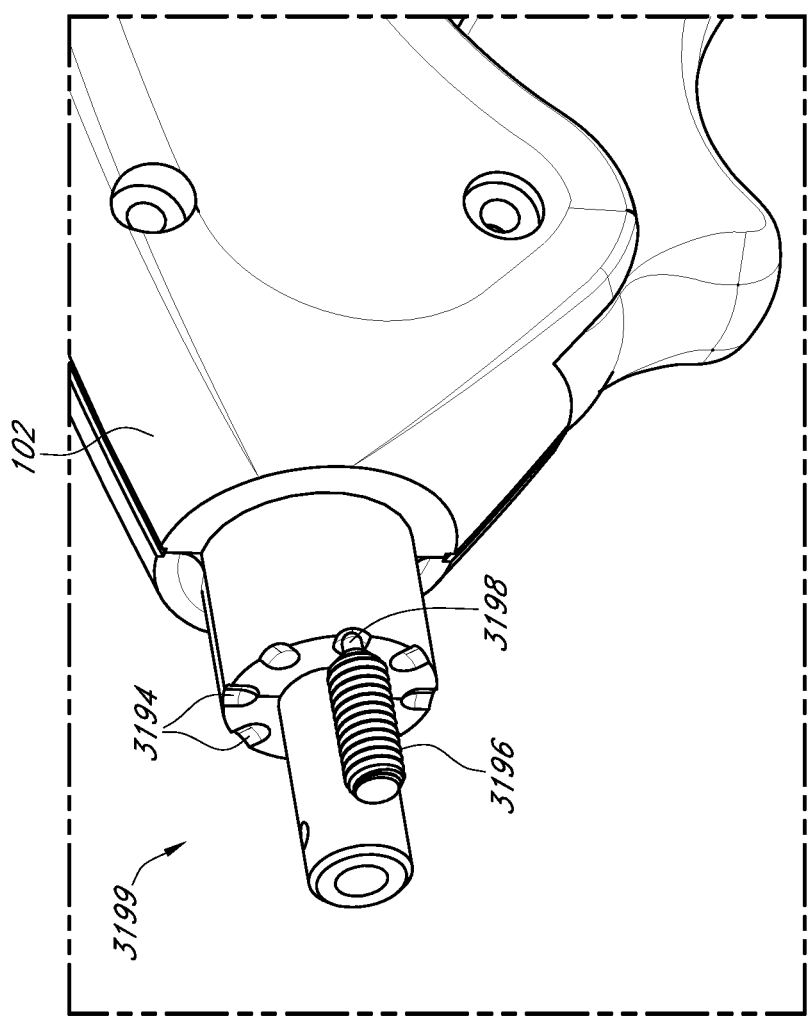

FIGS. 31A-31D illustrate another example embodiment of an automatic decoupling or release mechanism 3170 that can be used with any other embodiments of polypectomy devices disclosed herein. For example, the embodiment illustrated in FIGS. 31A-31D may be used with the distal end configuration of the embodiment of FIGS. 25A-25U, or with any of the other distal end configurations disclosed herein. The mechanism 3170 is similar in many respects to the mechanism 2970 illustrated in FIGS. 29A-29C. Accordingly, similar reference numbers are utilized, and this description focuses on differences in this embodiment with respect to other embodiments disclosed herein. The automatic decoupling or release mechanism 3170 comprises a housing 102, with a pivotally coupled trigger 112, and various components positioned within a cavity of the housing 102. FIG. 31A illustrates an outer side view of the mechanism 3170, and FIG. 31B illustrates a similar view, but with internal components shown in hidden lines. FIG. 31C illustrates a perspective view, with the housing 102 hidden. FIG. 31D illustrates a perspective view, with the hub 2591 hidden, to show a detent mechanism 3199.

One difference in the mechanism 3170 is the configuration of the bendable and/or spring-loaded connecting link or portion 2772, which engages the catch 2775. In the embodiment illustrated in FIG. 29C, the bendable and/or spring-loaded connecting link 2772 is coupled to actuator link 2971. In the embodiment of FIG. 31B, however, the bendable and/or spring-loaded connecting link 2772 desirably comprises a relatively thin piece of spring steel (or any other material that can perform a similar function) that is affixed to a proximal body 3152 using one or more fasteners 3154 (such as screws, rivets, and/or the like). The proximal body 3152 is configured to move proximally (to the right as shown in FIG. 31B) when the trigger 112 is squeezed. The proximal body 3152 is biased in the distal direction by proximal spring 3153. The proximal body 3152 and distal body (or actuating member) 2576 each comprise lateral protrusions 3160 configured to engage a corresponding channel or groove in the housing 102, to guide the sliding motion of the bodies 3152, 2576 in the longitudinal direction.

The bendable connecting link 2772 is desirably configured such that the connecting link 2772 engages the catch 2775 of the distal body 2576 when the proximal and distal bodies 3152, 2576 are in their distal most positions (as shown in FIG. 31B). As the proximal body 3152 is translated proximally by squeezing of the trigger 112 (with force transmitted through linkage 2760), the connecting link 2772 causes the distal body 2576 to also translate proximally. The distal body 2576 is desirably coupled to body 2620, so that body 2620 also translates proximally with distal body 2576. With continued squeezing of the trigger 112, as described above with reference to other embodiments, the bottom surface 3177 of the bendable connecting link 2772 will desirably engage cam surface 3178 of the housing, eventually forcing the distal portion of the connecting link 2772 to be forced upward and over the catch 2775 of the distal body 2576. Once the connecting link 2772 has disengaged the catch 2775, the distal spring 3151 is configured to cause the distal body 2576 to spring forward or in the distal direction. This will cause the inner tubular member 2514 to translate in the distal direction. Further, the helical groove 2621 of the body 2620 will desirably cause the inner tubular member 2514 to rotate about its longitudinal axis as the inner tubular member 2514 springs forward. The body 2620 is desirably coupled to the distal body 2576 in a way that allows rotation about the longitudinal axis of the body 2620 with respect to the distal body 2576. Finally, as the user releases pressure on the trigger 112, the proximal spring 3153 will desirably push the proximal body 3152 back to its distal most position, causing the connecting link 2772 to reengage the catch 2775. As described above with reference to other embodiments, bottom or angled surface 3179 of the connecting link 2772 will cooperate with cam surface 3180 to facilitate the distal end of the connecting link 2772 to move up and over the catch 2775 to re-engage the catch. The device is then ready for the next actuation. The proximal spring 3153 can be beneficial, for example, because it will allow the trigger 112 to be automatically "reset" to the extended position when a user released pressure from the trigger 112. In some embodiments, the proximal spring 3153 comprises a smaller spring rate than the distal spring 3151. This can be beneficial, for example, because the proximal spring 3153 is used to reset the trigger 112, which may be desired to be a less forceful and/or slower movement than the springing forward of the inner tubular body. In some embodiments, a damping mechanism may be included to damp the motion of the trigger 112 from the compressed to the extended position. It should be noted that, although this and other embodiments disclosed herein refer to a bendable portion that can elastically bend to engage or disengage a catch, any of these embodiments may also or alternatively comprise a portion that rotates instead of bends to engage or disengage the catch (such as shown in the embodiment of FIG. 28B).

The embodiment illustrated in FIGS. 31A-3D also illustrates another embodiment of a detent mechanism 3199 to selectively restrict rotation of the outer tubular body with respect to the handle. Specifically, FIG. 31D illustrates a portion of the handle 102 with the hub 2591 removed for clarity. Similarly to the detent mechanism 2599, the detent mechanism 3199 comprises a spring-loaded plunger 3198 positioned at least partially within the hub 2591 (not shown for clarity) and that can extend at least partially into one of a plurality of detents, depressions, grooves, and/or the like 3194 in a distal surface of the housing 102. The spring-loaded plunger 3198 can be held at least partially within one of the detents, depressions, grooves, and/or the like 3194 under its internal biasing force (e.g., a spring 3196 operatively positioned between the plunger and the hub), which can keep the outer tubular member 2504 in a specific rotational orientation with respect to the handle 102 until a sufficient rotational force is applied to force the ball or plunger 3198 out of the detent 3194. As with the detent mechanism described above, other forms of selective anti-rotation of the outer tubular member 2504 may also be used.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present invention herein disclosed should not be limited by the particular disclosed embodiments described above. The ranges disclosed herein also encompass any and all overlap, sub-ranges, and combinations thereof. Moreover, language such as "up to," "at least," "greater than," "less than," "between," and the like includes the number recited. Numbers or qualities or characteristics or amounts or quantities preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A polyp removal device, comprising:
    an outer tubular body having proximal and distal ends, the outer tubular body comprising an opening in a side wall near the distal end;
    an inner tubular body positioned within a lumen of the outer tubular body, the inner tubular body having proximal and distal ends and being longitudinally and rotationally movable with respect to the outer tubular body, the inner tubular body comprising a longitudinally extended position and a longitudinally retracted position with respect to the outer tubular body;
    a tubular cutter coupled to or formed as part of the distal end of the inner tubular body, the tubular cutter positioned adjacent the opening of the outer tubular body;
    a spring configured to bias the inner tubular body toward the extended position with respect to the outer tubular body;
    a handle coupled to the proximal end of the outer tubular body;
    a cam mechanism comprising a helical structure configured to cause the inner tubular body to rotate about a longitudinal axis as the inner tubular body moves from the longitudinally retracted position to the longitudinally extended position with respect to the outer tubular body; and
    a spring loaded cutter released mechanism or a trigger coupled to the handle and configured to selectively release the inner tubular body from the retracted position responsive to manipulation by a user of an actuation member movably coupled to the handle, allowing the spring to move the inner tubular body toward the extended position.

2. The polyp removal device of claim 1, wherein the outer tubular body is rotatable with respect to the handle, to enable changing of a rotational position of the opening with respect to the handle.

3. The polyp removal device of claim 2, further comprising a detent mechanism configured to selectively resist rotation of the outer tubular body with respect to the handle.

4. The polyp removal device of claim 3, wherein the detent mechanism comprises a spring-loaded ball or pin.

5. The polyp removal device of claim 1, wherein the helical structure of the cam mechanism comprises a helical cam groove coupled to or formed as part of the one of the inner tubular body or the handle.

6. The polyp removal device of claim 1, wherein the helical structure is configured to cause the inner tubular body to rotate at least 90 degrees about the longitudinal axis as the inner tubular body extends with respect to the outer tubular body.

7. The polyp removal device of claim 6, wherein the helical structure is configured to cause the inner tubular body to rotate no more than 270 degrees about the longitudinal axis as the inner tubular body extends with respect to the outer tubular body.

8. The polyp removal device of claim 1, wherein the cam mechanism further comprises a pin engaged with the helical structure, wherein the pin is coupled to or formed as part of one of the inner tubular body or the handle, and the helical structure comprises a helical cam groove coupled to or formed as part of the other of the inner tubular body or the handle.

9. The polyp removal device of claim 1, wherein the spring loaded cutter released mechanism or the trigger comprises a catch that engages an actuation surface of the inner tubular body or a component coupled to the inner tubular body, and wherein the catch is movable out of engagement with the actuation surface to allow the spring to move the inner tubular body toward the extended position.

10. The polyp removal device of claim 9, wherein the catch is pivotally movable to engage or disengage the actuation surface, and the spring loaded cutter released mechanism or the trigger further comprises a torsion spring that biases the catch toward engagement with the actuation surface.

11. The polyp removal device of claim 9, wherein the catch is biased toward engagement with the actuation surface, and the catch comprises an elastically bendable material that can bend to disengage the actuation surface.

12. The polyp removal device of claim 9, wherein, when the catch of the spring loaded cutter released mechanism or the trigger is in engagement with the actuation surface, movement of the actuation member with respect to the handle causes movement of the inner tubular body with respect to the handle; and
    wherein, when the catch of the spring loaded cutter released mechanism or the trigger is not in engagement with the actuation surface, movement of the actuation member with respect to the handle does not cause movement of the inner tubular body with respect to the handle.

13. The polyp removal device of claim 9, wherein the actuation member is configured to be manipulated by a user by at least one of sliding or rotating the actuation member with respect to the handle.

14. The polyp removal device of claim 13, wherein the spring loaded cutter released mechanism or the trigger further comprises a cam surface positioned to automatically cause the catch to disengage the actuation surface in response to movement of the actuation member with respect to the handle.

15. The polyp removal device of claim 14, wherein the cam surface is coupled to or formed as part of the handle.

16. The polyp removal device of claim 13, wherein the actuation member is coupled to the spring loaded cutter released mechanism or the trigger through a geartrain or linkage that converts pivotal movement of the actuation member into sliding movement of at least a portion of the spring loaded cutter released mechanism or the trigger.

17. The polyp removal device of claim 1, further comprising:
    a cutting block positioned at least partially distal to the opening, the cutting block comprising a proximally extending cutting portion positioned within the lumen of the outer tubular body, wherein the tubular cutter is sized to fit at least partially within a void between the lumen of the outer tubular body and an outer surface of the cutting portion of the cutting block when the inner tubular body is in the extended position with respect to the outer tubular body.

18. A method of removing a uterine polyp, comprising:

inserting a medical instrument into a uterus, the medical instrument comprising a working channel;

inserting the polyp removal device of claim 1 through the working channel of the medical instrument;

extending the distal end of the outer tubular body of the polyp removal device into the uterus beyond a distal end of the working channel of the medical device;

positioning at least a portion of a polyp through the opening in the outer tubular body of the polyp removal device;

manipulating the actuation member of the polyp removal device, causing the cutter to spring forward to separate the at least a portion of the polyp from the uterus; and transferring the separated portion of the polyp to a proximal end of the polyp removal device via suction.

19. The method of claim 18, wherein the medical instrument comprises a hysteroscope.

20. The method of claim 18, further comprising cutting and removing additional portions of the polyp from the uterus.

* * * * *